(12) United States Patent
Lampe et al.

(10) Patent No.: US 9,018,414 B2
(45) Date of Patent: Apr. 28, 2015

(54) SUBSTITUTED 3-PHENYLPROPIONIC ACIDS AND THE USE THEREOF

(71) Applicant: Bayer Intellectual Property GmbH, Monheim (DE)

(72) Inventors: Thomas Lampe, Düsseldorf (DE); Michael Hahn, Langenfeld (DE); Johannes-Peter Stasch, Solingen (DE); Karl-Heinz Schlemmer, Wuppertal (DE); Frank Wunder, Wuppertal (DE); Sherif El Sheikh, Essen (DE); Volkhart Min-Jian Li, Velbert (DE); Eva-Maria Becker-Pelster, Wuppertal (DE); Friederike Stoll, Düsseldorf (DE); Andreas Knorr, Erkrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/045,630

(22) Filed: Oct. 3, 2013

(65) Prior Publication Data

US 2014/0142069 A1    May 22, 2014

Related U.S. Application Data

(63) Continuation of application No. 12/914,101, filed on Oct. 28, 2010, now abandoned.

(30) Foreign Application Priority Data

Oct. 28, 2009 (DE) .......................... 10 2009 046 115

(51) Int. Cl.
| | | |
|---|---|---|
| C07C 205/00 | (2006.01) | |
| C07C 229/00 | (2006.01) | |
| C07C 233/88 | (2006.01) | |
| C07C 233/45 | (2006.01) | |
| C07C 205/38 | (2006.01) | |
| C07C 233/55 | (2006.01) | |
| C07C 255/60 | (2006.01) | |
| C07D 305/06 | (2006.01) | |
| A61K 31/196 | (2006.01) | |
| A61K 31/655 | (2006.01) | |
| C07C 231/02 | (2006.01) | |

(52) U.S. Cl.
CPC ............ C07C 233/88 (2013.01); C07C 233/45 (2013.01); C07C 205/38 (2013.01); C07C 233/55 (2013.01); C07C 255/60 (2013.01); C07C 2101/02 (2013.01); C07C 2101/04 (2013.01); C07C 2101/08 (2013.01); C07D 305/06 (2013.01); A61K 31/196 (2013.01); A61K 31/655 (2013.01); C07C 231/02 (2013.01)

(58) Field of Classification Search
CPC .... C07C 205/38; C07C 233/45; C07C 51/36; C07D 305/06

USPC .............................. 562/435, 433, 400; 549/511
See application file for complete search history.

(56) References Cited

U.S. PATENT DOCUMENTS

| | | | |
|---|---|---|---|
| 5,041,453 | A | 8/1991 | Huang et al. |
| 5,693,650 | A | 12/1997 | Müller et al. |
| 5,811,429 | A | 9/1998 | Connell et al. |
| 5,935,984 | A | 8/1999 | Goldmannn et al. |
| 6,667,334 | B1 | 12/2003 | Neises et al. |
| 6,693,102 | B2 | 2/2004 | Stasch et al. |
| 6,743,798 | B1 | 6/2004 | Stasch et al. |
| 6,833,364 | B1 | 12/2004 | Straub et al. |
| 6,835,752 | B2 | 12/2004 | Tani et al. |
| 6,884,821 | B1 | 4/2005 | Shinoda et al. |
| 7,005,440 | B1 | 2/2006 | Jayyosi et al. |
| 7,173,037 | B2 | 2/2007 | Alonso-Alija et al. |
| 7,176,204 | B2 | 2/2007 | Miyachi et al. |
| 7,238,716 | B2 | 7/2007 | Momose et al. |
| 7,241,785 | B2 | 7/2007 | Momose et al. |
| 7,244,861 | B2 | 7/2007 | Matsuura et al. |
| 7,368,578 | B2 | 5/2008 | Momose et al. |
| 7,371,777 | B2 | 5/2008 | Clark et al. |
| 7,465,825 | B2 | 12/2008 | Van Zandt et al. |
| 7,491,748 | B2 | 2/2009 | Tani et al. |
| 7,816,367 | B2 | 10/2010 | Akerman et al. |
| 2003/0105097 | A1 | 6/2003 | Simon et al. |
| 2005/0187266 | A1 | 8/2005 | Su |
| 2005/0234066 | A1 | 10/2005 | Bailey et al. |

(Continued)

FOREIGN PATENT DOCUMENTS

| | | |
|---|---|---|
| EP | 0 608 709 A1 | 8/1994 |
| EP | 1 229 010 A1 | 8/2002 |

(Continued)

OTHER PUBLICATIONS

U.S. Appl. No. 13/431,934, filed Mar. 27, 2012, published as US 2013-0079412.
Mase, et al.:"Synthesis of a Muscarinic Receptor Antagonist via a Diastereoselective Michael Reaction, Selective Deoxyfluorination and Aromatic Metal-Halogne Exchange Reaction," J. Org. Chem., 2001, 66: 6775-6786.
Moradi, et al.:"Palladium-Catalyzed α-Arylation of Esters," J. Am. Chem. Soc.,2001, 123: 7996-8002.
Sakai, et al.:"Rhodium-Catalyzed Conjugate Addition of Aryl- or 1-Alkenylboronic Acids to Enones," Organometallics, Sep. 30, 1997, 16(20): 4229-4231.

(Continued)

*Primary Examiner* — Andrew D Kosar
*Assistant Examiner* — Raymond Covington
(74) *Attorney, Agent, or Firm* — Buchanan Ingersoll & Rooney PC

(57) ABSTRACT

The present application relates to novel 3-phenylpropionic acid derivatives, to processes for their preparation, to their use for the treatment and/or prevention of diseases and to their use for preparing medicaments for the treatment and/or prevention of diseases, in particular for the treatment and/or prevention of cardiovascular disorders.

16 Claims, No Drawings

(56) References Cited

U.S. PATENT DOCUMENTS

| | | |
|---|---|---|
| 2011/0034450 A1 | 2/2011 | Hahn et al. |
| 2011/0092554 A1 | 4/2011 | Chesworth et al. |
| 2011/0130445 A1 | 6/2011 | Lampe et al. |
| 2012/0028971 A1 | 2/2012 | Lampe et al. |
| 2012/0172448 A1 | 7/2012 | Lampe et al. |
| 2013/0079412 A1 | 3/2013 | Hahn et al. |

FOREIGN PATENT DOCUMENTS

| | | |
|---|---|---|
| EP | 1285 908 A1 | 2/2003 |
| WO | 9612473 A1 | 5/1996 |
| WO | 9630036 A1 | 10/1996 |
| WO | 0064888 A1 | 11/2000 |
| WO | 2004099170 A2 | 11/2004 |
| WO | 2006050097 A1 | 5/2006 |

OTHER PUBLICATIONS

Varchi, et al.:"Copper Catalyzed Conjugate Addition of Highly Functionalized Arylmagnesium Compounds to Enones," Tetrahedron, 2000, 56: 2727-2731.

Weintraub, et al.:"Synthesis of Steroidal Vinyl Ethers Using Palladium Acetate-Phenanthroline as Catalyst," J.Org. Chem., 1997, 62:1560-1562.

Wolfe, et al.:"Palladium-Catalyzed Amination of Aryl Halides and Aryl Triflates: N-Hexyl-2-Methyl-4-Methoxyaniline and N-Methyl-N-(4-Chlorophenyl) Aniline," Organic Synthesis, Coll. vol. 10: 423 (2004); 78:23 (2002).

Evgenov et al., "NO-independent stimulators and activators of soluble guanylate cyclase: discovery and thereapeutic potential," Nature Reviews, 2006, 5(9):755-768.

Stasch et al., "NO- and haem-independent activation of soluble guanylyl cyclase: molecular basis and cardiovascular implications of a new pharmacological principle," British Journal of Pharmacology, 2002, 136(5):773-783.

Stasch et al., "Targeting the heme-oxidized nitric oxide receptor for selective vasodilatation of diseased blood vessels," Journal Clin. Invest., 2006, 116(9):2552-2561.

Hayashi, "Rhodium-Catalyzed Asymmetric 1,4-Addition of Organoboronic Acids and Their Derivatives to Electron Deficient Olefins," Synlett, 2001, SI: 879-887.

U.S. Appl. No. 13/312,230, filed Dec. 7, 2010.

U.S. Appl. No. 12/937,995, filed Oct. 14, 2010, published as US 2011-0034450.

U.S. Appl. No. 13/201,924, filed Oct. 6, 2011, published as US 2012-0028971.

SUBSTITUTED 3-PHENYLPROPIONIC ACIDS AND THE USE THEREOF

The present application relates to novel 3-phenylpropionic acid derivatives, to processes for their preparation, to their use for the treatment and/or prevention of diseases and to their use for preparing medicaments for the treatment and/or prevention of diseases, in particular for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. The latter is of central importance for the mechanism of activation. NO is able to bind to the iron atom of haem and thus markedly increase the activity of the enzyme. Haem-free preparations cannot, by contrast, be stimulated by NO. Carbon monoxide (CO) is also able to attach to the central iron atom of haem, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment [O. V. Evgenov et al., *Nature Rev. Drug Disc.* 5 (2006), 755].

Substances which directly stimulate soluble guanylate cyclase, i.e. without previous release of NO, have been identified in recent years. The indazole derivative YC-1 was the first NO-independent but haem-dependent sGC stimulator described [Evgenov et al., ibid.]. Based on YC-1, further substances were discovered which are more potent than YC-1 and show no relevant inhibition of phosphodiesterases (PDE). This led to the identification of the pyrazolopyridine derivatives BAY 41-2272, BAY 41-8543 and BAY 63-2521. Together with the recently published structurally different substances CMF-1571 and A-350619, these compounds form the new class of the sGC stimulators [Evgenov et al., ibid.]. A common characteristic of this substance class is an NO-independent and selective activation of the haem-containing sGC. In addition, the sGC stimulators in combination with NO have a synergistic effect on sGC activation based on a stabilization of the nitrosyl-haem complex. The exact binding site of the sGC stimulators at the sGC is still being debated. If the haem group is removed from the soluble guanylate cyclase, the enzyme still has a detectable catalytic basal activity, i.e. cGMP is still being formed. The remaining catalytic basal activity of the haem-free enzyme cannot be stimulated by any of the stimulators mentioned above [Evgenov et al., ibid.].

In addition, NO- and haem-independent sGC activators, with BAY 58-2667 as prototype of this class, have been identified. Common characteristics of these substances are that in combination with NO they only have an additive effect on enzyme activation, and that the activation of the oxidized or haem-free enzyme is markedly higher than that of the haem-containing enzyme [Evgenov et al., ibid.; J. P. Stasch et al., *Br. J. Pharmacol.* 136 (2002), 773; J. P. Stasch et al., *J. Clin. Invest.* 116 (2006), 2552]. Spectroscopic studies show that BAY 58-2667 displaces the oxidized haem group which, as a result of the weakening of the iron-histidine bond, is attached only weakly to the sGC. It has also been shown that the characteristic sGC haem binding motif Tyr-x-Ser-x-Arg is absolutely essential both for the interaction of the negatively charged propionic acids of the haem group and for the action of BAY 58-2667. Against this background, it is assumed that the binding site of BAY 58-2667 at the sGC is identical to the binding site of the haem group [J. P. Stasch et al., *J. Clin. Invest.* 116 (2006), 2552].

The compounds described in the present invention are now likewise capable of activating the haem-free form of soluble guanylate cyclase. This is also confirmed by the fact that these novel activators firstly have no synergistic action with NO at the haem-containing enzyme and that secondly their action cannot be blocked by the haem-dependent inhibitor of soluble guanylate cyclase, 1H-1,2,4-oxadiazolo[4,3-a]quinoxalin-1-one (ODQ), but is even potentiated by this inhibitor [cf. O. V. Evgenov et al., *Nature Rev. Drug Disc.* 5 (2006), 755; J. P. Stasch et al., *J. Clin. Invest.* 116 (2006), 2552].

Accordingly, it was an object of the present invention to provide novel compounds which act as activators of soluble guanylate cyclase in the manner described above and can be used as such in particular for the treatment and prevention of cardiovascular disorders.

WO 00/64888-A1, EP 1 216 980-A1, EP 1 375 472-A1, EP 1 452 521-A1, US 2005/0187266-A1 and US 2005/0234066-A1 describe various arylalkanecarboxylic acid derivatives as PPAR agonists for the treatment of diabetes, dyslipidemia, arteriosclerosis, obesity and other disorders. EP 1 312 601-A1 and EP 1 431 267-A1 disclose substituted arylalkanecarboxylic acids as PGE$_2$ receptor antagonists for the treatment of, for example, pain, urological disorders, Alzheimer's disease and cancer. Furthermore, arylalkanecarboxylic acids are claimed in WO 2005/086661-A2 as GPR40 modulators for the treatment of diabetes and dyslipidemias, and WO 2004/099170-A2, WO 2006/050097-A1 and WO 2006/055625-A2 describe phenyl-substituted carboxylic acids as PTP-1B inhibitors for the treatment of diabetes, cancer and neurodegenerative disorders. Furthermore, individual phenylacetamido-substituted phenylalkanecarboxylic acids which, in the form of non-covalent mixtures, improve the provision of active peptide compounds within the body are known from WO 96/12473-A1 and WO 96/30036-A1. Recently, oxohet-erocyclically substituted carboxylic acid derivatives which act as activators of soluble guanylate cyclase have been disclosed in WO 2009/127338-A1.

The present invention provides compounds of the general formula (I)

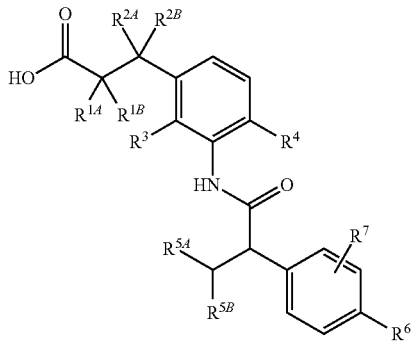

in which
R$^{1A}$ represents hydrogen, fluorine, methyl, trifluoromethyl, ethyl, 1,1-difluoroethyl, 2,2,2-trifluoroethyl, n-propyl, cyclopropyl or cyclobutyl,
R$^{1B}$ represents hydrogen or methyl,
R$^{2A}$ represents hydrogen, methyl, trifluoromethyl, ethyl, 1,1-difluoroethyl, 2,2,2-trifluoroethyl or n-propyl,
R$^{2B}$ represents hydrogen or methyl,
or
R$^{1A}$ and R$^{2A}$ are attached to one another and together with the carbon atoms to which they are attached form a cyclopropyl ring of the formula

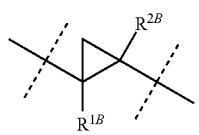

in which R$^{1B}$ and R$^{2B}$ have the meanings mentioned above,
or
R$^{2A}$ and R$^{2B}$ are attached to one another and together with the carbon atom to which they are attached form a cyclic group of the formula

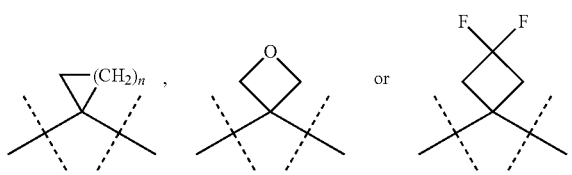

in which
n represents the number 1, 2 or 3, and
R$^{1A}$ and R$^{1B}$ have the meanings mentioned above,
R$^{3}$ represents hydrogen, fluorine, methyl or trifluoromethyl,
R$^{4}$ represents hydrogen, fluorine, chlorine, cyano, methyl, trifluoromethyl or ethyl,
R$^{5A}$ represents methyl, trifluoromethyl or ethyl,
R$^{5B}$ represents trifluoromethyl,
or
R$^{5A}$ and R$^{5B}$ are attached to one another and together with the carbon atom to which they are attached form a difluoro-substituted cycloalkyl ring of the formula

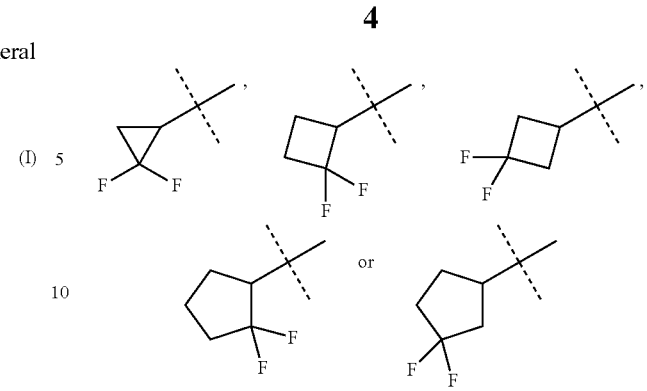

R$^{6}$ represents hydrogen, fluorine, chlorine, bromine, cyano, (C$_1$-C$_4$)-alkyl, (C$_2$-C$_4$)-alkenyl, cyclopropyl or cyclobutyl, where
(C$_1$-C$_4$)-alkyl and (C$_2$-C$_4$)-alkenyl may be substituted up to three times by fluorine
and
cyclopropyl and cyclobutyl may be substituted up to two times by fluorine,
and
R$^{7}$ represents hydrogen, fluorine, chlorine, cyano, methyl, trifluoromethyl, ethyl, methoxy or trifluoromethoxy,
and the salts, solvates and solvates of the salts thereof.

Compounds according to the invention are the compounds of the formula (I) and their salts, solvates and solvates of the salts; the compounds, encompassed by formula (I), of the formulae specified below and their salts, solvates and solvates of the salts; and the compounds, encompassed by formula (I), specified below as examples and their salts, solvates and solvates of the salts, where the compounds, encompassed by formula (I), specified below are not already salts, solvates and solvates of the salts.

The compounds according to the invention can exist in various stereoisomeric forms, i.e. in the form of configurational isomers or, if appropriate, also as conformational isomers (enantiomers and/or diastereomers, including those in the case of atrop isomers), depending on their structure. The present invention therefore includes the enantiomers and diastereomers and their particular mixtures. The stereoisomerically uniform constituents can be isolated from such mixtures of enantiomers and/or diastereomers in a known manner; chromatographical processes are preferably used for this, in particular HPLC chromatography on an achiral or chiral phase.

Where the compounds according to the invention can occur in tautomeric forms, the present invention includes all the tautomeric forms.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention also include in particular the salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropyl-amine, monoethanolamine, diethanolamine, triethanolamine, dicyclohexylamine, dimethylaminoethanol, procaine, dibenzylamine, N-methylmorpholine, N-methylpiperidine, arginine, lysine and ethylenediamine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

The present invention comprises in particular hydrolyzable ester derivatives of the carboxylic acids of the formula (I) according to the invention. These are to be understood as meaning esters which can be hydrolyzed to the free carboxylic acids, as the compounds that are mainly active biologically, in physiological media, under the conditions of the biological tests described later and in particular in vivo by enzymatic or chemical routes. $(C_1-C_4)$-alkyl esters, in which the alkyl group can be straight-chain or branched, are preferred as such esters. Particular preference is given to methyl, ethyl or tert-butyl esters.

In the context of the present invention, the substituents have the following meaning, unless specified otherwise:

$(C_1-C_4)$-Alkyl in the context of the invention represents a straight-chain or branched alkyl radical having 1 to 4 carbon atoms. There may be mentioned by way of example and preferably: methyl, ethyl, n-propyl, isopropyl, n-butyl, isobutyl, sec-butyl and tert-butyl.

$(C_2-C_4)$-Alkenyl and $(C_2-C_3)$-Alkenyl in the context of the invention represent a straight-chain or branched alkenyl radical having a double bond and 2 to 4 or, respectively, 2 or 3 carbon atoms. Preference is given to a straight-chain or branched alkenyl radical having 2 or 3 carbon atoms. There may be mentioned by way of example and preferably: vinyl, allyl, n-prop-1-en-1-yl, iso-propenyl, n-but-1-en-1-yl, n-but-2-en-1-yl, n-but-3-en-1-yl, 2-methylprop-1-en-1-yl and 2-methylprop-2-en-1-yl.

In the context of the present invention, for all the radicals which occur more than once, the meaning thereof is independent of each other. If radicals in the compounds according to the invention are substituted, the radicals can be mono- or polysubstituted, unless specified otherwise. Substitution by one or by two or by three individual or different substituents is preferred. Substitution by one or by two identical or different substituents is particularly preferred.

In a certain embodiment, the present invention embraces compounds of the formula (I) in which $R^{1A}$ represents hydrogen, fluorine, methyl, trifluoromethyl, ethyl, 1,1-difluoroethyl, 2,2,2-trifluoroethyl or n-propyl, $R^{1B}$ represents hydrogen or methyl, $R^{2A}$ represents hydrogen, methyl, trifluoromethyl, ethyl, 1,1-difluoroethyl, 2,2,2-trifluoroethyl or n-propyl, $R^{2B}$ represents hydrogen or methyl, or $R^{1A}$ and $R^{2A}$ are attached to one another and together with the carbon atoms to which they are attached form a cyclopropyl ring of the formula

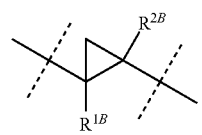

in which $R^{1B}$ and $R^{2B}$ have the meanings mentioned above, or $R^{2A}$ and $R^{2B}$ are attached to one another and together with the carbon atom to which they are attached form a cyclic group of the formula

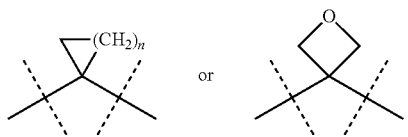

in which n represents the number 1, 2 or 3, and $R^{1A}$ and $R^{1B}$ have the meanings mentioned above, $R^3$ represents hydrogen, fluorine, methyl or trifluoromethyl, $R^4$ represents hydrogen, fluorine, chlorine, cyano, methyl, trifluoromethyl or ethyl, $R^{5A}$ represents methyl, trifluoromethyl or ethyl, $R^{5B}$ represents trifluoromethyl, or $R^{5A}$ and $R^{5B}$ are attached to one another and together with the carbon atom to which they are attached form a difluoro-substituted cycloalkyl ring of the formula

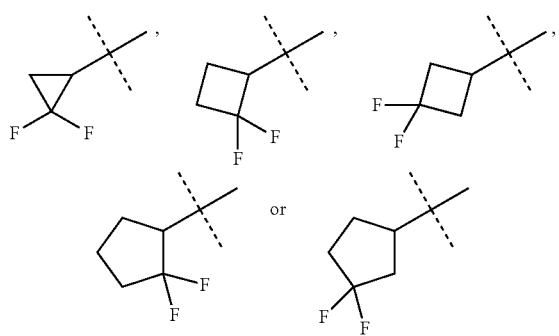

$R^6$ represents hydrogen, fluorine, chlorine, bromine, cyano, $(C_1-C_4)$-alkyl or $(C_2-C_4)$-alkenyl, where $(C_1-C_4)$-alkyl and $(C_2-C_4)$-alkenyl for their part may be substituted up to three times by fluorine, and $R^7$ represents hydrogen, fluorine, chlorine or methyl, and the salts, solvates, and solvates of the salts thereof.

In the context of the present invention, preference is given to compounds of the formula (I) in which $R^{1A}$ represents hydrogen, methyl, trifluoromethyl, ethyl, n-propyl, cyclopropyl or cyclobutyl, $R^{1B}$ represents hydrogen or methyl, $R^{2A}$ represents hydrogen, methyl, trifluoromethyl, ethyl or n-propyl, $R^{2B}$ represents hydrogen or methyl, or $R^{2A}$ and $R^{2B}$ are attached to one another and together with the carbon atom to which they are attached form a cyclic group of the formula

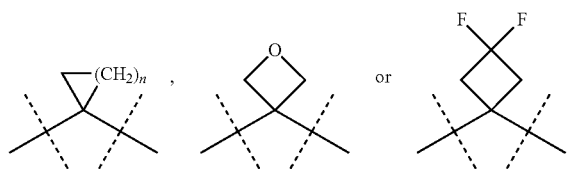

in which
n represents the number 1 or 2, and
$R^{1A}$ and $R^{1B}$ have the meanings mentioned above,
$R^3$ represents hydrogen, fluorine or methyl,
$R^4$ represents hydrogen, fluorine, chlorine, cyano, methyl or trifluoromethyl,
$R^{5A}$ represents methyl or ethyl,
$R^{5B}$ represents trifluoromethyl,
or
$R^{5A}$ and $R^{5B}$ are attached to one another and together with the carbon atom to which they are attached form a difluoro-substituted cycloalkyl ring of the formula

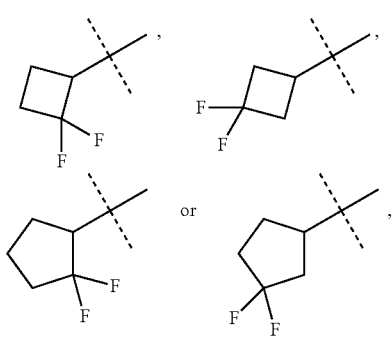

$R^6$ represents fluorine, chlorine, $(C_1-C_4)$-alkyl, $(C_2-C_3)$-alkenyl, cyclopropyl or cyclobutyl, where
$(C_1-C_4)$-alkyl and $(C_2-C_3)$-alkenyl may be substituted up to three times by fluorine
and
cyclopropyl and cyclobutyl may be substituted up to two times by fluorine,
and
$R^7$ represents hydrogen, fluorine, chlorine, methyl or methoxy,
and the salts, solvates, and solvates of the salts thereof.

A further preferred embodiment of the present invention embraces compounds of the formula (I) in which
$R^{1A}$ represents hydrogen, methyl, trifluoromethyl, ethyl or n-propyl,
$R^{1B}$ represents hydrogen or methyl,
$R^{2A}$ represents hydrogen, methyl, trifluoromethyl or ethyl,
$R^{2B}$ represents hydrogen or methyl,
or
$R^{2A}$ and $R^{2B}$ are attached to one another and together with the carbon atom to which they are attached form a cyclic group of the formula

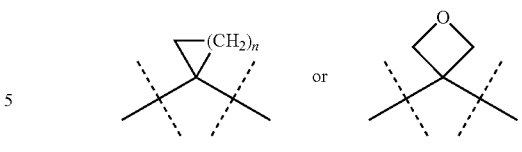

in which
n represents the number 1 or 2, and
$R^{1A}$ and $R^{1B}$ have the meanings mentioned above,
$R^3$ represents hydrogen or fluorine,
$R^4$ represents hydrogen, fluorine, chlorine, cyano, methyl or trifluoromethyl,
$R^{5A}$ represents methyl or ethyl,
$R^{5B}$ represents trifluoromethyl,
or
$R^{5A}$ and $R^{5B}$ are attached to one another and together with the carbon atom to which they are attached form a difluoro-substituted cycloalkyl ring of the formula

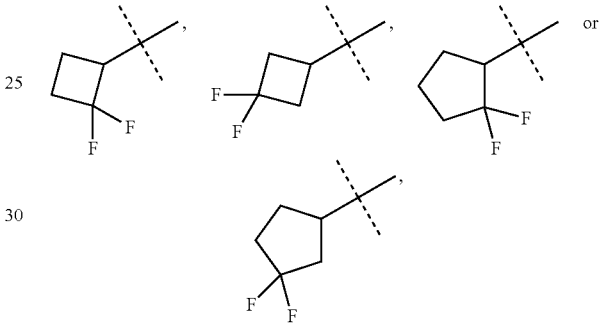

$R^6$ represents fluorine, chlorine, $(C_1-C_4)$-alkyl or $(C_2-C_3)$-alkenyl, where $(C_1-C_4)$-alkyl and $(C_2-C_3)$-alkenyl for their part may be substituted up to three times by fluorine,
and
$R^7$ represents hydrogen, fluorine or chlorine,
and the salts, solvates, and solvates of the salts thereof.

In the context of the present invention, particular preference is given to compounds of the formula (I) in which
$R^{1A}$ represents hydrogen, methyl or ethyl,
$R^{1B}$ represents hydrogen,
$R^{2A}$ represents hydrogen, methyl, trifluoromethyl, ethyl or n-Propyl,
$R^{2B}$ represents hydrogen or methyl,
or
$R^{2A}$ and $R^{2B}$ are attached to one another and together with the carbon atom to which they are attached form a cyclic group of the formula

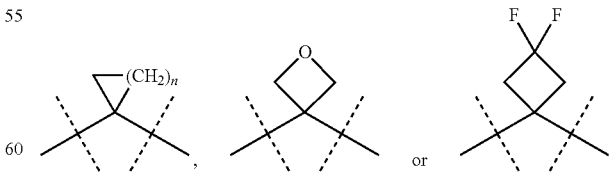

in which
n represents the number 1 or 2, and
$R^{1A}$ and $R^{1B}$ have the meanings mentioned above,
$R^3$ represents hydrogen,
$R^4$ represents fluorine, chlorine or methyl, $R^{5A}$ represents methyl,
$R^{5B}$ represents trifluoromethyl,
or
$R^{5A}$ and $R^{5B}$ are attached to one another and together with the carbon atom to which they are attached form a difluoro-substituted cyclopentyl ring of the formula

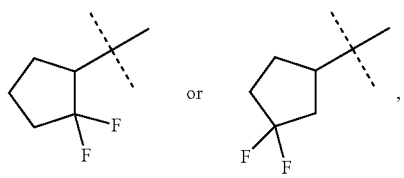

$R^6$ represents fluorine, chlorine, methyl, trifluoromethyl, ethyl, 1,1-difluoroethyl, 2,2,2-trifluoroethyl, isopropyl, tert-butyl, 1,1,1-trifluoro-2-methylpropan-2-yl, vinyl, 1-fluorovinyl, cyclopropyl, 2,2-difluorocyclopropyl, cyclobutyl or 3,3-difluorocyclobutyl,
and
$R^7$ represents hydrogen, fluorine, chlorine or methyl,
and the salts, solvates, and solvates of the salts thereof.

A further particularly preferred embodiment of the present invention embraces compounds of the formula (I) in which
$R^{1A}$ represents hydrogen, methyl or ethyl,
$R^{1B}$ represents hydrogen,
$R^{2A}$ represents hydrogen or methyl,
$R^{2B}$ represents hydrogen,
or
$R^{2A}$ and $R^{2B}$ are attached to one another and together with the carbon atom to which they are attached form a cyclic group of the formula

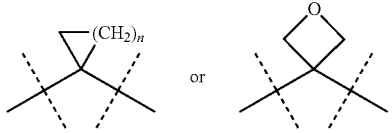

in which
n represents the number 1 or 2, and
$R^{1A}$ and $R^{1B}$ have the meanings mentioned above,
$R^3$ represents hydrogen,
$R^4$ represents fluorine, chlorine or methyl,
$R^{5A}$ represents methyl,
$R^{5B}$ represents trifluoromethyl,
or
$R^{5A}$ and $R^{5B}$ are attached to one another and together with the carbon atom to which they are attached form a difluoro-substituted cyclopentyl ring of the formula

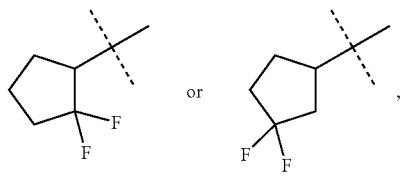

$R^6$ represents chlorine, methyl, trifluoromethyl, ethyl, 1,1-difluoroethyl, 2,2,2-trifluoroethyl, isopropyl, tert-butyl, 1,1,1-trifluoro-2-methylpropan-2-yl, vinyl or 1-fluorovinyl, and
$R^7$ represents hydrogen or fluorine,
and the salts, solvates, and solvates of the salts thereof.

A particular embodiment of the present invention embraces compounds of the formula (I) in which
$R^{1A}$ represents hydrogen, methyl or ethyl
and
$R^{1B}$, $R^{2A}$ and $R^{2B}$ each represent hydrogen,
and the salts, solvates, and solvates of the salts thereof.

A further particular embodiment of the present invention embraces compounds of the formula (I) in which
$R^{2A}$ represents methyl, trifluoromethyl, ethyl or n-propyl
and
$R^{1A}$, $R^{1B}$ and $R^{2B}$ each represent hydrogen,
and the salts, solvates, and solvates of the salts thereof.

A further particular embodiment of the present invention embraces compounds of the formula (I) in which
$R^{1A}$ and $R^{1B}$ each represent hydrogen
and
$R^{2A}$ and $R^{2B}$ each represent methyl,
and the salts, solvates, and solvates of the salts thereof.

A further particular embodiment of the present invention embraces compounds of the formula (I) in which
$R^{1A}$ and $R^{1B}$ each represent hydrogen
and
$R^{2A}$ and $R^{2B}$ are attached to one another and together with the carbon atom to which they are attached form a cyclopropyl or cyclobutyl ring of the formula

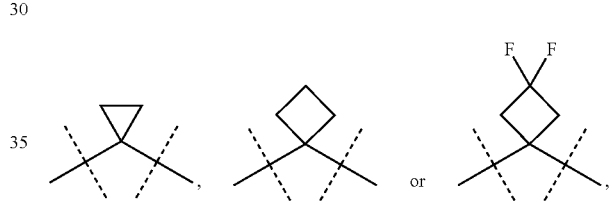

and the salts, solvates, and solvates of the salts thereof.

A further particular embodiment of the present invention embraces compounds of the formula (I) in which
$R^3$ represents hydrogen
and
$R^4$ represents fluorine or chlorine,
and the salts, solvates, and solvates of the salts thereof.

A further particular embodiment of the present invention embraces compounds of the formula (I) in which
$R^{5A}$ represents methyl
and
$R^{5B}$ represents trifluoromethyl,
or a salt, solvate or solvates of the salt thereof.

A further particular embodiment of the present invention embraces compounds of the formula (I) in which
$R^{5A}$ and $R^{5B}$ are attached to one another and together with the carbon atom to which they are attached form a difluoro-substituted cyclopentyl ring of the formula

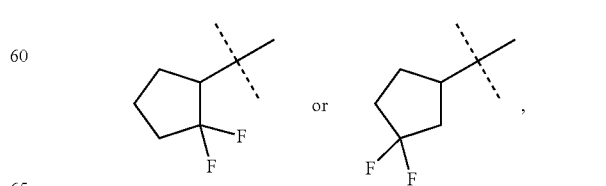

and the salts, solvates, and solvates of the salts thereof.

A further particular embodiment of the present invention embraces compounds of the formula (I-A)

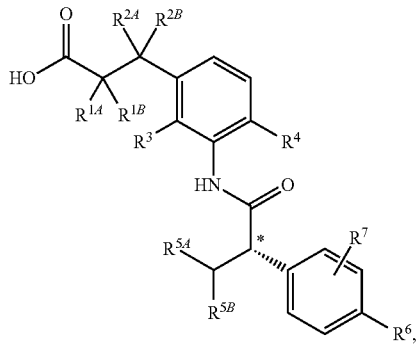

(I-A)

in which the carbon atom marked by an * sign of the phenylacetamide grouping has the S configuration shown
and
the radicals $R^{1A}$, $R^{1B}$, $R^{2A}$, $R^{2B}$, $R^3$, $R^4$, $R^{5A}$, $R^{5B}$, $R^6$ and $R^7$ each have the meanings given above,
and the salts, solvates, and solvates of the salts thereof.

The definitions of radicals indicated specifically in the respective combinations or preferred combinations of radicals are replaced as desired irrespective of the particular combinations indicated for the radicals also by definitions of radicals of other combinations.

Another embodiment of the present invention encompasses combinations of two or more of the abovementioned preferred definitions of substituents.

The invention furthermore provides a process for preparing the compounds of the formula (I) according to the invention, characterized in that a carboxylic acid of the formula (II)

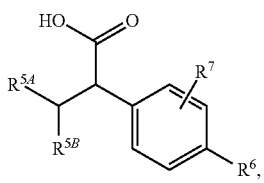

(II)

in which $R^{5A}$, $R^{5B}$, $R^6$ and $R^7$ have the meanings given above are coupled in an inert solvent with the aid of a condensing agent or via the intermediate of the corresponding carbonyl chloride in the presence of a base with an amine of the formula (III)

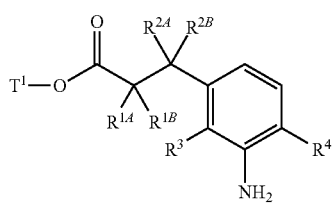

(III)

in which $R^{1A}$, $R^{1B}$, $R^{2A}$, $R^{5B}$, $R^3$ and $R^4$ have the meanings given above and
$T^1$ represents $(C_1-C_4)$-alkyl or benzyl,
to give a carboxamide of the formula (IV)

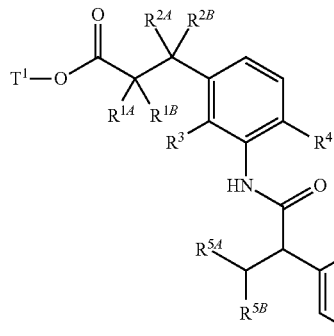

(IV)

in which $R^{1A}$, $R^{1B}$, $R^{2A}$, $R^{2B}$, $R^3$, $R^4$, $R^{5A}$, $R^{5B}$, $R^6$, $R^7$ and $T^1$ have the meanings given above,
the ester radical $T^1$ is then removed by basic or acidic solvolysis or, if $T^1$ represents benzyl, also by hydrogenolysis, giving the carboxylic acid of the formula (I),
and the compounds of the formula (I) are optionally separated by methods known to the person skilled in the art into their enantiomers and/or diastereomers, and/or optionally reacted with the appropriate (i) solvents and/or (ii) bases to give the solvates, salts and/or solvates of the salts thereof.

Inert solvents for the process step (II)+(III)→(IV) [amide coupling] are, for example, ethers such as diethyl ether, tert-butyl methyl ether, tetrahydrofuran, 1,4-dioxane, glycol dimethyl ether or diethylene glycol dimethyl ether, hydrocarbons such as benzene, toluene, xylene, hexane, cyclohexane or mineral oil fractions, halogenated hydrocarbons, such as dichloromethane, trichloromethane, carbon tetrachloride, 1,2-dichloroethane, trichloroethylene or chlorobenzene, or other solvents such as acetone, acetonitrile, ethyl acetate, pyridine, dimethyl sulphoxide (DMSO), N,N-dimethylformamide (DMF), N,N'-dimethylpropyleneurea (DMPU) or N-methylpyrrolidinone (NMP). It is also possible to use mixtures of the solvents mentioned. Preference is given to using dichloromethane, tetrahydrofuran, dimethylformamide or mixtures of these solvents.

Suitable condensing agents for this coupling reaction are, for example, carbodiimides such as N,N'-diethyl-, N,N'-dipropyl-, N,N'-diisopropyl-, N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, or isobutyl chloroformate, 1-chloro-2-methyl-1-dimethylamino-1-propene, propanephosphonic anhydride, diethyl cyanophosphonate, bis(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (Py-BOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), if appropriate in combination with further auxiliaries such as 1-hydroxybenzotriazole (HOBt) or N-hydroxysuccinimide (HOSu), and, as bases, alkali metal carbonates, for example sodium carbonate or potassium carbonate, or organic bases such as triethylamine, N-methylmorpholine, N-methylpiperidine, N,N-diisopropylethylamine, pyridine or 4-N,N-dimethylaminopyridine. Preference is given to using O-(7-azabenzotriazol-1-yl)-N,N,N',N'-tetramethyluronium hexafluorophosphate (HATU) or O-(benzotriazol-1-yl)-N,N,N',N'-tetramethyluronium tetrafluoroborate (TBTU), in each case in combination with pyridine or N,N-diisopropylethylamine, or N-(3-dimethylaminoisopropyl)-N'-ethylcarbodiimide hydrochloride (EDC) in combination with 1-hydroxybenzotriazole (HOBt) and triethylamine, or 1-chloro-2-methyl-1-dimethylamino-1-propene together with pyridine.

The reaction (II)+(III)→(IV) is generally carried out in a temperature range of from 0° C. to +60° C., preferably at from +10° C. to +40° C.

When a carbonyl chloride corresponding to the compound (II) is used, the coupling with the amine component (III) is carried out in the presence of a customary organic auxiliary base such as triethylamine, N-methylmorpholine, N-methylpiperidine, N,N-diisopropylethylamine, pyridine, 4-N,N-dimethylaminopyridine, 1,8-diazabicyclo[5.4.0]undec-7-ene (DBU) or 1,5-diazabicyclo-[4.3.0]non-5-ene (DBN). Preference is given to using triethylamine or N,N-diisopropylethylamine The reaction of the amine (III) with the carbonyl chloride is generally carried out in a temperature range of from −20° C. to +60° C., preferably in the range from −10° C. to +30° C.

The carbonyl chlorides may be prepared in a customary manner by treating the carboxylic acid (II) with thionyl chloride or oxalyl chloride.

The removal of the ester group $T^1$ in process step (IV)→(I) may be carried out by customary methods by treating the ester in inert solvents with acids or bases, where in the latter variant the salt initially formed is converted by treatment with acid into the free carboxylic acid. In the case of the tert-butyl esters, the ester cleavage is preferably carried out using acids. Benzyl esters are preferably cleaved by hydrogenolysis (hydrogenation) in the presence of a suitable catalyst, such as, for example, palladium on activated carbon.

Suitable inert solvents for these reactions are water or the organic solvents customary for ester cleavage. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichloromethane, dimethylformamide or dimethyl sulphoxide. It is also possible to use mixtures of the solvents mentioned. In the case of a basic ester hydrolysis, preference is given to using mixtures of water with dioxane, tetrahydrofuran, methanol and/or ethanol. In the case of the reaction with trifluoroacetic acid, preference is given to using dichloromethane, and in the case of the reaction with hydrogen chloride, preference is given to using tetrahydrofuran, diethyl ether, dioxane or water.

Suitable bases are the customary inorganic bases. These include in particular alkali metal or alkaline earth metal hydroxides such as, for example, lithium hydroxide, sodium hydroxide, potassium hydroxide or barium hydroxide, or alkali metal or alkaline earth metal carbonates such as sodium carbonate, potassium carbonate or calcium carbonate. Preference is given to lithium hydroxide, sodium hydroxide or potassium hydroxide.

Suitable acids for the ester cleavage are, in general, sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid or mixtures thereof, if appropriate with addition of water. Preference is given to hydrogen chloride or trifluoroacetic acid in the case of the tert-butyl esters and to hydrochloric acid in the case of the methyl esters.

The ester cleavage is generally carried out in a temperature range of from −20° C. to +100° C., preferably at from 0° C. to +60° C.

The intermediates of the formula (II) can be prepared, for example, by initially deprotonating a carboxylic ester of the formula (V)

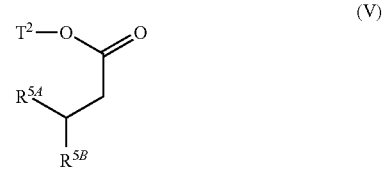

in which $R^{5A}$ and $R^{5B}$ have the meanings given above and
$T^2$ represents $(C_1$-$C_4)$-alkyl or benzyl,
in an inert solvent with the aid of a base, then arylating it in the presence of a suitable palladium catalyst with a phenyl bromide of the formula (VI)

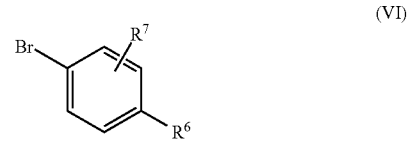

in which $R^6$ and $R^7$ have the meanings given above, to give a compound of the formula (VII)

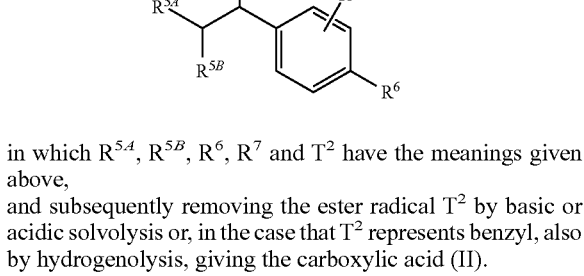

in which $R^{5A}$, $R^{5B}$, $R^6$, $R^7$ and $T^2$ have the meanings given above,
and subsequently removing the ester radical $T^2$ by basic or acidic solvolysis or, in the case that $T^2$ represents benzyl, also by hydrogenolysis, giving the carboxylic acid (II).

The arylation reaction in process step (V)+(VI)→(VII) is preferably carried out in toluene or toluene/tetrahydrofuran mixtures in a temperature range of from +20° C. to +100° C. Here, the base used for deprotonating the ester (V) is preferably lithium bis(trimethylsilyl)amide. Suitable palladium catalysts are, for example, palladium(II) acetate or tris(dibenzylideneacetone)dipalladium, in each case in combination with an electron-rich, sterically demanding phosphine ligand such as 2-dicyclohexylphosphino-2'-(N,N-dimethylamino) biphenyl or 2-di-tert-butylphosphino-2'-(N,N-dimethylamino)biphenyl [cf., for example, W. A. Moradi, S. L. Buchwald, *J. Am. Chem. Soc.* 123, 7996-8002 (2001)].

The removal of the ester group $T^2$ in process step (VII)→(II) may be carried out in a manner analogous to that described above for the ester radical $T^1$.

Alternatively, intermediates of the formula (II-A)

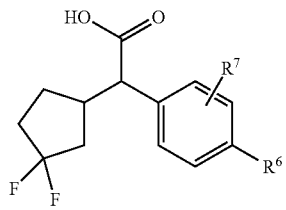
(II-A)

in which $R^6$ and $R^7$ have the meanings given above, can also be prepared by initially converting a phenylacetic ester of the formula (VIII)

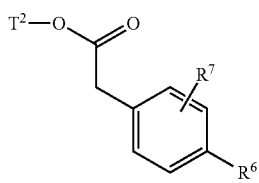
(VIII)

in which $R^6$, $R^7$ and $T^2$ have the meanings given above by base-induced addition to 2-cyclopenten-1-one into a compound of the formula (IX)

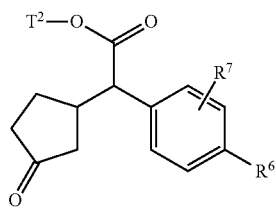
(IX)

in which $R^6$, $R^7$ and $T^2$ have the meanings given above, then fluorinating this compound with 1,1'-[(trifluoro-$\lambda^4$-sulphanyl)imino]bis(2-methoxyethane) under boron trifluoride catalysis to give a compound of the formula (VII-A)

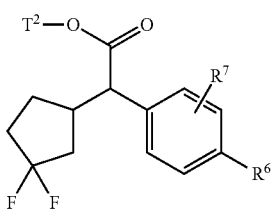
(VII-A)

in which $R^6$, $R^7$ and $T^2$ have the meanings given above, and subsequently again removing the ester group $T^2$ giving the carboxylic acid (II-A).

In process step (VIII)→(IX), for deprotonating the ester (VIII), preference is given to using an amide base such as lithium diisopropylamide or lithium bis(trimethylsilyl)amide. For the deoxy-fluorination in the transformation (IX)→(VII-A), instead of the 1,1'-[(trifluoro-$\lambda^4$-sulphanyl)-imino]bis(2-methoxyethane) ("Desoxofluor") mentioned above, it is also possible, if appropriate, to employ other known fluorinating agents, such as diethylaminosulphur trifluoride (DAST) or morpholinosulphur trifluoride (morpho-DAST) [for the reaction sequence (VIII)→(IX)→(VII-A), cf., for example, T. Mase et al., *J. Org. Chem.* 66 (20), 6775-6786 (2001)].

The intermediates of the formula (III) can be prepared, for example, either

[A] by reacting a phosphonoacetic ester of the formula (X)

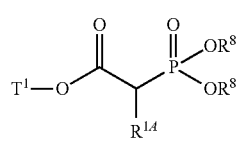
(X)

in which $R^{1A}$ and $T^1$ have the meanings given above and $R^8$ represents $(C_1\text{-}C_4)$-alkyl, in an inert solvent in a base-induced olefination reaction with a 3-nitrobenzoyl compound of the formula (XI)

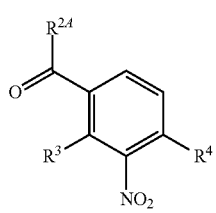
(XI)

in which $R^{2A}$, $R^3$ and $R^4$ have the meanings given above, to give a compound of the formula (XII)

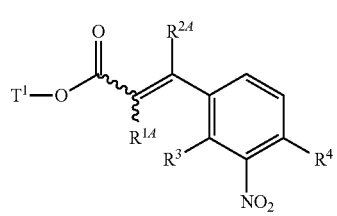
(XII)

in which $R^{1A}$, $R^{2A}$, $R^3$, $R^4$ and $T^1$ have the meanings given above, and then hydrogenating these in the presence of a suitable palladium or platinum catalyst to give a 3-(3-aminophenyl)propionic ester of the formula (III-A)

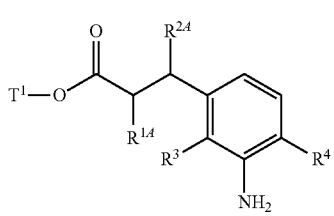
(III-A)

in which $R^{1A}$, $R^{2A}$, $R^3$, $R^4$ and $T^1$ have the meanings given above, or

[B] by reacting an acrylic ester of the formula (XIII)

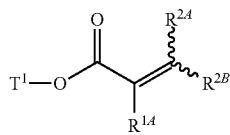
(XIII)

in which $R^{1A}$, $R^{2A}$, $R^{2B}$ and $T^1$ have the meanings given above in an inert solvent either (i) under rhodium(I) catalysis with a phenylboronic acid of the formula (XIV)

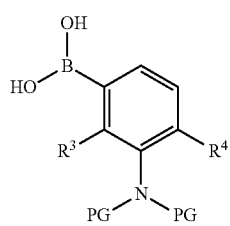
(XIV)

in which $R^3$ and $R^4$ have the meanings given above
and
PG represents benzyl or p-methoxybenzyl as inert aminoprotective group,
or (ii) under copper(I) catalysis with a phenylmagnesium reagent of the formula (XV)

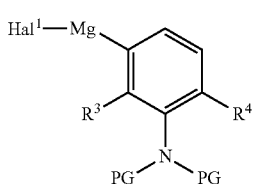
(XV)

in which $R^3$, $R^4$ and PG have the meanings given above
and
$Hal^1$ represents chlorine or bromine,
to give a compound of the formula (XVI)

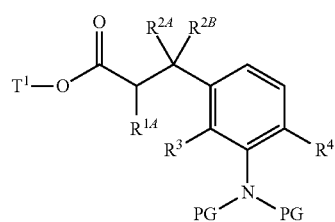
(XVI)

in which $R^{1A}$, $R^{2A}$, $R^{2B}$, $R^3$, $R^4$, PG and $T^1$ have the meanings given above, and subsequently removing the aminoprotective groups PG according to customary methods by hydrogenolysis or oxidatively, giving a 3-(3-aminophenyl)propionic ester of the formula (III-B)

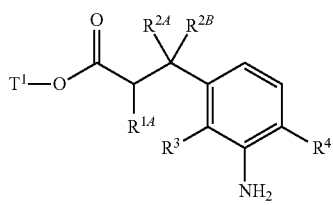
(III-B)

in which $R^{1A}$, $R^{2A}$, $R^{2B}$, $R^3$, $R^4$ and $T^1$ have the meanings given above, or

[C] by coupling an acrylic ester of the formula (XVII)

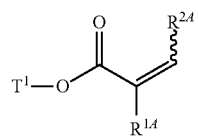
(XVII)

in which $R^{1A}$, $R^{2A}$ and $T^1$ have the meanings given above in an inert solvent under palladium catalysis with a 3-amino- or 3-nitrophenyl bromide of the formula (XVIII)

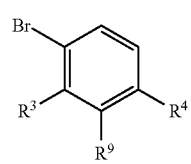
(XVIII)

in which $R^3$ and $R^4$ have the meanings given above
and
$R^9$ represents amino or nitro,
to give a compound of the formula (XIX)

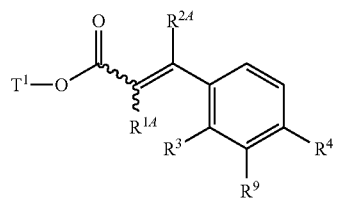
(XIX)

in which $R^{1A}$, $R^{2A}$, $R^3$, $R^4$, $R^9$ and $T^1$ have the meanings given above, and hydrogenating these in the presence of a suitable palladium or platinum catalyst to give the 3-(3-aminophenyl)propionic ester of the formula (III-C)

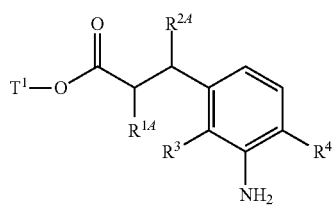
(III-C)

in which $R^{1A}$, $R^{2A}$, $R^3$, $R^4$ and $T^1$ have the meanings given above, or

[D] by alkylating an ester of the formula (XX)

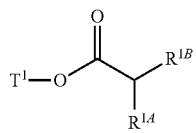
(XX)

in which $R^{1A}$, $R^{1B}$ and $T^1$ have the meanings given above in an inert solvent after α-deprotonation with a 3-bromobenzyl halide of the formula (XXI)

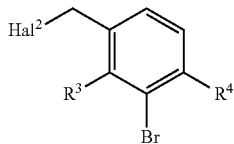
(XXI)

in which $R^3$ and $R^4$ have the meanings given above and $Hal^2$ represents chlorine, bromine or iodine, to give a compound of the formula (XXII)

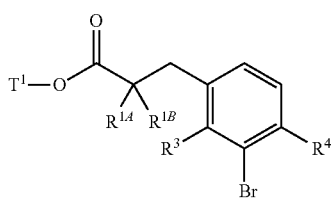
(XXII)

in which $R^{1A}$, $R^{1B}$, $R^3$, $R^4$ and $T^1$ have the meanings given above, then reacting it with benzylamine in the presence of a base and a palladium catalyst to give a compound of the formula (XXIII)

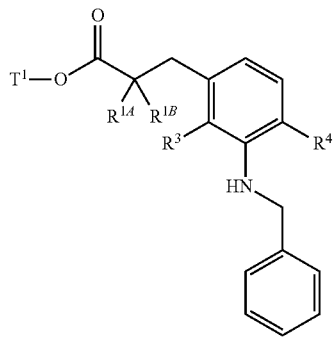
(XXIII)

in which $R^{1A}$, $R^{1B}$, $R^3$, $R^4$ and $T^1$ have the meanings given above, and then removing the N-benzyl group by hydrogenolysis, giving a 3-(3-aminophenyl)-propionic ester of the formula (III-D)

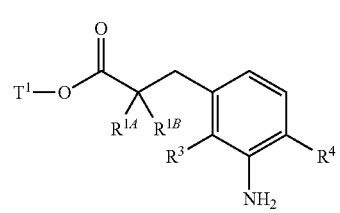
(III-D)

in which $R^{1A}$, $R^{1B}$, $R^3$, $R^4$ and $T^1$ have the meanings given above.

Suitable for deprotonating the phosphonic ester (X) in the olefination reaction (X)+(XI)→(XII) are in particular non-nucleophilic strong bases such as, for example, sodium hydride or potassium hydride, lithium bis(trimethylsilyl)amide, sodium bis(trimethylsilyl)amide or potassium bis(trimethylsilyl)amide or lithium diisopropylamide; preference is given to using sodium hydride.

The hydrogenation in the process step (XII)→(III-A) or (XIX)→(III-C) is generally carried out under a stationary hydrogen atmosphere at atmospheric pressure. Here, the catalyst used is preferably palladium on activated carbon (as support). The removal of the aminoprotective group(s) in the transformations (XVI)→(III-B) and (XXIII)→(III-D) is usually carried out by hydrogenolysis following the same procedure; in the case that PG in (XVI) represents p-methoxybenzyl, this may alternatively also take place oxidatively, for example with the aid of 2,3-dichloro-5,6-dicyano-1,4-benzoquinone (DDQ) or ammonium cerium(IV) nitrate.

A preferred palladium catalyst for the reaction (XVII)+(XVIII)→(XIX) [Heck reaction] is palladium(II) acetate in combination with a phosphine ligand such as, for example, triphenyl- or tri-2-tolylphosphine [for the reaction (XIII)+(XIV)→(XVI), cf., for example, N. Miyaura et al., *Organometallics* 16, 4229 (1997) and also T. Hayashi, *Synlett*, Special Issue 2001, 879-887; for the reaction (XIII)+(XV)→(XVI), cf., for example, P. Knochel et al., *Tetrahedron* 56, 2727-2731 (2000), *Angew. Chem.* 120, 6907-6911 (2008)].

Particularly suitable for the α-deprotonation of the ester (XX) in the alkylation reaction (XX)+(XXI)→(XXII) are likewise non-nucleophilic strong bases such as, for example, sodium hydride or potassium hydride, lithium bis(trimethylsilyl)amide, sodium bis(trimethylsilyl)amide or potassium bis(trimethylsilyl)amide or lithium diisopropylamide; here, preference is given to using lithium diisopropylamide.

For the reaction (XXII)+benzylamine→(XXIII) [Buchwald-Hartwig coupling], preference is given to using tris (dibenzylideneacetone)dipalladium(0) as palladium catalyst in combination with (±)-2,2'-bis(diphenylphosphino)-1,1'-binaphthyl as phosphine ligand and sodium tert-butoxide or potassium tert-butoxide as base [cf., for example, J. P. Wolfe and S. L. Buchwald, *Organic Syntheses*, Coll. Vol. 10, 423 (2004), Vol. 78, 23 (2002)].

The process steps described above can be carried out at atmospheric pressure, at elevated pressure or at reduced pressure (for example in the range of from 0.5 to 5 bar); in general, they are in each case carried out at atmospheric pressure.

Separation of the compounds according to the invention into the corresponding enantiomers and/or diastereomers can take place where appropriate, depending on expediency, even at the stage of the compounds (II), (III), (IV), (VII), (XVI), (XXII) or (XXIII), which are then reacted further in separated form in accordance with the above-described process sequences. Such a separation of the stereoisomers can be carried out by conventional methods known to the person skilled in the art. Preference is given to using chromatographic methods on achiral or chiral separation phases; in the case of carboxylic acids as intermediates or end products, separation may alternatively also be via diastereomeric salts.

The compounds of the formulae (V), (VI), (VIII), (X), (XI), (XIII), (XIV), (XV), (XVII), (XVIII), (XX) and (XXI) are either commercially available or described as such in the literature, or they can be prepared in a manner obvious to the person skilled in the art analogously to the methods published in the literature. Numerous detailed procedures and literature references for preparing the starting materials can also be found in the Experimental Part in the section on the preparation of the starting materials and intermediates.

The preparation of the compounds according to the invention can be illustrated in an exemplary manner by the reaction schemes below:

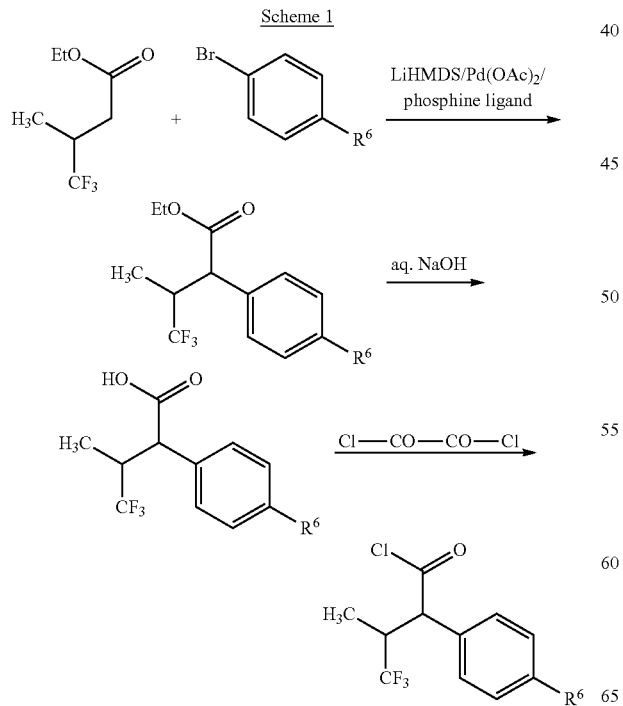

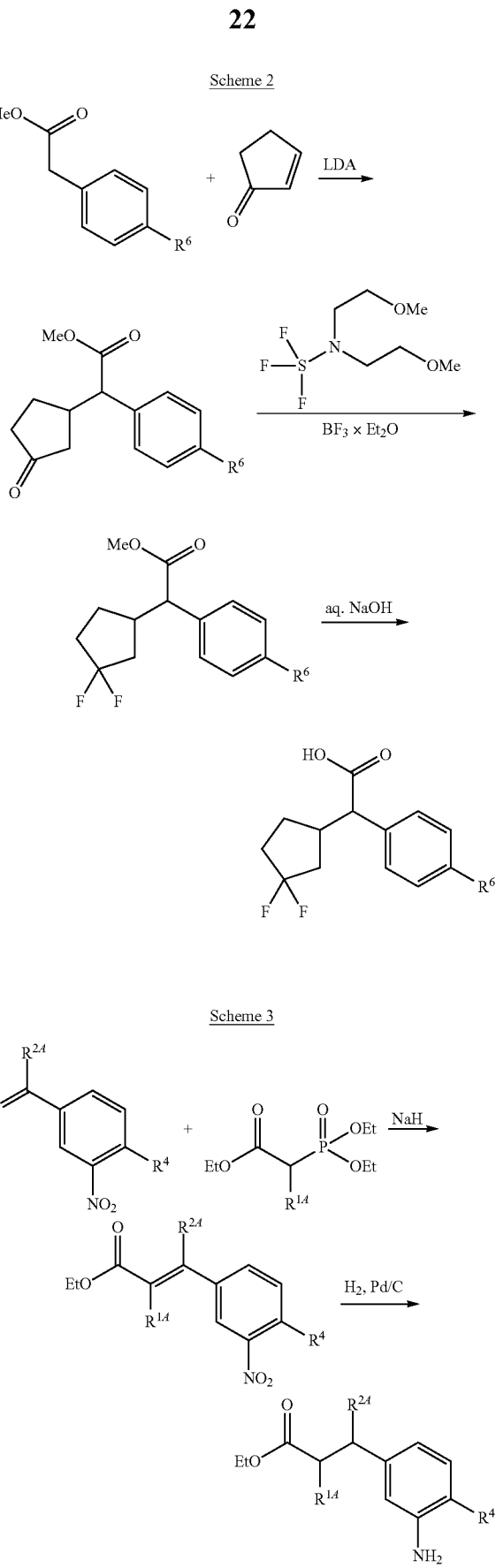

Scheme 4
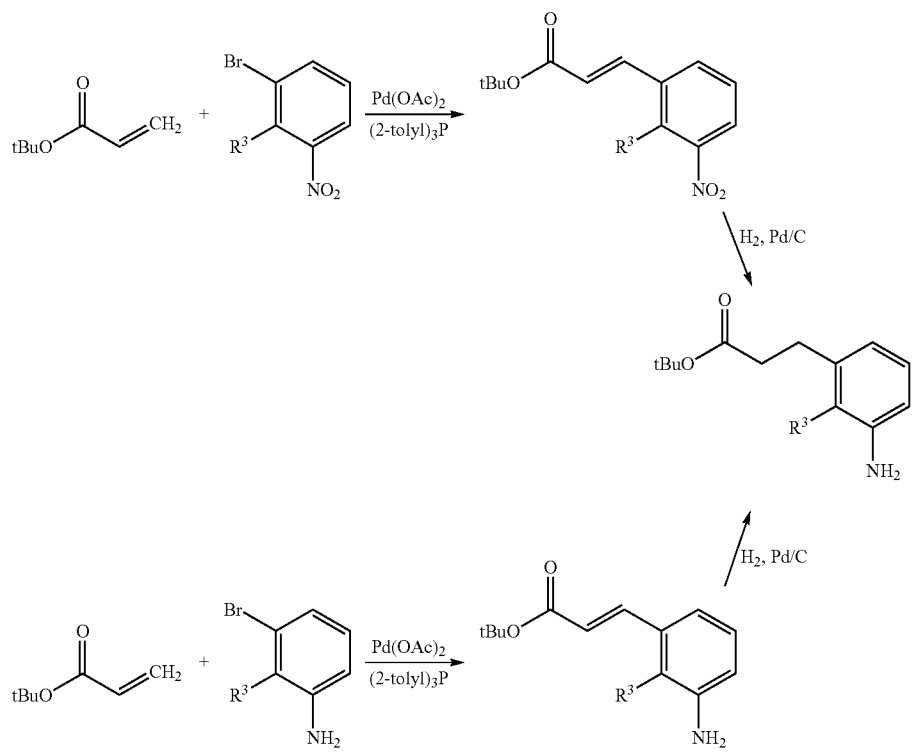
Scheme 5
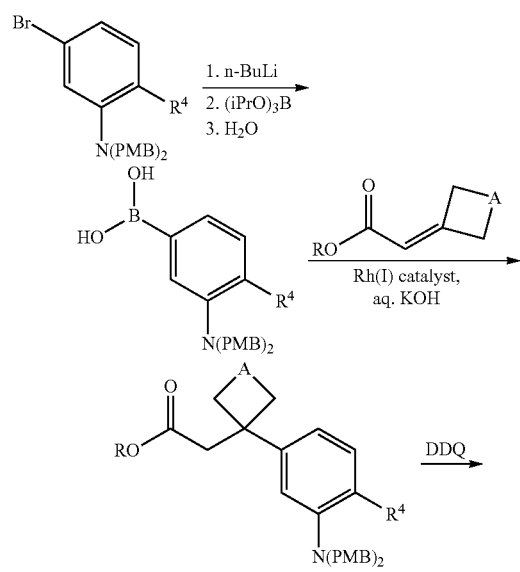
[PMB = p-methoxybenzyl; A = CH₂ or O; R = methyl or benzyl].
Scheme 6
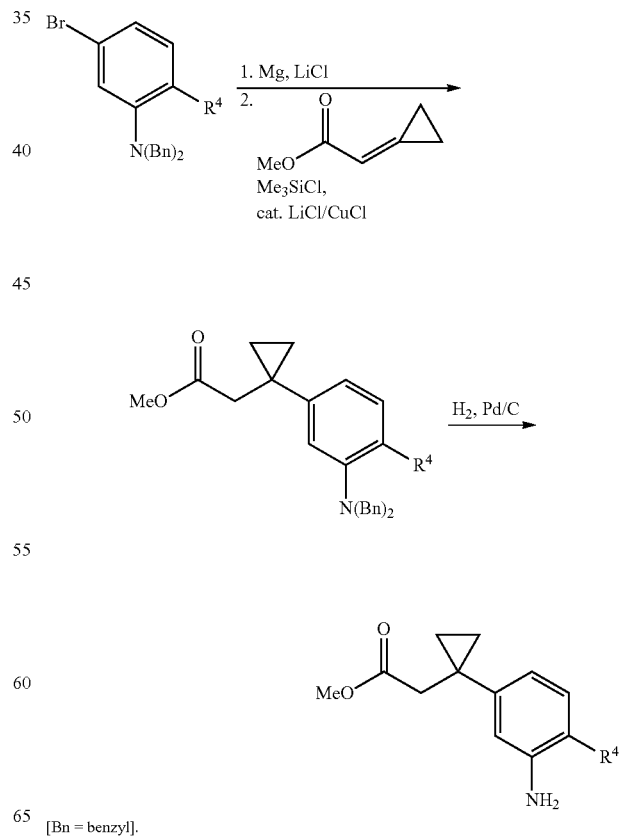
[Bn = benzyl].

Scheme 7

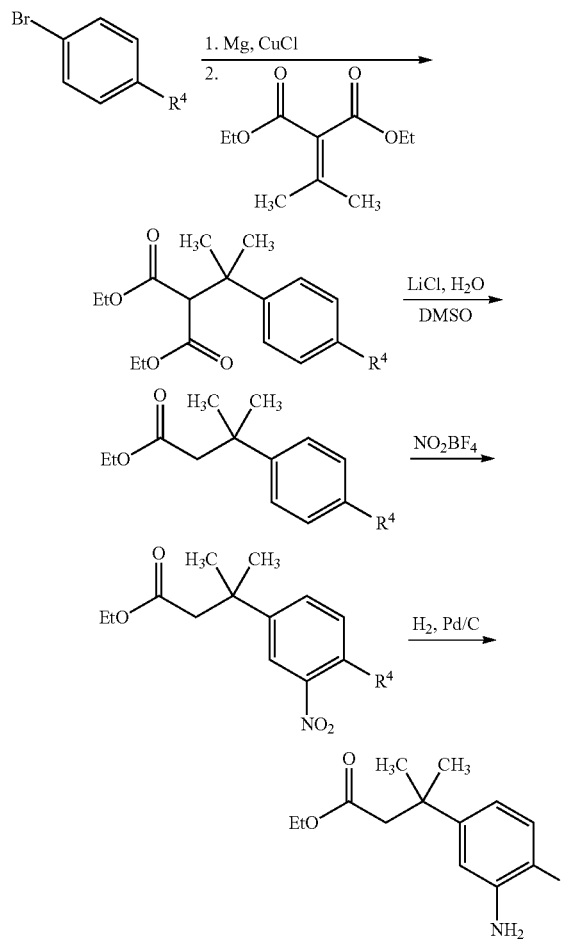

Scheme 8

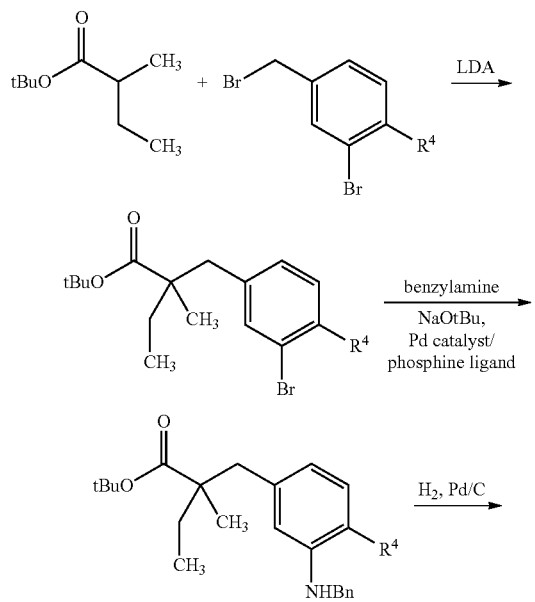

Scheme 9

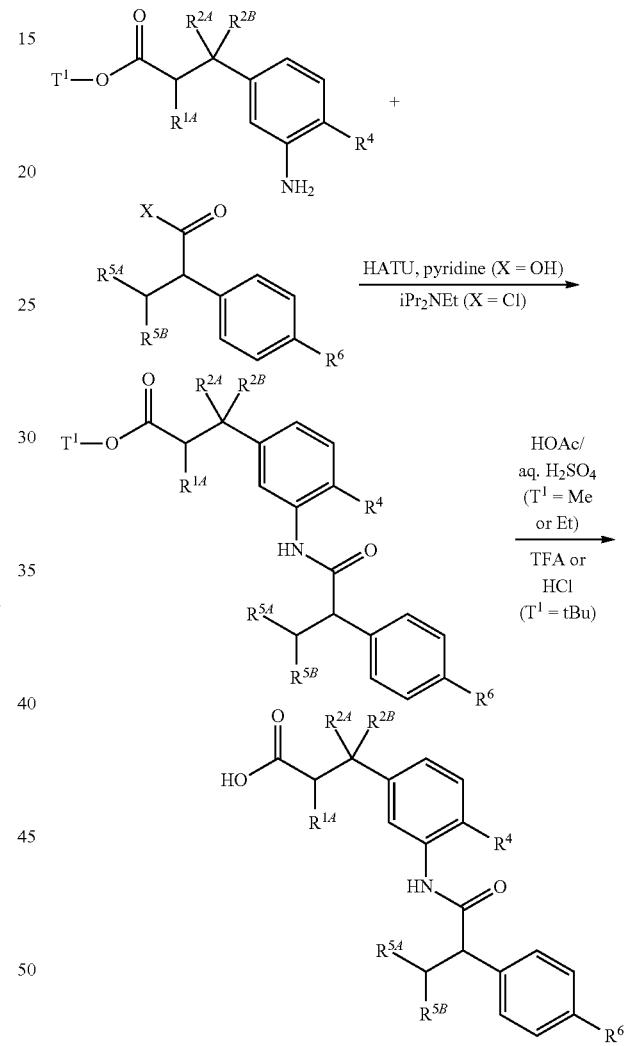

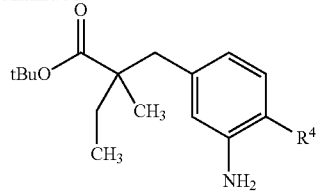

The compounds according to the invention have valuable pharmacological properties and can be used for the prevention and treatment of disorders in humans and animals.

The compounds according to the invention are potent activators of soluble guanylate cyclase. They lead to vasorelaxation, inhibition of platelet aggregation and lowering of blood pressure and increase of coronary blood flow. These effects are mediated by direct haem-independent activation of soluble guanylate cyclase and an increase of intracellular cGMP.

In addition, the compounds according to the invention have good pharmacokinetic properties, in particular with respect to their bioavailability and their half-life in the body.

The compounds according to the invention can therefore be employed in medicaments for the treatment and/or prevention of cardiovascular disorders such as, for example, of high blood pressure (hypertension) and heart failure, stable and unstable angina pectoris, pulmonary arterial hypertension (PAH) and other forms of pulmonary hypertension (PH), renal hypertension, peripheral and cardiac vascular disorders, and also of arrhythmias, for the treatment of thromboembolic disorders and ischemias such as myocardial infarction, stroke, transitory and ischemic attacks and also disturbances of peripheral blood flow, prevention of restenoses as after thrombolysis therapies, percutaneous transluminal angioplasties (PTAs), percutaneous transluminal coronary angioplasties (PTCAs) and bypass, for the treatment of arteriosclerosis, for promoting wound healing and for the treatment of osteoporosis, glaucoma and gastroparesis.

In the context of the present invention, the term heart failure includes both acute and chronic manifestations of heart failure, as well as more specific or related types of disease, such as acute decompensated heart failure, right heart failure, left heart failure, global failure, ischemic cardiomyopathy, dilated cardiomyopathy, hypertrophic cardiomyopathy, idiopathic cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and also diastolic and systolic heart failure.

The compounds according to the invention can additionally be used for the treatment and/or prevention of primary and secondary Raynaud's phenomenon, of microcirculation impairments, claudication, tinnitus, peripheral and autonomic neuropathies, diabetic microangiopathies, diabetic retinopathy, diabetic ulcers on the extremities, Crest syndrome, erythematosis, onchomycosis and rheumatic disorders.

In addition, the compounds according to the invention can be used for preventing ischemia- and/or reperfusion-related damage to organs or tissues and also as additives for perfusion and preservation solutions of organs, organ parts, tissues or tissue parts of human or animal origin, in particular for surgical interventions or in the field of transplantation medicine.

Furthermore, the compounds according to the invention are suitable for the treatment and/or prevention of kidney diseases, in particular of renal insufficiency and kidney failure. In the context of the present invention, the terms renal insufficiency and kidney failure comprise both acute and chronic manifestations thereof, as well as underlying or related kidney diseases such as renal hyperfusion, intradialytic hypertension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminurea, macroalbuminurea, lesions on glomerulae and arterioles, tubular dilatation, hyperphosphatemia and/or need for dialysis. The present invention also comprises the use of the compounds according to the invention for the treatment and/or prevention of sequelae of renal insufficiency, for example hypertension, pulmonary oedema, heart failure, uremia, anaemia, electrolyte disturbances (for example hypercalemia, hyponatremia) and disturbances in bone and carbohydrate mechanism In addition, the compounds according to the invention are suitable for the treatment and/or prevention of disorders of the urogenital system such as, for example, hyperactive bladder, disturbance of micturition, lower urinary tract syndrome (LUTS), incontinence, benign prostate hyperplasia (BPH), erectile dysfunction and female sexual dysfunction.

The compounds according to the invention can furthermore be used for the treatment of asthmatic disorders, chronic obstructive pulmonary disorders (COPD) and respiratory distress syndromes.

The compounds described in the present invention also represent active compounds for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions (Apoplexia cerebri) such as stroke, cerebral ischemias and craniocerebral trauma. The compounds according to the invention can likewise be employed for controlling states of pain.

In addition, the compounds according to the invention have antiinflammatory action and can therefore be used as antiinflammatory agents for the treatment and/or prevention of sepsis, multiple organ failure, inflammatory disorders of the kidney, chronic intestinal inflammations such as Colitis ulcerosa and Crohn's disease, pancreatitis, peritonitis, rheumatoid disorders, inflammatory skin diseases and inflammatory eye diseases.

By virtue of their activity profile, the compounds according to the invention are particularly suitable for the treatment and/or prevention of cardiovascular disorders such as heart failure, angina pectoris, hypertension, pulmonary hypertension, ischemias, vascular disorders, disturbances of microcirculation, thromboembolic disorders and arteriosclerosis.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to the use of the compounds according to the invention in a method for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active compounds. The present invention further relates to medicaments comprising at least one of the compounds according to the invention and one or more further active compounds, in particular for the treatment and/or prevention of the aforementioned disorders. Examples of suitable combination active compounds which may be preferably mentioned are:
- organic nitrates and NO donors such as, for example, sodium nitroprusside, nitroglycerin, isosorbide mononitrate, isosorbide dinitrate, molsidomine or SIN-1, and inhaled NO;
- compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;
- NO-independent but haem-dependent stimulators of guanylate cyclase, such as, in particular, the compounds described in WO 00/06568, WO 00/06569, WO 02/42301 and WO 03/095451;
- agents having antithrombotic activity, for example and preferably from the group of platelet aggregation inhibitors, of anticoagulants or of profibrinolytic substances;
- active compounds which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or
- active compounds which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidin or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide.

Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein (a) antagonists.

In a preferred embodiment of the invention, the compounds according to the invention are administered in combination with a CETP inhibitor such as, for example and preferably, torcetrapib (CP-529 414), JJT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, Cholesta-Gel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonary, nasal, sublingual, lingual, buccal, rectal, dermal, transdermal, conjunctival, otic routes or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral and intravenous administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavours and/or odours.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. Examples

Abbreviations and Acronyms abs. absolute
Ac acetyl
AIBN 2,2'-azobis(2-methylpropionitrile)
aq. aqueous, aqueous solution
ATP adenosine 5'-triphosphate
Bn benzyl
Brij® polyethylene glycol dodecyl ether
BSA bovine serum albumin
Ex. Example
Bu butyl
c concentration
cat. catalytic
CI chemical ionization (in MS)
d day(s)
DAST diethylaminosulphur trifluoride
TLC thin-layer chromatography
DCI direct chemical ionization (in MS)
DDQ 2,3-dichloro-5,6-dicyano-1,4-benzoquinone
de diastereomeric excess
DIBAH diisobutylaluminium hydride
DMF dimethylformamide
DMSO dimethyl sulphoxide
DTT dithiothreitol
EDC N'-(3-dimethylaminopropyl)-N-ethylcarbodiimide hydrochloride
ee enantiomeric excess
EI electron impact ionization (in MS)
ent enantiomerically pure, enantiomer
eq. equivalent(s)
ESI electrospray ionization (in MS)
Et ethyl
GC gas chromatography
sat. saturated
GTP guanosine 5'-triphosphate
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high-pressure, high-performance liquid chromatography
iPr isopropyl
conc. concentrated
LC-MS liquid chromatography-coupled mass spectroscopy
LDA lithium diisopropylamide
LiHMDS lithium hexamethyldisilazide [lithium bis(trimethylsilyl)amide]
Me methyl
min minute(s)
MS mass spectroscopy
NBS N-bromosuccinimide
NMR nuclear magnetic resonance spectroscopy
p para
Pd/C palladium on carbon
Ph phenyl
PMB p-methoxybenzyl
Pr propyl
rac racemic, racematee
$R_f$ retention index (in TLC)
RP reversed phase (in HPLC)
RT room temperature
$R_t$ retention time (in HPLC)
tBu tert-butyl
TEA triethanolamine
TFA trifluoroacetic acid
THF tetrahydrofuran
UV ultraviolet spectroscopy
v/v volume:volume ratio (of a solution)

GC-MS and LC-MS Methods:

Method 1 (GC-MS):
Instrument: Micromass GCT, GC 6890; Column: Restek RTX-35, 15 m×200 μm×0.33 μm; constant helium flow: 0.88 ml/min; Oven: 70° C.; inlet: 250° C.; gradient: 70° C., 30° C./min→310° C. (maintain for 3 min).

Method 2 (LC-MS):
MS instrument type: Micromass ZQ; HPLC instrument type: HP 1100 Series; UV DAD; Column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 3 (LC-MS):
MS instrument type: Micromass ZQ; HPLC instrument type: Waters Alliance 2795; Column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 4 (LC-MS):
Instrument: Micromass Quattro Premier with Waters UPLC Acquity; Column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 5 (LC-MS):
MS instrument type: Waters Micromass Quattro Micro; HPLC instrument type: Agilent 1100 Serie; Column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 6 (LC-MS):

Instrument: Waters Acquity SQD UPLC System; Column: Waters Acquity UPLC HSS T3 1.8μ, 50 mm×1 mm; mobile phase A: 1 l of water+0.25 ml 99% strength formic acid, mobile phase B: 1 l of acetonitrile+0.25 ml 99% strength formic acid; gradient: 0.0 min 90% A→1.2 min 5% A→2.0 min 5% A; flow rate: 0.40 ml/min; oven: 50° C.; UV detection: 210-400 nm.

Method 7 (LC-MS):

MS instrument type: Waters ZQ; HPLC instrument type: Agilent 1100 Series; UV DAD; Column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100% A (Flow rate 2.5 ml/min); oven: 55° C.; flow rate: 2 ml/min; UV detection: 210 nm.

Method 8 (GC-MS):

Instrument: Micromass GCT, GC 6890; Column: Restek RTX-35, 15 m×200 μm×0.33 μm; constant helium flow: 0.88 ml/min; oven: 70° C.; inlet: 250° C.; gradient: 70° C., 30° C./min→310° C. (maintain for 12 min)

Method 9 (LC-MS):

Instrument: Micromass Quattro Premier with Waters UPLC Acquity; Column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.3 min 90% A→3.0 min 10% A→4.8 min 10% A; flow rate: 0.33 ml/min; oven: 50° C.; UV detection: 210 nm.

Method 10 (GC-MS):

Instrument: Thermo DFS, Trace GC Ultra; Column: Restek RTX-35, 15 m×200 μm×0.33 μm; constant helium flow: 1.20 ml/min; Oven: 60° C.; Inlet: 220° C.; Gradient: 60° C., 30° C./min→300° C. (maintain for 3.33 min).

Starting Materials and Intermediates:

Example 1A tert-Butyl 3-(3-amino-2-methylphenyl)propanoate

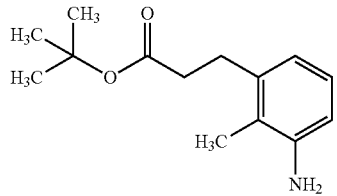 [SMILES: Cc1c(N)cccc1CCC(=O)OC(C)(C)C]

Under argon, 201 ml (1.39 mol) of tert-butyl-prop-2-enoate were added dropwise to a solution of 100 g (463 mmol) of 1-bromo-2-methyl-3-nitrobenzene, 322 ml (2.31 mol) of triethylamine, 28.18 g (92.58 mmol) of tri-2-tolylphosphine and 10.39 g (46.29 mmol) of palladium(II) acetate in 2 liters of DMF, and the mixture was then stirred at 125° C. for 36 h. After cooling to room temperature, the reaction mixture was stirred with saturated aqueous ammonium chloride solution and the organic phase was separated off. The aqueous phase was extracted three times with tert-butyl methyl ether, and the combined organic phases were washed with saturated sodium chloride solution and dried over sodium sulphate. After filtration, the solvent was removed to dryness under reduced pressure. The residue obtained was purified by flash chromatography on silica gel (mobile phase petroleum ether/ethyl acetate 9:1). This gave 89 g (338 mmol, 73% of theory) of the intermediate tert-butyl-(2E)-3-(2-methyl-3-nitrophenyl)prop-2-enoate as a colourless solid. 88 g (334 mmol) of this solid were dissolved in 2 liters of ethanol, 7 g of palladium on carbon (10%) were added at room temperature and the mixture was hydrogenated under atmospheric pressure for 18 h. After complete conversion, the reaction solution was filtered through kieselguhr and the filtrate obtained was concentrated under reduced pressure. This gave 61.3 g (260.5 mmol, 78% of theory) of the title compound as a colourless solid.

LC-MS (Method 2): $R_t$=1.84 min; m/z=236 (M+H)$^+$.

$^1$H-NMR (400 MHz, DMSO-$d_6$, δ/ppm): 6.77 (1H, t), 6.47 (1H, d), 6.36 (1H, d), 4.72 (2H, s), 2.14 (2H, t), 2.36 (2H, t), 1.95 (3H, s), 1.39 (9H, s).

Example 2A

Ethyl 3-(3-amino-2-methylphenyl)propanoate

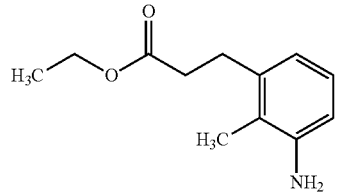

Under argon, 10.844 g (108 mmol) of ethyl prop-2-enoate were added dropwise to a solution of 7.8 g (36.1 mmol) of 1-bromo-2-methyl-3-nitrobenzene, 25 ml (180.5 mmol) of triethylamine, 2.197 g (7.22 mmol) of tri-2-tolylphosphine and 810 mg (3.6 mmol) of palladium(II) acetate in 200 ml of DMF, and the mixture was then stirred at 125° C. for 36 h. After cooling to room temperature, the reaction mixture was stirred with saturated aqueous ammonium chloride solution and the organic phase was separated off. The aqueous phase was extracted three times with tert-butyl methyl ether, and the combined organic phases were washed with saturated sodium chloride solution and dried over sodium sulphate. After filtration, the solvent was removed to dryness under reduced pressure. The residue obtained was purified by flash chromatography on silica gel (mobile phase petroleum ether/ethyl acetate 3:1). This gave 6.6 g (27.2 mmol, content 97%, 75% of theory) of the intermediate ethyl (2E)-3-(2-methyl-3-nitrophenyl)prop-2-enoate as a colourless solid. 6.6 g (27.2 mmol, content 97%) of this solid were dissolved in 200 ml of ethanol, 500 mg of palladium on carbon (10%) were added at room temperature and the mixture was hydrogenated under atmospheric pressure overnight. After the reaction had gone to completion, the reaction solution was filtered through kieselguhr and the filtrate obtained was concentrated under reduced pressure. This gave 5.47 g (26.38 mmol, content 97%, 97% of theory) of the title compound as a colourless solid.

LC-MS (Method 3): $R_t$=1.07 min; m/z=208 (M+H)$^+$.

Example 3A tert-Butyl (2E)-3-(4-fluoro-3-nitrophenyl)acrylate

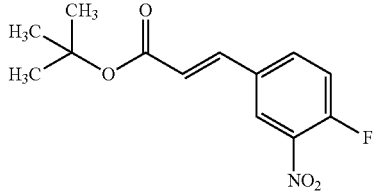 [SMILES: CC(C)(C)OC(=O)/C=C/c1ccc(F)c([N+](=O)[O-])c1]

Under argon, 0.65 g (16.3 mmol) of sodium hydride (as a 60% suspension in mineral oil) was initially charged in 25 ml of THF and cooled to 0° C. 4.29 g (17 mmol) of tert-butyl diethylphosphonoacetate were then slowly added dropwise. After 30 min, 2.5 g (14.8 mmol) of 4-fluoro-3-nitrobenzaldehyde were added. The reaction mixture was stirred at RT for 3 h and then poured into 100 ml of water and extracted three times with in each case 100 ml of ethyl acetate. The combined organic phases were dried over magnesium sulphate and concentrated. The residue was purified by flash chromatography (silica gel, mobile phase cyclohexane/ethyl acetate 50:1). This gave 3.37 g (85% of theory) of the title compound.

GC-MS (Method 1): $R_t$=6.45 min; m/z=211 (M–$^t$Bu)$^+$.

$^1$H-NMR (400 MHz, DMSO-$d_6$): δ [ppm]=1.49 (s, 9H), 6.69 (d, 1H), 7.59-7.76 (m, 2H), 8.19 (ddd, 1H), 8.50 (dd, 1H).

Example 4A tert-Butyl 3-(3-amino-4-fluorophenyl)propanoate

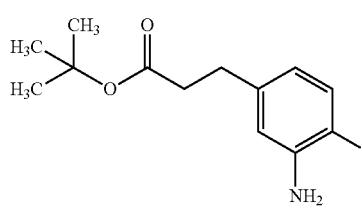

535 mg (2.00 mmol) of tert-butyl (2E)-3-(4-fluoro-3-nitrophenyl)prop-2-enoate were dissolved in 1 ml of ethanol and 1 ml of THF, and 21.3 mg of palladium on carbon (10%) were added. At RT, the mixture was hydrogenated under an atmosphere of hydrogen at atmospheric pressure overnight. The reaction mixture was then filtered off with suction through kieselguhr, the residue was washed with THF and the filtrate was concentrated. This gave 479 mg (100% of theory) of the title compound.

LC-MS (Method 6): $R_t$=1.06 min; m/z=184 (M–$C_4H_8$)$^+$.

$^1$H-NMR (400 MHz, DMSO-$d_6$): δ=6.84 (dd, 1H), 6.58 (dd, 1H), 6.36-6.29 (m, 1H), 5.00 (s, 2H), 2.64 (t, 2H), 2.42 (t, 2H), 1.36 (s, 9H).

Example 5A tert-Butyl (2E)-3-(4-chloro-3-nitrophenyl)prop-2-enoate

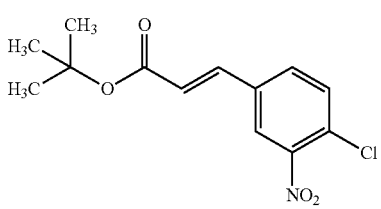 [SMILES: CC(C)(C)OC(=O)/C=C/c1ccc(Cl)c([N+](=O)[O-])c1]

Under argon, 1.19 g (29.64 mmol, 60%) of sodium hydride were suspended in 25 ml of toluene and 25 ml of THF, and the mixture was cooled to 0° C. 7.28 ml (30.99 mmol) of tert-butyl (diethoxyphosphoryl)acetate were then slowly added dropwise, and the mixture was stirred at 0° C. for 30 min. 5 g (26.94 mmol) of 4-chloro-3-nitrobenzaldehyde were then added to the reaction mixture, and the mixture was subsequently warmed to room temperature. The mixture was stirred at room temperature for 2 h, and 50 ml of water were then added. The organic phase was separated off, and the aqueous phase was then extracted three more times with ethyl acetate. The combined organic phases were dried over sodium sulphate. After filtration, the solvent was removed under reduced pressure. The crude product was purified chromatographically on silica gel (mobile phase cyclohexane/ethyl acetate 9:1). This gave 6.77 g (23.86 mmol, 77% of theory) of the title compound.

MS (DCI): m/z=301 (M+NH$_4$)$^+$.

$^1$H-NMR (400 MHz, DMSO-$d_6$): δ=8.46 (d, 1H), 8.07 (dd, 1H), 7.71 (d, 1H), 7.51 (d, 1H), 6.75 (d, 1H), 1.49 (s, 9H).

Example 6A tert-Butyl-3-(3-amino-4-chlorophenyl)propanoate

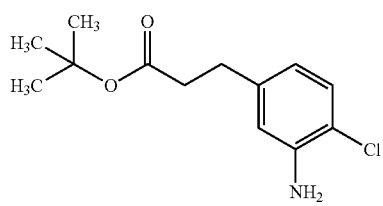 [SMILES: CC(C)(C)OC(=O)CCc1ccc(Cl)c(N)c1]

At room temperature, 500 mg of palladium on carbon (10%) were added to a solution of 6.74 g (23.76 mmol) of tert-butyl (2E)-3-(4-chloro-3-nitrophenyl)prop-2-enoate in 200 ml of ethanol and 20 ml of THF, and the mixture was hydrogenated under atmospheric pressure for 12 h. After the reaction had gone to completion (monitored by TLC; mobile phase cyclohexane/ethyl acetate 1:1), the reaction solution was filtered through kieselguhr and the filtrate was concentrated under reduced pressure. The crude product was purified chromatographically on silica gel (mobile phase cyclohexane/ethyl acetate 4:1→2:1). This gave 1.40 g (5.47 mmol, 23% of theory) of the title compound.

LC-MS (Method 6): $R_t$=1.14 min; m/z=256 (M+H)$^+$.

$^1$H-NMR (400 MHz, DMSO-$d_6$): δ=7.08 (d, 1H), 6.62 (s, 1H), 6.39 (dd, 1H), 5.22 (s, 2H), 2.66 (t, 2H), 2.45 (t, 2H), 1.37 (s, 9H).

Example 7A

Methyl 3-(3-amino-4-chlorophenyl)propanoate

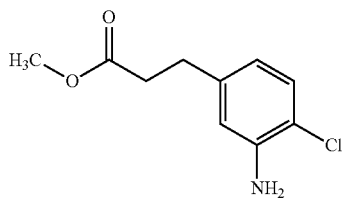

Under reflux, 0.86 ml (11.7 mmol) of thionyl chloride was added dropwise to a solution of 1.0 g (3.91 mmol) of tert-butyl 3-(3-amino-4-chlorophenyl)propanoate in 20 ml of methanol. The mixture was stirred under reflux for 1.5 h and then, after cooling, diluted with dichloromethane. The solution was added to water, and after phase separation the organic phase was washed with saturated sodium bicarbonate solution and saturated sodium chloride solution, dried over sodium sulphate and concentrated under reduced pressure. The residue was dried under high vacuum. This gave 745 mg (90.3% of theory) of the target compound.

LC-MS (Method 6): $R_t$=0.91 min; m/z=213/215 (M+H)$^+$.

$^1$H-NMR (400 MHz, DMSO-d$_6$): δ [ppm]=2.52-2.60 (m, 2H), 2.62-2.77 (m, 2H), 5.22 (s, 2H), 6.39 (dd, 1H), 6.62 (d, 1H), 7.06 (d, 1H).

Example 8A

Methyl {1-[3-(dibenzylamino)-4-fluorophenyl]cyclopropyl}acetate

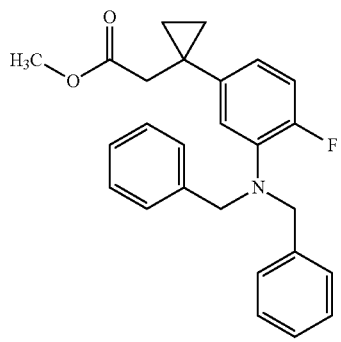 [SMILES: COC(=O)CC1(c2ccc(F)c(N(Cc3ccccc3)Cc3ccccc3)c2)CC1]

Preparation of solution A: Under argon, 688 mg (16.2 mmol) of lithium chloride were dissolved in 50 ml of THF, and 789 mg (32.5 mmol) of magnesium turnings and 23 μl (0.023 mmol) of a 1 M solution of diisobutylaluminium hydride in THF were then added. The reaction solution was stirred at room temperature for 10 min and then cooled to –10° C. 5 g (13.5 mmol) of N,N-dibenzyl-5-bromo-2-fluoroaniline (CAS Reg.-No. 869529-97-5) were then added, and the solution was stirred at –10° C. for about 1 h.

Preparation of solution B: Under argon, 110 mg (2.6 mmol) of lithium chloride and 128 mg (1.3 mmol) of copper(I) chloride were suspended at room temperature in 10 ml of THF, and 1.65 ml (12.98 mmol) of chloro(trimethyl)silane and 1.46 g (12.98 mmol) of methyl cyclopropylidene acetate (CAS Reg.-No. 110793-87-8) were then added. Subsequently, the solution was stirred at RT for another 1 h.

Solution A obtained above was cooled to –40° C. Solution B was then slowly added dropwise. The combined solutions were slowly warmed to –20° C. and stirred at this temperature for 1 h. 50 ml of an ice-cold semi-saturated ammonium chloride solution were then added to the reaction mixture. The phases were separated, the aqueous phase was then extracted three more times with ethyl acetate and the combined organic phases were dried over magnesium sulphate and concentrated to dryness. The crude product obtained was purified chromatographically on silica gel (mobile phase cyclohexane/ethyl acetate 10:1). This gave 2.1 g (5.2 mmol, 39% of theory) of the title compound.

$^1$H-NMR (400 MHz, DMSO-d$_6$, δ/ppm): 7.33-7.25 (8H, m), 7.25-7.18 (2H, m), 7.02-6.94 (1H, m), 6.78-6.69 (2H, m), 4.27 (4H, s), 3.43 (3H, s), 2.48 (2H, s), 0.78-0.73 (2H, m), 0.63-0.58 (2H, m).

LC-MS (Method 5): $R_t$=2.99 min; m/z=404 (M+H)$^+$.

Example 9A

Methyl [1-(3-amino-4-fluorophenyl)cyclopropyl]acetate

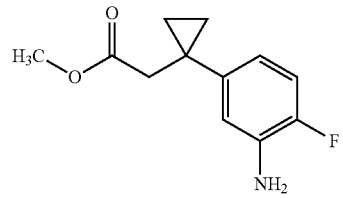

At room temperature, 200 mg of palladium on carbon (10%) were added to a solution of 2.1 g (5.2 mmol) of methyl {1-[3-(dibenzylamino)-4-fluorophenyl]cyclopropyl}acetate in 100 ml of ethanol, and the mixture was hydrogenated at atmospheric pressure for 12 h. After the reaction had gone to completion (monitored by TLC; mobile phase cyclohexane/ethyl acetate 1:1), the reaction solution was filtered through kieselguhr and the filtrate was concentrated under reduced pressure. The crude product was purified chromatographically on silica gel (mobile phase cyclohexane/ethyl acetate 10:1). This gave 647 mg (2.9 mmol, 56% of theory) of the title compound.

$^1$H-NMR (400 MHz, DMSO-d$_6$, δ/ppm): 6.88-6.78 (1H, m), 6.70-6.62 (1H, m), 6.44-6.35 (1H, m), 4.98 (2H, br. s), 3.51 (3H, s), 2.55 (2H, s), 0.84-0.79 (2H, m), 0.78-0.73 (2H, m).

GC-MS (Method 1): $R_t$=5.67 min; m/z=224 (M+H)$^+$.

Example 10A

5-Bromo-2-chloro-N,N-bis(4-methoxybenzyl)aniline

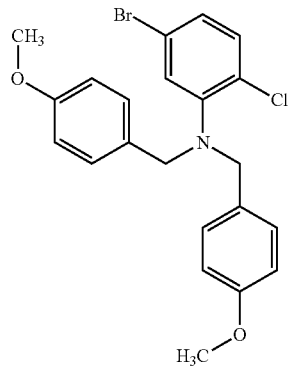 [SMILES: COc1ccc(CN(Cc2ccc(OC)cc2)c2cc(Br)ccc2Cl)cc1]

Under argon, 5.07 g (126.93 mmol, 60%) of sodium hydride were suspended in 150 ml of THF, and the mixture was cooled to 0° C. 10.70 g (51.81 mmol) of 5-bromo-2-chloroaniline dissolved in 10 ml of THF were then slowly added dropwise, and the mixture was stirred at 0° C. for 30 min. 25 g (124.34 mmol) of 4-methoxybenzyl chloride were then added to the reaction mixture, and the mixture was subsequently warmed to room temperature. The mixture was stirred at RT for 2 h and then slowly poured onto 150 ml of ice-water. The organic phase was separated off, and the aqueous phase was extracted three more times with ethyl acetate. The combined organic phases were dried over sodium sulphate. After filtration, the solvent was removed under reduced pressure. The crude product was purified chromatographically [column: Kromasil Si 6012, 350 mm×30 mm; mobile phase A: isohexane, mobile phase B: ethyl acetate; gradient: 0 min 98% A→4.65 min 98% A→13 min 87% A→13.01 min 98% A→13.28 min 98% A; flow rate: 70 ml/min; temperature: 20° C.; UV detection: 265 nm]. This gave 12.37 g (27.69 mmol, 57% of theory) of the title compound.

$^1$H-NMR (400 MHz, DMSO-d$_6$, δ/ppm): 7.37 (1H, d), 7.26-7.19 (5H, m), 7.19-7.14 (1H, m), 6.86 (4H, d), 4.11 (4H, s), 3.71 (6H, s).

LC-MS (Method 4): R$_t$=1.68 min; m/z=446 (M)$^+$.

Example 11A

{3-[Bis(4-methoxybenzyl)amino]-4-chlorophenyl}boronic acid

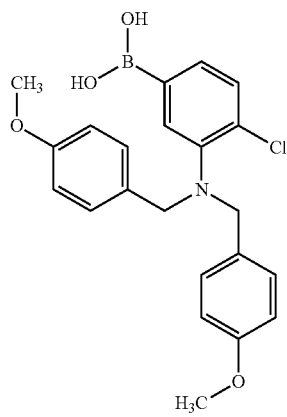 [SMILES: COc1ccc(CN(Cc2ccc(OC)cc2)c2cc(B(O)O)ccc2Cl)cc1]

Under argon and at −78° C., 6.1 ml (15.25 mmol) of a 2.5 M solution of n-butyllithium in hexane were slowly added dropwise to a solution of 5.2 g (11.64 mmol) of 5-bromo-2-chloro-N,N-bis(4-methoxybenzyl)aniline in 100 ml of THF/diethyl ether (1:1). The reaction solution was stirred at −78° C. for 60 min, and 4.3 ml (18.62 mmol) of triisopropyl borate were then added slowly. The reaction solution was then stirred at −78° C. for another 15 min, then slowly warmed to room temperature and stirred at this temperature for another 3 h. 150 ml of ice-water were then metered in. The organic phase was separated off, and the aqueous phase was then extracted three more times with ethyl acetate. The combined organic phases were dried over sodium sulphate. After filtration, the solvent was removed under reduced pressure. The crude product was purified chromatographically on silica gel (mobile phase: initially cyclohexane/ethyl acetate 10:1→9:1→4:1, then dichloromethane/methanol 95:5). This gave 2.54 g (6.17 mmol, 53% of theory) of the title compound.

LC-MS (Method 6): R$_t$=1.20 min; m/z=412 (M+H)$^+$.

Example 12A

Benzyl oxetan-3-ylideneacetate

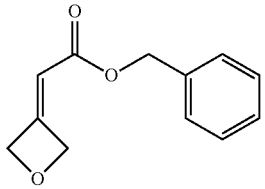 [SMILES: O=C(C=C1COC1)OCc1ccccc1]

Under argon and at 0° C., 3.0 g (41.63 mmol) of oxetan-3-one (CAS Reg.-No. 6704-31-0) were dissolved in 50 ml of dichloromethane, and 18.8 g (45.79 mmol) of benzyl (triphenyl-λ$^5$-phosphanylidene)acetate were then added. The reaction mixture was then slowly warmed to room temperature and stirred for another 15 minutes. The reaction solution was then concentrated to dryness. The residue was taken up in 25 ml of diethyl ether and stirred, and the mixture was kept at 4° C. for 12 h. The precipitated triphenylphosphine oxide was filtered off and the filtrate was concentrated to dryness. The crude product obtained was purified chromatographically on silica gel (mobile phase cyclohexane/ethyl acetate 4:1→1:1). This gave 4.2 g (20.57 mmol, 49% of theory) of the title compound.

$^1$H-NMR (400 MHz, DMSO-d$_6$, δ/ppm): 7.42-7.30 (5H, m), 5.85-5.80 (1H, m), 5.39-5.34 (2H, m), 5.27-5.22 (2H, m), 5.13 (2H, s).

MS (DCI): m/z=205 (M+H)$^+$.

Example 13A

Benzyl (3-{3-[bis(4-methoxybenzyl)amino]-4-chlorophenyl}oxetan-3-yl)acetate

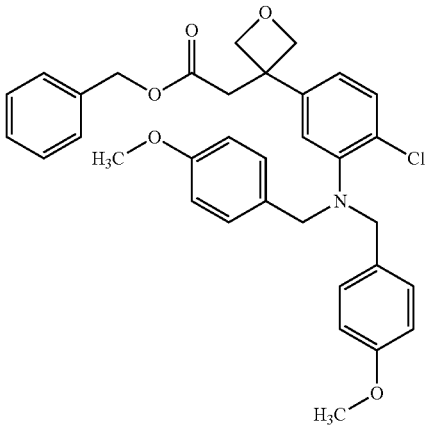 [SMILES: COc1ccc(CN(Cc2ccc(OC)cc2)c2cc(C3(CC(=O)OCc4ccccc4)COC3)ccc2Cl)cc1]

Under argon and at room temperature, 1.6 ml (2.37 mmol) of a 1.5 M aqueous potassium hydroxide solution, 272 mg (1.82 mmol) of benzyl oxetan-3-ylideneacetate and 750 mg (1.82 mmol) of {3-[bis(4-methoxybenzyl)amino]-4-chlorophenyl}boronic acid were added successively to a solution of 45 mg (0.09 mmol) of (1Z,5Z)-cycloocta-1,5-diene/rhodium(I) chloride dimer in 25 ml of dioxane. The reaction solution was then stirred at room temperature for 4 h. After the reaction had gone to completion, the solution was concentrated to dryness and the residue was taken up in 25 ml of water and 25 ml of ethyl acetate. The phases were separated and the aqueous phase was extracted three more times with ethyl acetate, and the combined organic phases were dried over magnesium sulphate and concentrated to dryness. The crude product obtained was purified chromatographically on silica gel (mobile phase cyclohexane/ethyl acetate 4:1→1:1). This gave 669 mg (1.17 mmol, 64% of theory) of the title compound.

$^1$H-NMR (400 MHz, DMSO-d$_6$, δ/ppm): 7.34-7.26 (4H, m), 7.18-7.13 (4H, m), 7.12-7.07 (2H, m), 6.86-6.76 (6H, m), 4.90 (2H, s), 4.72 (2H, d), 4.57 (2H, d), 4.01 (6H, s), 3.08 (2H, s).

LC-MS (Method 6): R$_t$=1.45 min; m/z=572 (M)$^+$.

The following compound was obtained analogously to synthesis Example 13A:

| Example | Name/Structure/Starting Materials | Analytical Data |
|---|---|---|
| 14A | Methyl (1-{3-[bis(4-methoxybenzyl)amino]-4-chlorophenyl}cyclobuytl)acetate 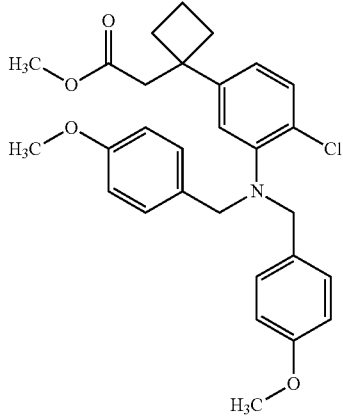<br>(from {3-[bis(4-methoxybenzyl)amino]-4-chloropheny}boronic acid and methyl cyclobulylideneacetate [prepared according to A. Goti et al., *Tetrahedron* 48 (25), 5283-5300 (1992)]) | $^1$H-NMR (400 MHz, DMSO-$d_6$, δ/ppm): 7.29 (1H, d), 7.19 (4H, d), 6.83 (4H, d), 6.79-6.74 (2H, m), 4.04 (4H, s), 3.70 (6H, s), 3.35 (3H, s), 2.69 (2H, s), 2.26-2.17 (2H, m), 2.16-2.06 (2H, m), 2.03-1.89 (1H, m), 1.71-1.58 (1H, m).<br>LC-MS (Method 6):<br>$R_t$ = 1.50 min; m/z = 494 (M)$^+$. |

Example 15A

Benzyl [3-(3-amino-4-chlorophenyl)oxetan-3-yl]acetate

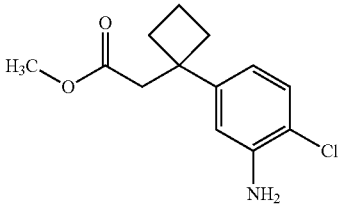

At room temperature, 576 mg (2.54 mmol) of 2,3-dichloro-5,6-dicyano-1,4-benzoquinone (DDQ) were added to a solution of 660 mg (1.15 mmol) of benzyl (3-{3-[bis(4-methoxybenzyl)amino]-4-chlorophenyl}oxetan-3-yl) acetate in 30 ml of dichloromethane and 6 ml of water, and the mixture was stirred for 2 h. After the reaction had gone to completion (monitored by TLC; mobile phase cyclohexane/ethyl acetate 2:1), 25 ml of saturated sodium bicarbonate solution were added to the reaction solution. The phases were separated and the aqueous phase was then extracted three more times with dichloromethane, and the combined organic phases were dried over magnesium sulphate and concentrated to dryness. The crude product obtained was purified chromatographically on silica gel (mobile phase cyclohexane/ethyl acetate 5:1). This gave 360 mg (0.98 mmol, content 90%, 85% of theory) of the title compound.

LC-MS (Method 4): $R_t$=1.18 min; m/z=332 (M+H)$^+$.

The following compound was obtained analogously to synthesis Example 15A:

| Example | Name/Structure/Starting Materials | Analytical Data |
|---|---|---|
| 16A | Methyl [1-(3-amino-4-chlorophenyl)-cyclobutyl]acetate <br>(from methyl (1-{3-[bis(4-methoxybenzyl)-amino]-4-chlorophenyl}cyclobutyl)acetate) | $^1$H-NMR (400 MHz, DMSO-$d_6$, δ/ppm): 7.06 (1H, d), 6.59 (1H, s), 6.32 (1H, d), 5.21 (2H, br. s), 3.43 (3H, s), 2.73 (2H, s), 2.31-2.19 (4H, m), 2.09-1.94 (1H, m), 1.82-1.67 (1H, m).<br>LC-MS (Method 4):<br>$R_t$ = 1.20 min; m/z = 254 (M + H)$^+$. |

Example 17A

3-Bromo-2-fluoroaniline

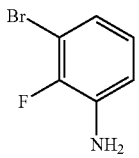

2.0 g (9.09 mmol) of 3-bromo-2-fluoronitrobenzene were dissolved in 10 ml of dioxane, and 8.62 g (45.45 mmol) of tin(II) chloride were added at RT. After addition of a few drops of 1 N hydrochloric acid, the mixture was heated at 70° C. for 2 h. After cooling, the reaction mixture was concentrated under reduced pressure and the residue was taken up in ethyl acetate. The solution was washed successively twice with 1N aqueous sodium hydroxide solution, water and saturated sodium chloride solution, dried over magnesium sulphate and concentrated under reduced pressure. The crude product was purified by chromatography on silica gel (mobile phase cyclohexane/ethyl acetate 10:1). This gave 997 mg (57.7% of theory) of the target compound.

LC-MS (Method 6): $R_t$=0.88 min; m/z=189/191 (M+H)$^+$.

$^1$H-NMR (400 MHz, DMSO-d$_6$): δ [ppm]=5.43 (s, 2H), 6.66-6.85 (m, 3H).

Example 18A tert-Butyl (2E)-3-(3-amino-2-fluorophenyl)acrylate

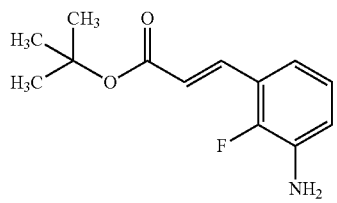 [SMILES: CC(C)(C)OC(=O)/C=C/c1cccc(N)c1F]

5.2 ml (37.1 mmol) of triethylamine were added to a solution of 1.41 g (7.42 mmol) of 3-bromo-2-fluoroaniline and 2.85 g (22.3 mmol) of tert-butyl acrylate in 8 ml of DMF. Three times, the flask was evacuated and vented with argon, and 451 mg (1.48 mmol) of tri-2-tolylphosphine and 166.6 mg (0.74 mmol) of palladium(II) acetate were then added. Once more, the reaction vessel was twice evacuated and vented with argon, and the mixture was then heated to about 140° C. After 2 h of vigorous stirring, the reaction mixture was cooled and added to saturated sodium bicarbonate solution. The mixture was extracted three times with ethyl acetate, and the combined organic phases were dried over magnesium sulphate and concentrated under reduced pressure. The residue was purified by chromatography on silica gel (mobile phase cyclohexane/ethyl acetate 10:1). This gave 1660 mg of the target product (94.3% of theory).

LC-MS (Method 6): $R_t$=1.12 min; m/z=279 (M+H+CH$_3$CN)$^+$.

$^1$H-NMR (400 MHz, DMSO-d$_6$): δ [ppm]=1.48 (s, 9H), 5.27 (s, 2H), 6.45 (d, 1H), 6.73-7.02 (m, 3H), 7.59 (d, 1H).

Example 19A tert-Butyl 3-(3-amino-2-fluorophenyl)propanoate

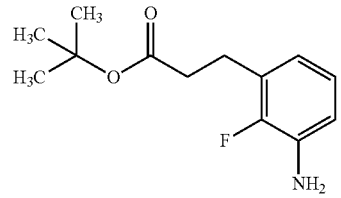 [SMILES: CC(C)(C)OC(=O)CCc1cccc(N)c1F]

Palladium on carbon (10%) was added to a solution of 1660 mg (7.0 mmol) of tert-butyl (2E)-3-(3-amino-2-fluorophenyl)acrylate in a mixture of 5 ml of ethanol and 3 ml of THF, and the mixture was stirred vigorously at atmospheric pressure under an atmosphere of hydrogen overnight. The reaction mixture was then filtered through kieselguhr and the filter residue was washed repeatedly with ethanol/THF. The combined filtrates were concentrated under reduced pressure and the residue was purified by chromatography on silica gel (mobile phase cyclohexane/ethyl acetate 20:1→10:1). This gave 1350 mg of the target product (80.6% of theory).

LC-MS (Method 6): $R_t$=1.07 min; m/z=225.

$^1$H-NMR (400 MHz, DMSO-d$_6$): δ [ppm]=1.36 (s, 9H), 2.45 (t, 2H), 2.74 (t, 2H), 5.00 (s, 2H), 6.24-6.46 (m, 1H), 6.51-6.66 (m, 1H), 6.66-6.82 (m, 1H).

Example 20A

Ethyl (E/Z)-3-(4-fluoro-3-nitrophenyl)-2-methyl-prop-2-enoate

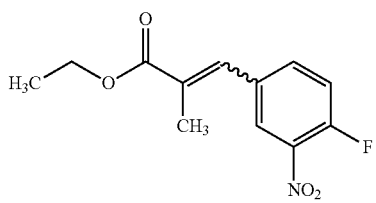 [SMILES: CCOC(=O)C(C)=Cc1ccc(F)c([N+](=O)[O-])c1]

3.17 g of sodium hydride (60% suspension in mineral oil, 79.36 mmol) were suspended in 90 ml of a THF/DMF mixture (2:1). The mixture was cooled to 0° C., and a solution of 19.76 g (82.96 mmol) of triethyl 2-phosphonopropionate in 60 ml of THF/DMF (2:1) was added dropwise. After 30 min, a solution of 12.2 g (72.14 mmol) of 4-fluoro-3-nitrobenzaldehyde in 60 ml of THF/DMF (2:1) was added dropwise at 0° C. After the addition had ended, the reaction mixture was slowly warmed to RT and stirred at this temperature for 2 h. The reaction mixture was then added to water. The mixture was extracted three times with ethyl acetate, and the combined organic phases were concentrated under reduced pressure. The residue was purified by chromatography on silica gel (mobile phase cyclohexane/ethyl acetate 20:1). This gave 15.2 g (83.2% of theory) of the target product as an E/Z isomer mixture (E/Z 91:9).

LC-MS (Method 6): Z isomer: $R_t$=1.11 min; m/z=254 (M+H)$^+$; E isomer: $R_t$=1.14 min; m/z=254 (M+H)$^+$.

$^1$H-NMR (400 MHz, DMSO-$d_6$): E isomer: δ [ppm]=1.28 (t, 3H), 4.22 (q, 2H), 7.59-7.73 (m, 2H), 7.92 (ddd, 1H), 8.24 (dd, 1H).

Example 21A

Ethyl (+/−)-3-(3-amino-4-fluorophenyl)-2-methyl-propanoate

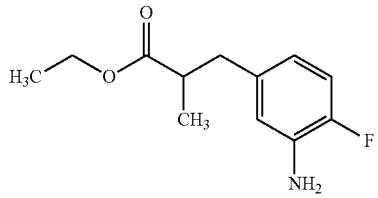 [SMILES: CCOC(=O)C(C)Cc1ccc(F)c(N)c1]

Palladium on carbon (10%) was added to 15.2 g (60.02 mmol) of ethyl (E/Z)-3-(4-fluoro-3-nitrophenyl)-2-methyl-prop-2-enoate (E/Z 91:9) in a mixture of 100 ml of ethanol and 100 ml of THF, and the mixture was stirred vigorously at atmospheric pressure under an atmosphere of hydrogen overnight. The reaction mixture was then filtered through celite, the residue was washed with ethanol/dichloromethane and the combined filtrates were concentrated under reduced pressure. The product was dried under high vacuum. This gave 13.34 g of the target product (98.7% of theory).

LC-MS (Method 6): $R_t$=0.98 min; m/z=226 (M+H)$^+$.

$^1$H-NMR (400 MHz, DMSO-$d_6$): δ [ppm]=1.04 (d, 3H), 1.12 (t, 3H), 2.46-2.50 (m, 1H), 2.55-2.66 (m, 1H), 2.66-2.78 (m, 1H), 4.01 (q, 2H), 5.00 (s, 2H), 6.18-6.35 (m, 1H), 6.55 (dd, 1H), 6.84 (dd, 1H).

The racematee obtained above was separated into the enantiomers by preparative HPLC on a chiral phase [column: Daicel Chiralpak AD-H, 5 μm, 250 mm×20 mm; injection volume: 0.15 ml; temperature: 30° C.; mobile phase: 90% isohexane/10% ethanol; flow rate: 15 ml/min; detection: 220 nm]. 7.25 g of racematee gave 3.43 g of enantiomer 1 (Example 22A) and 3.35 g of enantiomer 2 (Example 23A):

Example 22A

Ethyl (+)-(2S)-3-(3-amino-4-fluorophenyl)-2-methyl-ylpropanoate

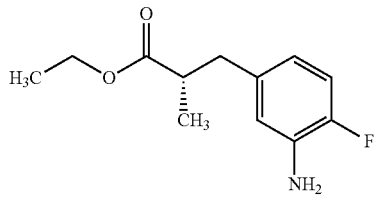 [SMILES: CCOC(=O)[C@@H](C)Cc1ccc(F)c(N)c1]

Yield: 3.43 g

LC-MS (Method 6): $R_t$=0.97 min; m/z=226 (M+H)$^+$.

$^1$H-NMR (400 MHz, DMSO-$d_6$): δ [ppm]=1.04 (d, 3H), 1.12 (t, 3H), 2.46-2.50 (m, 1H), 2.55-2.66 (m, 1H), 2.66-2.78 (m, 1H), 4.01 (q, 2H), 5.00 (s, 2H), 6.18-6.35 (m, 1H), 6.55 (dd, 1H), 6.84 (dd, 1H).

$[\alpha]_D^{20}$=+18.30°, c=0.465, chloroform.

Example 23A

Ethyl (−)-(2R)-3-(3-amino-4-fluorophenyl)-2-methylpropanoate

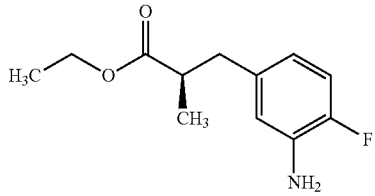 [SMILES: CCOC(=O)[C@H](C)Cc1ccc(F)c(N)c1]

Yield: 3.35 g

LC-MS (Method 6): $R_t$=0.97 min; m/z=226 (M+H)$^+$.

$^1$H-NMR (400 MHz, DMSO-$d_6$): δ [ppm]=1.04 (d, 3H), 1.12 (t, 3H), 2.46-2.50 (m, 1H), 2.55-2.66 (m, 1H), 2.68-2.79 (m, 1H), 4.01 (q, 2H), 5.00 (br. s, 2H), 6.30 (dd, 1H), 6.55 (dd, 1H), 6.84 (dd, 1H).

$[\alpha]_D^{20}$=−31.4°, c=0.520, chloroform.

Example 24A

Ethyl (E/Z)-3-(4-chloro-3-nitrophenyl)-2-methyl-prop-2-enoate

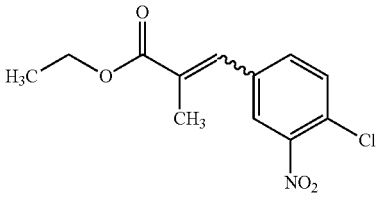 [SMILES: CCOC(=O)C(C)=Cc1ccc(Cl)c([N+](=O)[O-])c1]

4.74 g of sodium hydride (60% suspension in mineral oil, 118.56 mmol) were suspended in 93 ml of a THF/DMF mixture (1:1). The mixture was cooled to 0° C., and 26.6 ml (123.95 mmol) of triethyl 2-phosphonopropionate were added dropwise. After 30 min, 20.0 g (107.78 mmol) of 4-chloro-3-nitrobenzaldehyde were added at 0° C. After the addition had ended, the reaction mixture was slowly warmed to RT and stirred at this temperature for another 3 h. The reaction mixture was then added to water. The mixture was extracted three times with ethyl acetate, and the combined organic phases were concentrated under reduced pressure. The residue was purified by chromatography on silica gel (mobile phase cyclohexane/ethyl acetate 70:1→50:1). This gave 26.7 g (91.9% of theory) of the target product as an E/Z isomer mixture (E/Z 91:9).

LC-MS (Method 4): Z isomer: $R_t$=1.32 min; m/z=255; E isomer: $R_t$=1.36 min; m/z=270 (M+H)$^+$.

$^1$H-NMR (400 MHz, DMSO-$d_6$): E isomer: δ [ppm]=1.28 (t, 3H), 2.06 (d, 3H), 4.22 (q, 2H), 7.56-7.67 (m, 1H), 7.75-7.87 (m, 2H), 8.17 (d, 1H).

Example 25A

Ethyl (+/−)-3-(3-amino-4-chlorophenyl)-2-methyl-propanoate

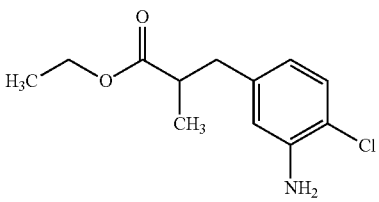 [SMILES: CCOC(=O)C(C)Cc1ccc(Cl)c(N)c1]

10.0 g (37.08 mmol) of ethyl (E/Z)-3-(4-chloro-3-nitrophenyl)-2-methylprop-2-enoate (E/Z 91:9) were dissolved in 25 ml of ethyl acetate and 25 ml of acetic acid, and palladium on carbon (10%) was added. The reaction mixture was stirred vigorously at atmospheric pressure under an atmosphere of hydrogen for a total of 6 h, with another 25 ml of acetic acid and further portions of 10% palladium on carbon being added after 2 h. The mixture was then filtered through celite and the residue was washed with ethanol/dichloromethane. The combined filtrates were washed with saturated sodium bicarbonate solution, dried over sodium sulphate and concentrated under reduced pressure. The crude product was purified by chromatography on silica gel (mobile phase cyclohexane/ethyl acetate 30:1→10:1). This gave 4.01 g of the target product (44.7% of theory).

LC-MS (Method 6): $R_t$=1.06 min; m/z=242 (M+H)$^+$.

$^1$H-NMR (400 MHz, DMSO-d$_6$): δ [ppm]=1.05 (d, 3H), 1.12 (t, 3H), 2.47-2.50 (m, 1H), 2.56-2.67 (m, 1H), 2.67-2.78 (m, 1H), 4.02 (q, 2H), 5.23 (s, 2H), 6.35 (dd, 1H), 6.58 (d, 1H), 7.05 (d, 1H).

The racematee obtained above was separated into the enantiomers by preparative HPLC on a chiral phase [column: Daicel Chiralpak OJ-H, 5 μm, 250 mm×20 mm; injection volume: 0.15 ml; temperature: 35° C.; mobile phase: 50% isohexane/50% isopropanol; flow rate: 15 ml/min; detection: 220 nm]. 10.3 g of racematee gave 4.0 g of enantiomer 1 (Example 26A) and 3.7 g of enantiomer 2 (Example 27A):

Example 26A

Ethyl (−)-(2R)-3-(3-amino-4-chlorophenyl)-2-methylpropanoate

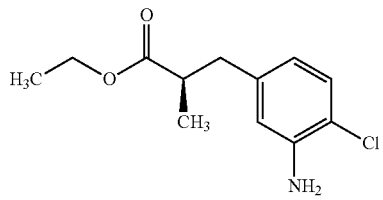

Yield: 4.0 g

LC-MS (Method 7): $R_t$=2.27 min; m/z=196/198.

$^1$H-NMR (400 MHz, DMSO-d$_6$): δ [ppm]=1.05 (d, 3H), 1.12 (t, 3H), 2.47-2.50 (m, 1H), 2.54-2.66 (m, 2H), 2.68-2.80 (m, 1H), 4.02 (q, 2H), 5.23 (s, 2H), 6.35 (dd, 1H), 6.58 (d, 1H), 7.05 (d, 1H).

$[α]_D^{20}$=−35.8°, c=0.560, chloroform.

Example 27A

Ethyl (+)-(2S)-3-(3-amino-4-chlorophenyl)-2-methylpropanoate

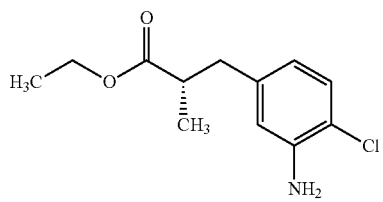

Yield: 3.7 g $^1$H-NMR (400 MHz, DMSO-d$_6$): δ [ppm]=1.05 (d, 3H), 1.12 (t, 3H), 2.47-2.50 (m, 1H), 2.56-2.67 (m, 1H), 2.67-2.81 (m, 1H), 4.02 (q, 2H), 5.23 (br. s, 2H), 6.35 (dd, 1H), 6.58 (d, 1H), 7.05 (d, 1H).

$[α]_D^{20}$=+35.1°, c=0.525, chloroform.

Example 28A

Ethyl (2E/Z)-2-(4-chloro-3-nitrobenzylidene)butanoate

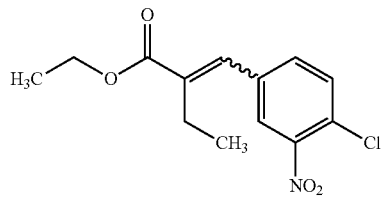 [SMILES: CCOC(=O)C(=Cc1ccc(Cl)c([N+](=O)[O-])c1)CC]

1.19 g of sodium hydride (60% suspension in mineral oil, 29.64 mmol) were suspended in 50 ml of a THF/DMF mixture (1:1). The mixture was cooled to 0° C., and 7.3 ml (30.99 mmol) of triethyl 2-phosphonobutyrate were added dropwise. After 30 min, 5.0 g (26.94 mmol) of 4-chloro-3-nitrobenzaldehyde were added a little at a time at −10° C. After the addition had ended, the reaction mixture was stirred at 0° C. for 5 h and then slowly warmed to RT overnight. The reaction mixture was then added to water. The mixture was extracted three times with ethyl acetate, and the combined organic phases were concentrated under reduced pressure. The residue was purified by chromatography on silica gel (mobile phase cyclohexane/ethyl acetate 6:1). This gave 7.05 g (92.1% of theory) of the target product as an E/Z isomer mixture.

LC-MS (Method 6): $R_t$=1.24 min and 1.26 min; no ionization.

Example 29A (+/−)-Ethyl 2-(3-amino-4-chlorobenzyl)butanoate

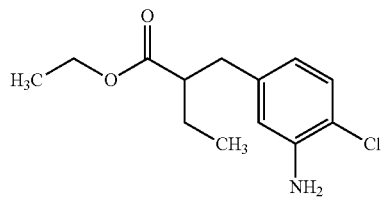

7.05 g (24.84 mmol) of ethyl (2E/Z)-2-(4-chloro-3-nitrobenzylidene)butanoate were dissolved in 35 ml of ethyl acetate and 35 ml of acetic acid, and palladium on carbon (10%) was added. The reaction mixture was stirred vigorously at atmospheric pressure under an atmosphere of hydrogen for a total of 6 h, with further portions of 10% palladium on carbon being added after 4 h. The mixture was then filtered through celite and the residue was washed with ethyl acetate/THF. The combined filtrates were washed with saturated sodium bicarbonate solution, dried over sodium sulphate and concentrated under reduced pressure. The crude product was purified by chromatography on silica gel (mobile phase cyclohexane/ethyl acetate 30:1→10:1). This gave 4.12 g of the target product (64.9% of theory).

LC-MS (Method 6): $R_t$=1.14 min; m/z=210.

¹H-NMR (400 MHz, DMSO-d₆): δ [ppm]=0.84 (t, 3H), 1.10 (t, 3H), 1.42-1.59 (m, 2H), 2.40-2.80 (m, 4H), 4.01 (q, 2H), 5.23 (s, 2H), 6.34 (dd, 1H), 6.58 (d, 1H), 7.05 (d, 1H).

The racematee obtained above was separated into the enantiomers by preparative HPLC on a chiral phase [column: Daicel Chiralpak OJ-H, 5 μm, 250 mm×20 mm; injection volume: 0.43 ml; temperature: 30° C.; mobile phase: ethanol; flow rate: 15 ml/min; detection: 220 nm]. 3.22 g of racematee gave 1.22 g of enantiomer 1 (Example 30A) and 1.27 g of enantiomer 2 (Example 31A):

Example 30A (−)-Ethyl (2R)-2-(3-amino-4-chlorobenzyl)butanoate

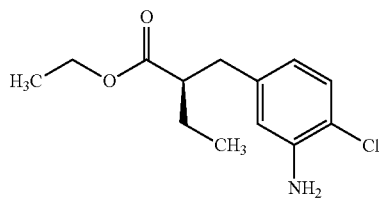 [SMILES: CCOC(=O)[C@H](CC)Cc1ccc(Cl)c(N)c1]

Yield: 1.22 g

LC-MS (Method 6): R$_t$=1.14 min; m/z=210.

¹H-NMR (400 MHz, DMSO-d₆): δ [ppm]=0.84 (t, 3H), 1.10 (t, 3H), 1.42-1.56 (m, 2H), 2.39-2.48 (m, 1H), 2.56-2.73 (m, 3H), 4.01 (q, 2H), 5.11-5.27 (m, 2H), 6.34 (dd, 1H), 6.58 (d, 1H), 7.05 (d, 1H).

[α]$_D^{20}$=−28.1°, c=0.510, chloroform.

Example 31A (+)-Ethyl (2S)-2-(3-amino-4-chlorobenzyl)butanoate

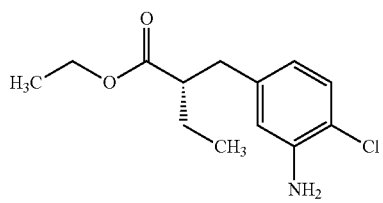 [SMILES: CCOC(=O)[C@@H](CC)Cc1ccc(Cl)c(N)c1]

Yield: 1.27 g

LC-MS (Method 6): R$_t$=1.15 min; m/z=210.

¹H-NMR (400 MHz, DMSO-d₆): δ [ppm]=0.84 (t, 3H), 1.10 (t, 3H), 1.46-1.55 (m, 2H), 2.42-2.49 (m, 1H), 2.54-2.69 (m, 3H), 4.01 (q, 2H), 5.22 (s, 2H), 6.34 (dd, 1H), 6.57 (d, 1H), 7.05 (d, 1H).

[α]$_D^{20}$=+34.1°, c=0.550, chloroform.

Example 32A tert-Butyl (2E/Z)-3-(4-chloro-3-nitrophenyl)but-2-enoate

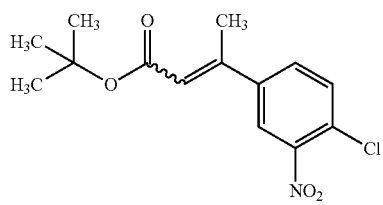 [SMILES: CC(=CC(=O)OC(C)(C)C)c1ccc(Cl)c([N+](=O)[O-])c1]

2.87 g of sodium hydride (60% suspension in mineral oil, 71.65 mmol) were suspended in 80 ml of THF. The mixture was cooled to 0° C., and 17.6 ml (74.9 mmol) of tert-butyl (diethoxyphosphoryl)acetate were added dropwise. After 30 min at 0° C., 13.0 g (65.1 mmol) of 4-chloro-3-nitroacetophenone were added. After the addition had ended, the reaction mixture was slowly warmed to RT and stirred at RT for another 1.5 h, and the mixture was then added to water. The mixture was extracted three times with ethyl acetate, and the combined organic phases were concentrated under reduced pressure. The residue was purified by chromatography on silica gel (mobile phase cyclohexane/ethyl acetate 20:1→10:1). This gave 17.03 g (87.8% of theory) of the target product as an E/Z isomer mixture (E/Z about 1:1).

LC-MS (Method 5): isomer 1: R$_t$=2.61 min; m/z=255; isomer 2: R$_t$=2.77 min; m/z=224.

Example 33A tert-Butyl (+/−)-3-(3-amino-4-chlorophenyl)butanoate

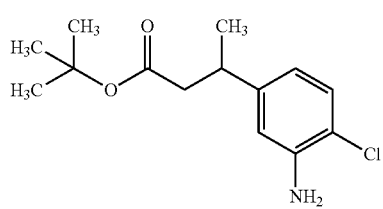

11.5 g (38.62 mmol) of tert-butyl (2E/Z)-3-(4-chloro-3-nitrophenyl)but-2-enoate (E/Z about 1:1) were dissolved in 60 ml of ethyl acetate and 60 ml of acetic acid, and palladium on carbon (10%) was added. The reaction mixture was stirred vigorously at atmospheric pressure under an atmosphere of hydrogen for 6 h. The mixture was then filtered through celite and the residue was washed with ethyl acetate. The combined filtrates were washed with saturated sodium bicarbonate solution, dried over sodium sulphate and concentrated under reduced pressure. The crude product was purified by chromatography on silica gel (mobile phase cyclohexane/ethyl acetate 30:1). This gave 3.90 g (37.4% of theory) of the target product.

¹H-NMR (400 MHz, DMSO-d₆): δ [ppm]=1.14 (d, 3H), 1.31 (s, 9H), 2.38 (dd, 2H), 2.95 (q, 1H), 5.21 (br. s, 2H), 6.42 (dd, 1H), 6.65 (d, 1H), 7.06 (d, 1H).

The racematee obtained above was separated into the enantiomers by preparative HPLC on a chiral phase [column: Daicel Chiralpak AD-H, 5 μm, 250 mm×20 mm; injection volume: 0.15 ml; temperature: 30° C.; mobile phase: 90% isohexane/10% ethanol; flow rate: 15 ml/min; detection: 220 nm]. 5.0 g of racematee gave 2.1 g of enantiomer 1 (Example 34A) and 1.8 g of enantiomer 2 (Example 35A):

Example 34A tert-Butyl (+)-(3S)-3-(3-amino-4-chlorophenyl)butanoate

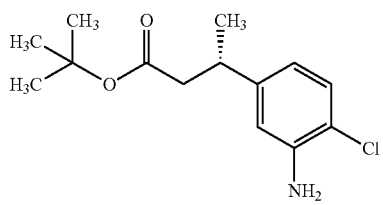 [SMILES: CC(CC(=O)OC(C)(C)C)c1ccc(Cl)c(N)c1]

LC-MS (Method 4): $R_t$=1.34 min; m/z=270 (M+H)$^+$.
$^1$H-NMR (400 MHz, DMSO-$d_6$): δ [ppm]=1.14 (d, 3H), 1.31 (s, 9H), 2.19-2.45 (m, 2H), 2.95 (q, 1H), 5.20 (s, 2H), 6.42 (dd, 1H), 6.65 (d, 1H), 7.06 (d, 1H).
$[α]_D^{20}$=+20.9°, c=0.670, chloroform.

Example 35A tert-Butyl (−)-(3R)-3-(3-amino-4-chlorophenyl)butanoate

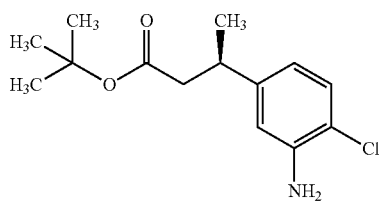 [SMILES: C[C@H](CC(=O)OC(C)(C)C)c1ccc(Cl)c(N)c1]

LC-MS (Method 4): $R_t$=1.34 min; m/z=214 (M+H—$C_4H_8$)$^+$.
$^1$H-NMR (400 MHz, DMSO-$d_6$): δ [ppm]=1.14 (d, 3H), 1.31 (s, 9H), 2.38 (dd, 2H), 2.95 (q, 1H), 5.20 (br. s, 2H), 6.42 (dd, 1H), 6.65 (d, 1H), 7.06 (d, 1H).
$[α]_D^{20}$=−24.1°, c=0.570, chloroform.

Example 36A tert-Butyl (2E/Z)-3-(4-fluoro-3-nitrophenyl)but-2-enoate

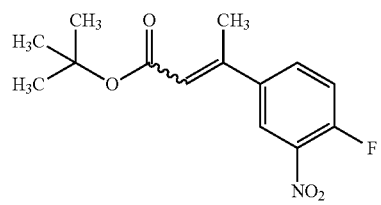 [SMILES: CC(=CC(=O)OC(C)(C)C)c1ccc(F)c([N+](=O)[O-])c1]

4.81 g of sodium hydride (60% suspension in mineral oil, 120.13 mmol) were suspended in a mixture of 120 ml of THF and 120 ml of DMF. The mixture was cooled to 0° C., and 29.5 ml (125.59 mmol) of tert-butyl (diethoxyphosphoryl)acetate were added dropwise. After 30 min, 20.0 g (109.21 mmol) of 4-fluoro-3-nitroacetophenone were added at 0° C. After the addition had ended, the reaction mixture was slowly warmed to RT and stirred at RT for another 3.5 h, after which the mixture was added to water. The mixture was extracted three times with ethyl acetate, and the combined organic phases were concentrated under reduced pressure. The residue was purified by chromatography on silica gel (mobile phase cyclohexane/ethyl acetate 50:1). This gave 7.24 g (23.6% of theory) of the target product as an E/Z isomer mixture (E/Z about 1.2:1).
LC-MS (Method 4): isomer 1: $R_t$=1.34 min; m/z=208; isomer 2: $R_t$=1.42 min; m/z=208.

Example 37A tert-Butyl (+/−)-3-(3-amino-4-fluorophenyl)butanoate

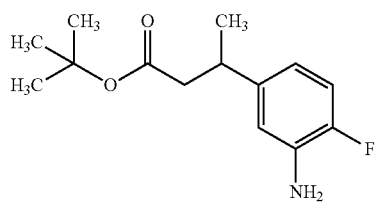

7.24 g (25.74 mmol) of tert-butyl (2E/Z)-3-(4-fluoro-3-nitrophenyl)but-2-enoate (E/Z about 1.2:1) were dissolved in 200 ml of ethanol, and palladium on carbon (10%) was added. The reaction mixture was stirred vigorously at atmospheric pressure under an atmosphere of hydrogen overnight. The mixture was then filtered through celite, and the residue was washed twice with ethyl acetate. The combined filtrates were concentrated under reduced pressure and the residue was dried under high vacuum. This gave 6.02 g of the target product (92.4% of theory).
$^1$H-NMR (400 MHz, DMSO-$d_6$): δ [ppm]=1.14 (d, 3H), 1.31 (s, 9H), 2.37 (dd, 2H), 2.95 (q, 1H), 4.98 (s, 2H), 6.36 (ddd, 1H), 6.62 (dd, 1H), 6.85 (dd, 1H).
The racemate obtained above was separated into the enantiomers by preparative HPLC on a chiral phase [column: Daicel Chiralpak OJ-H, 5 μm, 250 mm×20 mm; injection volume: 0.15 ml; temperature: 35° C.; mobile phase: 65% isohexane/35% ethanol; flow rate: 15 ml/min; detection: 220 nm]. 6.0 g of racematee gave 2.44 g of enantiomer 1 (Example 38A) and 1.92 g of enantiomer 2 (Example 39A):

Example 38A tert-Butyl (+)-(3S)-3-(3-amino-4-fluorophenyl)butanoate

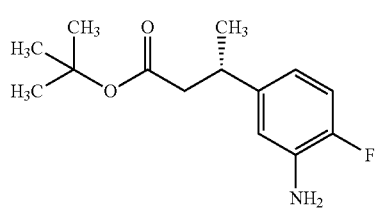 [SMILES: C[C@@H](CC(=O)OC(C)(C)C)c1ccc(F)c(N)c1]

LC-MS (Method 6): $R_t$=1.11 min; m/z=254 (M+H)$^+$.

$^1$H-NMR (400 MHz, DMSO-d$_6$): δ [ppm]=1.14 (d, 3H), 1.31 (s, 9H), 2.18-2.46 (m, 2H), 2.95 (q, 1H), 4.99 (br. s, 2H), 6.36 (ddd, 1H), 6.61 (dd, 1H), 6.85 (dd, 1H).

$[α]_D^{20}$=+22.5°, c=0.570, chloroform.

Example 39A tert-Butyl (−)-(3R)-3-(3-amino-4-fluorophenyl)butanoate

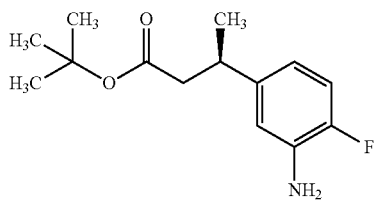 [SMILES: C[C@H](CC(=O)OC(C)(C)C)c1ccc(F)c(N)c1]

LC-MS (Method 6): $R_t$=1.11 min; m/z=254 (M+H)$^+$.

$^1$H-NMR (400 MHz, DMSO-d$_6$): δ [ppm]=1.14 (d, 3H), 1.31 (s, 9H), 2.26-2.45 (m, 2H), 2.95 (q, 1H), 4.99 (br. s, 2H), 6.36 (ddd, 1H), 6.62 (dd, 1H), 6.85 (dd, 1H).

$[α]_D^{20}$=−23.2°, c=0.510, chloroform.

Example 40A

Ethyl 3-(3-bromo-4-fluorophenyl)acrylate

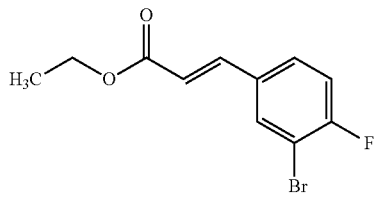

9.65 g (111 mmol) of manganese dioxide were added to a solution of 6.5 g (31.7 mmol) of 3-bromo-4-fluorobenzyl alcohol and 13.25 g (38 mmol) of ethoxycarbonylmethylenephosphorane in 390 ml of toluene. The reaction mixture was heated at reflux, a further 9.65 g of manganese dioxide were added after 1 h and heating under reflux was continued overnight. After cooling, the mixture was filtered through celite and the filtrate was concentrated. The residue was purified by flash chromatography on silica gel (mobile phase cylclohexane/ethyl acetate 5:1). This gave 7.05 g (81% of theory) of the target product in the form of an E/Z isomer mixture.

LC-MS (Method 4): $R_t$=1.33 min and 1.35 min; m/z=273/275 (M+H)$^+$.

Example 41A rac-Ethyl 2-(3-bromo-4-fluorophenyl)-trans-cyclopropanecarboxylate

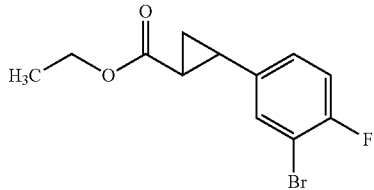 [SMILES: CCOC(=O)C1CC1c1ccc(F)c(Br)c1]

Under argon, 381 mg (9.52 mmol) of sodium hydride (60% in paraffin oil) were initially charged in 20 ml of DMSO, and 2.1 g (9.52 mmol) of trimethylsulphoxonium iodide were added in one portion at RT. After the evolution of gas had ceased, 2.0 g (7.3 mmol) of ethyl 3-(3-bromo-4-fluorophenyl)acrylate, dissolved in 10 ml of DMSO, were slowly added dropwise. The reaction mixture was heated at 50° C. overnight, then cooled to RT and, without further work-up, purified by flash chromatography on silica gel (mobile phase isohexane/ethyl acetate 100:1). This gave 907 mg (43% of theory) of the target product.

LC-MS (Method 6): $R_t$=1.20 min; m/z=289 (M+H)$^+$.

GC-MS (Method 1): $R_t$=5.85 min; m/z=287/289 (M+H)$^+$.

$^1$H-NMR (500 MHz, CDCl$_3$): δ [ppm]=1.20-1.33 (m, 4H), 1.56-1.63 (m, 1H), 1.80-1.88 (m, 1H), 2.43-2.52 (m, 1H), 4.17 (q, 2H), 7.00-7.06 (m, 2H), 7.28 (d, 1H).

Example 42A rac-Ethyl 2-[3-(benzylamino)-4-fluorophenyl]-trans-cyclopropanecarboxylate

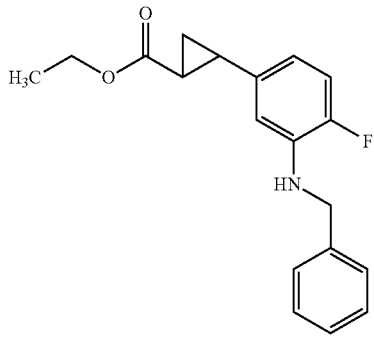 [SMILES: CCOC(=O)C1CC1c1ccc(F)c(NCc2ccccc2)c1]

Under argon, 361.5 m (3.8 mmol) of sodium tert-butoxide were suspended in 12.9 ml of toluene, and 900 mg (3.1 mmol) of (+/−)-trans-ethyl 2-(3-bromo-4-fluorophenyl)cyclopropanecarboxylate, 403 mg (3.8 mmol) of benzylamine, 28.7 mg (0.03 mmol) of tris(dibenzylideneacetone)dipalladium and 19.5 mg (0.03 mmol) of rac-2,2'-bis(diphenylphosphino)-1,1'-binaphthyl were added successively. The mixture was heated at 110° C. for 4 h. The reaction mixture was then cooled to RT, 100 ml of ethyl acetate and 50 ml of saturated ammonium chloride solution were added and the mixture was filtered through celite. The organic phase was separated off, washed with in each case 50 ml of saturated ammonium chloride solution and saturated sodium chloride solution, dried over magnesium sulphate and concentrated. The crude product was purified by preparative HPLC. This gave 262 mg of the target compound of a purity of 66% (18% of theory).

LC-MS (Method 6): $R_t$=1.28 min; m/z=314 (M+H)$^+$.

Example 43A rac-Ethyl 2-[3-amino-4-fluorophenyl]-trans-cyclopropanecarboxylate

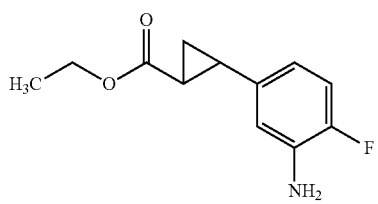

262 mg (purity 66%, 0.55 mmol) of (+/−)-ethyl 2-[3-(benzylamino)-4-fluorophenyl]-trans-cyclopropanecarboxylate were dissolved in 5 ml of ethanol/THF (1:1), 26 mg of palladium on carbon (10%) were added and the mixture was hydrogenated at RT using a hydrogen pressure of 1 bar for 24 h. The reaction mixture was then filtered through celite, the residue was washed with ethanol and the filtrate was concentrated. The crude product obtained in this manner was purified by preparative HPLC. This gave 87 mg (69% of theory) of the target compound.

LC-MS (Method 6): $R_t$=0.96 min; m/z=224 (M+H)$^+$.

$^1$H-NMR (400 MHz, DMSO-$d_6$): δ [ppm]=1.17-1.23 (m, 3H), 1.23-1.28 (m, 1H), 1.39 (dt, 1H), 1.67-1.81 (m, 1H), 2.21-2.31 (m, 1H), 4.09 (q, 2H), 6.31 (ddd, 1H), 6.55 (dd, 1H), 6.86 (dd, 1H).

Example 44A

3-Amino-4-fluoroacetophenone

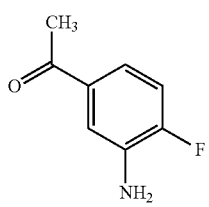

At 0° C., a solution of 11.1 g (89 mmol) of tin chloride dihydrate in 12 ml of water was added dropwise over a period of 15 min to a solution of 3 g (16.4 mmol) of 4-fluoro-3-nitroacetophenone in 7.8 ml of 12 N hydrochloric acid. The reaction mixture was then heated at reflux for 15 min and subsequently stirred at RT overnight. The reaction mixture was then poured on ice, adjusted to pH 12 using 50% strength aqueous sodium hydroxide solution and extracted with ethyl acetate. The organic phase was washed with saturated sodium chloride solution, dried over magnesium sulphate and concentrated. This gave 2.47 g (purity 90%, 87% of theory) of the target compound.

LC-MS (Method 5): $R_t$=1.32 min; m/z=154 (M+H)$^+$.

Example 45A and Example 46A

Ethyl (2E)-3-(3-amino-4-fluorophenyl)-2-methylbut-2-enoate and Ethyl (2Z)-3-(3-amino-4-fluorophenyl)-2-methylbut-2-enoate

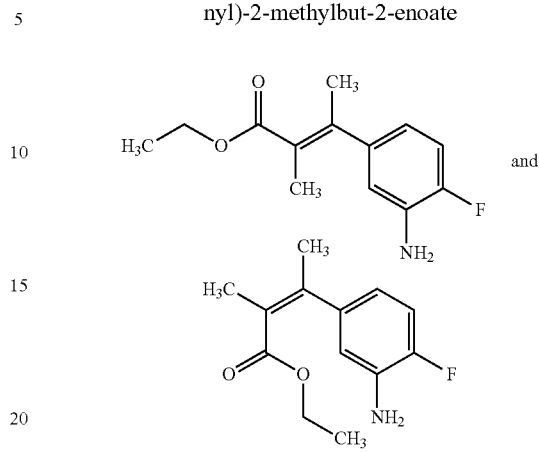

At 0° C., 6.92 ml (7.68 g, 32.3 mmol) of triethyl 2-phosphonopropionate were slowly added dropwise to a suspension of 1.29 g of sodium hydride (60% in paraffin oil; 32.3 mmol) in 24.7 ml of THF. The reaction mixture was stirred for 30 min, and 2.47 g (purity 90%, 14.5 mmol) of 3-amino-4-fluoroacetophenone were then added. The reaction mixture was stirred initially at RT for 1 h and then under reflux for 2 h, then cooled back to RT and stirred overnight. The mixture was then poured into water and extracted three times with in each case 100 ml of ethyl acetate. The combined organic phases were dried over magnesium sulphate and concentrated and the residue was purified by flash chromatography on silica gel (mobile phase toluene/ethyl acetate 5:1). This gave, in separated form, 612 mg (15% of theory) of the 2E isomer (Example 45A) and 529 mg (13% of theory) of the 2Z isomer (Example 46A).

2E Isomer

Example 45A

LC-MS (Method 6): $R_t$=1.05 min; m/z=238 (M+H)$^+$.

$^1$H-NMR (400 MHz, DMSO-$d_6$): δ [ppm]=1.22-1.29 (m, 3H), 1.69 (d, 3H), 2.11 (d, 3H), 4.17 (d, 2H), 6.30 (ddd, 1H), 6.56 (dd, 1H), 6.97 (dd, 1H).

2Z Isomer

Example 46A

LC-MS (Method 6): $R_t$=0.99 min; m/z=238 (M+H)$^+$.

$^1$H-NMR (400 MHz, DMSO-$d_6$): δ [ppm]=0.85 (t, 3H), 1.86-1.92 (m, 3H), 1.94-2.01 (m, 3H), 3.82 (q, 2H), 6.24 (ddd, 1H), 6.51 (dd, 1H), 6.87 (dd, 1H).

Example 47A rac-threo-Ethyl 3-(3-amino-4-fluorophenyl)-2-methylbutanoate

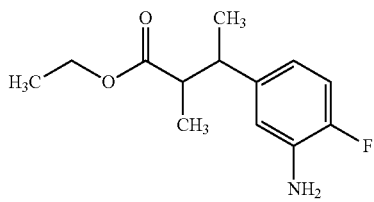 [SMILES: CCOC(=O)C(C)C(C)c1ccc(F)c(N)c1]

4.8 mg of palladium on carbon (10%) were added to a solution of 48 mg (0.2 mmol) of ethyl (2E)-3-(3-amino-4-fluorophenyl)-2-methylbut-2-enoate in 5 ml of methanol. The reaction mixture was hydrogenated at a hydrogen pressure of 1 bar overnight. The mixture was then filtered through celite and the filtrate was concentrated. This gave 35.8 mg (74% of theory) of the title compound which contained about 20% of the erythro isomer.

LC-MS (Method 6): $R_t$=1.02 min; m/z=240 (M+H)$^+$.

Example 48A rac-eythro-Ethyl 3-(3-amino-4-fluorophenyl)-2-methylbutanoate

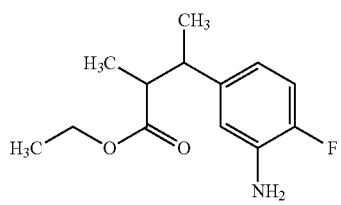

3 mg of palladium on carbon (10%) were added to a solution of 30 mg (0.13 mmol) of ethyl (2Z)-3-(3-amino-4-fluorophenyl)-2-methylbut-2-enoate in 3.1 ml of methanol. The reaction mixture was hydrogenated at a hydrogen pressure of 1 bar overnight. The mixture was then filtered through celite and the filtrate was concentrated. This gave 22.5 mg (74% of theory) of the title compound which contained about 5% of the threo isomer.

LC-MS (Method 6): $R_t$=1.04 min; m/z=240 (M+H)$^+$.

Example 49A tert-Butyl (2E)-3-(4-fluoro-3-nitrophenyl)acrylate

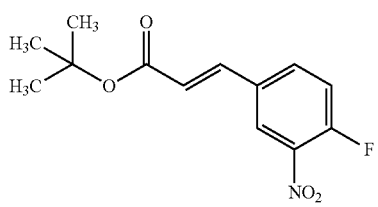

Under argon, 0.65 g of sodium hydride (60% in paraffin oil; 16.3 mmol) was initially charged in 25 ml of THF, and the mixture was cooled to 0° C. 4.29 g (17 mmol) of tert-butyl diethylphosphonoacetate were then slowly added dropwise. After 30 min of stirring, 2.5 g (14.8 mmol) of 4-fluoro-3-nitrobenzaldehyde were added. The reaction mixture was stirred at RT for 3 h, then poured into 100 ml of water and extracted three times with in each case 100 ml of ethyl acetate. The combined organic phases were dried over magnesium sulphate and concentrated. The residue was purified by flash chromatography on silica gel (mobile phase cyclohexane/ethyl acetate 50:1). This gave 3.37 g (85% of theory) of the target product.

GC-MS (Method 1): $R_t$=6.45 min; m/z=211 (M–$^t$Bu)$^+$.

$^1$H-NMR (400 MHz, DMSO-d$_6$): δ [ppm]=1.49 (s, 9H), 6.69 (d, 1H), 7.59-7.76 (m, 2H), 8.19 (ddd, 1H), 8.50 (dd, 1H).

Example 50A tert-Butyl (2E)-3-(4-cyano-3-nitrophenyl)acrylate

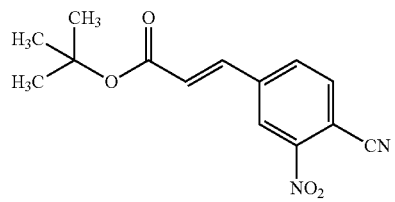 [SMILES: CC(C)(C)OC(=O)/C=C/c1ccc(C#N)c([N+](=O)[O-])c1]

134 mg (2.06 mmol) of potassium cyanide were added to a solution of 500 mg (1.87 mmol) of tert-butyl (2E)-3-(4-fluoro-3-nitrophenyl)acrylate in 5.4 ml of DMF. The reaction mixture was stirred at RT overnight and then purified directly by flash chromatography on silica gel (mobile phase cyclohexane/ethyl acetate mixture). This gave 57 mg (11% of theory) of the title compound.

LC-MS (Method 5): $R_t$=2.40 min; m/z=292 (M+NH$_4$)$^+$.

$^1$H-NMR (400 MHz, DMSO-d$_6$): δ [ppm]=1.39-1.58 (m, 9H), 6.91 (d, 1H), 7.73 (d, 1H), 8.19 (d, 1H), 8.26-8.38 (m, 1H), 8.72 (d, 1H).

Example 51A tert-Butyl 3-(3-amino-4-cyanophenyl)propanoate

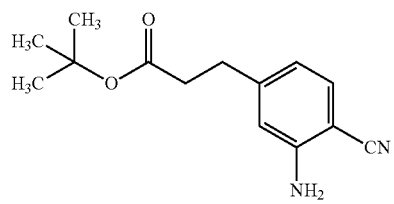 [SMILES: CC(C)(C)OC(=O)CCc1ccc(C#N)c(N)c1]

4.9 mg of palladium on carbon (10%) were added to a solution of 48.9 mg (0.18 mmol) of tert-butyl (2E)-3-(4-cyano-3-nitrophenyl)acrylate in 4.4 ml of ethanol. The reaction mixture was hydrogenated using a hydrogen pressure of 1 bar at RT overnight. The mixture was then filtered through celite and the filtrate was concentrated. This gave 43.5 mg (99% of theory) of the target compound of a purity of 85%.

LC-MS (Method 6): $R_t$=1.06 min; m/z=247 (M+H)$^+$.

Example 52A

Ethyl (3R)-4,4,4-trifluoro-3-methylbutanoate

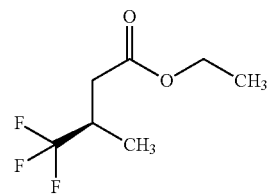

At room temperature, 133 ml (1.82 mmol) of thionyl chloride were added slowly to 287 g (1.65 mol) of (3R)-4,4,4-trifluoro-3-methylbutanoic acid [A. Gerlach and U. Schulz, *Speciality Chemicals Magazine* 24 (4), 37-38 (2004); CAS Acc.-No. 142:179196] in 580 ml of ethanol. The reaction solution was then heated to 80° C. and stirred at this temperature for 2 h. The mixture was then cooled to room temperature, 250 ml of water were added slowly and the mixture was extracted three times with in each case 150 ml of tert-butyl methyl ether. The combined organic phases were dried over sodium sulphate. After filtration, the solvent was removed under a reduced pressure of 300 mbar at 30° C. The crude product was then distilled at 100 mbar and a head temperature of 65° C. This gave 225.8 g (113 mol, 74% of theory) of the title compound as a colourless liquid.

$^1$H-NMR (400 MHz, DMSO-$d_6$, δ/ppm): 4.10 (2H, q), 2.88-2.72 (1H, m), 2.66-2.57 (1H, m), 2.46-2.36 (1H, m), 1.19 (3H, t), 1.11 (3H, d).

GC-MS (Method 1): $R_t$=1.19 min; m/z=184 (M)$^+$.

$[α]_D^{20}$=+16.1°, c=0.41, methanol

Example 53A

Ethyl 4,4,4-trifluoro-3-methyl-2-(4-methylphenyl)butanoate (diastereomer mixture)

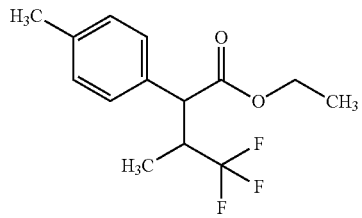 [SMILES: CCOC(=O)C(c1ccc(C)cc1)C(C)C(F)(F)F]

Under argon, 196.9 mg (0.88 mmol) of palladium(II) acetate and 724.8 mg (1.84 mmol) of 2-dicyclohexylphosphino-2'-(N,N-dimethylamino)biphenyl were initially charged in 50 ml of anhydrous toluene. 43.8 ml (43.8 mmol) of a 1 M solution of lithium hexamethyldisilazide in THF were then added slowly, and the reaction solution was stirred at RT for 10 min. The reaction solution was then cooled to −10° C., 7 g (38.0 mmol) of (+/−)-ethyl 4,4,4-trifluoro-3-methylbutanoate were added slowly and the mixture was stirred at −10° C. for 10 min 5 g (29.2 mmol) of 4-bromotoluene, dissolved in 50 ml of toluene, were then added dropwise, and the reaction solution was warmed initially to RT and then to 80° C. The mixture was stirred at this temperature for 2 h, then cooled to RT and stirred overnight. After the reaction had gone to completion (monitored by TLC; mobile phase cyclohexane/dichloromethane 2:1), the reaction mixture was filtered through kieselguhr, the residue was washed repeatedly with ethyl acetate and dichloromethane and the combined filtrates were concentrated under reduced pressure. The crude product obtained was purified chromatographically on silica gel (mobile phase petroleum ether/dichloromethane 4:1→3:1). This gave 3.91 g (14.3 mmol, 48.8% of theory) of the title compound as a colourless liquid.

$^1$H-NMR (400 MHz, DMSO-$d_6$, δ/ppm): 7.26 (2H, d), 7.20-7.12 (2H, m), 4.17-3.95 (2H, m), 3.74 (0.25H, d), 3.66 (0.75H, d), 3.35-3.07 (1H, m), 2.29 (2.25H, s), 2.28 (0.75H, s), 1.17 (0.75H, d), 1.11 (3H, t), 0.76 (2.25H, d).

GC-MS (Method 1): $R_t$=4.20 min; m/z=275 (M+H)$^+$ (diastereomer 1); $R_t$=4.23 min; m/z=275 (M+H)$^+$ (diastereomer 2).

Example 54A

Ethyl (3R)-2-(4-chlorophenyl)-4,4,4-trifluoro-3-methylbutanoate

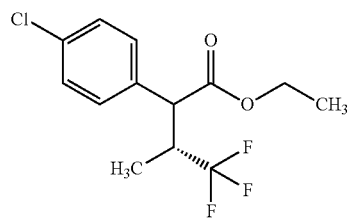 [SMILES: CCOC(=O)C(c1ccc(Cl)cc1)[C@@H](C)C(F)(F)F]

Preparation of solution A: Under argon, 163.9 ml of a 1 M solution of lithium hexamethyldisilazide in toluene were cooled to from −10° C. to −20° C. (cooling with acetone/dry ice), and 20 g (108.6 mmol) of ethyl (3R)-4,4,4-trifluoro-3-methylbutanoate, dissolved in 150 ml of toluene, were added slowly, where care was being taken not to exceed a temperature of −10° C. The solution was then stirred at not more than −10° C. for 10 min.

Preparation of solution B: Under argon, 27.03 g (141.2 mmol) of 1-bromo-4-chlorobenzene were dissolved in 100 ml of toluene at RT, and 731 mg (3.26 mmol) of palladium(II) acetate and 2.693 g (6.84 mmol) of 2'-(dicyclohexylphosphanyl)-N,N-dimethylbiphenyl-2-amine were added. The solution was stirred at RT for 10 min.

Initially, the cooling bath was removed from solution A. Solution B was then slowly added dropwise to solution A, which was still cold. The combined solutions were slowly warmed to RT and stirred at this temperature for 1 h. The reaction solution was then warmed to 80° C. (internal temperature) and stirred at this temperature for 3 h. The reaction solution was then slowly cooled to RT and stirred for another 12 h. The reaction mixture was then filtered through kieselguhr, the residue was washed repeatedly with toluene and the combined filtrates were concentrated under reduced pressure. The crude product obtained was purified chromatographically on silica gel (mobile phase cyclohexane/dichloromethane 4:1). This gave 27.4 g (92.98 mmol, 86% of theory) of the title compound as a yellow oil in a diastereomer ratio of 3:1.

GC-MS (Method 1): $R_t$=4.45 min; m/z=294 (M)$^+$ (diastereomer 1); $R_t$=4.48 min; m/z=294 (M)$^+$ (diastereomer 2).

The following compounds were obtained analogously to synthesis Examples 53A and 54A:

| Example | Name/Structure/Starting Materials | Analytical Data |
|---|---|---|
| 55A | Ethyl (3R)-4,4,4-trifluoro-2-(4-isopropylphenyl)-3-methylbutanoate<br>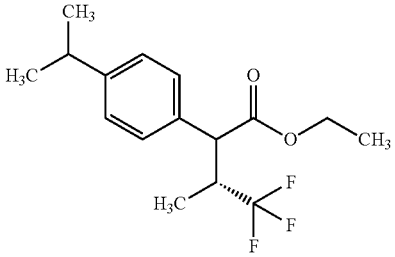<br>(from 1-bromo-4-isopropylbenzene and ethyl (3R)-4,4,4-trifluoro-3-methylbutanoate) | GC-MS (Method 1): $R_t$ = 4.61 min; m/z = 302 (M)$^+$ (diastereomer 1); $R_t$ = 4.64 min; m/z = 302 (M)$^+$ (diastereomer 2). |
| 56A | Ethyl (3R)-2-(4-tert-butylphenyl)-4,4,4-trifluoro-3-methylbutanoate<br>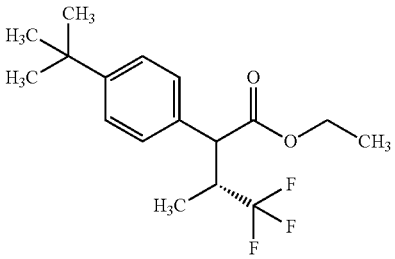<br>(from 1-bromo-4-tert-butylbenzene and ethyl (3R)-4,4,4-trifluoro-3-methylbutanoate) | GC-MS (Method 1): $R_t$ = 4.83 min; m/z = 317 (M + H)$^+$ (diastereomer 1); $R_t$ = 4.85 min; m/z = 317 (M + H)$^+$ (diastereomer 2). MS (DCI): m/z = 334 (M + NH$_4$)$^+$. |
| 57A | Ethyl (3R)-4,4,4-trifluoro-3-methyl-2-[4-(trifluoromethyl)phenyl]butanoate<br>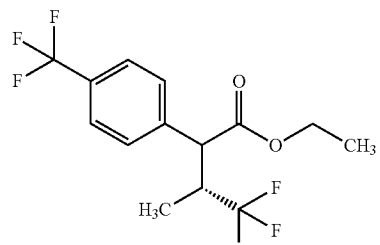<br>(from 1-bromo-4-(trifluoromethyl)benzene and ethyl (3R)-4,4,4-trifluoro-3-methylbutanoate) | GC-MS (Method 1): $R_t$ = 3.38 min; m/z = 328 (M)$^+$ (diastereomer 1); $R_t$ = 3.42 min; m/z = 328 (M)$^+$ (diastereomer 2). |
| 58A | Ethyl (3R)-4,4,4-trifluoro-3-methyl-2-[4-(1,1,1-trifluoro-2-methylpropan-2-yl)phenyl]butanoate<br>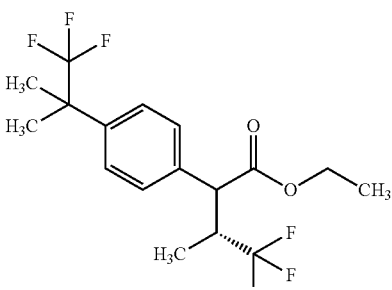<br>(from 1-bromo-4-(1,1,1-trifluoro-2-methylpropan-2-yl)-benzene and ethyl (3R)-4,4,4-trifluoro-3-methylbutanoate) | GC-MS (Method 1): $R_t$ = 4.68 min; m/z = 370 (M)$^+$. |

Example 59A

Ethyl 2-[4-(bromomethyl)phenyl]-4,4,4-trifluoro-3-methylbutanoate

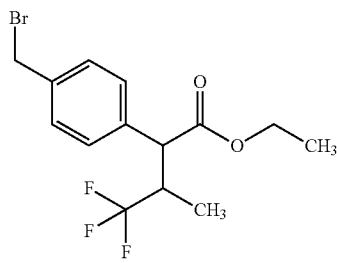 [SMILES: CCOC(=O)C(c1ccc(CBr)cc1)C(C)C(F)(F)F]

2.25 g (8.2 mmol) of ethyl 4,4,4-trifluoro-3-methyl-2-(4-methylphenyl)butanoate, 1.53 g (8.6 mmol) of N-bromosuccinimide and 67 mg (0.41 mmol) of 2,2'-azobis-2-methylpropanenitrile in 36 ml of trichloromethane were stirred under reflux overnight. After the reaction had gone to completion, the succinimide was filtered off, the filter residue was washed with dichloromethane and the filtrate was concentrated under reduced pressure. The crude product was purified chromatographically on silica gel (mobile phase cyclohexane/ethyl acetate 40:1). This gave 2.667 g (7.5 mmol, 92% of theory) of a yellowish oil.

GC-MS (Method 1): $R_t$=5.72 min; m/z=373 (M−Br)$^+$ (diastereomer 1); $R_t$=5.74 min; m/z=373 (M−Br)$^+$ (diastereomer 2).

Example 60A

Ethyl 4,4,4-trifluoro-3-methyl-2-[4-(2,2,2-trifluoroethyl)phenyl]butanoate

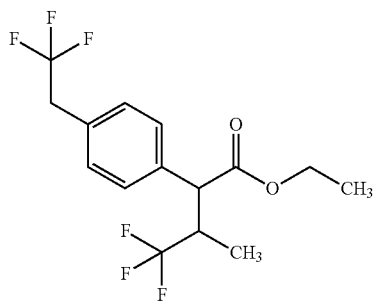 [SMILES: CCOC(=O)C(c1ccc(CC(F)(F)F)cc1)C(C)C(F)(F)F]

529 mg (2.78 mmol) of copper(I) iodide and 4 g (20.82 mmol) of methyl 2,2-difluoro-2-(fluorosulphonyl) acetate were added to 3.77 g (10.67 mmol) of ethyl 2-[4-(bromomethyl)phenyl]-4,4,4-trifluoro-3-methylbutanoate in 40 ml of 1-methylpyrrolidin-2-one, and the mixture was stirred at 80° C. overnight. After the reaction had gone to completion, the reaction solution was slowly poured onto 100 ml of ice-water. The mixture obtained was then extracted three times with diethyl ether. The combined organic phases were dried over magnesium sulphate. After filtration, the solvent was removed under reduced pressure. The crude product obtained was purified chromatographically on silica gel (mobile phase cyclohexane/dichloromethane 4:1). This gave 1.48 g (4.32 mmol, 41% of theory) of the title compound as a yellowish oil.

GC-MS (Method 1): $R_t$=4.06 min; m/z=342 (M)$^+$ (diastereomer 1); $R_t$=4.09 min; m/z=342 (M)$^+$ (diastereomer 2).

MS (DCI): m/z=360 (M+NH$_4$)$^+$.

Example 61A

1-Bromo-4-(2-bromo-1-fluoroethyl)benzene

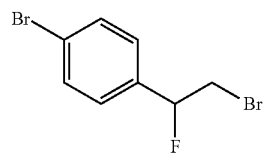 [SMILES: FC(CBr)c1ccc(Br)cc1]

5.0 g (27.31 mmol) of 4-bromostyrene were dissolved in 40 ml of dichloromethane and cooled to 0° C., and 13.21 g (81.94 mmol) of triethylamine trihydrofluoride were added. 5.83 g (32.78 mmol) of N-bromosuccinimide were then added in three portions. The mixture was stirred at RT overnight. After dilution with dichloromethane, the reaction mixture was poured onto ice-water. The organic phase was washed successively with 1 N hydrochloric acid, water and saturated sodium bicarbonate solution, dried over magnesium sulphate and concentrated under reduced pressure. The residue was purified by chromatography on silica gel (mobile phase pentane). This gave 4.14 g (53.8% of theory) of the title compound.

GC-MS (Method 1): $R_t$=4.94 min; m/z=277/281/283 (M+H)$^+$ $^1$H-NMR (400 MHz, DMSO-d$_6$): δ [ppm]=3.75-4.04 (m, 2H), 5.84 (dt, 1H), 7.31-7.51 (m, 2H), 7.55-7.78 (m, 2H).

Example 62A

1-Bromo-4-(1-fluorovinyl)benzene

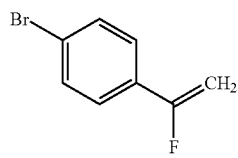

796 mg (7.09 mmol) of potassium tert-butoxide were added in several portions to a solution, cooled to 0° C., of 1.0 g (3.55 mmol) of 1-bromo-4-(2-bromo-1-fluoroethyl)benzene in 10 ml of pentane. The resulting suspension was stirred at 0° C. for 30 min and then at RT for 1 h. The solid was filtered off, and the filtrate was washed with saturated ammonium chloride solution, dried over magnesium sulphate and carefully concentrated under reduced pressure. This gave 0.61 g (85.6% of theory) of the title compound.

GC-MS (Method 1): $R_t$=3.14 min; m/z=200/202 (M+H)$^+$ $^1$H-NMR (400 MHz, DMSO-d$_6$): δ [ppm]=5.10 (dd, 1H), 5.47 (dd, 1H), 7.48-7.61 (m, 2H), 7.62-7.72 (m, 2H).

Example 63A

Ethyl (3R)-2-(4-ethylphenyl)-4,4,4-trifluoro-3-methylbutanoate (diastereomer mixture)

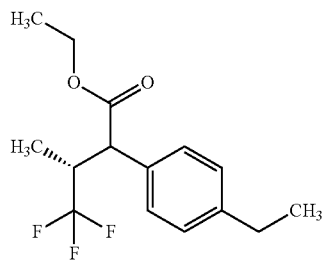 [SMILES: CCOC(=O)C(c1ccc(CC)cc1)[C@@H](C)C(F)(F)F]

24.4 ml (24.4 mmol) of a 1 M solution of lithium hexamethyldisilazide in toluene were cooled to −10° C., and a solution of 3.0 g (16.29 mmol) of ethyl (3R)-4,4,4-trifluoro-3-methylbutanoate in 15 ml of abs. toluene was added dropwise. The mixture was stirred for 10 min. At −10° C., a solution, prepared beforehand, of 3.92 g (21.18 mmol) of 1-bromo-4-ethylbenzene, 110 mg (0.49 mmol) of palladium (II) acetate and 404 mg (1.03 mmol) of 2'-dicyclohexylphosphino-2-(N,N-dimethylamino)biphenyl in 20 ml of abs. toluene was then added dropwise. The resulting reaction mixture was stirred initially at RT for 1 h, then at 80° C. for 3 h. The mixture was then concentrated under reduced pressure and the residue was taken up in ethyl acetate and added to water. The aqueous phase was back-extracted with ethyl acetate, and the combined organic phases were washed with saturated ammonium chloride solution and saturated sodium chloride solution, dried over magnesium sulphate and concentrated under reduced pressure. The residue gave, after chromatography on silica gel (mobile phase: initially cyclohexane, then gradient cyclohexane/ethyl acetate 200:1→50:1), 3.051 g of the title compound (64.9% of theory, diastereomer ratio about 3:1).

LC-MS (Method 4): $R_t$=1.52 min; m/z=289 (M+H)$^+$ (minor diastereomer); $R_t$=1.54 min; m/z=289 (M+H)$^+$ (major diastereomer).

$^1$H-NMR (400 MHz, DMSO-d$_6$): major diastereomer: δ [ppm]=0.76 (d, 3H), 1.13 (t, 3H), 1.17 (t, 3H), 2.55-2.63 (m, 2H), 3.21-3.31 (m, 1H), 3.67 (d, 1H), 3.95-4.16 (m, 2H), 7.15-7.23 (m, 2H), 7.25-7.31 (m, 2H).

The two compounds below were prepared in an analogous manner from ethyl (3R)-4,4,4-trifluoro-3-methylbutanoate and the appropriate phenyl bromide:

Example 64A

Ethyl (3R)-4,4,4-trifluoro-3-methyl-2-(4-vinylphenyl)butanoate (diastereomer mixture)

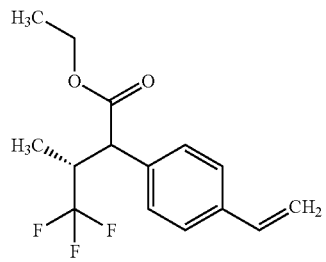 [SMILES: C=Cc1ccc(C(C(=O)OCC)[C@@H](C)C(F)(F)F)cc1]

GC-MS (Method 1): $R_t$=4.64 min and 4.66 min; m/z=286 (M)$^+$.

$^1$H-NMR (400 MHz, DMSO-d$_6$): major diastereomer: δ [ppm]=0.79 (d, 3H), 1.12 (t, 3H), 3.22-3.32 (m, 1H), 3.73 (d, 1H), 3.99-4.17 (m, 2H), 5.28 (d, 1H), 5.84 (d, 1H), 6.72 (dd, 1H), 7.34-7.40 (m, 2H), 7.45-7.51 (m, 2H).

Example 65A

Ethyl (3R)-4,4,4-trifluoro-2-[4-(1-fluorovinyl)phenyl]-3-methylbutanoate

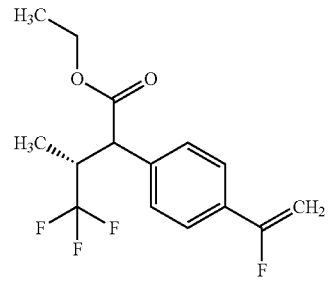 [SMILES: C=C(F)c1ccc(C(C(=O)OCC)[C@@H](C)C(F)(F)F)cc1]

GC-MS (Method 1): $R_t$=4.60 min and 4.63 min; m/z=304 (M)$^+$.

LC-MS (Method 6): $R_t$=1.29 min and 1.30 min; m/z=279.

$^1$H-NMR (400 MHz, DMSO-d$_6$): major diastereomer: δ [ppm]=0.79 (d, 3H), 1.12 (t, 3H), 3.34-3.38 (m, 1H), 3.81 (d, 1H), 3.99-4.17 (m, 2H), 4.97 (dd, 1H), 5.42 (dd, 1H), 7.46-7.49 (m, 2H), 7.63 (d, 2H).

Example 66A

Methyl (4-chlorophenyl)(3-oxocyclopentyl)acetate

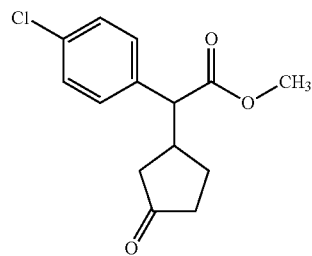 [SMILES: COC(=O)C(c1ccc(Cl)cc1)C1CCC(=O)C1]

Under argon, 14.8 ml (105.6 mmol) of diisopropylamine were initially charged in 150 ml of THF, the mixture was cooled to −30° C. and 42.3 ml (105.75 mmol) of a 2.5 M solution of n-butyllithium in hexane were added slowly. The reaction solution was then warmed to −20° C., 15 g (81.25 mmol) of methyl (4-chlorophenyl)acetate, dissolved in 90 ml of THF, were added slowly and the mixture was stirred at this temperature for 2 h. The reaction solution was then cooled to −78° C., and 7.2 ml (86.1 mmol) of 2-cyclopentene-1-one, dissolved in 60 ml of THF, were added slowly. After the addition had ended, the solution was stirred at this temperature for 1 h. After TLC check (mobile phase cyclohexane/ethyl acetate 9:1), saturated ammonium chloride solution was added and the mixture was taken up in ethyl acetate. The aqueous phase was extracted twice with ethyl acetate. The combined organic phases were dried over magnesium sulphate. After filtration, the solvent was removed under reduced pressure. The crude product was purified chromatographically on silica gel (mobile phase cyclohexane/ethyl acetate 4:1). This gave 15.65 g (58.67 mmol, 72% of theory) of the title compound as a yellowish oil.

GC-MS (Method 1): $R_t$=7.02 min; m/z=266 (M)$^+$ (diastereomer 1); $R_t$=7.04 min; m/z=266 (M)$^+$ (diastereomer 2).

MS (DCI): m/z=284 (M+NH$_4$)$^+$.

Example 67A

Methyl (4-chlorophenyl)(3,3-difluorocyclopentyl)acetate

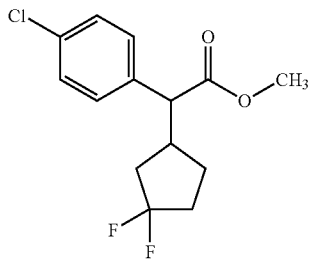 [SMILES: COC(=O)C(c1ccc(Cl)cc1)C1CCC(F)(F)C1]

Under argon, 82.5 ml (82.14 mmol) of a 50% strength solution of 1,1'-[(trifluoro-λ$^4$-sulphanyl)-imino]bis(2-methoxyethane) (Desoxofluor) in THF, diluted with 200 ml of toluene, were initially charged and cooled to 5° C., and 744 µl (5.87 mmol) of a 1 M solution of boron trifluoride/diethyl ether complex were added slowly. The mixture was stirred at 5° C. for 2 h. 15.65 g (58.67 mmol) of methyl (4-chlorophenyl)(3-oxocyclopentyl)acetate, dissolved in 200 ml of toluene, were then added slowly, and the mixture was subsequently warmed to 55° C. and stirred at this temperature for 60 h. The reaction mixture was then added to a mixture, cooled to 0° C., consisting of 100 ml of toluene and 100 ml of 2 M aqueous sodium hydroxide solution. The organic phase was separated off, and the aqueous phase was extracted three more times with ethyl acetate. The combined organic phases were dried over sodium sulphate. After filtration, the solvent was removed under reduced pressure. The crude product was purified chromatographically on silica gel (mobile phase cyclohexane/ethyl acetate 7:1). This gave 13.24 g (45.86 mmol, 78% of theory) of the title compound as a colourless oil.

MS (DCI): m/z=306 (M+NH$_4$)$^+$.

GC-MS (Method 1): $R_t$=5.83 min; m/z=288 (M)$^+$ (diastereomer 1); $R_t$=5.86 min; m/z=288 (M)$^+$ (diastereomer 2).

Example 68A (+/−)-Ethyl (2,2-difluorocyclopentyl)acetate

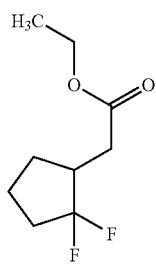

At RT, 17.0 g (99.88 mmol) of (+/−)-ethyl 2-oxocyclopentylacetate were added dropwise to a solution of 52.8 ml (399.5 mmol) of diethylaminosulphur trifluoride (DAST) in 150 ml of abs. dichloromethane. The mixture was heated under reflux overnight. After cooling, a further 13.2 ml (99.88 mmol) of diethylaminosulphur trifluoride (DAST) were added, and the mixture was once more stirred under reflux for 36 h. After cooling, the mixture was diluted with dichloromethane, saturated sodium bicarbonate solution was added carefully and the mixture was then stirred vigorously. The organic phase was washed successively with saturated sodium bicarbonate solution, twice with 1 N hydrochloric acid and with saturated sodium chloride solution, dried over magnesium sulphate and concentrated under reduced pressure. From the dark brown residue, the product was isolated by column chromatography on silica gel (mobile phase pentane/dichloromethane 10:1→1:1). This gave 7.52 g (39% of theory) of the title compound.

GC-MS (Method 1): $R_t$=2.88 min; m/z=172.

$^1$H-NMR (400 MHz, DMSO-d$_6$): δ [ppm]=1.18 (t, 3H), 1.33-1.48 (m, 1H), 1.61-1.77 (m, 2H), 1.92-2.20 (m, 3H), 2.24-2.38 (m, 1H), 2.43-2.60 (m, 2H), 4.07 (q, 2H).

Example 69A

Ethyl (4-chlorophenyl)(2,2-difluorocyclopentyl)acetate (diastereomer mixture)

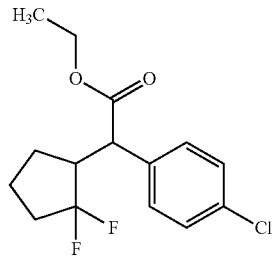 [SMILES: CCOC(=O)C(c1ccc(Cl)cc1)C1CCCC1(F)F]

22.6 ml (22.6 mmol) of a 1 M solution of lithium hexamethyldisilazide in toluene were cooled to −20° C., and a solution of 2.90 g (15.09 mmol) of (+/−)-ethyl (2,2-difluorocyclopentyl)acetate in 20 ml of abs. toluene was added dropwise. The mixture was stirred at −20° C. for 10 min Cooling was removed, and a solution, prepared beforehand, of 3.75 g (19.61 mmol) of 4-bromo-chlorobenzene, 110 mg (0.49 mmol) of palladium(II) acetate and 374 mg (0.95 mmol) of 2'-dicyclohexylphosphino-2-(N,N-dimethylamino)biphenyl in 20 ml of abs. toluene was then added dropwise. The resulting reaction mixture was stirred initially at RT for 1 h, and then at 90° C. for 2 h. After cooling, the reaction mixture was added to water. The aqueous phase was extracted three times with ethyl acetate, and the combined organic phases were dried over magnesium sulphate and concentrated under reduced pressure. The residue gave, after chromatography on silica gel (mobile phase cyclohexane/ethyl acetate 50:1), 2.70 g of the title compound (59.1% of theory, diastereomer ratio about 1:4.3).

GC-MS (Method 1): $R_t$=6.09 min and 6.20 min.

$^1$H-NMR (400 MHz, DMSO-d$_6$): δ [ppm]=1.01-1.27 (m, 3H), 1.37-1.50 (m, 1H), 1.51-1.75 (m, 3H), 1.94-2.23 (m, 3H), 2.84-3.07 (m, 1H), 3.55-3.79 (m, 1H), 3.93-4.20 (m, 2H), 7.29-7.53 (m, 4H).

Example 70A (+)-(2S,3R)-2-(4-chlorophenyl)-4,4,4-trifluoro-3-methylbutanoic acid

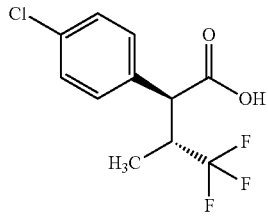 [SMILES: C[C@H]([C@H](C(=O)O)c1ccc(Cl)cc1)C(F)(F)F]

5.086 g (17.26 mmol) of ethyl (3R)-2-(4-chlorophenyl)-4,4,4-trifluoro-3-methylbutanoate were dissolved in 68 ml of dioxane, and 34 ml of 1 N aqueous sodium hydroxide solution were added. The mixture was stirred at 50° C. for 2 h. The reaction mixture was then acidified to pH 1 with 1 N hydrochloric acid and extracted repeatedly with dichloromethane. The combined organic phases were washed with saturated sodium chloride solution, dried over sodium sulphate and concentrated under reduced pressure. This gave 3.9 g (14.63 mmol, 85% of theory, 83% de) of the target compound.

$^1$H-NMR (400 MHz, DMSO-d$_6$, δ/ppm): 12.95-12.73 (1H, br. s), 7.49-7.34 (4H, m), 3.68 (1H, d), 3.31-3.18 (1H, m), 1.20 (0.25H, d), 0.78 (2.75H, d).

GC-MS (Method 1): R$_t$=4.85 min; m/z=266 (M)$^+$.

[α]$_D^{20}$=+57.2°, c=0.41, methanol.

The compounds listed in the table below were prepared analogously to synthesis Example 70A:

| Example | Name/Structure/Starting materials | Analytical data |
|---|---|---|
| 71A | 4,4,4-trifluoro-3-methyl-2-(4-methylphenyl)-butanoic acid<br><br>(from ethyl 4,4,4-trifluroro-3-methyl-2-(4-methyl-phenyl)butanoate) | GC-MS (Method 1):<br>R$_t$ = 4.48 min; m/z = 246 (M)$^+$. |
| 72A | (2S,3R)-4,4,4-triflura-2-(4-isopropylphenyl)-3-methylbutanoic acid<br><br>(from ethyl (3R)-4,4,4-trifluoro-2-(4-isopropylphenyl)-3-methylbutanoate) | $^1$H-NMR (400 MHz, DMSO-d$_6$, δ/ppm): 12.56 (1H, br. s), 7.25 (4H, q), 3.56 (1H, d), 3.28-3.16 (1H, m), 2.94-2.81 (1H, m), 1.19 (6H, d), 0.75 (3H, d).<br>GC-MS (Method 1):<br>R$_t$ = 4.93 min; m/z = 274 (M)$^+$. |
| 73A | (2S,3R)-2-(4-tert-butylphenyl)-4,4,4-trifluoro-3-methylbutanoic acid<br><br>(from ethyl (2S,3R)-2-(4-tert-butylphenyl)-4,4,4-trifluoro-3-methylbutanoate) | GC-MS (Method 1):<br>R$_t$ = 5.15 min; m/z = 288 (M)$^+$. |

| Example | Name/Structure/Starting materials | Analytical data |
|---|---|---|
| 74A | (2S,3R)-4,4,4-trifluro-3-methyl-2-[4-(trifluoromethyl)phenyl]butanoic acid<br>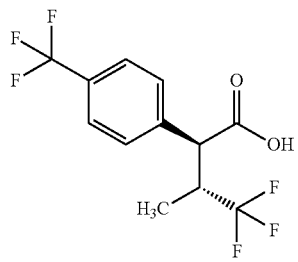<br>(from ethyl (2S,3R)-4,4,4-trifluoro-3-methyl-2-[4-(trifluoromethyl)phenyl]butanonate) | GC-MS (Method 1):<br>$R_t$ = 3.85 min; m/z = 300 (M)$^+$. |
| 75A | (2S,3R)-4,4,4-trifluro-3-methyl-2-[4-(1,1,1-trifluoro-2-methylpropan-2-yl)phenyl]butanoic acid<br>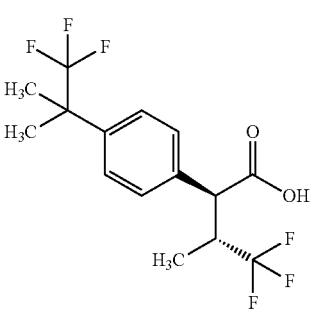<br>(from ethyl (2S,3R)-4,4,4-trifluoro-3-methyl-2-[4-(1,1,1-trifluoro-2-methylpropan-2-yl)phenyl]-butanoate) | $^1$H-NMR (400 MHz, DMSO-d$_6$, δ/ppm): 12.90-12.40 (1H, br. s), 7.53 (2H, d), 7.40 (2H, d), 3.69 (0.11H, d), 3.64 (0.89H, d), 3.30-3.20 (1H, m), 1.55 (6H, s), 1.21 (0.33H, d), 0.76 (2.67H, d).<br>LC-MS (Method 6:)<br>$R_t$ = 1.19 min; m/z = 341 (M − H)$^-$. |
| 76A | 4,4,4-trifluoro-3-methyl-2-[4-(2,2,2-trifluoroethyl)phenyl]butanoic acid<br>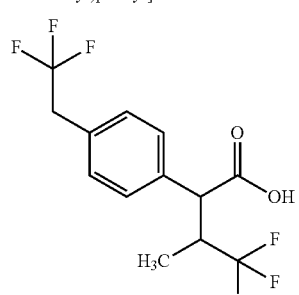<br>(from ethyl 4,4,4-trifluoro-3-methyl-2-[4-(2,2,2-trifluoroethyl)phenyl]butanoate) | $^1$H-NMR (400 MHz, DMSO-d$_6$, δ/ppm): 12.95-12.59 (1H, br. s), 7.37 (4H, q), 3.70-3.57 (3H, m), 3.30-3.18 (1H, m), 0.76 (3H, d).<br>GC-MS (Method 8): $R_t$ = 4.45 min; m/z = 315 (M + H)$^+$. |

-continued

| Example | Name/Structure/Starting materials | Analytical data |
|---|---|---|
| 77A | (4-chlorophenyl)(3,3-difluorocyclopentyl)acetic acid<br>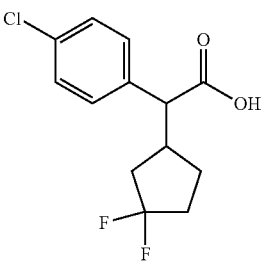<br>(from methyl (4-chlorophenyl)(3,3-difluoro-cyclopentyl)acetate) | $^1$H-NMR (400 MHz, DMSO-d$_6$, δ/ppm): 12.59 (1H, br. s), 7.38 (4H, q), 3.51 (0.5H, d), 3.48 (0.5H, d), 2.77-2.60 (1H, m), 2.42-2.27 (0.5H, m), 2.26-1.20 (5.5H, m).<br>GC-MS (Method 1):<br>R$_t$ = 6.33 min; m/z = 274 (M)$^+$ (diastereomer 1);<br>R$_t$ = 6.38 min; m/z = 274 (M)$^+$ (diastereomer 2). |

Example 78A (3R)-2-(4-ethylphenyl)-4,4,4-trifluoro-3-methylbutanoic acid (diastereomer mixture)

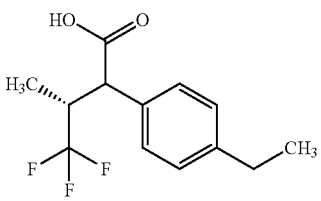 [SMILES: CCc1ccc(C(C(=O)O)[C@@H](C)C(F)(F)F)cc1]

3.0 g of ethyl (3R)-2-(4-ethylphenyl)-4,4,4-trifluoro-3-methylbutanoate (purity about 88%, about 9.16 mmol; diastereomer mixture) were dissolved in a mixture of in each case 12.4 ml of methanol, THF and water, and 5.49 g (137.35 mmol) of sodium hydroxide were added a little at a time. The reaction mixture was stirred at 40° C. for 9 h. After cooling, most of the volatile solvents were removed under reduced pressure and the residue was diluted with water. The mixture was acidified by addition of hydrochloric acid, and the aqueous phase was extracted three times with ethyl acetate. The combined organic phases were dried over sodium sulphate and concentrated under reduced pressure, and the residue was dried under high vacuum. This gave 2.61 g of the title compound as a crude product which was not purified any further (diastereomer ratio about 9:1).

LC-MS (Method 6): R$_t$=1.08 min; m/z=259 (M−H)$^−$ (minor diastereomer); R$_t$=1.11 min; m/z=259 (M−H)$^−$ (major diastereomer).

$^1$H-NMR (400 MHz, DMSO-d$_6$): major diastereomer: δ [ppm]=0.76 (d, 3H), 1.17 (t, 3H), 2.54-2.66 (m, 4H), 3.10-3.29 (m, 1H), 3.56 (d, 1H), 7.14-7.22 (m, 2H), 7.22-7.32 (m, 2H), 12.58 (br. s, 1H).

In a similar manner (reaction temperature: RT to 40° C.; reaction time: 9-12 h), the two carboxylic acid derivatives below were prepared from the corresponding esters:

Example 79A (3R)-4,4,4-trifluoro-3-methyl-2-(4-vinylphenyl)butanoic acid (diastereomer mixture)

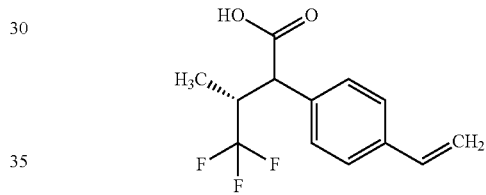

Diastereomer ratio about 10:1.
LC-MS (Method 6): R$_t$=1.04 min; m/z=257 (M−H)$^−$ (minor diastereomer); R$_t$=1.06 min; m/z=257 (M−H)$^−$ (major diastereomer).

$^1$H-NMR (400 MHz, DMSO-d$_6$): major diastereomer: δ [ppm]=0.78 (d, 3H), 3.18-3.31 (m, 1H), 3.62 (d, 1H), 5.28 (d, 1H), 5.84 (d, 1H), 6.73 (dd, 1H), 7.31-7.39 (m, 2H), 7.40-7.54 (m, 2H), 12.74 (br. s, 1H).

Example 80A (3R)-4,4,4-trifluoro-2-[4-(1-fluorovinyl)phenyl]-3-methylbutanoic acid (diastereomer mixture)

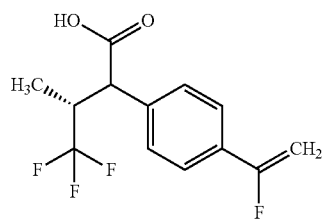 [SMILES: C=C(F)c1ccc(C(C(=O)O)[C@@H](C)C(F)(F)F)cc1]

Diastereomer ratio about 9:1.
GC-MS (Method 1): R$_t$=4.97 min; m/z=276.
$^1$H-NMR (400 MHz, DMSO-d$_6$): major diastereomer: δ [ppm]=0.78 (d, 3H), 3.16-3.29 (m, 1H), 3.70 (d, 1H), 4.96

(dd, 1H), 5.34 (d, 1H), 5.47 (d, 1H), 7.39-7.51 (m, 2H), 7.58-7.69 (m, 2H), 12.83 (br. s, 1H).

Example 81A (4-chlorophenyl)(2,2-difluorocyclopentyl)acetic acid (diastereomer mixture)

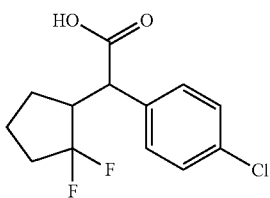 [SMILES: O=C(O)C(c1ccc(Cl)cc1)C1CCCC1(F)F]

2.70 g (8.92 mmol) of ethyl (4-chlorophenyl)(2,2-difluorocyclopentyl)acetate (diastereomer mixture) were dissolved in 10 ml of methanol, 10 ml of THF and 5 ml of water, and 7.13 g (89.18 mmol) of 50% strength aqueous sodium hydroxide solution were added at RT. The reaction mixture was stirred at RT overnight. The mixture was then diluted with water and acidified with hydrochloric acid. The aqueous phase was extracted three times with ethyl acetate, the combined organic phases were dried over magnesium sulphate and concentrated under reduced pressure and the residue was dried under high vacuum. This gave 2.39 g of the title compound (97.6% of theory, diastereomer ratio about 1:1).

LC-MS (Method 6): $R_t$=1.05 min and 1.07 min; m/z=273 (M-H)⁻.

Example 82A (2S,3R)-2-(4-chlorophenyl)-4,4,4-trifluoro-3-methylbutanoyl chloride

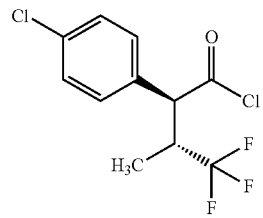 [SMILES: C[C@H]([C@H](C(=O)Cl)c1ccc(Cl)cc1)C(F)(F)F]

19.5 g (73.13 mmol) of (2S,3R)-2-(4-chlorophenyl)-4,4,4-trifluoro-3-methylbutanoic acid were dissolved in 860 ml of dichloromethane, and 0.5 ml of DMF was added. At from −5° C. to −10° C. (ice/acetone cooling bath), 73 ml (146.26 mmol) of a 2 M solution of oxalyl chloride in dichloromethane were then slowly added dropwise, and the mixture was stirred at this temperature for 1 h. After the reaction had gone to completion, the reaction solution was evaporated under reduced pressure and the residue obtained was taken up in 200 ml dichloromethane and then once more concentrated to dryness. This gave 20.1 g (70.5 mmol, 96% of theory) of the title compound as a colourless oil. Without further purification and without further spectroscopic characterization, the product obtained in this manner was used for subsequent reactions.

The compounds listed in the table below were prepared in an analogous manner

| Example | Name/Structure | Starting material |
|---|---|---|
| 83A | (2S,3R)-4,4,4-trifluoro-2-(4-isopropylphenyl)-3-methylbutanol chloride | (2S,3R)-4,4,4-trifluoro-2-(4-isopropylphenyl)-3-methylbutanoic acid |
| 84A | (2S,3R)-2-(4-tert-butylphenyl)-4,4,4-trifluoro-3-methylbutanoyl chloride | (2S,3R)-2-(4-tert-butylphenyl)-4,4,4-trifluoro-3-methylbutanoic acid |

-continued

| Example | Name/Structure | Starting material |
| --- | --- | --- |
| 85A | (2S,3R)-4,4,4-trifluoro-3-methyl-2-[4-(trifluoromethyl)phenyl]butanoyl chloride | (2S,3R)-4,4,4-trifluoro-3-methyl-2-[4-(trifluoromethyl)phenyl]butanoic acid |
| 86A | (2S,3R)-4,4,4-trifluoro-3-methyl-2-[4-(1,1,1-trifluoro-2-methylpropan-2-yl)phenyl]butanoyl chloride | (2S,3R)-4,4,4-trifluoro-3-methyl-2-[4-(1,1,1-trifluoro-2-methylpropan-2-yl)phenyl]butanoic acid |
| 87A | 4,4,4-trifluoro-3-methyl-2-[4-(2,2,2-trifluoroethyl)phenyl]butanoyl chloride | 4,4,4-trifluoro-3-methyl-2-[4-(2,2,2-trifluoroethyl)phenyl]butanoic acid |
| 88A | (4-chlorophenyl)(3,3-difluorocyclopentyl)acetyl chloride | (4-chlorophenyl)-(3,3-difluorocyclopentyl)-acetic acid |

Example 89A tert-butyl-3-(4-chloro-3-{[(2S,3R)-2-(4-chlorophenyl)-4,4,4-trifluoro-3-methylbutanoyl]amino}-phenyl)propanoate

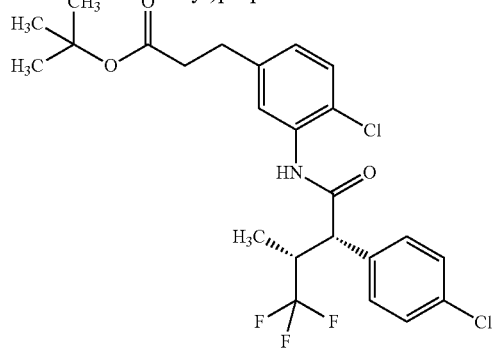

18 g (70.38 mmol) of (2S,3R)-2-(4-chlorophenyl)-4,4,4-trifluoro-3-methylbutanoyl chloride were dissolved in 500 ml of THF, 18.4 ml (105.57 mmol) of N,N-diisopropylethylamine were added and the mixture was cooled to −10° C. 20.07 g (70.38 mmol) of tert-butyl-3-(3-amino-4-chlorophenyl)-propanoate, dissolved in 500 ml of THF, were then added slowly, while care was being taken not to exceed a reaction temperature of 0° C. during the addition. The mixture was then stirred for another 1 h. Water and ethyl acetate were then added to the reaction solution, the organic phase was separated off and the aqueous phase was extracted three more times with ethyl acetate. The combined organic phases were dried over sodium sulphate and concentrated on a rotary evaporator. The residue was purified by chromatography on silica gel (mobile phase cyclohexane/ethyl acetate 20:1). This gave 30.13 g (59.74 mmol, 85% of theory) of the title compound.

$^1$H-NMR (400 MHz, DMSO-$d_6$, δ/ppm): 9.82 (1H, s), 7.50-7.42 (4H, m), 7.39-7.32 (2H, m), 7.07-7.01 (1H, m), 4.12 (1H, d), 3.42-3.29 (1H, m), 2.75 (2H, t), 2.46 (2H, t), 1.31 (9H, s), 0.80 (3H, d).

LC-MS (Method 7): $R_t$=3.03 min; m/z=502/504 (M−H)$^-$.

The compounds listed in the table below were obtained in an analogous manner

| Example | Name/Structure/Starting materials | Analytical data |
|---|---|---|
| 90A | tert-butyl 3-(4-chloro-3-{[(2S,3R)-4,4,4-trifluoro-2-(4-isopropylphenyl)-3-methylbutanoyl]-amino}phenyl)propanoate<br><br>(from (2S,3R)-4,4,4-trifluoro-2-(4-isopropylphenyl)-3-methylbutanoyl chloride and tert-butyl 3-(3-amino-4-chlorophenyl)propanoate) | $^1$H-NMR (400 MHz, DMSO-$d_6$, δ/ppm): 9.70 (1H, s), 7.47-7.42 (1H, m), 7.34 (3H, t), 7.23 (2H, d), 7.04-6.99 (1H, m), 4.07 (1H, d), 3.40-3.26 (1H, m), 2.94-2.81 (1H, m), 2.75 (2H, t), 2.45 (2H, t), 1.31 (9H, s), 1.19 (6H, d), 0.78 (3H, d). LC-MS (Method 4): $R_t$ = 1.72 min; m/z = 510/512 (M − H)$^-$. |
| 91A | tert-butyl 3-(3-{[(2S,3R)-2-(4-tert-butylphenyl)-4,4,4-trifluoro-3-methylbutanoyl]amino}-4-chlorophenyl)propanoate<br><br>(from (2S,3R)-2-(4-tert-butylphenyl)-4,4,4-trifluoro-3-methylbutanoyl chloride and tert-butyl 3-(3-amino-4-chlorophenyl)propanoate) | $^1$H-NMR (400 MHz, DMSO-$d_6$, δ/ppm): 9.71 (1H, s), 7.49-7.43 (1H, m), 7.41-7.35 (4H, m), 7.34 (1H, d), 7.04-6.98 (1H, m), 4.08 (1H, d), 3.39-3.25 (1H, m), 2.75 (2H, t), 2.45 (2H, t), 1.31 (9H, s), 1.27 (9H, s), 0.78 (3H, d). LC-MS (Method 6): $R_t$ = 1.52 min; m/z = 524/526 (M − H)$^-$. |

| Example | Name/Structure/Starting materials | Analytical data |
|---------|-----------------------------------|-----------------|
| 92A | tert-butyl 3-[4-chloro-3-({(2S,3R)-4,4,4-trifluoro-3-methyl-2-[4-(trifluoromethyl)phenyl]butanoyl}-amino)phenyl]propanoate<br>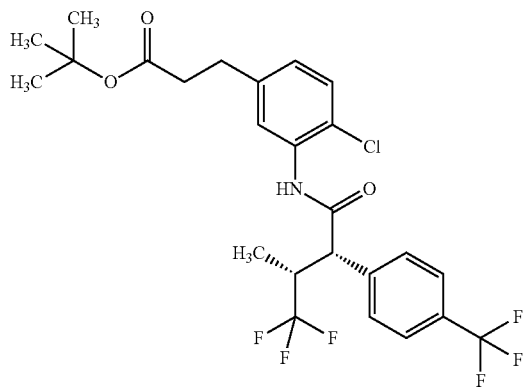<br>(from (2S,3R)-4,4,4-trifluoro-3-methyl-2-[4-(trifluoromethyl)phenyl]butanoylchloride and tert-butyl 3-(3-amino-4-chlorophenyl)propanoate) | $^1$H-NMR (400 MHz, DMSO-$d_6$, δ/ppm): 9.89 (1H, s), 7.76 (2H, d), 7.69 (2H, d), 7.37 (1H, d), 7.35 (1H, d), 7.04 (1H, dd), 4.24 (1H, d), 3.48-3.36 (1H, m), 2.75 (2H, t), 2.45 (2H, t), 1.29 (9H, s), 0.80 (3H, d).<br>LC-MS (Method 6): $R_t$ = 1.43 min; m/z = 536 (M − H)$^-$. |
| 93A | tert-butyl 3-[4-chloro-3-({(2S,3R)-4,4,4-trifluoro-3-methyl-2-[4-(1,1,1-trifluoro-2-methylpropan-2-yl)-phenyl]butanoyl}amino)phenyl]propanoate<br>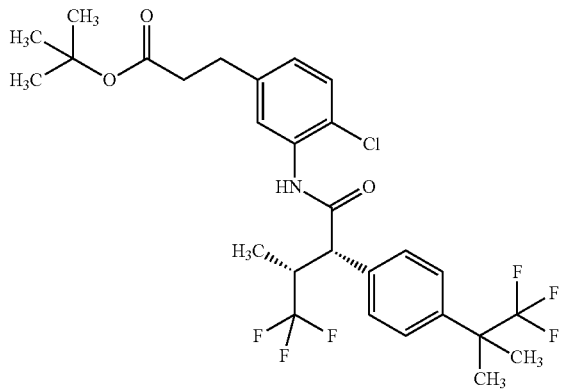<br>(from (2S,3R)-4,4,4-trifluoro-3-methyl-2-[4-(1,1,1-trifluoro-2-methylpropan-2-yl)phenyl]butanoyl-chloride and tert-butyl 3-(3-amino-4-chlorophenyl)-propanoate) | LC-MS (Method 6): $R_t$ = 1.48 min; m/z = 579 (M − H)$^-$. |

| Example | Name/Structure/Starting materials | Analytical data |
|---|---|---|
| 94A | tert-butyl-3-[4-chloro-3-({4,4,4-trifluoro-3-methyl-2-[4-(2,2,2-trifluoroethyl)phenyl]butanoyl}amino)-phenyl] propanoate<br><br>(from 4,4,4-trifluoro-3-methyl-2-[4-(2,2,2-trifluoroethyl)phenyl]butanoyl chloride and tert-butyl 3-(3-amino-4-chlorophenyl)propanoate) | $^1$H-NMR (400 MHz, DMSO-$d_6$, δ/ppm): 9.78 (1H, s), 7.46 (2H, d), 7.41 (1H, d), 7.35 (3H, t), 7.02 (1H, dd), 4.11 (1H, d), 3.63 (2H, q), 3.42-3.28 (1H, m), 2.75 (2H, t), 2.45 (2H, t), 1.30 (9H, s), 0.79 (3H, d).<br>LC-MS (Method 6): $R_t$ = 1.41 min; m/z = 550 (M − H)$^-$. |
| 95A | tert-butyl 3-(4-chloro-3-{[(4-chlorophenyl)(3,3-difluorocyclopentyl)acetyl]amino}phenyl)-propanoate<br><br>(from (4-chlorophenyl)(3,3-difluorocyclopentyl)-acetyl chloride and tert-butyl 3-(3-amino-4-chlorophenyl)propanoate) | LC-MS (Method 5): $R_t$ = 3.01 min; m/z = 510/512 (M − H)$^-$. |
| 96A | Ethyl (2S)-3-(4-chloro-3-{[(4-chlorophenyl)-(3,3-difluorocyclopentyl)acetyl]amino}phenyl)-2-methylpropanoate<br><br>(from (4-chlorophenyl)(3,3-difluorocyclopentyl)-acetyl chloride and ethyl-(2S)-3-(3-amino-4-chloro-phenyl)-2-methylpropanoate) | LC-MS (Method 7): $R_t$ = 2.94 min; m/z = 498 (M)$^+$. |

-continued

| Example | Name/Structure/Starting materials | Analytical data |
|---|---|---|
| 97A | Ethyl (2R)-3-(4-chloro-3-{[(4-chlorophenyl)-(3,3-difluorocyclopentyl)acetyl]amino}phenyl)-2-methylpropanoate<br><br>(from (4-chlorophenyl)(3,3-difluorocyclopentyl)-acetyl chloride and ethyl (2R)-3-(3-amino-4-chloro-phenyl)-2-methylpropanoate) | LC-MS (Method 7): $R_t$ = 2.94 min; m/z = 498 (M)$^+$. |
| 98A | Methyl [1-(4-chloro-3-{[(3R)-2-(4-chlorophenyl)-4,4,4-trifluoro-3-methylbutanoyl]amino}phenyl)-cyclobutyl]acetate<br><br>(from (2S,3R)-2-(4-chlorophenyl)-4,4,4-trifluoro-3-methylbutanoyl chloride and methyl [1-(3-amino-4-chlorophenyl)cyclobutyl]acetate) | $^1$H-NMR (400 MHz, DMSO-d$_6$, δ/ppm): 9.95 (0.33H, s), 9.81 (0.66H, s), 7.54-7.30 (6H, m), 7.02-6.93 (1H, m), 4.14 (1H, d), 3.41-3.28 (1H, m), 3.37 (3H, s), 2.80-2.74 (2H, m), 2.35-2.19 (4H, m), 2.11-1.97 (1H, m), 1.82-1.69 (1H, m), 1.25 (1H, d), 0.80 (2H, d). LC-MS (Method 7): $R_t$ = 2.96 min; m/z = 500/502 (M − H)$^−$. |
| 99A | Benzyl [3-(4-chloro-3-{[(2S,3R)-2-(4-chlorophenyl)-4,4,4-trifluoro-3-methylbutanoyl]amino}phenyl)-oxetan-3-yl]acetate<br><br>(from (2S,3R)-2-(4-chlorophenyl)-4,4,4-trifluoro-3-methylbutanoyl chloride and benzyl [3-(3-amino-4-chlorophenyl)oxetan-3-yl]acetate) | $^1$H-NMR (400 MHz, DMSO-d$_6$, δ/ppm): 9.88 (1H, s), 7.51 (1H, d), 7.45 (4H, q), 7.38 (1H, d), 7.33-7.23 (3H, m), 7.17-7.10 (2H, m), 7.03 (1H, dd), 4.92 (2H, s), 4.78-4.67 (4H, m), 4.17 (1H, d), 3.42-3.28 (1H, m), 3.18 (2H, s), 0.80 (3H, d). LC-MS (Method 7): $R_t$ = 2.87 min; m/z = 578 (M − H)$^−$. |

Example 100A

Methyl [1-(3-{[(2S,3R)-2-(4-chlorophenyl)-4,4,4-trifluoro-3-methylbutanoyl]amino}-4-fluorophenyl)cyclopropyl]acetate

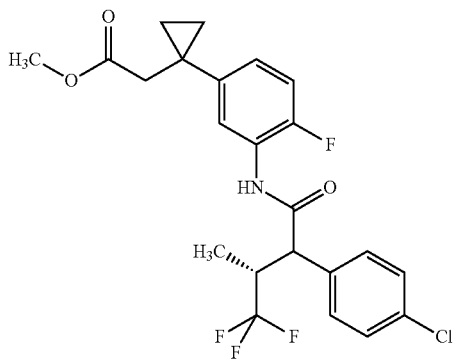 [SMILES: COC(=O)CC1(c2ccc(F)c(NC(=O)C(c3ccc(Cl)cc3)[C@@H](C)C(F)(F)F)c2)CC1]

A solution of 70 mg (0.31 mmol) of (2S,3R)-2-(4-chlorophenyl)-4,4,4-trifluoro-3-methylbutanoic acid, 84 mg (0.31 mmol) of methyl [1-(3-amino-4-fluorophenyl)cyclopropyl]acetate, 179 mg (0.47 mmol) of 2-(1H-7-azabenzotriazol-1-yl)-1,1,3,3-tetramethyluronium hexafluorophosphate (HATU) and 0.6 ml of pyridine in 2.4 ml of DMF was stirred at room temperature overnight. After the reaction had ended, the mixture was separated directly, without further work-up, by preparative HPLC. This gave 106 mg (0.22 mmol, 72% of theory) of the title compound as a colourless oil.

$^1$H-NMR (400 MHz, DMSO-$d_6$, δ/ppm): 10.02 (1H, s), 7.71 (1H, dd), 7.52-7.38 (4H, m), 7.15-7.06 (1H, m), 7.05-6.98 (1H, m), 4.11 (1H, d), 3.48 (3H, s), 3.42-3.25 (1H, m), 2.57 (2H, s), 0.90-0.84 (2H, m), 0.81-0.74 (5H, m).

LC-MS (Method 6): $R_t$=1.33 min; m/z=472 (M+H)$^+$.

The following compound was obtained in an analogous manner:

General Procedure 1

HATU-mediated amide coupling of 4,4,4-trifluoro-3-methyl-2-phenylbutanoic acid derivatives with anilines At RT, HATU (1.0 to 2.0 eq.) is added to a solution of the 4,4,4-trifluoro-3-methyl-2-phenylbutanoic acid derivative in question (about 0.8 to 1.5 eq., 0.15 to 1.5 mol/l) and an aniline (about 0.8 to 1.5 eq., 0.15 to 1.5 mol/l) in a mixture of DMF and pyridine (mixing ratio about 3:1 to 1.5:1). Alternatively, instead of pyridine, it is also possible to use N,N-diisopropylethylamine (2.0 to 5.0 eq.). The resulting mixture is stirred at a temperature of from RT to 60° C. for 4 h to 48 h. If appropriate, a further portion of aniline or of carboxylic acid and HATU is added after 24 h. After the reaction has ended, the crude product can be purified, after removal of the solvent under reduced pressure, by preparative RP-HPLC (mobile phase: acetonitrile/water gradient) or alternatively, after aqueous work-up of the reaction mixture, by chromatography on silica gel (mobile phase: cyclohexane/ethyl acetate or dichloromethane/methanol mixtures).

The following examples were prepared in accordance with the General Procedure 1:

| Example | Name/Structure/Starting materials | Analytical data |
|---|---|---|
| 101A | Methyl [1-(3-{[(2S,3R)-2-(4-ethylphenyl)-4,4,4-trifluoro-3-methylbutanoyl]amino}-4-fluorophenyl)cyclopropyl]acetate<br><br>(from (2S,3R)-2-(4-ethylphenyl)-4,4,4-trifluoro-3-methylbutanoic acid and methyl [1-(3-amino-4-fluorophenyl)cyclopropyl]acetate) | $^1$H-NMR (400 MHz, DMSO-$d_6$, δ/ppm): 9.96 (1H, s), 7.74 (1H, dd), 7.34 (2H, d), 7.20 (2H, d), 7.12-7.05 (1H, m), 7.03-6.96 (1H, m), 4.04 (1H, d), 3.47 (3H, s), 3.41-3.25 (1H, m), 2.63-2.52 (4H, m), 1.17 (3H, t), 0.89-0.84 (2H, m), 0.81-0.73 (5H, m). LC-MS (Method 4): $R_t$ = 1.53 min; m/z = 466 (M + H)$^+$. |

| Example | Name/Structure | Analytical data |
|---|---|---|
| 102A | tert-butyl (+/−)-3-(3-{[2-(4-chlorophenyl)-4,4,4-trifluoro-3-methylbutanoyl]amino}-2-fluorophenyl)propanoate (diastereomer 1)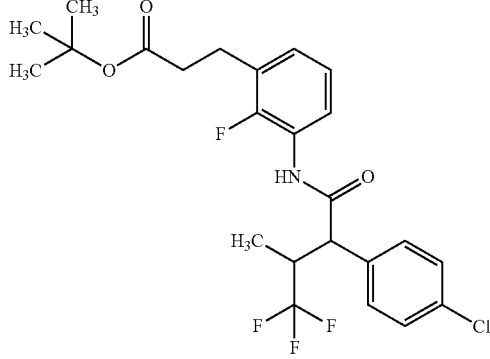 | LC-MS (Method 4): $R_t$ = 1.64 min; m/z = 487 (M − H)⁻. $^1$H-NMR (400 MHz, DMS0-$d_6$): δ [ppm] = 0.79 (d, 3H), 1.32 (s, 9H), 2.48 (t, 2H), 2.81 (t, 2H), 3.34-3.45 (m, 1H), 4.12 (d, 1H), 6.88-7.12 (m, 2H), 7.36-7.52 (m, 4H), 7.63 (td, 1H), 10.03 (s, 1H). |
| 103A | tert-butyl (+/−)-3-(3-{[2-(4-chlorophenyl)-4,4,4-trifluoro-3-methylbutanoyl]amino}-2-fluorophenyl)propanoate (diastereomer 2)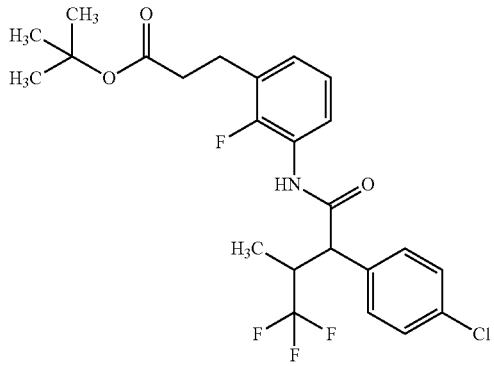 | $^1$H-NMR (400 MHz, DMSO-$d_6$): δ [ppm] = 1.22 (d, 3H), 1.32 (s, 9H), 2.49 (t, 2H), 2.82 (t, 2H), 3.21 (dd, 1H), 4.15 (d, 1H), 6.93-7.12 (m, 2H), 7.35-7.43 (m, 2H), 7.43-7.52 (m, 2H), 7.54-7.74 (m, 1H), 10.12 (s, 1H). |
| 104A | tert-butyl (+/−)-3-(3-{[2-(4-chlorophenyl)-4,4,4-trifluoro-3-methylbutanoyl]amino}-4-fluorophenyl)propanoate (diastereomer 1)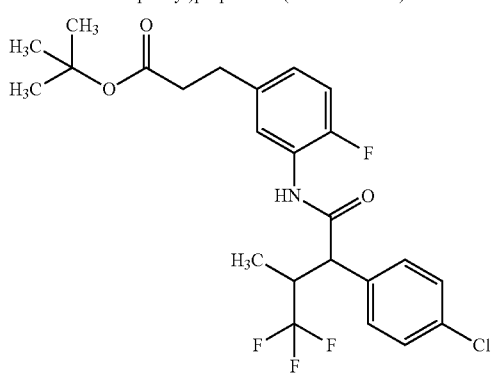 | LC-MS (Method 4): $R_t$ = 1.63 min; m/z = 486 (M − H)⁻. $^1$H-NMR (400 MHz, DMSO-$d_6$): δ [ppm] = 0.78 (d, 3H), 1.31 (m, 9H), 2.44 (t, 2H), 2.74 (t, 2H), 3.33-3.48 (m, 1H), 4.11 (d, 1H), 6.92-7.04 (m, 1H), 7.12 (dd, 1H), 7.35-7.52 (m, 4H), 7.65 (dd, 1H), 10.02 (s, 1H). |

| Example | Name/Structure | Analytical data |
|---|---|---|
| 105A | tert-butyl (+/−)-3-(3-{[2-(4-chlorophenyl)-4,4,4-trifluoro-3-methylbutanoyl]amino}-4-fluorophenyl)propanoate (diastereomer 2)<br />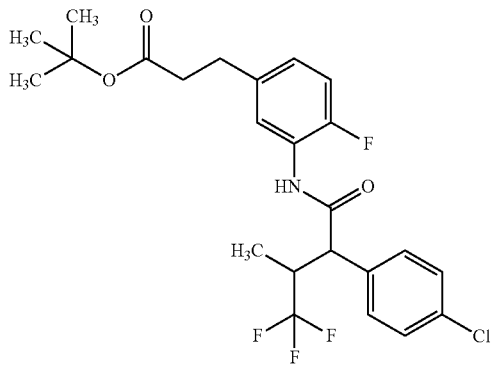 | LC-MS (Method 4): $R_t$ = 1.63 min; m/z = 486 (M − H)$^-$.<br />$^1$H-NMR (400 MHz, DMSO-d$_6$): δ [ppm] = 1.21 (d, 3H), 1.31 (s, 9H), 2.45 (t, 2H), 2.74 (t, 2H), 3.21 (dd, 1H), 4.13 (d, 1H), 6.89-7.06 (m, 1H), 7.14 (dd, 1H), 7.36-7.44 (m, 2H), 7.45-7.55 (m, 2H), 7.62 (dd, 1H), 10.12 (s, 1H). |
| 106A | tert-butyl (+)-3-(3-{[(2S,3R)-2-(4-chlorophenyl)-4,4,4-trifluoro-3-methylbutanoyl]amino}-4-fluorophenyl)propanoate<br />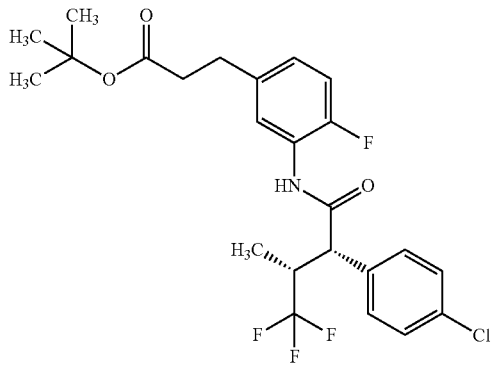 | LC-MS (Method 6): $R_t$ = 1.43 min; m/z = 486 (M − H)$^-$.<br />$^1$H-NMR (400 MHz, DMSO-d$_6$): δ [ppm] = 0.78 (d, 3H), 1.31 (s, 9H), 2.44 (t, 2H), 2.74 (t, 2H), 3.34-3.43 (m, 1H), 4.11 (d, 1H), 6.87-7.02 (m, 1H), 7.12 (dd, 1H), 7.36-7.51 (m, 4H), 7.65 (dd, 1H), 10.03 (s, 1H).<br />$[\alpha]_D^{20}$ = +127°, c = 0.52, Chloroform. |
| 107A | tert-butyl (+)-3-(4-fluoro-3-{[(2S,3R)-4,4,4-trifluoro-3-methyl-2-(4-vinylphenyl)butanoyl]amino}phenyl)propanoate<br />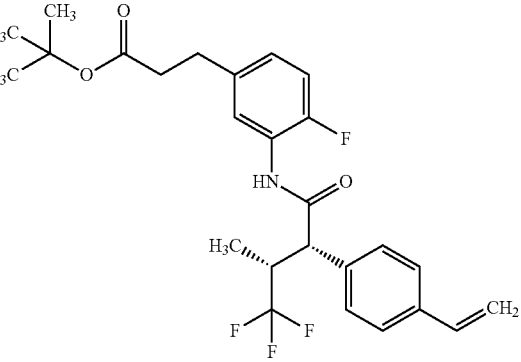 | LC-MS (Method 6): $R_t$ = 1.39 min; m/z = 478 (M − H)$^-$.<br />$^1$H-NMR (400 MHz, DMSO-d$_6$): δ [ppm] = 0.79 (d, 3H), 1.31 (s, 9H), 2.44 (t, 2H), 2.74 (t, 2H), 3.35-3.43 (m, 1H), 4.08 (d, 1H), 5.26 (d, 1H), 5.83 (d, 1H), 6.72 (dd, 1H), 6.97 (td, 1H), 7.11 (dd, 1H), 7.32-7.51 (m, 4H), 7.66 (dd, 1H), 9.99 (s, 1H).<br />$[\alpha]_D^{20}$ = +119°, c = 0.455, Chloroform. |

| Example | Name/Structure | Analytical data |
|---|---|---|
| 108A | Ethyl 3-(3-{[(2S,3R)-2-(4-chlorophenyl)-4,4,4-trifluoro-3-methylbutanoyl]amino}-4-fluorophenyl)-2-methylpropanoate (diastereomer mixture)<br>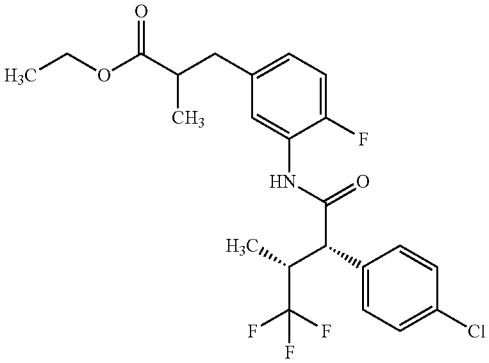 | LC-MS (Method 6): $R_t$ = 1.35 min; m/z = 474 (M + H)$^+$.<br>$^1$H-NMR (400 MHz, DMSO-$d_6$): δ [ppm] = 0.78 (d, 3H), 1.01-1.11 (m, 6H), 2.56-2.69 (m, 2H), 2.69-2.83 (m, 1H), 3.34-3.44 (m, 1H), 3.87- 3.99 (m, 2H), 4.11 (d, 1H), 6.88- 7.00 (m, 1H), 7.12 (dd, 1H), 7.39-7.48 (m, 4H), 7.55-7.66 (m, 1H), 10.03 (s, 1H). |
| 109A | tert-butyl (+)-3-(4-chloro-3-{[(2S,3R)-4,4,4-trifluoro-3-methyl-2-(4-vinylphenyl)butanoyl]amino}phenyl)propanoate<br>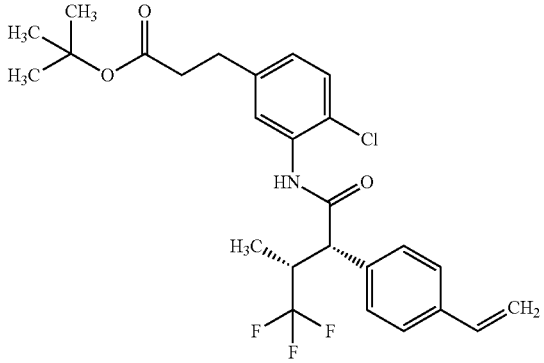 | LC-MS (Method 6): $R_t$ = 1.43 min; m/z = 496 (M + H)$^+$.<br>$^1$H-NMR (400 MHz, DMSO-$d_6$): δ [ppm] = 0.80 (d, 3H), 1.31 (s, 9H), 2.45 (t, 2H), 2.75 (t, 2H), 3.34-3.43 (m, 1H), 4.09 (d, 1H), 5.27 (d, 1H), 5.84 (d, 1H), 6.72 (dd, 1H), 7.03 (dd, 1H), 7.29-7.53 (m, 6H), 9.78 (s, 1H).<br>$[α]_D^{20}$ = +105.2°, c = 0.315, chloroform. |
| 110A | tert-butyl (+)-3-(3-{[(2S,3R)-2-(4-ethylphenyl)-4,4,4-trifluoro-3-methylbutanoyl]amino}-4-fluorophenyl)propanoate<br>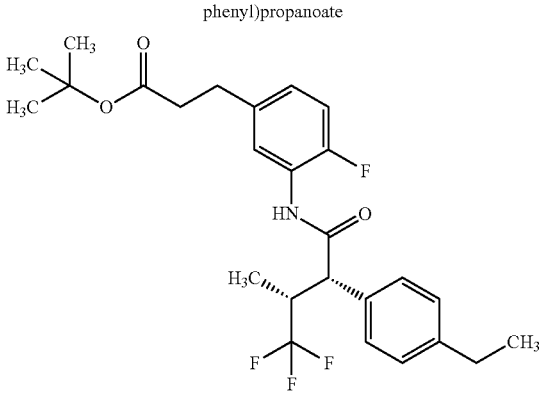 | LC-MS (Method 6): $R_t$ = 1.46 min; m/z = 480 (M – H)$^-$.<br>$^1$H-NMR (400 MHz, DMSO-$d_6$): δ [ppm] = 0.77 (d, 3H), 1.17 (t, 3H), 1.31 (s, 9H), 2.44 (t, 2H), 2.60 (q, 2H), 2.74 (t, 2H), 3.29-3.34 (m, 1H), 4.05 (d, 1H), 6.86-7.00 (m, 1H), 7.11 (dd, 1H), 7.16-7.26 (m, 2H), 7.28-7.41 (m, 2H), 7.69 (dd, 1H), 9.96 (s, 1H).<br>$[α]_D^{20}$ = +108.7°, c = 0.500, Chloroform. |

| Example | Name/Structure | Analytical data |
|---|---|---|
| 111A | tert-butyl (+)-3-(4-chloro-3-{[(2S,3R)-2-(4-ethylphenyl)-4,4,4-trifluoro-3-methylbutanoyl]amino}phenyl)propanoate 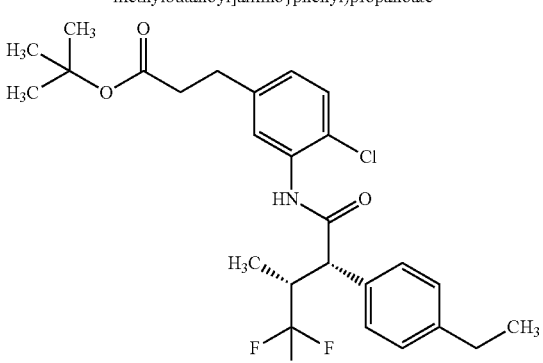 | LC-MS (Method 6): $R_t$ = 1.51 min; m/z = 496 (M − H)$^-$.<br>$^1$H-NMR (400 MHz, DMSO-d$_6$): δ [ppm] = 0.78 (d, 3H), 1.17 (t, 3H), 1.31 (s, 9H), 2.45 (t, 2H), 2.59 (q, 2H), 2.75 (t, 2H), 3.34-3.40 (m, 1H), 4.06 (d, 1H), 7.02 (dd, 1H), 7.20 (d, 2H), 7.34 (dd, 3H), 7.42 (d, 1H), 9.73 (s, 1H).<br>$[α]_D^{20}$ = +62.7°, c = 0.475, Chloroform. |
| 112A | Ethyl 3-(4-chloro-3-{[(2S,3R)-2-(4-ethylphenyl)-4,4,4-trifluoro-3-methylbutanoyl]amino}phenyl)-2-methylpropanoate (diastereomer mixture) 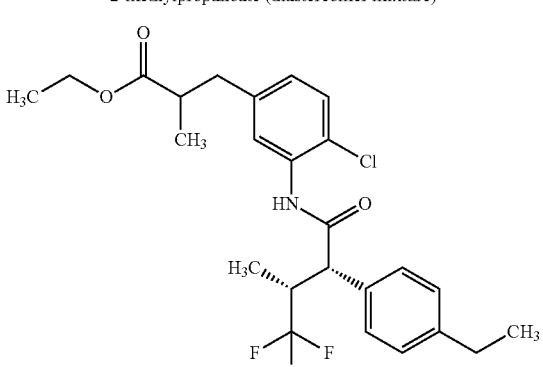 | LC-MS (Method 4): $R_t$ = 1.61 min; m/z = 484 (M + H)$^+$.<br>$^1$H-NMR (400 MHz, DMSO-d$_6$): δ [ppm] = 0.78 (d, 3H), 1.03-1.07 (m, 5H), 1.17 (t, 3H), 2.55-2.69 (m, 4H), 2.74-2.83 (m, 1H), 3.27-3.40 (m, 2H), 3.96 (qd, 2H), 4.03-4.12 (m, 1H), 6.97 (dd, 1H), 7.20 (d, 2H), 7.33-7.41 (d, 4H), 9.73 (s, 1H). |
| 113A | Ethyl 3-(3-{[(2R,3R)-2-(4-ethylphenyl)-4,4,4-trifluoro-3-methylbutanoyl]amino}-4-fluorophenyl)-2-methylpropanoate {diastereomer mixture) 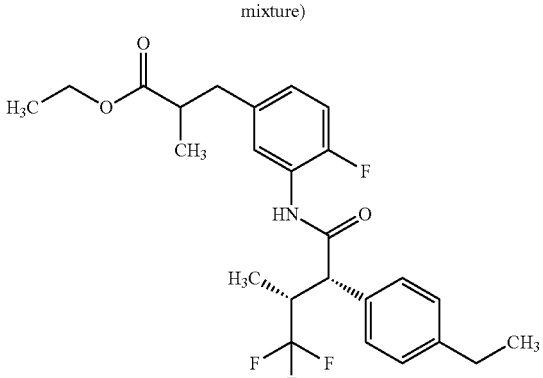 | LC-MS (Method 4): $R_t$ = 1.57 min; m/z = 468 (M + H)$^+$.<br>$^1$H-NMR (400 MHz, DMSO-d$_6$): δ [ppm] = 0.77 (d, 3H), 0.99-1.11 (m, 6H), 1.11-1.23 (m, 3H), 2.52-2.68 (m, about 5H), 2.70-2.85 (m, 1H), 3.28-3.32 (m, about 1H), 3.90-4.00 (m, 2H), 4.00-4.08 (m, 1H), 6.82-6.96 (m, 1H), 7.11 (dd, 1H), 7.16-7.25 (m, 2H), 7.27-7.41 (m, 2H), 7.65 (dd, 1H), 9.96 (s, 1H). |

| Example | Name/Structure | Analytical data |
|---|---|---|
| 114A | Ethyl 3-(4-chloro-3-{[(2S,3R)-2-(4-chlorophenyl)-4,4,4-trifluoro-3-methylbutanoyl]amino}phenyl)-2-methylpropanoate (diastereomer mixture) | LC-MS (Method 5): $R_t$ = 2.95 min; m/z = 490/492 (M + H)$^+$. $^1$H-NMR (400 MHz, DMSO-d$_6$): δ [ppm] = 0.80 (d, 3H), 1.00-1.12 (m, 6H), 2.59-2.72 (m, 2H), 2.74-2.86 (m, 1H), 3.34-3.42 (m, 1H), 3.96 (qd, 2H), 4.12 (d, 1H), 6.99 (dd, 1H), 7.26-7.39 (m, 2H), 7.39-7.54 (m, 4H), 9.81 (s, 1H). |
| 115A | tert-butyl 3-(4-chloro-3-{[(2S,3R)-2-(4-ethylphenyl)-4,4,4-trifluoro-3-methylbutanoyl]amino}phenyl)butanoate (diastereomer mixture) | LC-MS (Method 6): $R_t$ = 1.55 min; m/z = 510 (M – H)$^-$. $^1$H-NMR (400 MHz, DMSO-d$_6$): δ [ppm] = 0.79 (d, 3H), 1.10-1.19 (m, 6H), 1.24/1.26 (2s, together 9H), 2.32-2.46 (m, 2H), 2.59 (q, 2H), 2.97-3.11 (m, 1H), 3.33-3.40 (m, 1H), 4.02-4.14 (m, 1H), 7.06 (d, 1H), 7.20 (d, 2H), 7.35 (d, 3H), 7.48 (dd, 1H), 9.72 (s, 1H). |
| 116A | Methyl (+)-3-[4-chloro-3-({(2S,3R)-4,4,4-trifluoro-2-[4-(1-fluorovinyl)phenyl]-3-methylbutanoyl}amino)phenyl]propanoate | LC-MS (Method 6): $R_t$ = 1.30 min; m/z = 472/474 (M + H)$^+$. $^1$H-NMR (400 MHz, DMSO-d$_6$): δ [ppm] = 0.80 (d, 3H), 2.54-2.60 (m, 2H), 2.73-2.88 (m, 2H), 3.35-3.45 (m, 1H), 4.15 (d, 1H), 4.96 (dd, 1H), 5.40 (dd, 1H), 7.04 (dd, 1H), 7.28-7.40 (m, 2H), 7.45-7.55 (m, 2H), 7.59-7.71 (m, 2H), 9.84 (s, 1H). $[α]_D^{20}$ = +66.3°, c = 0.455, Chloroform. |

-continued

| Example | Name/Structure | Analytical data |
|---|---|---|
| 117A | tert-butyl 3-(3-{[(2S,3R)-2-(4-chlorophenyl)-4,4,4-trifluoro-3-methylbutanoyl]amino}-4-chlorophenyl)butanoate (diastereomer mixture) | LC-MS (Method 4): $R_t$ = 1.66 min; m/z = 516/517 (M + H)$^+$. $^1$H-NMR (400 MHz, DMSO-d$_6$): δ [ppm] = 0.80 (d, 3H), 1.16 (d, 3H), 1.24/1.26 (2s, together 9H), 2.34-2.47 (m, 2H), 3.01-3.14 (m, 1H), 3.33-3.42 (m, 1H), 4.10-4.18 (m, 1H), 7.08 (d, 1H), 7.36 (d, 1H), 7.40-7.51 (m, 5H), 9.80 (s, 1H). |
| 118A | tert-butyl (3S)-3-(4-chloro-3-{[(4-chlorophenyl)(2,2-difluorocyclopentyl)acetyl]amino}phenyl)butanoate (diastereomer mixture) | LC-MS (Method 6): $R_t$ = 1.45 min; m/z = 524/526 (M − H)$^-$ and $R_t$ = 1.46 min; m/z = 524/526 (M − H)$^-$. $^1$H-NMR (400 MHz, DMSO-d$_6$): δ [ppm] = 1.16 (d, 3H), 1.24/1.26 (2s, together 9H), 1.48-1.78 (m, 3H), 1.96-2.25 (m, 3H), 2.33-2.47 (m, 2H), 2.89-3.18 (m, 2H), 4.06 (ddd, 1H), 7.07 (ddd, 1H), 7.30-7.50 (m, 6H), 9.60/9.81 (2s, together 1H). |
| 119A | tert-butyl 3-(3-{[(2S,3R)-2-(4-chlorophenyl)-4,4,4-trifluoro-3-methylbutanoyl]amino}-4-fluorophenyl)butanoate (diastereomer mixture) | LC-MS (Method 6): $R_t$ = 1.45 min; m/z = 500 (M − H)$^-$. $^1$H-NMR (400 MHz, DMSO-d$_6$): δ [ppm] = 0.79 (d, 3H), 1.16 (d, 3H), 1.23/1.24 (2s, together 9H), 1.58-1.72 (m, 1H), 2.30-2.47 (m, 2H), 2.99-3.10 (m, 1H), 3.32-3.43 (m, 1H), 4.12 (d, 1H), 6.97-7.06 (m, 1H), 7.13 (dd, 1H), 7.38-7.54 (m, 4H), 7.62-7.79 (m, 1H), 10.02 (s, 1H). |

| Example | Name/Structure | Analytical data |
|---|---|---|
| 120A | tert-butyl 3-(4-chloro-3-{[(4-chlorophenyl)(2,2-difluorocyclopentyl)-acetyl]amino}phenyl)propanoate (diastereomer mixture) | LC-MS (Method 6): $R_t$ = 1.44 min; m/z = 510/512 (M − H)⁻ and $R_t$ = 1.45 min; m/z = 510/512 (M − H)⁻. <br> ¹H-NMR (400 MHz, DMSO-$d_6$): δ [ppm] = 1.07-1.25 (m, 1H), 1.31 (s, 9H), 1.46-1.75 (m, 3H), 1.95-2.25 (m, 2H), 2.42-2.47 (m, 2H), 2.70-2.81 (m, 2H), 2.87-3.20 (m, 1H), 4.03/4.06 (2d, together 1H), 6.97-7.12 (m, 1H), 7.29-7.54 (m, 6H), 9.63/9.84 (2s, together 1H). |
| 121A | Ethyl (2S)-3-(4-chloro-3-{[(4-chlorophenyl)(2,2-difluorocyclopentyl)acetyl]amino}phenyl)-2-methylpropanoate (diastereomer mixture) | LC-MS (Method 6): $R_t$ = 1.40 min; m/z = 498/500 (M + H)⁺ and $R_t$ = 1.41 min; m/z = 498/500 (M + H)⁺. <br> ¹H-NMR (400 MHz, DMSO-$d_6$): δ [ppm] = 0.98-1.08 (m, 6H), 1.10-1.24 (m, 1H), 1.48-1.80 (m, 3H), 1.96-2.26 (m, 2H), 2.57-2.70 (m, 2H), 2.70-2.86 (m, 1H), 2.90-3.22 (m, 1H), 3.90-4.10 (m, 3H), 6.98 (ddd, 1H), 7.30-7.51 (m, 6H), 9.63/9.83 (2s, together 1H). |
| 122A | Ethyl 2-(4-chloro-3-{[(2S,3R)-2-(4-chlorophenyl)-4,4,4-trifluoro-3-methylbutanoyl]amino}benzyl)-butanoate (diastereomer mixture) | LC-MS (Method 6): $R_t$ = 1.45 min; m/z = 504 (M + H)⁺. <br> ¹H-NMR (400 MHz, DMSO-$d_6$): δ [ppm] = 0.77-0.88 (m, about 6H), 0.98-1.07 (m, about 3H), 1.44-1.56 (m, 2H), 2.42-2.48 (m, 1H), 2.72 (d, 2H), 3.33-3.43 (m, 1H), 3.88-4.01 (m, 2H), 4.12 (d, 1H), 6.98 (dd, 1H), 7.30-7.37 (m, 2H), 7.40-7.51 (m, 4H), 9.81 (s, 1H). |

Example 123A

Ethyl (2R)-3-(4-chloro-3-{[(2S,3R)-2-(4-chlorophenyl)-4,4,4-trifluoro-3-methylbutanoyl]amino}-phenyl)-2-methylpropanoate

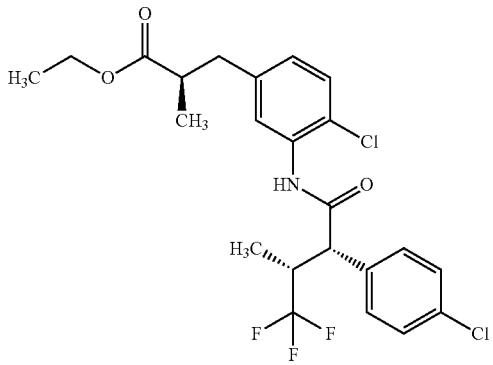 [SMILES: CCOC(=O)[C@H](C)Cc1ccc(Cl)c(NC(=O)[C@H](c2ccc(Cl)cc2)[C@@H](C)C(F)(F)F)c1]

500 mg (2.07 mmol) of ethyl (−)-(2R)-3-(3-amino-4-chlorophenyl)-2-methylpropanoate and 607 mg (2.28 mmol) of (2S,3R)-2-(4-chlorophenyl)-4,4,4-trifluoro-3-methylbutanoic acid were dissolved in a mixture of 2.0 ml of DMF and 1.0 ml of pyridine, and 1022 mg (2.69 mmol) of HATU were added at room temperature. The reaction mixture was stirred at RT overnight. The mixture was diluted with ethyl acetate, and the solution was washed successively with 1 N hydrochloric acid, water, saturated sodium bicarbonate solution and saturated sodium chloride solution. The organic phase was dried over magnesium sulphate and concentrated under reduced pressure. The residue was purified by chromatography on silica gel (mobile phase cyclohexane/ethyl acetate 40:1). This gave 998 mg (98.4% of theory) of the target compound.

LC-MS (Method 6): $R_t$=1.41 min; m/z=490/492 (M+H)$^+$.

$^1$H-NMR (400 MHz, DMSO-d$_6$): δ [ppm]=0.80 (d, 3H), 0.99-1.09 (m, 6H), 1.54-1.74 (m, 1H), 2.59-2.73 (m, 2H), 2.74-2.88 (m, 1H), 3.97 (q, 2H), 4.12 (d, 1H), 6.99 (dd, 1H), 7.25-7.37 (m, 2H), 7.40-7.55 (m, 4H), 9.81 (s, 1H).

Example 124A (+)-Ethyl (2S)-3-(4-chloro-3-{[(2S,3R)-2-(4-chlorophenyl)-4,4,4-trifluoro-3-methylbutanoyl]amino}phenyl)-2-methylpropanoate

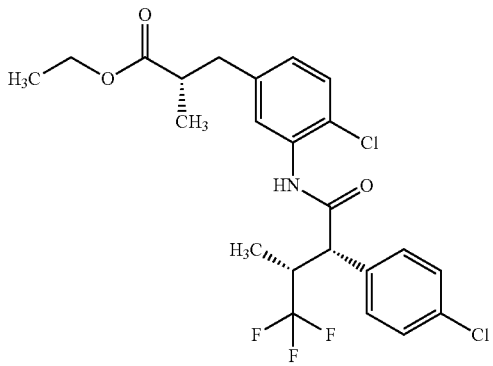 [SMILES: CCOC(=O)[C@@H](C)Cc1ccc(Cl)c(NC(=O)[C@H](c2ccc(Cl)cc2)[C@@H](C)C(F)(F)F)c1]

Method A:

1.50 g (6.21 mmol) of ethyl (+)-(2S)-3-(3-amino-4-chlorophenyl)-2-methylpropanoate and 1.82 g (6.83 mmol) of (3R)-2-(4-chlorophenyl)-4,4,4-trifluoro-3-methylbutanoic acid (as an about 9:1 diastereomer mixture) were dissolved in a mixture of 6.3 ml of DMF and 3.2 ml of pyridine, and 2.83 g (7.45 mmol) of HATU were added at RT. The reaction mixture was stirred at RT overnight. The mixture was then diluted with ethyl acetate, and the solution was washed successively with saturated ammonium chloride solution and saturated sodium chloride solution. The organic phase was dried over magnesium sulphate and concentrated under reduced pressure. The residue was purified by chromatography on silica gel (mobile phase cyclohexane/ethyl acetate 50:1→40:1). A mixed fraction (which contained the minor diastereomer) obtained during the purification was separated by another chromatography on silica gel (mobile phase cyclohexane/ethyl acetate 40:1). This gave a total of 2.46 g (80.8% of theory) of the target compound.

Method B:

30 ml of dichloromethane and one drop of DMF were added to 7.60 g (28.50 mmol) of (3R)-2-(4-chlorophenyl)-4,4,4-trifluoro-3-methylbutanoic acid (about 9:1-diastereomer mixture). 4.48 ml (51.3 mmol) of oxalyl chloride were added dropwise to the solution, which had been cooled to −10° C., such that the temperature did not exceed −5° C. The reaction mixture was stirred at from −5° C. to 0° C. for 1 h and then for about 30 min without cooling with warming to RT and subsequently concentrated under reduced pressure. The residue was taken up in dichloromethane and the solution was once more concentrated under reduced pressure. This procedure was repeated once more, and the acid chloride obtained was then briefly dried under high vacuum and directly, without further purification, reacted further.

6.1 ml (35.04 mmol) of N,N-diisopropylethylamine were added to a solution of 6.05 g (25.03 mmol) of ethyl (+)-(2S)-3-(3-amino-4-chlorophenyl)-2-methylpropanoate in 25 ml of abs. THF. The resulting solution was cooled to −10° C., and a solution of the acid chloride prepared above (7.85 g, 27.5 mmol) in about 10 ml of abs. THF was added dropwise, the temperature being kept below 0° C. The reaction mixture was then stirred at from −10° C. to 0° C. for 1 h, and ethyl acetate and three drops of water were then added. After 10 min, the mixture, which had been diluted further with ethyl acetate, was washed successively with 1 N hydrochloric acid, saturated sodium bicarbonate solution and saturated sodium chloride solution, dried over magnesium sulphate and concentrated under reduced pressure. The crude product was triturated with 50 ml of diisopropyl ether for 4 h. After filtration, the solid obtained was once more triturated with 40 ml of diisopropyl ether. The solid obtained was dried thoroughly under high vacuum. This gave 8.32 g of the target compound. The filtrates obtained above were combined and concentrated under reduced pressure. The residue gave, after chromatography on silica gel (mobile phase cyclohexane/ethyl acetate 50:1), a further 1.75 g of product. In this manner, a total of 10.07 g (82.1% of theory) of the title compound were obtained.

LC-MS (Method 7): $R_t$=2.95 min; m/z=490 (M+H)$^+$.

$^1$H-NMR (400 MHz, DMSO-d$_6$): δ [ppm]=0.80 (d, 3H), 1.00-1.10 (m, 6H), 2.58-2.72 (m, 2H), 2.72-2.83 (m, 1H), 3.34-3.44 (m, 1H), 3.96 (q, 2H), 4.12 (d, 1H), 6.99 (dd, 1H), 7.27-7.38 (m, 2H), 7.42-7.51 (m, 4H), 9.82 (s, 1H).

$[α]_D^{20}$=+94°, c=0.58, chloroform.

Example 125A

Ethyl (+)-(2S)-2-(4-chloro-3-{[(2S,3R)-2-(4-chlorophenyl)-4,4,4-trifluoro-3-methylbutanoyl]amino}benzyl)butanoate

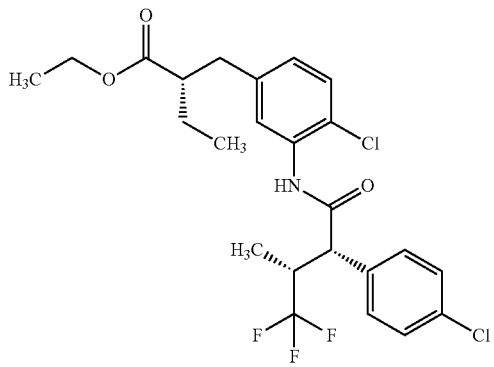 [SMILES: CCOC(=O)[C@@H](CC)Cc1ccc(Cl)c(NC(=O)[C@H](c2ccc(Cl)cc2)[C@@H](C)C(F)(F)F)c1]

13 ml of dichloromethane and one drop of DMF were added to 3.3 g (12.38 mmol) of (3R)-2-(4-chlorophenyl)-4,4,4-trifluoro-3-methylbutanoic acid (as an about 9:1 diastereomer mixture). 1.94 ml (22.28 mmol) of oxalyl chloride were added dropwise to the solution, which had been cooled to −10° C., such that the temperature did not exceed −5° C. The reaction mixture was then stirred at from −5° C. to 0° C. for 1 h and subsequently concentrated under reduced pressure. The residue was taken up in dichloromethane, and the solution was once more concentrated under reduced pressure. This procedure was repeated once more, and the acid chloride obtained was then briefly dried under high vacuum and directly, without further purification, reacted further.

1.2 ml (6.68 mmol) of N,N-diisopropylethylamine were added to a solution of 1.22 g (4.77 mmol) of (+)-ethyl (2S)-2-(3-amino-4-chlorobenzyl)butanoate in 4.8 ml of abs. THF. The resulting solution was cooled to −10° C., and a solution of the acid chloride prepared above (1.5 g, 5.25 mmol) in 2 ml of abs. THF was added dropwise, the temperature being kept below 0° C. The reaction mixture was then stirred at from −10° C. to 0° C. for 1 h and ethyl acetate and three drops of water were then added. After 10 min, the mixture, which had been diluted further with ethyl acetate, was washed successively with 1 N hydrochloric acid, saturated sodium bicarbonate solution and saturated sodium chloride solution, dried over magnesium sulphate and concentrated under reduced pressure. The desired product was isolated by chromatography of the residue on silica gel (mobile phase cyclohexane/ethyl acetate 40:1). This gave 2.13 g (88.5% of theory) of the title compound.

LC-MS (Method 6): $R_t$=1.46 min; m/z=504 (M+H)$^+$.

$^1$H-NMR (400 MHz, DMSO-d$_6$): δ [ppm]=0.76-0.88 (m, 6H), 1.02 (t, 3H), 1.45-1.56 (m, 2H), 2.47 (d, 1H), 2.72 (d, 2H), 3.34-3.43 (m, 1H), 3.93 (qd, 2H), 4.12 (d, 1H), 6.98 (dd, 1H), 7.29-7.38 (m, 2H), 7.40-7.52 (m, 4H), 9.81 (s, 1H).

$[α]_D^{20}$=+62.6°, c=0.515, chloroform.

The following compound was prepared according to an analogous procedure:

Example 126A

Ethyl (+)-(2R)-2-(4-chloro-3-{[(2S,3R)-2-(4-chlorophenyl)-4,4,4-trifluoro-3-methylbutanoyl]amino}benzyl)butanoate

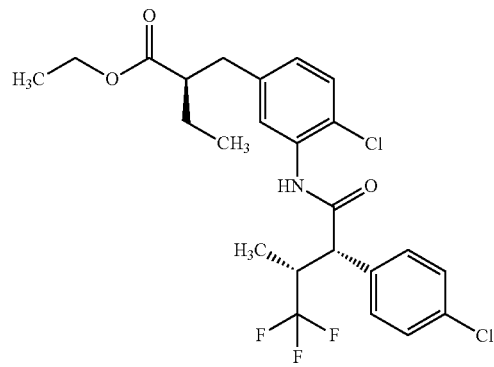 [SMILES: CCOC(=O)[C@H](CC)Cc1ccc(Cl)c(NC(=O)[C@H](c2ccc(Cl)cc2)[C@@H](C)C(F)(F)F)c1]

LC-MS (Method 6): $R_t$=1.46 min; m/z=504/506 (M+H)$^+$.

$^1$H-NMR (400 MHz, DMSO-d$_6$): δ [ppm]=0.79 (d, 3H), 0.84 (t, 3H), 1.04 (t, 3H), 1.46-1.56 (m, 2H), 2.45-2.49 (m, 1H), 2.70-2.74 (m, 2H), 3.34-3.42 (m, 1H), 3.95 (q, 2H), 4.12 (d, 1H), 6.98 (dd, 1H), 7.30-7.37 (m, 2H), 7.42-7.50 (m, 4H), 9.81 (s, 1H).

$[α]_D^{20}$=+52.3°, c=0.485, chloroform.

Example 127A

Ethyl 2-(3-{[(2S,3R)-2-(4-chlorophenyl)-4,4,4-trifluoor-3-methylbutanoyl]amino}-4-fluorophenyl)-trans-cyclopropanecarboxylate

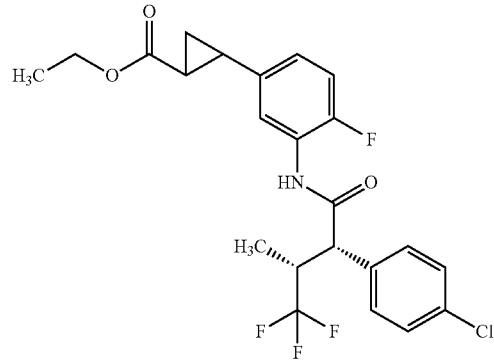 [SMILES: CCOC(=O)C1CC1c1ccc(F)c(NC(=O)[C@H](c2ccc(Cl)cc2)[C@@H](C)C(F)(F)F)c1]

167 mg (0.44 mmol) of HATU were added to a solution of 90 mg (0.34 mmol) of (2S,3R)-2-(4-chlorophenyl)-4,4,4-trifluoro-3-methylbutanoic acid in 1.5 ml of a 4:1 mixture of DMF and pyridine. After 30 min of stirring at RT, 83 mg (0.37 mmol) of rac-ethyl 2-[3-amino-4-fluorophenyl]-trans-cyclopropanecarboxylate were added. The reaction mixture was stirred at RT overnight, then diluted with ethyl acetate (about 50 ml) and washed with saturated sodium chloride solution. The organic phase was dried over magnesium sulphate and concentrated and the residue was purified by preparative HPLC. This gave 123 mg (77% of theory) of the title compound.

LC-MS (Method 6): $R_t$=1.35 min; m/z=472 (M+H)$^+$.

$^1$H-NMR (400 MHz, DMSO-$d_6$): δ [ppm]=0.79 (d, 3H), 1.19 (t, 3H), 1.25-1.34 (m, 1H), 1.42 (dt, 1H), 1.73-1.91 (m, 1H), 2.31-2.45 (m, 1H), 3.96-4.20 (m, 3H), 6.83-7.00 (m, 1H), 7.13 (dd, 1H), 7.45 (s, 4H), 7.57-7.68 (m, 1H), 10.06 (s, 1H).

Example 128A

Ethyl threo-3-(3-{[(2S,3R)-2-(4-chlorophenyl)-4,4,4-trifluoro-3-methylbutanoyl]amino}-4-fluoro-phenyl)-2-methylbutanoate

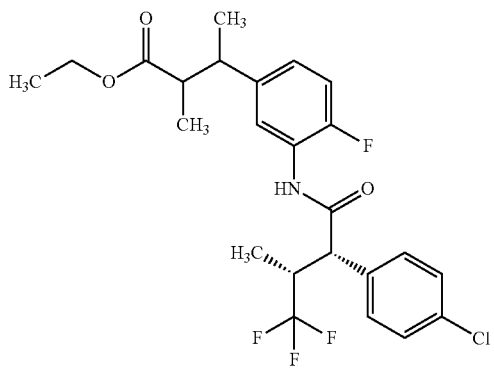 [SMILES: CCOC(=O)C(C)C(C)c1ccc(F)c(NC(=O)[C@H](c2ccc(Cl)cc2)[C@@H](C)C(F)(F)F)c1]

15 µl (0.19 mmol) of pyridine and 75.8 mg (0.2 mmol) of HATU were added to a solution of 35.5 mg (0.13 mmol) of (2S,3R)-2-(4-chlorophenyl)-4,4,4-trifluoro-3-methylbutanoic acid in 0.98 ml of DMF. The reaction mixture was stirred at RT for 30 min, and 35 mg (0.15 mmol) of rac-threo-ethyl 3-(3-amino-4-fluorophenyl)-2-methylbutanoate were then added. The reaction mixture was stirred overnight and then purified directly by preparative HPLC. This gave 34 mg (52% of theory) of the title compound.

LC-MS (Method 5): $R_t$=2.89 min; m/z=488 (M+H)$^+$.

Example 129A

Ethyl erythro-3-(3-{[(2S,3R)-2-(4-chlorophenyl)-4,4,4-trifluoro-3-methylbutanoyl]amino}-4-fluorophenyl)-2-methylbutanoate

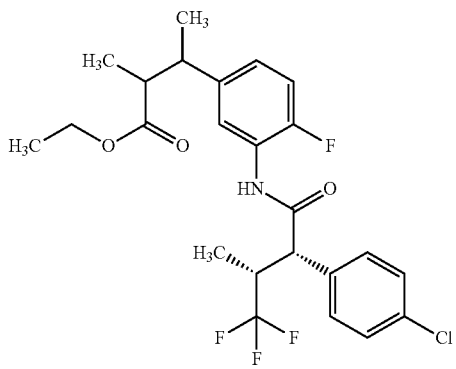 [SMILES: CCOC(=O)C(C)C(C)c1ccc(F)c(NC(=O)[C@H](c2ccc(Cl)cc2)[C@@H](C)C(F)(F)F)c1]

9.5 µl (117 µmol) of pyridine and 47.7 mg (125 µmol) of HATU were added to a solution of 22.3 mg (84 µmol) of (2S,3R)-2-(4-chlorophenyl)-4,4,4-trifluoro-3-methylbutanoic acid in 0.62 ml of DMF. The reaction mixture was stirred at RT for 30 min, and 22 mg (92 µmol) of rac-erythro-ethyl 3-(3-amino-4-fluorophenyl)-2-methylbutanoate were then added. The reaction mixture was stirred overnight and then purified directly by preparative HPLC. This gave 10.7 mg (24% of theory) of the title compound.

LC-MS (Method 4): $R_t$=1.57 min; m/z=488 (M+H)$^+$.

Example 130A tert-butyl 3-(3-{[(2S,3R)-2-(4-chlorophenyl)-4,4,4-trifluoro-3-methylbutanoyl]amino}-4-cyano-phenyl)propanoate

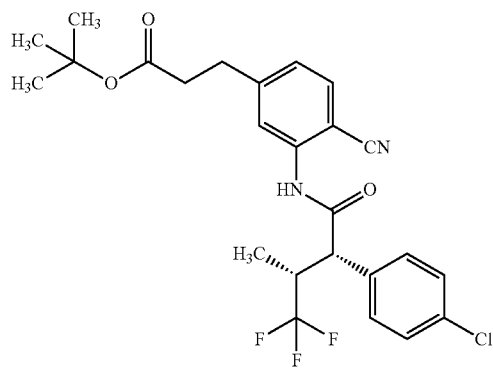 [SMILES: C[C@H]([C@H](C(=O)Nc1cc(CCC(=O)OC(C)(C)C)ccc1C#N)c1ccc(Cl)cc1)C(F)(F)F]

At 0° C., 155 µl (0.31 mmol) of a 2 M solution of oxalyl chloride in dichloromethane and one drop of DMF were added to a solution of 41.3 mg (0.16 mmol) of (2S,3R)-2-(4-chlorophenyl)-4,4,4-trifluoro-3-methylbutanoic acid in 1.16 ml of dichloromethane. After 1 h of stirring at 0° C., the mixture was concentrated, the residue that remained was dissolved in 1 ml of THF, 32 µl (0.19 mmol) of N,N-diisopropylethylamine were added, the mixture was cooled to 0° C. and a solution of 42 mg (0.17 mmol) of tert-butyl 3-(3-amino-4-cyanophenyl)propanoate in 2 ml of THF was added. The reaction mixture was stirred at RT overnight. The mixture was then poured into 10 ml of water and extracted with ethyl acetate. The combined organic phases were dried over magnesium sulphate and concentrated. The residue was purified by preparative HPLC. This gave 16.5 mg (22% of theory) of the title compound.

LC-MS (Method 7): $R_t$=2.86 min; m/z=439 (M−$_t$Bu)$^+$.

$^1$H-NMR (400 MHz, DMSO-$d_6$): δ [ppm]=0.81 (d, 3H), 1.27-1.35 (m, 9H), 2.83 (t, 2H), 4.01 (d, 1H), 7.21 (dd, 1H), 7.30 (s, 1H), 7.40-7.52 (m, 4H), 7.69 (d, 1H), 10.47 (s, 1H).

Example 131A

Methyl (2E)-3-(2-methyl-3-nitrophenyl)acrylate

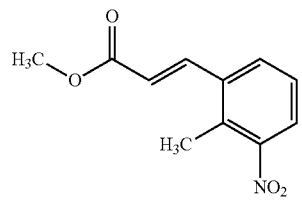 [SMILES: COC(=O)/C=C/c1cccc([N+](=O)[O-])c1C]

Under argon, 119.5 g (1.39 mol) of methyl acrylate were added dropwise to a mixture of 100 g (0.463 mol) of 2-bromo-6-nitrotoluene, 323 ml (2.31 mol) of triethylamine, 28.2 g (92.6 mmol) of tri-2-tolylphosphine and 10.4 g (46.3 mmol) of palladium(II) acetate in 2.0 liters of DMF, and the mixture was then stirred at 125° C. for 36 h. After cooling to room temperature, the reaction mixture was stirred with 4 liters of saturated aqueous ammonium chloride solution and extracted three times with a total of 5 liters of diethyl ether. The combined organic phases were washed with water and saturated sodium chloride solution and dried over sodium sulphate. After filtration, the solvent was removed to dryness under reduced pressure. The residue obtained was purified by flash chromatography on silica gel (mobile phase petroleum ether/ethyl acetate 6:1). The product was triturated with heptane, and the solid obtained was filtered off with suction and dried under high vacuum. This gave 48.7 g of the title compound (46.6% of theory).

MS: m/z=162 (M–$C_2H_3O_2$)$^+$.

$^1$H-NMR (400 MHz, DMSO-$d_6$): δ [ppm]=2.41 (s, 3H), 3.76 (s, 3H), 6.63 (d, 1H), 7.48 (t, 1H), 7.84-7.95 (m, 2H), 8.00 (d, 1H).

Example 132A

Methyl 3-(3-amino-2-methylphenyl)propanoate

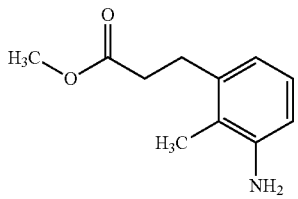

48.7 g (220.1 mmol) of methyl (2E)-3-(2-methyl-3-nitrophenyl)acrylate were dissolved in 2.2 liters of methanol, and the solution was hydrogenated in a continuous-flow hydrogenation reactor ("H-Cube midi" from Thales Nano, Budapest) at a flow rate of 6-10 ml/min and at a reaction temperature of 35-40° C. and at maximum hydrogen pressure. After the reaction had ended, the product-containing solution was concentrated under reduced pressure. This gave 40.0 g of the target product as a solid (92.1% of theory).

MS: m/z=194 (M+H)$^+$.

$^1$H-NMR (400 MHz, DMSO-$d_6$): δ [ppm]=1.97 (s, 3H), 2.45 (t, 2H), 2.78 (t, 2H), 3.58 (s, 3H), 4.75 (s, 2H), 6.37 (d, 1H), 6.50 (d, 1H), 6.79 (t, 1H).

Example 133A

Methyl 3-(3-amino-4-chloro-2-methylphenyl)propanoate

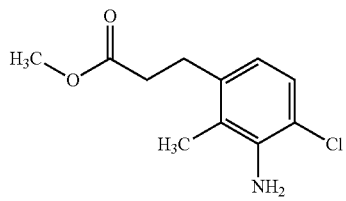

At RT, 1.38 g (10.3 mmol) of N-chlorosuccinimide were added to a solution of 2.0 g (10.3 mmol) of methyl 3-(3-amino-2-methylphenyl)propanoate in 10 ml of acetonitrile. The reaction mixture was stirred for 30 min and then diluted with ethyl acetate. The mixture was washed successively with sat. sodium bicarbonate solution and sat. sodium chloride solution, dried over magnesium sulphate and concentrated under reduced pressure. The crude product gave, after chromatography on silica gel (mobile phase cyclohexane/ethyl acetate 10:1), 279 mg of the target product (11.8% of theory).

LC-MS (Method 4): R$_t$=1.11 min; m/z=228 (M+H)$^+$.

$^1$H-NMR (500 MHz, DMSO-$d_6$): δ [ppm]=2.06 (s, 3H), 2.46 (t, 2H), 2.78 (t, 2H), 3.58 (s, 3H), 4.94 (s, 2H), 6.42 (d, 1H), 6.98 (d, 1H).

Example 134A 3-bromo-6-chloro-2-methylaniline

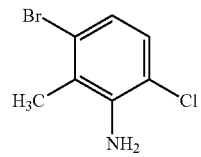

At RT, 8.61 g (64.5 mmol) of N-chlorosuccinimide were added to a solution of 12.0 g (64.5 mmol) of 3-bromo-2-methylaniline in 150 ml of acetonitrile. The reaction mixture was stirred at 60° C. for 7 h and, after cooling, concentrated under reduced pressure. The residue was taken up in dichloromethane, and the mixture was washed successively with sat. sodium bicarbonate solution and sat. sodium chloride solution, dried over sodium sulphate and concentrated under reduced pressure. The crude product gave, after chromatography on silica gel (mobile phase cyclohexane/ethyl acetate 40:1 to 20:1), 3.78 g of the target product (26.6% of theory).

GC-MS (Method 1): R$_t$=5.07 min; m/z=218/220 (M+H)$^+$.

$^1$H-NMR (400 MHz, DMSO-$d_6$): δ [ppm]=2.24 (s, 3H), 5.39 (s, 2H), 6.80 (d, 1H), 7.03 (d, 1H).

Example 135A tert-butyl (2E)-3-(3-amino-4-chloro-2-methylphenyl)-2-methylacrylate and tert-butyl 2-(3-amino-4-chloro-2-methylbenzyl)acrylate

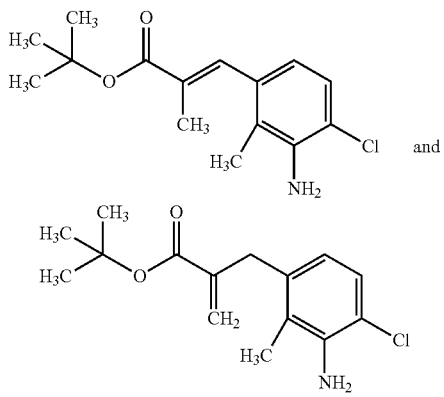

1.50 g (6.80 mmol) of 3-bromo-6-chloro-2-methylaniline, 2.90 g (20.4 mmol) of tert-butyl methacrylate and 4.74 ml (34.0 mmol) of triethylamine were dissolved in 10.0 ml of DMF. Three times, the reaction solution was evacuated and in each case vented again with argon. After addition of 152.7 mg (0.68 mmol) of palladium(II) acetate and 414.1 mg (1.36 mmol) of tri-2-tolylphosphine, the mixture was once more evacuated twice and in each case vented with argon. The reaction mixture was then stirred at 150° C. for 2 h. After cooling, the mixture was filtered through celite and the residue was washed with DMF. The filtrate was concentrated under reduced pressure and the residue was purified by chromatography on silica gel (mobile phase cyclohexane/ethyl acetate 100:1). This gave 1.59 g of a mixture of the two title compounds (ratio about 2:1, 83% of theory).

LC-MS (Method 4): $R_t$=1.45 min; m/z=226 $(M-C_4H_8)^+$ and $R_t$=1.49 min; m/z=282 $(M+H)^+$.

$^1$H-NMR (400 MHz, DMSO-$d_6$): tert-butyl (2E)-3-(3-amino-4-chloro-2-methylphenyl)-2-methylacrylate: δ [ppm]=1.49 (s, 9H), 1.75 (d, 3H), 2.02 (s, 3H), 5.12 (s, 2H), 6.44 (d, 1H), 7.11 (d, 1H), 7.51 (s, 1H).

$^1$H-NMR (400 MHz, DMSO-$d_6$): tert-butyl 2-(3-amino-4-chloro-2-methylbenzyl)acrylate: δ [ppm]=1.42 (s, 9H), 1.98 (s, 3H), 3.45 (s, 2H), 4.97 (s, 2H), 5.15 (d, 1H), 6.01 (d, 1H), 6.38 (d, 1H), 7.02 (d, 1H).

Example 136A (+/−)-tert-butyl 3-(3-amino-4-chloro-2-methylphenyl)-2-methylpropanoate

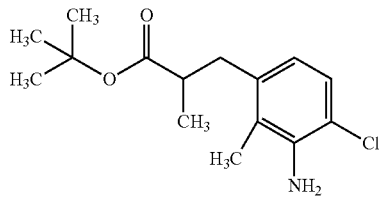 [SMILES: Cc1c(CC(C)C(=O)OC(C)(C)C)ccc(Cl)c1N]

A solution of 1.58 g (5.61 mmol) of a mixture of tert-butyl (2E)-3-(3-amino-4-chloro-2-methylphenyl)-2-methylacrylate and tert-butyl 2-(3-amino-4-chloro-2-methylbenzyl)acrylate (Example 135A) in 5.0 ml of methanol was added to 354 mg (14.6 mmol) of magnesium turnings and a few grains of iodine. The mixture was stirred at RT (initially with cooling) overnight. 50 ml of 1 N hydrochloric acid were then added with ice-cooling. By addition of 10% strength aqueous sodium hydroxide solution, the pH of the mixture was then adjusted to about 10. The mixture was extracted three times with ethyl acetate. The combined organic phases were dried over magnesium sulphate and concentrated under reduced pressure. The crude product gave, after chromatography on silica gel (mobile phase cyclohexane/ethyl acetate 50:1 to 40:1), 962 mg of the target product (60.5% of theory).

LC-MS (Method 9): $R_t$=2.30 min; m/z=284 $(M+H)^+$.

$^1$H-NMR (400 MHz, DMSO-$d_6$): δ [ppm]=1.02 (d, 3H), 1.32 (s, 9H), 2.06 (s, 3H), 2.46 (dd, 1H), 2.80 (dd, 1H), 4.94 (br. s, 2H), 6.38 (d, 1H), 6.97 (d, 1H).

The racemate obtained above was separated into the enantiomers by preparative HPLC on a chiral phase [column: Daicel Chiralpak OJ-H, 5 μm, 250 mm×20 mm; flow rate: 20 ml/min; detection: 220 nm; injection volume: 0.28 ml; temperature: 22° C.; mobile phase: 93% isohexane/7% isopropanol]. 962 mg of racemate gave 434 mg of enantiomer 1 (Example 137A) and 325 mg of enantiomer 2 (Example 138A):

Example 137A (−)-tert-butyl (2R)-3-(3-amino-4-chloro-2-methylphenyl)-2-methylpropanoate

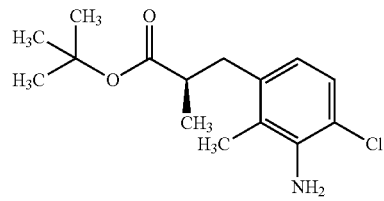 [SMILES: Cc1c(C[C@@H](C)C(=O)OC(C)(C)C)ccc(Cl)c1N]

Yield: 434 mg

LC-MS (Method 4): $R_t$=1.44 min; m/z=284 $(M+H)^+$.

$^1$H-NMR (400 MHz, DMSO-$d_6$): δ [ppm]=1.03 (d, 3H), 1.32 (s, 9H), 2.06 (s, 3H), 2.46 (dd, 1H), 2.80 (dd, 1H), 4.93 (s, 2H), 6.38 (d, 1H), 6.97 (d, 1H).

$[α]_D^{20}$=−37.30°, c=0.455, chloroform.

Example 138A (+)-tert-butyl (2S)-3-(3-amino-4-chloro-2-methylphenyl)-2-methylpropanoate

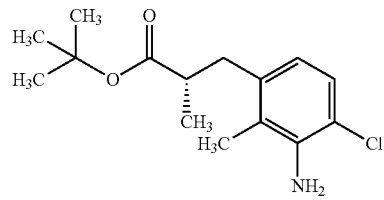 [SMILES: Cc1c(C[C@H](C)C(=O)OC(C)(C)C)ccc(Cl)c1N]

Yield: 325 mg

LC-MS (Method 4): $R_t$=1.44 min; m/z=284 $(M+H)^+$.

$^1$H-NMR (400 MHz, DMSO-$d_6$): δ [ppm]=1.03 (d, 3H), 1.32 (s, 9H), 2.06 (s, 3H), 2.46 (dd, 1H), 2.80 (dd, 1H), 4.93 (s, 2H), 6.38 (d, 1H), 6.97 (d, 1H).

$[α]_D^{20}$=+35.0°, c=0.455, chloroform.

Example 139A

Ethyl 4,4,4-trifluoro-3-(4-fluoro-3-nitrophenyl)but-2-enoate

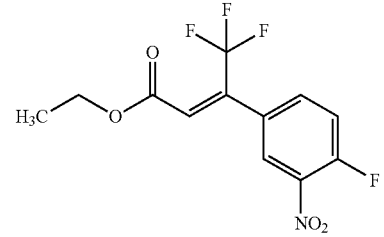 [SMILES: CCOC(=O)/C=C(/c1ccc(F)c([N+](=O)[O-])c1)C(F)(F)F]

10.9 g (48.5 mmol) of ethyl diethylphosphonoacetate were slowly added dropwise to an ice-cooled suspension of 1.86 g (60% in mineral oil, 46.4 mmol) of sodium hydride in a mixture of 70 ml of THF and 20 ml of DMF. After the addition had ended, the mixture was stirred at 0° C. for another 30 min, and 10.0 g (42.2 mmol) of 2,2,2-trifluoro-1-(4-fluoro-3-nitrophenyl)ethanone were then added. The reaction mixture was stirred at RT overnight and then added to water. The mixture was extracted three times with ethyl acetate, and the combined organic phases were concentrated under reduced pressure. The crude product gave, after chromatography on silica gel (mobile phase cyclohexane/ethyl acetate 20:1 to 10:1), 9.23 g of the target product (71.2% of theory).

GC-MS (Method 1): $R_t$=4.51 min; m/z=262 (M−$C_2H_5O$)$^+$.

$^1$H-NMR (400 MHz, DMSO-$d_6$): δ [ppm]=1.04 (t, 3H), 4.03 (q, 2H), 6.96 (d, 1H), 7.67-7.76 (m, 1H), 7.78-7.86 (m, 1H), 8.16 (dd, 1H).

Example 140A (+/−)-Ethyl 3-(3-amino-4-fluorophenyl)-4,4,4-trifluorobutanoate

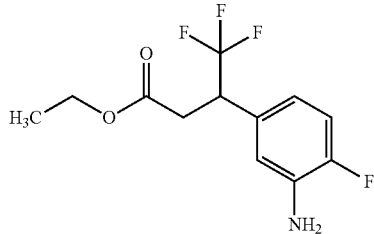

5.0 g (16.3 mmol) of ethyl 4,4,4-trifluoro-3-(4-fluoro-3-nitrophenyl)but-2-enoate were dissolved in 133 ml of ethanol, and 866 mg of palladium on carbon (10%) were added under argon. At RT, the reaction mixture was stirred vigorously under an atmosphere of hydrogen (atmospheric pressure) overnight. The mixture was then filtered off through celite and the residue was washed with ethyl acetate. The filtrate was concentrated under reduced pressure and the residue obtained was purified by chromatography on silica gel (mobile phase cyclohexane/ethyl acetate 50:1). This gave 3.91 g of the target product (85.9% of theory).

LC-MS (Method 6): $R_t$=0.97 min; m/z=280 (M+H)$^+$.

$^1$H-NMR (400 MHz, DMSO-$d_6$): δ [ppm]=1.08 (t, 3H), 2.85 (dd, 1H), 2.99 (dd, 1H), 3.81-3.92 (m, 1H), 3.94-4.07 (m, 2H), 5.21 (s, 2H), 6.40-6.58 (m, 1H), 6.77 (dd, 1H), 6.96 (dd, 1H).

Example 141A tert-butyl 2-methylbutanoate

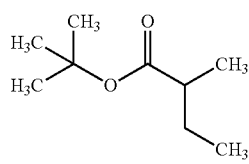

15.0 g (124.4 mmol) of 2-methylbutyryl chloride were dissolved in 150 ml of abs. THF and cooled to 0° C., and 114 ml (114 mmol) of a 1 M solution of potassium tert-butylate in THF were added dropwise. After the addition had ended, the mixture was stirred at 0° C. for 1 h and then at RT for h, and about half of the solvent were removed under reduced pressure. After addition of diethyl ether, sat. sodium bicarbonate solution was added dropwise with vigorous stirring. After phase separation, the aqueous phase was extracted with diethyl ether, and the combined organic phases were washed with sat. sodium carbonate solution, dried over sodium sulphate and concentrated under reduced pressure. The crude product was purified by vacuum distillation (19 mm Hg, 40-45° C.). This gave a total of 6.35 g of the target product (32.3% of theory).

GC-MS (Method 1): $R_t$=1.53 min; m/z=85.

$^1$H-NMR (400 MHz, DMSO-$d_6$): δ [ppm]=0.84 (m, 3H), 1.01 (d, 3H), 1.33-1.41 (m, 1H), 1.39 (s, 9H), 1.48-1.55 (m, 1H), 2.13-2.26 (m, 1H).

Example 142A 2-bromo-4-(bromomethyl)-1-chlorobenzene

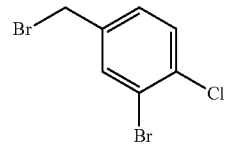

Step 1:
199.0 g (0.845 mol) of 3-bromo-4-chlorobenzoic acid were dissolved in 2.5 liters of THF, the mixture was cooled to −10° C. and 1.69 liters (1.69 mol) of a 1 M solution of borane in THF were added at this temperature. The reaction mixture was warmed to RT overnight, and saturated aqueous ammonium chloride solution was then added. After the addition of water, the mixture was extracted twice with ethyl acetate and the combined organic phases were dried over magnesium sulphate and concentrated under reduced pressure. This gave, as a crude product, 206 g of (3-bromo-4-chlorophenyl)methanol which were used in the subsequent step without further purification.

Step 2:
260 g (about 1.05 mol) of crude (3-bromo-4-chlorophenyl)methanol were dissolved in 2.86 liters of dichloromethane, the mixture was cooled to −5° C. and 127.1 g (44.6 ml, 460 mmol) of phosphorous tribromide were added slowly. After the addition had ended, stirring at −5° C. was continued for 1 h, and the mixture was then diluted with dichloromethane and water. The organic phase was separated off, dried over magnesium sulphate and concentrated under reduced pressure. This gave, as a crude product, 280.5 g (about 84% of theory) of 2-bromo-4-(bromomethyl)-1-chlorobenzene.

GC-MS (Method 1): $R_t$=5.36 min; m/z=281/283/285 (M+H)$^+$.

$^1$H-NMR (400 MHz, DMSO-$d_6$): δ [ppm]=4.71 (s, 2H), 7.49 (dd, 1H), 7.63 (d, 1H), 7.89 (d, 1H).

Example 143A (+/−)-tert-butyl 2-(3-bromo-4-chlorobenzyl)-2-methylbutanoate

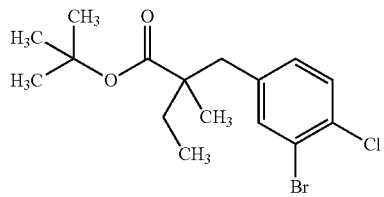 [SMILES: CCC(C)(Cc1ccc(Cl)c(Br)c1)C(=O)OC(C)(C)C]

Under argon, 5.8 ml (41.6 mmol) of diisopropylamine were dissolved in 50 ml of dry THF, and the mixture was cooled to −30° C. 16.6 ml (41.6 mmol) of n-butyllithium solution (2.5 M in hexane) were added dropwise, and the resulting mixture was warmed to 0° C. and then cooled to −70° C. A solution of 5.06 g (32.0 mmol) of tert-butyl 2-methylbutanoate in 20 ml of THF was added, the reaction temperature being kept below −60° C. After 4 h of stirring at −60° C., a solution of 10.0 g (35.2 mmol) of 2-bromo-4-(bromomethyl)-1-chlorobenzene in 30 ml of THF was added, and the temperature was once more kept below −60° C. The reaction mixture was then slowly warmed to RT overnight, and saturated aqueous ammonium chloride solution and ethyl acetate were then added. After phase separation, the aqueous phase was extracted twice with ethyl acetate. The combined organic phases were dried over magnesium sulphate and concentrated under reduced pressure. The crude product was purified by chromatography on silica gel (mobile phase cyclohexane/ethyl acetate 100:1). This gave 7.62 g (65.9% of theory) of the title compound.

GC-MS (Method 1): $R_t$=6.52 min; m/z=306 (M−$C_4H_7$)±.

$^1$H-NMR (400 MHz, DMSO-$d_6$): δ [ppm]=0.83 (t, 3H), 0.93 (s, 3H), 1.32-1.45 (m, 10H), 1.60-1.73 (m, 1H), 2.62 (d, 1H), 2.91 (d, 1H), 7.18 (dd, 1H), 7.47-7.56 (m, 2H).

Example 144A (+/−)-tert-butyl 2-[3-(benzylamino)-4-chlorobenzyl]-2-methylbutanoate

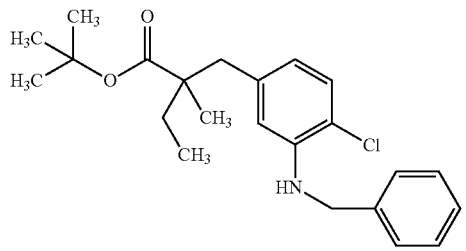 [SMILES: CCC(C)(Cc1ccc(Cl)c(NCc2ccccc2)c1)C(=O)OC(C)(C)C]

Under argon, 1.59 g (16.6 mmol) of sodium tert-butoxide were weighed out into a dry flask, and 34.6 ml of abs. toluene were added. 5.0 g (13.8 mmol) of (+/−)-tert-butyl-2-(3-bromo-4-chlorobenzyl)-2-methylbutanoate, 1.8 ml (16.6 mmol) of benzylamine, 633 mg (0.69 mmol) of tris(dibenzylidenacetone)dipalladium and 344 mg (0.55 mmol) of (+/−)-2,2'-bis(diphenylphosphino)-1,1'-binaphthyl were added in succession. The reaction mixture was then stirred at 110° C. for 2.0 h. After cooling, saturated aqueous ammonium chloride solution and ethyl acetate were added and the reaction mixture was filtered off with suction through kieselguhr. After phase separation, the organic phase was washed with sat ammonium chloride solution and sat. sodium chloride solution, dried over magnesium sulphate and concentrated under reduced pressure. The crude product was purified by chromatography on silica gel (mobile phase cyclohexane/ethyl acetate 80:1). This gave 4.44 g of the title compound in still slightly contaminated form (about 83% of theory).

LC-MS (Method 6): $R_t$=1.57 min; m/z=388 (M+H)$^+$.

$^1$H-NMR (400 MHz, DMSO-$d_6$): δ [ppm]=0.70 (t, 3H), 1.13-1.22 (m, 1H), 1.35 (s, 9H), 1.39 (s, 3H), 1.39-1.50 (m, 1H), 2.42 (d, 1H), 2.66 (d, 1H), 4.26-4.46 (m, 2H), 6.00 (t, 1H), 6.26-6.35 (m, 1H), 7.11 (d, 1H), 7.16-7.23 (m, 1H), 7.28-7.34 (m, 4H), 7.45-7.55 (m, 1H).

Example 145A (+/−)-tert-butyl 2-(3-amino-4-chlorobenzyl)-2-methylbutanoate

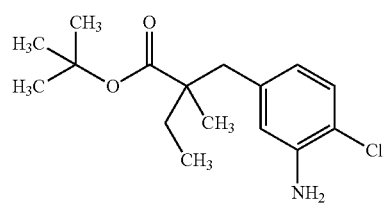 [SMILES: CCC(C)(Cc1ccc(Cl)c(N)c1)C(=O)OC(C)(C)C]

2.20 g (about 5.67 mmol) of (+/−)-tert-butyl 2-[3-(benzylamino)-4-chlorobenzyl]-2-methylbutanoate were dissolved in 130 ml of ethyl acetate, and 100 mg of palladium on carbon (10%) were added. At RT, the reaction mixture was stirred under an atmosphere of hydrogen at atmospheric pressure overnight. The reaction mixture was then filtered off with suction through kieselguhr, the residue was washed thoroughly with ethyl acetate and the combined filtrate was concentrated. The crude product was purified by chromatography on silica gel (mobile phase cyclohexane/ethyl acetate 50:1 to 30:1). This gave 924 mg (54.7% of theory) of the target compound.

LC-MS (Method 6): $R_t$=1.34 min; m/z=298 (M+H)$^+$.

The racemate obtained above was separated into the enantiomers by preparative HPLC on a chiral phase [column: Daicel Chiralpak OJ-H, 5 μm, 250 mm×20 mm; flow rate: 20 ml/min; detection: 220 nm; injection volume: 0.30 ml; temperature: 35° C.; mobile phase: 70% isohexane/30% ethanol]. 924 mg of racemate gave 405 mg of enantiomer 1 (Example 146A) and 403 mg of enantiomer 2 (Example 147A):

Example 146A (−)-tert-butyl 2-(3-amino-4-chlorobenzyl)-2-methylbutanoate (enantiomer 1)

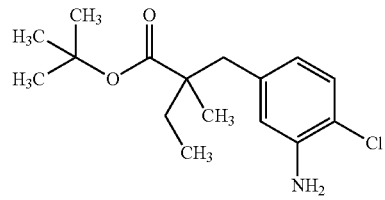

Yield: 405 mg

LC-MS (Method 6): $R_t$=1.32 min; m/z=298 (M+H)$^+$.

$^1$H-NMR (400 MHz, DMSO-$d_6$): δ [ppm]=0.81 (t, 3H), 0.93 (s, 3H), 1.28-1.37 (m, 1H), 1.38 (s, 9H), 1.59-1.71 (m, 1H), 2.45 (d, 1H), 2.74 (d, 1H), 5.14-5.22 (m, 2H), 6.31 (dd, 1H), 6.57 (d, 1H), 7.04 (d, 1H).

[α]$_D^{20}$=−11.8°, c=0.50, chloroform.

Example 147A (+)-tert-butyl-2-(3-amino-4-chlorobenzyl)-2-methylbutanoate (enantiomer 2)

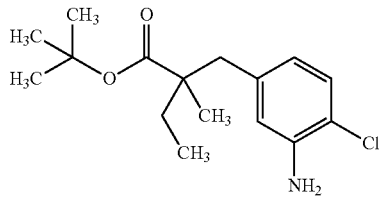

Yield: 403 mg

LC-MS (Method 6): $R_t$=1.32 min; m/z=298 (M+H)$^+$.

$^1$H-NMR (400 MHz, DMSO-$d_6$): δ [ppm]=0.75-0.85 (m, 3H), 0.93 (s, 3H), 1.30-1.37 (m, 1H), 1.39 (s, 9H), 1.58-1.70 (m, 1H), 2.45 (d, 1H), 2.74 (d, 1H), 5.09-5.23 (m, 2H), 6.31 (dd, 1H), 6.57 (d, 1H), 7.04 (d, 1H).

$[α]_D^{20}$=+12.0°, c=0.420, chloroform.

Example 148A 2,2,2-trifluoro-1-(3-nitrophenyl)ethanone

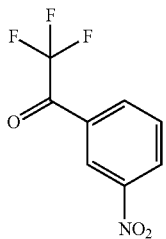

20.0 g (114.9 mmol) of 2,2,2-trifluoroacetophenone were initially charged in 80 ml of conc. sulphuric acid, and the mixture was cooled to −10° C. A solution, prepared beforehand at −10° C., of 4.8 ml (114.8 mmol) of nitric acid in 20 ml of conc. sulphuric acid was added dropwise to this mixture such that the reaction temperature did not exceed −5° C. After the addition had ended, the reaction mixture was stirred between −10° C. and 0° C. for 1 h and then added carefully to ice-water. By addition of 50% strength aqueous sodium hydroxide solution, the pH of the mixture was adjusted to about 9-10. The mixture was extracted three times with ethyl acetate, and the combined organic phases were dried over magnesium sulphate and concentrated under reduced pressure. The residue was purified by chromatography on silica gel (mobile phase initially cyclohexane/dichloromethane 2:1 to 1:1, finally pure dichloromethane). This gave 19.2 g of the target product (76.2% of theory).

LC-MS (Method 6): $R_t$=0.81 min; m/z=236.

GC-MS (Method 1): $R_t$=3.19 min; m/z=150 (M−CF$_3$)$^+$.

Example 149A tert-butyl (2E/Z)-4,4,4-trifluoro-3-(3-nitrophenyl)but-2-enoate

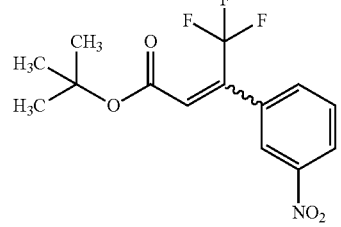

25.9 ml (110.4 mmol) of tert-butyl (diethoxyphosphoryl)acetate were added dropwise to a suspension, cooled to 0° C., of 4.41 g (60% in mineral oil, 110.4 mmol) of sodium hydride in a mixture of 37.2 ml of THF and 37.2 ml of DMF. After 30 min, 18.6 g (84.9 mmol) of 2,2,2-trifluoro-1-(3-nitrophenyl)ethanone were added, the cooling bath was removed and the reaction mixture was stirred at RT for 2 h. The reaction mixture was then added to water and, after saturation with sodium chloride, extracted three times with ethyl acetate. The combined organic phases were dried over magnesium sulphate and concentrated under reduced pressure. The residue was purified by chromatography on silica gel (mobile phase cyclohexane/ethyl acetate 100:1 to 20:1). This gave 18.0 g of the target product as an E/Z isomer mixture (66.8% of theory).

LC-MS (Method 6): $R_t$=1.25 min; no ionization.

MS (DCI): m/z=335 (M+H$_2$O)$^+$.

$^1$H-NMR (400 MHz, DMSO-$d_6$): δ [ppm]=1.17/1.50 (2s, together 9H), 6.93/7.14 (2d, together 1H), 7.74-7.94 (m, 2H), 8.16/8.23 (2s, together 1H), 8.30-8.42 (m, 1H).

Example 150A (+/−)-tert-butyl 3-(3-aminophenyl)-4,4,4-trifluorobutanoate

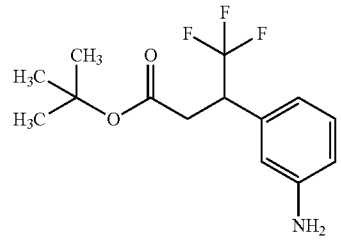 [SMILES: CC(C)(C)OC(=O)CC(c1cccc(N)c1)C(F)(F)F]

18.0 g (56.7 mmol) of tert-butyl (2E/Z)-4,4,4-trifluoro-3-(3-nitrophenyl)but-2-enoate were dissolved in 100 ml of ethanol and deoxygenated with argon. After addition of 1.21 g of palladium on carbon (10%), the mixture was stirred vigorously at RT under an atmosphere of hydrogen at atmospheric pressure overnight. The reaction mixture was then filtered through celite, the residue was washed thoroughly with ethanol, the filtrate was concentrated under reduced pressure and the product obtained was dried under high vacuum overnight. This gave 13.7 g of the target product (83.7% of theory).

LC-MS (Method 6): $R_t$=1.02 min; m/z=290 (M+H)$^+$.
$^1$H-NMR (400 MHz, DMSO-d$_6$): δ [ppm]=1.27 (s, 9H), 2.70 (dd, 1H), 2.89 (dd, 1H), 3.62-3.79 (m, 1H), 5.11-5.17 (m, 2H), 6.43-6.56 (m, 3H), 6.99 (t, 1H).

Example 151A (+/−)-tert-butyl 3-(3-amino-4-chlorophenyl)-4,4,4-trifluorobutanoate

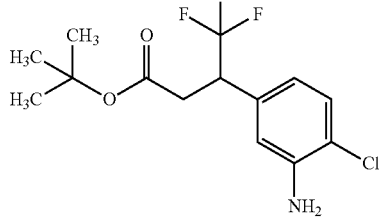

13.6 g (47.0 mmol) of (+/−)-tert-butyl-3-(3-aminophenyl)-4,4,4-trifluorobutanoate were initially charged in 100 ml of acetonitrile, and 6.28 g (47.0 mmol) of N-chlorosuccinimide were added at RT. The reaction mixture was initially stirred at 60° C. for 12 h and then allowed to stand at RT for 3 days. After concentration under reduced pressure, the residue was separated by chromatography on silica gel (mobile phase cyclohexane/ethyl acetate 100:1), and the desired target product was isolated. This gave 4.49 g of the title compound (29.5% of theory).

LC-MS (Method 6): $R_t$=1.17 min; m/z=324 (M+H)$^+$.
$^1$H-NMR (400 MHz, DMSO-d$_6$): δ [ppm]=1.27 (s, 9H), 2.72 (dd, 1H), 2.91 (dd, 1H), 3.74-3.86 (m, 1H), 5.43 (s, 2H), 6.55 (dd, 1H), 6.79 (d, 1H), 7.17 (d, 1H).

The racemate obtained above was separated into the enantiomers by preparative HPLC on a chiral phase [column: Daicel Chiralpak OJ-H, 5 μm, 250 mm×20 mm; flow rate: 15 ml/min; detection: 220 nm; injection volume: 0.20 ml; temperature: 35° C.; mobile phase: 70% isohexane/30% isopropanol]. 4.49 g of racemate gave 2.02 g of enantiomer 1 (Example 152A) and 2.04 g of enantiomer 2 (Example 153A):

Example 152A (−)-tert-butyl (3R)-3-(3-amino-4-chlorophenyl)-4,4,4-trifluorobutanoate

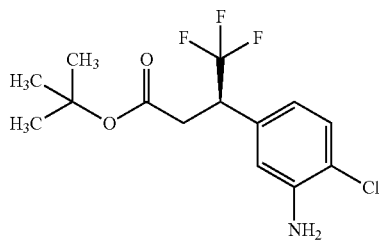 [SMILES: CC(C)(C)OC(=O)C[C@H](c1ccc(Cl)c(N)c1)C(F)(F)F]

Yield: 2.02 g
LC-MS (Method 6): $R_t$=1.17 min; m/z=324 (M+H)$^+$.
$^1$H-NMR (400 MHz, DMSO-d$_6$): δ [ppm]=1.27 (s, 9H), 2.72 (dd, 1H), 2.91 (dd, 1H), 3.75-3.85 (m, 1H), 5.40-5.46 (m, 2H), 6.55 (dd, 1H), 6.79 (d, 1H), 7.17 (d, 1H).
$[α]_D^{20}$=−69.4°, c=0.520, chloroform.

Example 153A (+)-tert-butyl (3S)-3-(3-amino-4-chlorophenyl)-4,4,4-trifluorobutanoate

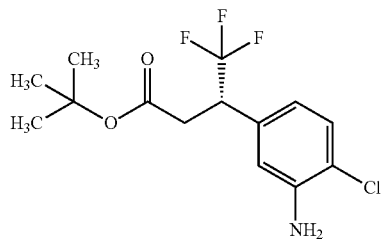 [SMILES: CC(C)(C)OC(=O)C[C@@H](c1ccc(Cl)c(N)c1)C(F)(F)F]

Yield: 2.04 g
LC-MS (Method 6): $R_t$=1.17 min; m/z=324 (M+H)$^+$.
$^1$H-NMR (400 MHz, DMSO-d$_6$): δ [ppm]=1.27 (s, 9H), 2.71 (dd, 1H), 2.91 (dd, 1H), 3.74-3.86 (m, 1H), 5.38-5.46 (m, 2H), 6.55 (dd, 1H), 6.73-6.80 (m, 1H), 7.17 (d, 1H).
$[α]_D^{20}$=+66.3°, c=0.495, chloroform.

Example 154A tert-butyl cyclobutylacetate

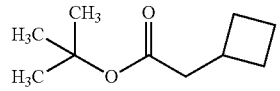

4.0 g (35.0 mmol) of cyclobutylacetic acid were dissolved in 20 ml of dichloromethane, a drop of DMF was added and 4.0 ml (45.6 mmol) of oxalyl chloride were added dropwise after cooling to 0° C. The reaction mixture was stirred between 0° C. and 10° C. for 2 h and then concentrated in the cold under reduced pressure. The residue was taken up in abs. dichloromethane and once more concentrated in the cold under reduced pressure. This procedure was repeated once more, and the acid chloride obtained was then briefly dried under high vacuum for 5 min. The residue was then taken up in 20 ml of abs. THF and cooled to 0° C., and 28 ml (28 mmol) of a 1 M solution of potassium tert-butoxide in THF were added dropwise. After the addition had ended, cooling was removed and the mixture was stirred at RT for 1 h and then added to water. The mixture was extracted three times with dichloromethane, and the combined organic phases were dried over magnesium sulphate and concentrated under reduced pressure. This gave 3.88 g of the crude target product (about 65% of theory).

GC-MS (Method 1): $R_t$=2.29 min; m/z=97 (M−C$_3$H$_5$O$_2$)$^+$.
$^1$H-NMR (400 MHz, DMSO-d$_6$): δ [ppm]=1.38 (s, 9H), 1.60-1.89 (m, 5H), 1.95-2.11 (m, 2H), 2.28 (d, 2H).

Example 155A tert-butyl cyclopropylacetate

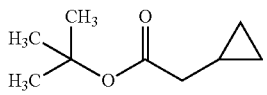

10.0 g (99.9 mmol) of cyclopropylacetic acid were dissolved in 50 ml of dichloromethane, a drop of DMF was added and 9.6 ml (109.9 mmol) of oxalyl chloride were added dropwise after cooling to 0° C. The reaction mixture was stirred between 0° C. and 10° C. for 2 h and then concentrated in the cold under reduced pressure. The residue was briefly (about 5 min) dried under high vacuum and then taken up in 20 ml of abs. THF and cooled to 0° C., and 89.9 ml (89.9 mmol) of a 1 M solution of potassium tert-butoxide in THF were added dropwise. After the addition had ended, cooling was removed and the mixture was stirred at RT for 2 h, before most of the THF was removed under reduced pressure (up to 150 mm Hg, water bath about 30° C.). Diethyl ether and 0.5 N aqueous sodium hydroxide solution were added to the residue. After phase separation, the organic phase was dried over magnesium sulphate and concentrated under reduced pressure and the residue was briefly dried under high vacuum. This gave 8.38 g of the crude target product (about 53% of theory).

GC-MS (Method 1): $R_t$=1.80 min; m/z=100 (M−$C_4H_8$)$^+$.

$^1$H-NMR (400 MHz, DMSO-$d_6$): δ [ppm]=0.05-0.14 (m, 2H), 0.38-0.51 (m, 2H), 0.81-0.99 (m, 1H), 1.40 (s, 9H), 2.10 (d, 2H).

Example 156A (+/−)-tert-butyl 3-(3-bromo-4-chlorophenyl)-2-cyclobutylpropanoate

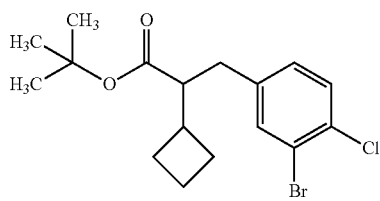 [SMILES: CC(C)(C)OC(=O)C(Cc1ccc(Cl)c(Br)c1)C1CCC1]

Under argon, 2.9 ml (20.8 mmol) of diisopropylamine were dissolved in 30 ml of dry THF, and the mixture was cooled to −20° C. 8.3 ml (20.8 mmol) of n-butyllithium solution (2.5 M in hexane) were added dropwise, and the resulting mixture was stirred to −20° C. for 30 min and then cooled to −78° C. At this temperature, a solution of 2.60 g (about 15.3 mmol, crude) of tert-butyl cyclobutylacetate in 10 ml of THF was added. After 4 h of stirring at −78° C., a solution of 3.95 g (13.9 mmol) of 2-bromo-4-(bromomethyl)-1-chlorobenzene in 10 ml of THF was added. The reaction mixture was slowly warmed to RT overnight, and saturated aqueous ammonium chloride solution was then added. The mixture was extracted three times with ethyl acetate. The combined organic phases were dried over magnesium sulphate and concentrated under reduced pressure. The solid that remained was triturated with 30 ml of cyclohexane/dichloromethane (1:1) and filtered off. The solid was once more triturated with 10 ml of cyclohexane/dichloromethane (1:1) and again filtered off; this procedure was repeated once more. All filtrates were collected, combined and concentrated under reduced pressure. This residue was then purified further by chromatography on silica gel (mobile phase from pure cyclohexane to cyclohexane/dichloromethane 20:1 to 10:1). This gave 2.24 g of the title compound (43.2% of theory).

GC-MS (Method 1): $R_t$=6.92 min; m/z=318 (M−$C_4H_7$)$^+$.

$^1$H-NMR (400 MHz, DMSO-$d_6$): δ [ppm]=1.27 (s, 9H), 1.71-1.84 (m, 4H), 1.90-1.94 (m, 1H), 1.96-2.04 (m, 1H), 2.33-2.44 (m, 1H), 2.53-2.60 (m, 1H), 2.61-2.71 (m, 1H), 7.22 (dd, 1H), 7.52 (d, 1H), 7.57 (d, 1H).

The example below was obtained in an analogous manner

Example 157A tert-butyl 3-(3-bromo-4-chlorophenyl)-2-cyclopropylpropanoate

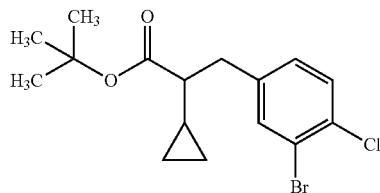 [SMILES: CC(C)(C)OC(=O)C(Cc1ccc(Cl)c(Br)c1)C1CC1]

From tert-butyl cyclopropylacetate and 2-bromo-4-(bromomethyl)-1-chlorobenzene, 3.13 g of the title compound were obtained (45% of theory).

GC-MS (Method 1): $R_t$=6.41 min; m/z=301/304 (M−$C_4H_8$)$^+$.

$^1$H-NMR (400 MHz, DMSO-$d_6$): δ [ppm]=0.22 (tt, 2H), 0.40-0.50 (m, 2H), 0.82-0.93 (m, 1H), 1.28 (s, 9H), 1.82-1.88 (m, 1H), 2.81-2.89 (m, 2H), 7.24 (dd, 1H), 7.52 (d, 1H), 7.60 (d, 1H).

Example 158A (+/−)-tert-butyl 3-[3-(benzylamino)-4-chlorophenyl]-2-cyclobutylpropanoate

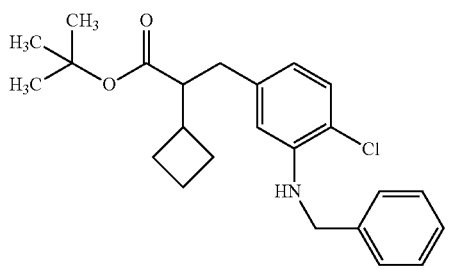 [SMILES: CC(C)(C)OC(=O)C(Cc1ccc(Cl)c(NCc2ccccc2)c1)C1CCC1]

Under argon, 848.6 mg (8.83 mmol) of sodium tert-butoxide, 337 mg (0.39 mmol) of tris(dibenzylidenacetone)dipalladium and 183 mg (0.29 mmol) of rac-2,2'-bis(diphenylphosphino)-1,1'-binaphthyl were weighed out into a dry flask, kept under high vacuum for 10 min and then vented with argon. 5 ml of abs. toluene, 0.96 ml (8.83 mmol) of benzylamine and a solution of 2.75 g (7.36 mmol) of (+/−)-tert-butyl 3-(3-bromo-4-chlorophenyl)-2-cyclobutylpropanoate in 5 ml of abs. toluene were added in succession. Three more times, the reaction mixture was evacuated and in each case vented with argon, and the mixture was then stirred at 110° C. for 3 h. After cooling, the reaction mixture was added to saturated aqueous ammonium chloride solution. The mixture was extracted three times with ethyl acetate. The organic phases were combined, dried over magnesium sulphate and concentrated under reduced pressure. The crude product was purified by chromatography on silica gel (mobile phase cyclohexane/dichloromethane 4:1 to 2:1, then pure dichloromethane) This gave 1.95 g of the title compound (65.1% of theory).

LC-MS (Method 4): $R_t$=1.90 min; m/z=400 (M+H)$^+$.

$^1$H-NMR (400 MHz, DMSO-d$_6$): δ [ppm]=1.26 (s, 9H), 1.54-1.76 (m, 4H), 1.78-1.86 (m, 2H), 2.19-2.38 (m, 2H), 2.38-2.45 (m, 2H), 4.33-4.44 (m, 2H), 5.95 (t, 1H), 6.25-6.40 (m, 2H), 7.11 (d, 1H), 7.23 (td, 1H), 7.27-7.37 (m, 4H).

The example below was obtained in an analogous manner

Example 159A tert-butyl 3-[3-(benzylamino)-4-chlorophenyl]-2-cyclopropylpropanoate

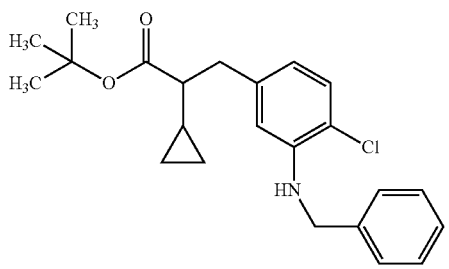 [SMILES: CC(C)(C)OC(=O)C(Cc1ccc(Cl)c(NCc2ccccc2)c1)C1CC1]

From tert-butyl 3-(3-bromo-4-chlorophenyl)-2-cyclopropylpropanoate and benzylamine, 2.51 g of the title compound were obtained (74.7% of theory).

LC-MS (Method 6): $R_t$=1.55 min; m/z=386 (M+H)$^+$.

Example 160A (+/−)-tert-butyl 3-(3-amino-4-chlorophenyl)-2-cyclobutylpropanoate

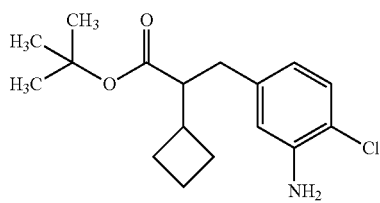

1.85 g (4.63 mmol) of (+/−)-tert-butyl 3-[3-(benzylamino)-4-chlorophenyl]-2-cyclobutylpropanoate were dissolved in 10 ml of ethyl acetate and deoxygenated with argon, and 98 mg (0.093 mmol) of palladium on carbon (10%) were added. The reaction mixture was stirred at RT under an atmosphere of hydrogen at atmospheric pressure for 4 h and then allowed to stand over the weekend. The mixture was filtered through celite, the residue was washed with ethyl acetate, the filtrate was concentrated under reduced pressure and the residue of the filtrate was dried under high vacuum. This residue (about 1:1 mixture of starting material and target product) was once more dissolved in about 10 ml of ethyl acetate and deoxygenated with argon, and once more 98 mg (0.093 mmol) of palladium on carbon (10%) were added. Again, the reaction mixture was stirred at RT under an atmosphere of hydrogen at atmospheric pressure for 4 h. The mixture was then filtered through celite, the residue was washed with ethyl acetate, the filtrate was concentrated under reduced pressure and the residue was dried under high vacuum. Chromatographic purification on silica gel (mobile phase cyclohexane/ethyl acetate 20:1) gave 1.12 g of the target product (78.2% of theory).

LC-MS (Method 6): $R_t$=1.34 min; m/z=310 (M+H)$^+$, 254 (M−C$_4$H$_7$)$^+$.

$^1$H-NMR (400 MHz, DMSO-d$_6$): δ [ppm]=1.29 (s, 9H), 1.68-1.86 (m, 4H), 1.87-1.95 (m, 1H), 1.96-2.07 (m, 1H), 2.32-2.48 (m, 4H), 5.21 (s, 2H), 6.33 (dd, 1H), 6.57 (d, 1H), 7.04 (d, 1H).

The racemate obtained above was separated into the enantiomers by preparative HPLC on a chiral phase [column: Daicel Chiralpak AD-H, 5 μm, 250 mm×20 mm; flow rate: 20 ml/min; detection: 230 nm; injection volume: 0.80 ml; temperature: 25° C.; mobile phase: 95% isohexane/5% ethanol]. 790 mg of racemate gave 318 mg of enantiomer 1 (Example 161A) and 339 mg of enantiomer 2 (Example 162A):

Example 161A tert-butyl 3-(3-amino-4-chlorophenyl)-2-cyclobutylpropanoate (enantiomer 1)

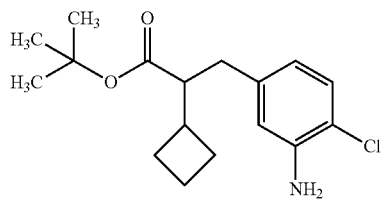

Yield: 318 mg

LC-MS (Method 4): $R_t$=1.70 min; m/z=254 (M−C$_4$H$_7$)$^+$.

$^1$H-NMR (400 MHz, DMSO-d$_6$): δ [ppm]=1.29 (s, 9H), 1.68-1.85 (m, 4H), 1.87-1.94 (m, 1H), 1.96-2.06 (m, 1H), 2.31-2.48 (m, 4H), 5.21 (s, 2H), 6.33 (dd, 1H), 6.57 (d, 1H), 7.04 (d, 1H).

Example 162A tert-butyl 3-(3-amino-4-chlorophenyl)-2-cyclobutylpropanoate (enantiomer 2)

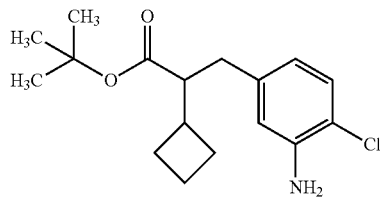 [SMILES: CC(C)(C)OC(=O)C(Cc1ccc(Cl)c(N)c1)C1CCC1]

Yield: 339 mg

LC-MS (Method 4): $R_t$=1.71 min; m/z=254 (M−C$_4$H$_7$)$^+$.

$^1$H-NMR (400 MHz, DMSO-$d_6$): δ [ppm]=1.29 (s, 9H), 1.67-1.84 (m, 4H), 1.87-1.94 (m, 1H), 1.95-2.05 (m, 1H), 2.32-2.48 (m, 4H), 5.22 (s, 2H), 6.33 (dd, 1H), 6.57 (d, 1H), 7.04 (d, 1H).

Example 163A (+/−)-tert-butyl 3-(3-amino-4-chlorophenyl)-2-cyclopropylpropanoate

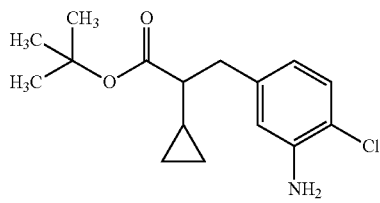

2.50 g (4.63 mmol) of (+/−)-tert-butyl 3-[3-(benzylamino)-4-chlorophenyl]-2-cyclopropylpropanoate were dissolved in 160 ml of ethyl acetate, the mixture was deoxygenated with argon and 150 mg of palladium on carbon (10%) were added. The reaction mixture was stirred at RT under an atmosphere of hydrogen at atmospheric pressure for 8 h. The mixture was then filtered through celite, the residue was washed with ethyl acetate, the filtrate was concentrated under reduced pressure and the residue was dried under high vacuum. The residue was purified by chromatography on silica gel (mobile phase pure cyclohexane to cyclohexane/ethyl acetate 20:1). This gave 1.41 g of the target product (73.6% of theory).

LC-MS (Method 6): $R_t$=1.28 min; m/z=240 (M−$C_4H_7$)$^+$.

$^1$H-NMR (400 MHz, DMSO-$d_6$): δ [ppm]=0.10-0.18 (m, 1H), 0.19-0.26 (m, 1H), 0.37-0.52 (m, 2H), 0.79-0.92 (m, 1H), 1.30 (s, 9H), 1.73 (td, 1H), 2.65-2.74 (m, 2H), 5.10-5.25 (m, 2H), 6.35 (dd, 1H), 6.59 (d, 1H), 6.99-7.06 (m, 1H).

Example 164A

Methyl 3-(3-amino-4-chlorophenyl)hex-2-enoate and methyl 3-(3-amino-4-chlorophenyl)hex-3-enoate

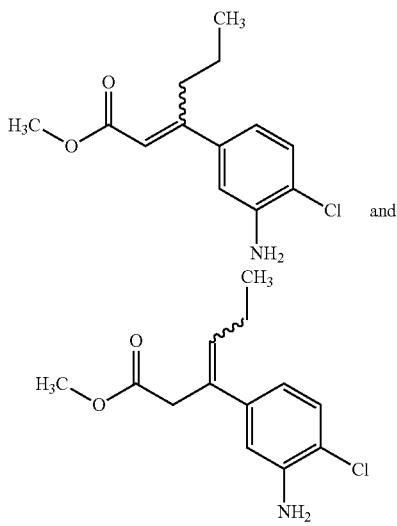

33.8 ml (242.2 mmol) of triethylamine were added to a mixture of 10.0 g (48.4 mmol) of 5-bromo-2-chloraniline and 8.69 g (67.8 mmol) of methyl (2E)-hex-2-enoate in 100 ml of DMF. Three times, the mixture was evacuated and in each case vented with argon. After addition of 1.09 g (4.84 mmol) of palladium(II) acetate and 2.95 g (9.69 mmol) of tri-2-tolylphosphine, the mixture was evacuated two more times and in each case vented with argon, and the reaction mixture was then stirred at 150° C. for 4 h. After cooling, the mixture was added to water, saturated with sodium chloride and extracted three times with ethyl acetate. The combined organic phases were dried over magnesium sulphate and concentrated under reduced pressure, finally under high vacuum. The residue was purified by chromatography on silica gel (mobile phase cyclohexane/ethyl acetate 50:1). This gave 7.70 g of a mixture of the two title compounds (62.7% of theory, ratio about 1.5:1 in favour of the α,β-unsaturated isomer).

LC-MS (Method 6): Methyl 3-(3-amino-4-chlorophenyl)hex-2-enoate: $R_t$=1.04 min, m/z=254 (M+H)$^+$; methyl 3-(3-amino-4-chlorophenyl)hex-3-enoate: $R_t$=1.12 min, m/z=254 (M+H)$^+$.

$^1$H-NMR (400 MHz, DMSO-$d_6$): Methyl 3-(3-amino-4-chlorophenyl)hex-2-enoate: δ [ppm]=0.85 (t, 3H), 1.29-1.41 (m, 2H), 2.92-3.00 (m, 2H), 3.46 (s, 3H), 5.45 (s, 2H), 5.98 (s, 1H), 6.69 (dd, 1H), 6.94 (d, 1H), 7.20 (d, 1H).

$^1$H-NMR (400 MHz, DMSO-$d_6$): Methyl 3-(3-amino-4-chlorophenyl)hex-3-enoate: δ [ppm]=1.00 (t, 3H), 2.15 (quin, 2H), 3.56 (s, 3H), 3.66 (s, 2H), 5.26-5.31 (m, 2H), 5.84 (t, 1H), 6.54 (dd, 1H), 6.79 (d, 1H), 7.09 (d, 1H).

Example 165A (+/−)-Methyl 3-(3-amino-4-chlorophenyl)hexanoate

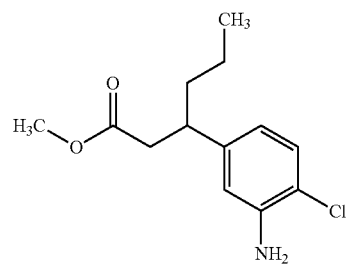 [SMILES: CCCC(CC(=O)OC)c1ccc(Cl)c(N)c1]

7.70 g (30.3 mmol) of the mixture of methyl 3-(3-amino-4-chlorophenyl)hex-2-enoate and methyl 3-(3-amino-4-chlorophenyl)hex-3-enoate (about 1.5:1, Example 164A) were dissolved in 45 ml of ethyl acetate, 646 mg (0.303 mmol) of palladium on carbon (5%) were added and the mixture was stirred under an atmosphere of hydrogen at atmospheric pressure and RT. After 10 h, the reaction mixture was filtered off through celite, the residue was washed with ethyl acetate and the filtrate was concentrated. The residue was taken up in about 50 ml of ethyl acetate, another about 650 mg of palladium on carbon (5%) were added and the mixture was stirred under an atmosphere of hydrogen at atmospheric pressure and RT. After a further 36 h, the reaction mixture was once more filtered off through celite, the residue was washed with ethyl acetate and the filtrate was concentrated. The residue was taken up in 800 ml of ethyl acetate, once more about 650 mg of palladium on carbon (5%) were added and the mixture was stirred under an atmosphere of hydrogen at atmospheric pressure and RT for 24 h. Again, the reaction mixture was filtered off through celite, the residue was washed with ethyl acetate and the filtrate was concentrated. The residue was purified by chromatography on silica gel (mobile phase cyclohexane/ethyl acetate 50:1 to 10:1). This gave a total of 4.79 g of a mixture of target product and starting material. This mixture was dissolved in 180 ml of ethyl acetate, another 603 mg (0.566 mmol) of palladium on carbon (10%) were added and the mixture was stirred under an atmosphere of hydrogen at atmospheric pressure and RT overnight. The reaction mixture was filtered off through celite, the residue was washed with ethyl acetate, the filtrate was concentrated and the residue was dried under high vacuum. This gave 4.45 g (about 57% of theory) of the target product.

LC-MS (Method 4): $R_t$=1.50 min; m/z=256 (M+H)$^+$.

$^1$H-NMR (400 MHz, DMSO-$d_6$): δ [ppm]=0.80 (t, 3H), 1.03-1.15 (m, 2H), 1.39-1.56 (m, 2H), 2.46 (dd, 1H), 2.59 (dd, 1H), 2.78-2.89 (m, 1H), 3.50 (s, 3H), 5.22 (br. s, 2H), 6.39 (dd, 1H), 6.61 (d, 1H), 7.06 (d, 1H).

Example 166A and Example 167A

Methyl 3-(3-amino-4-chlorophenyl)pent-2-enoate and methyl 3-(3-amino-4-chlorophenyl)pent-3-enoate

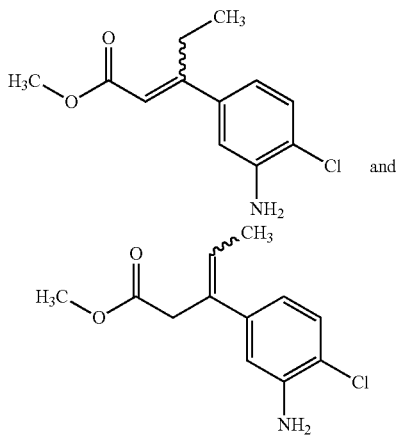

16.9 ml (121 mmol) of triethylamine were added to a mixture of 5.0 g (24.2 mmol) of 5-bromo-2-chloraniline and 5.53 g (48.4 mmol) of methyl 2-pentenoate in 50 ml of DMF. Three times, the mixture was evacuated and in each case vented with argon. After addition of 544 mg (2.42 mmol) of palladium(II) acetate and 1.47 g (4.84 mmol) of tri-2-tolylphosphine, the mixture was evacuated two more times and in each case vented with argon, and the reaction mixture was then stirred at 150° C. for 6 h. After cooling, the mixture was kept at RT overnight and then added to water. The mixture was extracted three times with ethyl acetate. The organic phases were combined, dried over magnesium sulphate, concentrated under reduced pressure and the residue was dried under high vacuum. The residue gave, by chromatography on silica gel (mobile phase cyclohexane/ethyl acetate 50:1 to 10:1), the two isomeric target products in separated form. This gave 0.85 g of methyl 3-(3-amino-4-chlorophenyl)pent-2-enoate (14.6% of theory) and 3.05 g of methyl 3-(3-amino-4-chlorophenyl)pent-3-enoate (52.5% of theory).

Methyl 3-(3-amino-4-chlorophenyl)pent-2-enoate

Example 166A

LC-MS (Method 6): $R_t$=1.09 min; m/z=240 (M+H)$^+$.

$^1$H-NMR (400 MHz, DMSO-$d_6$): δ [ppm]=0.97 (t, 3H), 2.98 (q, 2H), 3.66 (s, 3H), 5.45 (s, 2H), 5.96 (s, 1H), 6.70 (dd, 1H), 6.95 (d, 1H), 7.21 (d, 1H).

Methyl 3-(3-amino-4-chlorophenyl)pent-3-enoate

Example 167A

LC-MS (Method 6): $R_t$=1.00 min; m/z=240 (M+H)$^+$.

$^1$H-NMR (400 MHz, DMSO-$d_6$): δ [ppm]=1.75 (d, 3H), 3.47 (s, 2H), 3.56 (s, 3H), 5.28 (s, 2H), 5.94 (q, 1H), 6.54 (dd, 1H), 6.77 (d, 1H), 7.09 (d, 1H).

Example 168A (+/−)-Methyl 3-(3-amino-4-chlorophenyl)pentanoate

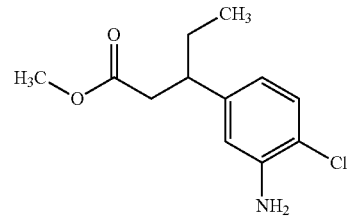 [SMILES: CCC(CC(=O)OC)c1ccc(Cl)c(N)c1]

3.05 g (12.7 mmol) of methyl 3-(3-amino-4-chlorophenyl)pent-3-enoate and 0.85 g (3.55 mmol) of methyl 3-(3-amino-4-chlorophenyl)pent-2-enoate were dissolved together in 500 ml of ethyl acetate, 346 mg (0.325 mmol) of palladium on carbon (10%) were added and the mixture was stirred at RT under an atmosphere of hydrogen at atmospheric pressure overnight. The reaction mixture was then filtered off through celite, the residue was washed with ethyl acetate and the filtrate was concentrated. Drying of the residue under high vacuum gave 3.73 g of the target product (94.8% of theory).

GC-MS (Method 1): $R_t$=6.07 min; m/z=242 (M)$^+$.

$^1$H-NMR (400 MHz, DMSO-$d_6$): δ [ppm]=0.71 (t, 3H), 1.42-1.49 (m, 1H), 1.55-1.61 (m, 1H), 2.42-2.48 (m, 1H), 2.60 (dd, 1H), 2.68-2.78 (m, 1H), 3.50 (s, 3H), 5.22 (s, 2H), 6.39 (dd, 1H), 6.61 (d, 1H), 7.05-7.08 (m, 1H).

Example 169A

Ethyl (3R)-2-(4-chloro-2-fluorophenyl)-4,4,4-trifluoro-3-methylbutanoate (diastereomer mixture)

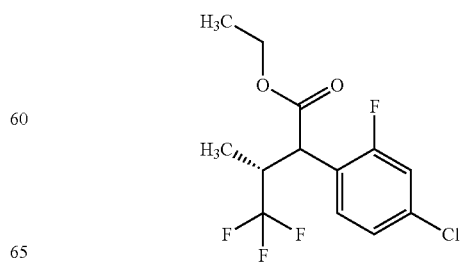

81.5 ml (81.5 mmol) of a 1 M solution of lithium hexamethyldisilazide in toluene were cooled to −20° C., and a solution of 10.0 g (50.3 mmol) of ethyl (3R)-4,4,4-trifluoro-3-methylbutanoate in 50 ml of abs. toluene was added dropwise. The mixture was stirred for 10 min At −20° C., a solution, prepared beforehand, of 14.8 g (70.6 mmol) of 1-bromo-4-chloro-2-fluorobenzene, 366 mg (1.63 mmol) of palladium(II) acetate and 1.35 g (3.42 mmol) of 2-dicyclohexylphosphino-2'-(N,N-dimethylamino)biphenyl in 50 ml of abs. toluene was then added dropwise. After the addition had ended, cooling was removed and the resulting reaction mixture was initially stirred at RT for 1 h and then at 80° C. overnight. After cooling, the mixture was filtered through celite, the residue was washed repeatedly with toluene and the filtrate obtained was concentrated under reduced pressure. The residue gave, after chromatography on silica gel (mobile phase cyclohexane/ethyl acetate 100:1→100:4), 4.26 g of the title compound (25.1% of theory).

GC-MS (Method 1): $R_t$=4.21 min; m/z=312 (M)$^+$.

The example below was obtained in an analogous manner:

Example 170A

Ethyl (3R)-2-(4-chloro-3-fluorophenyl)-4,4,4-trifluoro-3-methylbutanoate (diastereomer mixture)

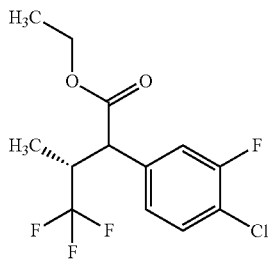

From 2.0 g of ethyl (3R)-4,4,4-trifluoro-3-methylbutanoate and 2.96 g of 1-bromo-4-chloro-3-fluorobenzene, 2.47 g of the target compound were obtained.

GC-MS (Method 1): $R_t$=4.33 min+4.36 min; both m/z=312 (M)$^+$.

$^1$H-NMR (400 MHz, DMSO-d$_6$): major diastereomer δ [ppm]=0.80 (d, 3H), 1.08-1.19 (m, 3H), 3.34-3.41 (m, 1H), 3.88 (d, 1H), 4.01-4.18 (m, 2H), 7.28-7.34 (m, 1H), 7.51-7.64 (m, 2H).

Example 171A

Ethyl (3R)-2-(4-chloro-2-methylphenyl)-4,4,4-trifluoro-3-methylbutanoate (diastereomer mixture)

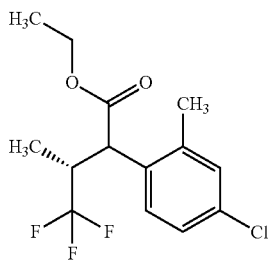 [SMILES: CCOC(=O)C(c1ccc(Cl)cc1C)[C@@H](C)C(F)(F)F]

22.5 ml (22.5 mmol) of a 1 M solution of lithium hexamethyldisilazide in toluene were cooled to −20° C., and a solution of 2.76 g (50.3 mmol) of ethyl (3R)-4,4,4-trifluoro-3-methylbutanoate in 15 ml of abs. toluene was added dropwise. The mixture was stirred for 10 min. At −20° C., a solution, prepared beforehand, of 4.0 g (19.5 mmol) of 2-bromo-5-chlorotoluene, 101 mg (0.45 mmol) of palladium (II) acetate and 371 mg (0.94 mmol) of 2-dicyclohexylphosphino-2'-(N,N-dimethylamino)biphenyl in 15 ml of abs. toluene was then added dropwise. After the addition had ended, cooling was removed and the resulting reaction mixture was stirred initially at RT for 1 h and then at 100° C. overnight. After cooling, the mixture was filtered through celite, the residue was washed repeatedly with toluene and the filtrate obtained was concentrated under reduced pressure. This gave 3.10 g of the title compound as a crude product which was directly reacted further.

GC-MS (Method 1): $R_t$=4.72 min; m/z=308 (M)$^+$.

Example 172A

Ethyl (3R)-2-(4-chloro-3-methylphenyl)-4,4,4-trifluoro-3-methylbutanoate (diastereomer mixture)

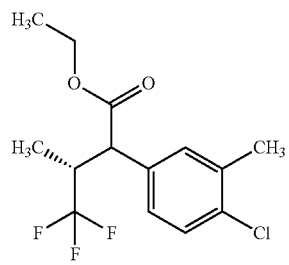 [SMILES: CCOC(=O)C(c1ccc(Cl)c(C)c1)[C@@H](C)C(F)(F)F]

29.2 ml (29.2 mmol) of a 1 M solution of lithium hexamethyldisilazide in toluene were cooled to −10° C., and a solution of 4.30 g (23.4 mmol) of ethyl (3R)-4,4,4-trifluoro-3-methylbutanoate in 26 ml of abs. toluene was added dropwise. The mixture was stirred for 10 min At −10° C., a solution, prepared beforehand, of 5.0 g (19.5 mmol, 80% pure) of 5-bromo-2-chlorotoluene, 131 mg (0.58 mmol) of palladium(II) acetate and 483 mg (1.23 mmol) of 2-dicyclohexylphosphino-2'-(N,N-dimethylamino)biphenyl in 26 ml of abs. toluene was then added dropwise. The resulting reaction mixture was initially stirred at RT for 1 h and then at 80° C. for 4 h. After cooling, the mixture was diluted with ethyl acetate, washed twice with sat. aqueous sodium bicarbonate solution and once with sat. sodium chloride solution, dried over sodium sulphate and concentrated under reduced pressure. This gave 7.80 g of the title compound as a crude product which was directly reacted further.

LC-MS (Method 4): $R_t$=1.55 min; m/z=309 (M+H)$^+$.

The example below was obtained in an analogous manner

Example 173A

Ethyl (3R)-2-(3,4-dichlorophenyl)-4,4,4-trifluoro-3-methylbutanoate (diastereomer mixture)

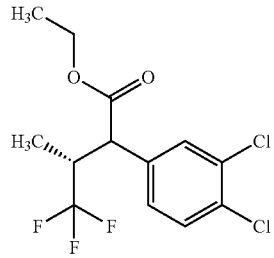 [SMILES: CCOC(=O)C(c1ccc(Cl)c(Cl)c1)[C@@H](C)C(F)(F)F]

From 3.91 g of ethyl (3R)-4,4,4-trifluoro-3-methylbutanoate and 5.0 g of 4-bromo-1,2-dichloro-benzene, 7.54 g of the target compound were obtained as a crude product.

LC-MS (Method 4): $R_t$=1.54 min; m/z=329 (M+H)$^+$.

$^1$H-NMR (400 MHz, DMSO-$d_6$): both diastereomers δ [ppm]=0.80/1.17 (2d, together 3H), 1.10-1.15 (m, 3H), 3.30-3.41 (m, 1H), 3.89/3.94 (2d, together 1H), 4.01-4.18 (m, 2H), 7.38-7.48 (m, about 1H), 7.59-7.68 (m, about 1H), 7.74/7.75 (2d, together 1H).

Example 174A (3R)-2-(4-Chloro-2-fluorophenyl)-4,4,4-trifluoro-3-methylbutanoic acid (diastereomer mixture)

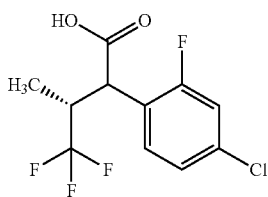 [SMILES: C[C@H](C(C(=O)O)c1ccc(Cl)cc1F)C(F)(F)F]

4.26 g (13.6 mmol) of ethyl (3R)-2-(4-chloro-2-fluorophenyl)-4,4,4-trifluoro-3-methylbutanoate (diastereomer mixture) were dissolved in a mixture of 22 ml of methanol, 22 ml of THF and 11 ml of water, and 10.9 g of 50% strength aqueous sodium hydroxide solution were added at 0° C. The reaction mixture was stirred at RT overnight. Most of the organic solvents were then removed under reduced pressure. The mixture that remained was diluted with water and extracted with diethyl ether. After phase separation, the organic phase was discarded and the aqueous phase was acidified with semiconcentrated hydrochloric acid (pH about 2) and extracted repeatedly with ethyl acetate. The combined ethyl acetate phases were dried over sodium sulphate and concentrated under reduced pressure. This gave 3.38 g (76.7% of theory) of the target product as a mixture of diastereomers which could be used without further purification for subsequent reactions.

LC-MS (Method 4): $R_t$=1.25 min; m/z=283 (M−H)$^-$.

$^1$H-NMR (400 MHz, DMSO-$d_6$): major diastereomer δ [ppm]=0.87 (d, 3H), 3.27-3.37 (m, 1H), 4.02 (d, 1H), 7.35 (dd, 1H), 7.45-7.52 (m, 2H), 13.02 (br. s, 1H).

The two carboxylic acids below were obtained in an analogous manner:

Example 175A (3R)-2-(4-Chloro-3-fluorophenyl)-4,4,4-trifluoro-3-methylbutanoic acid (diastereomer mixture)

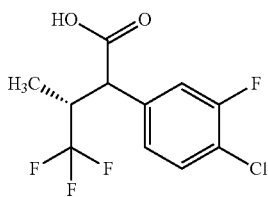 [SMILES: C[C@H](C(C(=O)O)c1ccc(Cl)c(F)c1)C(F)(F)F]

Diastereomer ratio about 1:1.
GC-MS (Method 1): $R_t$=4.79 min; m/z=284 (M)$^+$.

$^1$H-NMR (400 MHz, DMSO-$d_6$): both diastereomers δ [ppm]=0.80/1.19 (2d, together 3H), 3.18-3.29 (m, 1H), 3.74/3.77 (2dd, together 1H), 7.28 (d, 1H), 7.43-7.65 (m, 2H), 12.91/13.24 (2 br. s, together 1H).

Example 176A (3R)-2-(4-Chloro-3-methylphenyl)-4,4,4-trifluoro-3-methylbutanoic acid (diastereomer mixture)

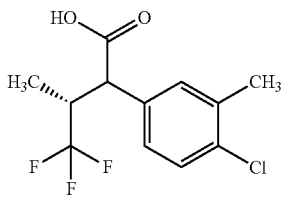 [SMILES: Cc1cc(C(C(=O)O)[C@@H](C)C(F)(F)F)ccc1Cl]

Diastereomer ratio about 5:1.

$^1$H-NMR (400 MHz, DMSO-$d_6$): both diastereomers δ [ppm]=0.78/1.11 (2d, together 3H), 2.31/2.32 (2s, together 3H), 3.24-3.30 (m, 1H), 3.61/3.64 (2d, together 1H), 7.20-7.50 (m, 5H), 12.80 (br. s, 1H).

Example 177A (3R)-2-(4-Chloro-2-methylphenyl)-4,4,4-trifluoro-3-methylbutanoic acid (diastereomer mixture)

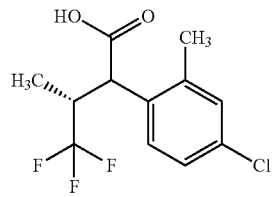 [SMILES: Cc1cc(Cl)ccc1C(C(=O)O)[C@@H](C)C(F)(F)F]

3.10 g (crude, about 10.04 mmol) of ethyl (3R)-2-(4-chloro-2-methylphenyl)-4,4,4-trifluoro-3-methylbutanoate (diastereomer mixture) were dissolved in a mixture of 10 ml of methanol, 10 ml of THF and 5 ml of water, and 8.03 g of 50% strength aqueous sodium hydroxide solution were added at 0° C. The reaction mixture was stirred at RT overnight. The mixture was then acidified with 1 N hydrochloric acid (pH about 2) and extracted three times with ethyl acetate. The combined organic phases were washed with sat. sodium chloride solution, dried over magnesium sulphate and concentrated under reduced pressure. The residue was purified by chromatography on silica gel (mobile phase cyclohexane/ethyl acetate 50:1 to 4:1). This gave 1.46 g (51.8% of theory) of the target product as a mixture of diastereomers (about 5:1).

GC-MS (Method 1): $R_t$=5.14 min; m/z=280 (M)$^+$.

$^1$H-NMR (400 MHz, DMSO-$d_6$): both diastereomers δ [ppm]=0.76/1.11 (2d, together 3H), 2.34/2.36 (2s, together 3H), 3.33-3.38 (m, about 1H, obscured), 3.81/3.88 (2d, together 1H), 7.27-7.41 (m, 3H), 12.81 (br. s, 1H).

Example 178A (3R)-2-(3,4-Dichlorophenyl)-4,4,4-trifluoro-3-methylbutanoic acid (diastereomer mixture)

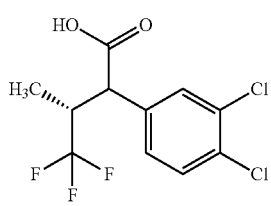 [SMILES: C[C@H](C(C(=O)O)c1ccc(Cl)c(Cl)c1)C(F)(F)F]

3.77 g (crude, about 11.5 mmol) of ethyl (3R)-2-(3,4-dichlorophenyl)-4,4,4-trifluoro-3-methylbutanoate (diastereomer mixture) were dissolved in a mixture of 14 ml of methanol, 14 ml of THF and 5 ml of water, and 9.16 g of 50% strength aqueous sodium hydroxide solution were added at 0° C. The reaction mixture was stirred at 40° C. for about 6 h. The mixture was then acidified with 1 N hydrochloric acid (pH about 2) and extracted three times with ethyl acetate. The combined organic phases were washed with sat. sodium chloride solution, dried over sodium sulphate and concentrated under reduced pressure. This gave 3.94 g of the target compound as a crude product which could be used without further purification for subsequent reactions.

$^1$H-NMR (400 MHz, DMSO-$d_6$): both diastereomers δ [ppm]=0.80/1.19 (2d, together 3H), 3.21-3.30 (m, 1H), 3.69-3.82 (m, 1H), 7.42 (dd, 1H), 7.63-7.67 (m, 1H), 7.70-7.73 (m, 1H), 12.97 (br. s, 1H).

Example 179A (3R)-2-(4-Chloro-2-fluorophenyl)-4,4,4-trifluoro-3-methylbutanoyl chloride (diastereomer mixture)

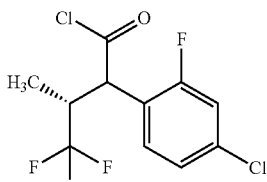

660 mg (2.32 mmol) of (3R)-2-(4-chloro-2-fluorophenyl)-4,4,4-trifluoro-3-methylbutanoic acid (diastereomer mixture) were dissolved in 2 ml of dichloromethane. After addition of a small drop of DMF, the reaction solution was cooled to from −5° C. to 0° C., and 0.4 ml (4.64 mmol) of oxalyl chloride was added dropwise. Cooling was removed and the reaction mixture was stirred at RT for 1 h until the evolution of gas had ceased. The mixture was then concentrated under reduced pressure. The residue was twice taken up in abs. dichloromethane, in each case reconcentrated under reduced pressure and the residue was finally dried under high vacuum. This gave 640 mg of the target product which was directly, without further purification, reacted further.

The examples below were prepared according to General Procedure 1 (HATU-mediated amide coupling of 4,4,4-trifluoro-3-methyl-2-phenylbutanoic acid derivatives with anilines in DMF using pyridine or N,N-diisopropylethylamine as base):

| Example | Name/Structure/Starting Materials | Analytical Data |
|---|---|---|
| 180A | (+)-tert-Butyl 3-(4-chloro-3-{[(2S,3R)-2-(4-chloro-3-fluorophenyl)-4,4,4-trifluoro-3-methylbutanoyl]-amino}phenyl)propanoate<br>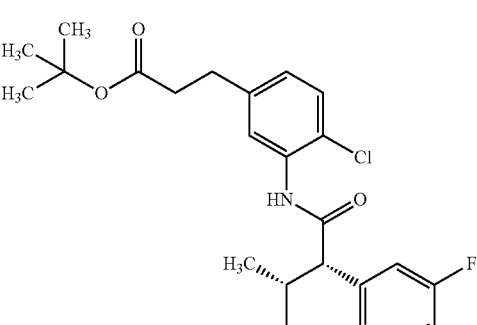<br>(from tert-butyl 3-(3-amino-4-chlorophenyl)propanoate and (3R)-2-(4-chloro-3-fluorophenyl)-4,4,4-trifluoro-3-methylbutanoic acid (diastereomer mixture)) | LC-MS (Method 6): $R_t$ = 1.44 min; m/z = 520 (M − H)$^-$.<br>$^1$H-NMR (400 MHz, DMSO-$d_6$): δ [ppm] = 0.83 (d, 3H), 1.30 (s, 9H), 2.42-2.48 (m, 2H), 2.76 (t, 2H), 3.35-3.46 (m, 1H), 4.09-4.19(m, 1H), 7.05 (dd, 1H), 7.26-7.41 (m, 3H), 7.49 (dd, 1H), 7.62 (t, 1H), 9.86 (s, 1H).<br>$[α]_D^{20}$ = +66.9°, c = 0.46, chloroform. |

| Example | Name/Structure/Starting Materials | Analytical Data |
|---|---|---|
| 181A | (+)-Ethyl (2S)-3-(4-chloro-3-{[(2S,3R)-2-(4-chloro-3-fluorophenyl)-4,4,4-trifluoro-3-methylbutanoyl]-amino}phenyl)-2-methylpropanoate<br>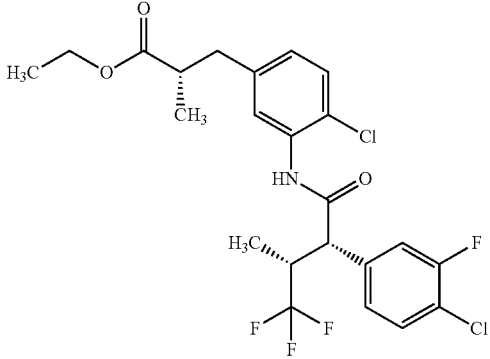<br>(from ethyl (+)-(2S)-3-(3-amino-4-chlorophenyl)-2-methylpropanoate and (3R)-2-(4-chloro-3-fluorophenyl)-4,4,4-trifluoro-3-methylbutanoic acid (diastereomer mixture)) | LC-MS (Method 6): $R_t$ = 1.40 min; m/z = 508 (M + H)$^+$.<br>$^1$H-NMR (400 MHz, DMSO-$d_6$): δ [ppm] = 0.83 (d, 3H), 1.01-1.10 (m, 6H), 2.60-2.71 (m, 2H), 2.74-2.84 (m, 1H), 3.35-3.49 (m, 1H), 3.96 (q, 2H), 4.15 (d, 1H), 7.00 (dd, 1H), 7.24-7.39 (m, 3H), 7.49 (dd, 1H), 7.62 (t, 1H), 9.87 (s, 1H).<br>$[α]_D^{20}$ = +98.6°, c = 0.45, chloroform. |
| 182A | (+)-Ethyl (2S)-3-(4-chloro-3-{[(2S,3R)-2-(4-chloro-2-methylphenyl)-4,4,4-trifluoro-3-methylbutanoyl]-amino}phenyl)-2-methylpropanoate<br>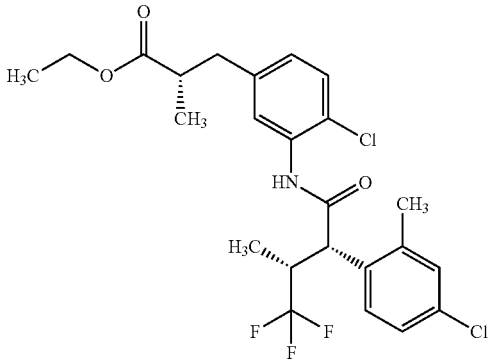<br>(from ethyl (+)-(2S)-3-(3-amino-4-chlorophenyl)-2-methylpropanoate and (3R)-2-(4-chloro-2-methyl-phenyl)-4,4,4-trifluoro-3-methylbutanoic acid (diastereomer mixture)) | LC-MS (Method 6): $R_t$ = 1.46 min; m/z = 504 (M + H)$^+$.<br>$^1$H-NMR (400 MHz, DMSO-$d_6$): δ [ppm] = 0.75 (d, 3H), 1.02-1.12 (m, 6H), 2.61-2.72 (m, 2H), 2.77-2.84 (m, 1H), 3.33-3.42 (m, 1H), 3.98 (q, 2H), 4.15 (d, 1H), 7.02 (dd, 1H), 7.24-7.30 (m, 2H), 7.32-7.38 (m, 2H), 7.52 (d, 1H), 9.88 (s, 1H).<br>$[α]_D^{20}$ = +112.3°, c = 0.40, chloroform. |

| Example | Name/Structure/Starting Materials | Analytical Data |
|---|---|---|
| 183A | tert-Butyl 3-(4-chloro-3-{[(2S,3R)-2-(4-chloro-3-methylphenyl)-4,4,4-trifluoro-3-methylbutanoyl]-amino}phenyl)propanoate<br>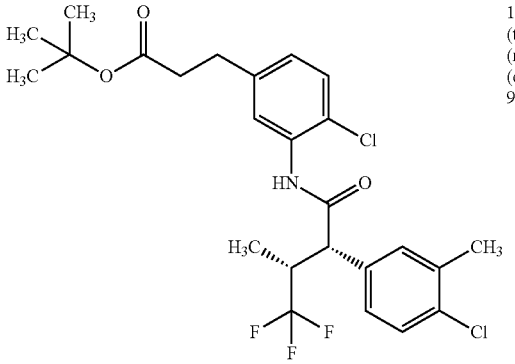<br>(from tert-butyl 3-(3-amino-4-chlorophenyl)-propanoate and (3R)-2-(4-chloro-3-methylphenyl)-4,4,4-trifluoro-3-methylbutanoic acid) | LC-MS (Method 4): $R_t$ = 1.69 min; m/z = 516/518 (M − H)−.<br>$^1$H-NMR (400 MHz, DMSO-$d_6$): δ [ppm] = 0.80 (d, 3H), 1.31 (s, 9H), 2.33 (s, 3H), 2.46 (t, 2H), 2.75 (t, 2H), 3.34-3.41 (m, 1H), 4.07 (d, 1H), 7.03 (dd, 1H), 7.27-7.45 (m, 5H), 9.80 (s, 1H). |
| 184A | Ethyl (2S)-3-(4-chloro-3-{[(2S,3R)-2-(4-chloro-3-methylphenyl)-4,4,4-trifluoro-3-methylbutanoyl]-amino}phenyl)-2-methylpropanoate<br>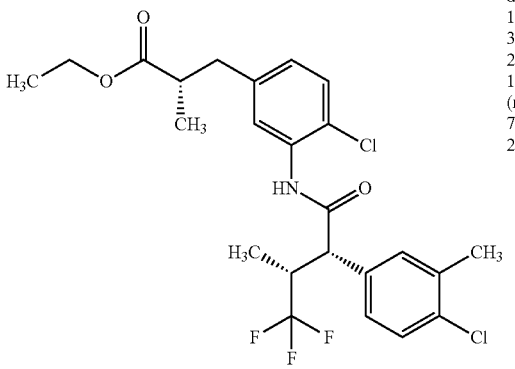<br>(from ethyl (+)-(2S)-3-(3-amino-4-chlorophenyl)-2-methylpropanoate and (3R)-2-(4-chloro-3-methylphenyl)-4,4,4-trifluoro-3-methylbutanoic acid) | LC-MS (Method 4): $R_t$ = 1.64 min; m/z = 502/504 (M − H)−.<br>$^1$H-NMR (400 MHz, DMSO-$d_6$): δ [ppm] = 0.80 (d, 3H), 1.02-1.09 (m, 6H), 2.33 (s, 3H), 2.59-2.72 (m, 2H), 2.74-2.85 (m, 1H), 3.34-3.44 (m, 1H), 3.96 (q, 2H), 4.04-4.11 (m, 1H), 6.99 (dd, 1H), 7.26-7.38 (m, 3H), 7.39-7.44 (m, 2H), 9.80 (s, 1H). |
| 185A | Ethyl (2S)-3-(4-chloro-3-{[(2S,3R)-2-(3,4-dichlorophenyl)-4,4,4-trifluoro-3-methylbutanoyl]-amino}phenyl)-2-methylpropanoate<br>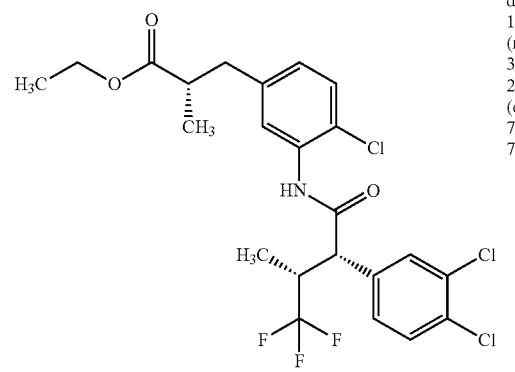<br>(from ethyl (+)-(2S)-3-(3-amino-4-chlorophenyl)-2-methylpropanoate and (3R)-2-(3,4-dichlorophenyl)-4,4,4-trifluoro-3-methylbutanoic acid) | LC-MS (Method 6): $R_t$ = 1.44 min; m/z = 524/526 (M + H)+.<br>$^1$H-NMR (400 MHz, DMSO-$d_6$): δ [ppm] = 0.83 (d, 3H), 1.01-1.08 (m, 6H), 2.60-2.70 (m, 2H), 2.75-2.83 (m, 1H), 3.35-3.48 (m, 1H), 3.96 (q, 2H), 4.09-4.16 (m, 1H), 7.01 (dd, 1H), 7.30-7.38 (m, 2H), 7.45 (dd, 1H), 7.67 (d, 1H), 7.72 (d, 1H), 9.87 (s, 1H). |

| Example | Name/Structure/Starting Materials | Analytical Data |
|---|---|---|
| 186A | tert-Butyl 3-(4-chloro-3-{[(2S,3R)-2-(3,4-dichlorophenyl)-4,4,4-trifluoro-3-methylbutanoyl]-amino}phenyl)propanoate<br>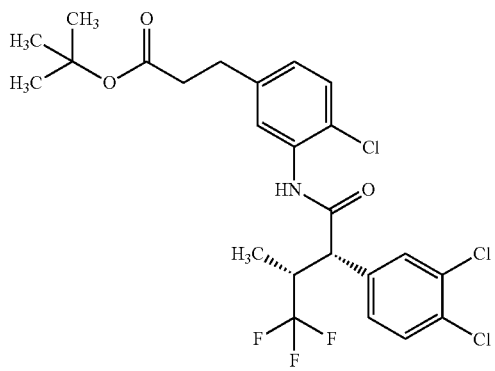<br>(from tert-butyl-3-(3-amino-4-chlorophenyl)-propanoate and (3R)-2-(3,4-dichlorophenyl)-4,4,4-trifluoro-3-methylbutanoic acid) | LC-MS (Method 6): $R_t$ = 1.48 min; m/z = 536/538 (M − H)⁻.<br>¹H-NMR (400 MHz, DMSO-$d_6$): δ [ppm] = 0.83 (d, 5H), 1.30 (s, 9H), 2.42-2.48 (m, 2H), 2.72-2.80 (m, 2H), 3.34-3.48 (m, 1H), 4.07-4.17 (m, 1H), 7.05 (dd, 1H), 7.31-7.39 (m, 2H), 7.45 (dd, 1H), 7.67 (d, 1H), 7.72 (d, 1H), 9.87 (s, 1H). |
| 187A | tert-Butyl 3-(4-chloro-3-{[(2S,3R)-2-(4-chlorophenyl)-4,4,4-trifluoro-3-methylbutanoyl]amino}-2-methylphenyl)-2-methylpropanoate (diastereomer mixture)<br>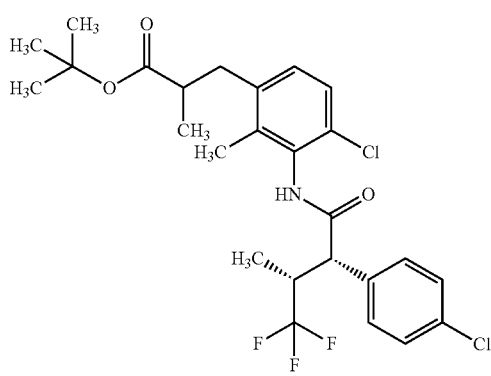 [SMILES: Cc1c(CC(C)C(=O)OC(C)(C)C)ccc(Cl)c1NC(=O)[C@H](c1ccc(Cl)cc1)[C@@H](C)C(F)(F)F]<br>(from (+/−)-tert-butyl 3-(3-amino-4-chloro-2-methylphenyl)-2-methylpropanoate and (+)-(2S,3R)-2-(4-chlorophenyl)-4,4,4-trifluoro-3-methylbutanoic acid) | LC-MS (Method 6): $R_t$ = 1.45 min; m/z = 530/532 (M − H)⁻.<br>¹H-NMR (400 MHz, DMSO-$d_6$): δ [ppm] = 0.80 (d, 3H), 1.03 (br. s, about 3H), 1.29 (s, about 9H), 1.51 (br. s, about 1H), 1.56 (br. s, about 1H), 2.15 (br. s, 1H), 2.77 (br. s, 1H), 3.34-3.43 (m, 1H), 3.86-4.02 (m, 1H), 6.97-7.08 (m, 1H), 7.15 (br. s, 1H), 7.23 (br. s, 1H), 7.38-7.53 (m, 5H), 9.87 (br. s, 1H) [because of rotamers, the signals are very broad]. |

-continued

| Example | Name/Structure/Starting Materials | Analytical Data |
|---------|-----------------------------------|-----------------|
| 188A | Ethyl 3-(3-{[(2S,3R)-2-(4-chlorophenyl)-4,4,4-trifluoro-3-methylbutanoyl]amino}-4-fluorophenyl)-4,4,4-trifluorobutanoate<br>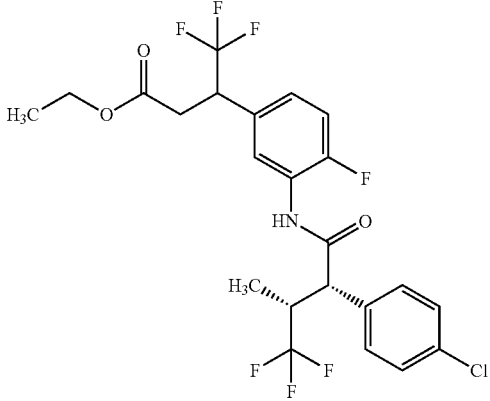 [SMILES: CCOC(=O)CC(c1ccc(F)c(NC(=O)[C@H](c2ccc(Cl)cc2)[C@@H](C)C(F)(F)F)c1)C(F)(F)F]<br>(from (+/−)-ethyl 3-(3-amino-4-fluorophenyl)-4,4,4-trifluorobutanoate and (+)-(2S,3R)-2-(4-chlorophenyl)-4,4,4-trifluoro-3-methylbutanoic acid) | LC-MS (Method 4): $R_t$ = 1.65 min; m/z = 526 (M − H)⁻.<br>¹H-NMR (400 MHz, DMSO-$d_6$): both diastereomers<br>δ [ppm] = 0.79 (d, 3H), 1.03 (t, 3H), 2.91 (dd, 1H), 3.03 (dd, 1H), 3.34-3.46 (m, 1H), 3.89-4.00 (m, 2H), 4.04-4.18 (m, 2H), 7.15-7.32 (m, 2H), 7.42-7.55 (m, 4H), 7.85-8.06 (m, 1H), 10.17 (s, 1H). |
| 189A | tert-Butyl 2-(4-chloro-3-{[(2S,3R)-2-(4-chlorophenyl)-4,4,4-trifluoro-3-methylbutanoyl]-amino)benzyl)-2-methylbutanoate (diastereomer mixture)<br>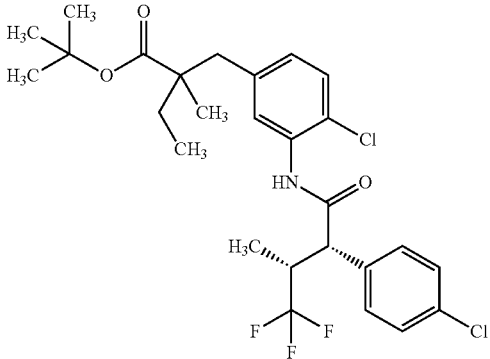 [SMILES: CCC(C)(Cc1ccc(Cl)c(NC(=O)[C@H](c2ccc(Cl)cc2)[C@@H](C)C(F)(F)F)c1)C(=O)OC(C)(C)C]<br>(from (+/−)-tert-butyl-2-(3-amino-4-chlorophenyl)-2-methylbutanoate and (+)-(2S,3R)-2-(4-chlorophenyl)-4,4,4-trifluoro-3-methylbutanoic acid) | LC-MS (Method 6): $R_t$ = 1.64 min; m/z = 544/546 (M − H)⁻.<br>'H-NMR (400 MHz, DMSO-$d_6$): both diastereomers<br>δ [ppm] = 0.74-0.84 (m, 6H), 0.88/0.91 (2d, together 3H), 1.22/1.32 (2s, together 9H), 1.32-1.40 (m, 1H), 1.58-1.68 (m, 1H), 2.57 (d, 1H), 2.84/2.85 (2d, together 1H), 3.35-3.43 (m, 1H), 4.03-4.08/4.10 (2d, together 1H), 6.95 (dd, 1H), 7.26-7.38 (m, 2H), 7.39-7.52 (m, 4H), 9.81/9.83 (2s, together 1H). |

| Example | Name/Structure/Starting Materials | Analytical Data |
|---|---|---|
| 190A | tert-Butyl 2-(4-chloro-3-{[(2S,3R)-2-(4-chlorophenyl)-4,4,4-trifluoro)-3-methylbutanoyl]-amino)benzyl)-2-methylbutanoate (diastereomer B)<br>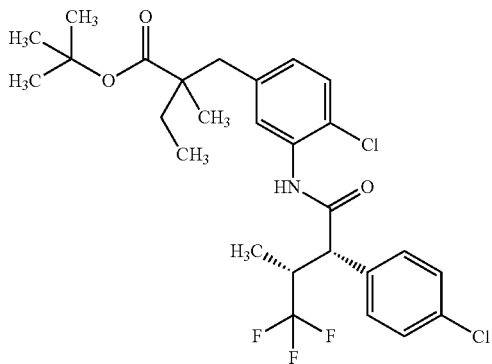 [SMILES: CCC(C)(Cc1ccc(Cl)c(NC(=O)[C@H](c2ccc(Cl)cc2)[C@@H](C)C(F)(F)F)c1)C(=O)OC(C)(C)C]<br>(from (+)-tert-butyl-2-(3-amino-4-chlorobenzyl)-2-methylbutanoate (enantiomer 2) and (+)-(2S,3R)-2-(4-chlorophenyl)-4,4,4-trifluoro-3-methylbutanoic acid) | LC-MS (Method 6): $R_t$ = 1.57 min; m/z = 544/546 (M − H)⁻.<br>¹H-NMR (400 MHz, DMSO-$d_6$): δ [ppm]= 0.75-0.82 (m, 6H), 0.88 (s, 3H), 1.22 (s, 9H), 1.27-1.38 (m, 1H), 1.56-1.70 (m, 1H), 2.54 (d, about 1H, obscured), 2.84 (d, 1H), 3.35-3.43 (m, 1H), 4.01-4.14 (m, 1H), 6.95 (d, 1H), 7.17-7.32 (m, 1H), 7.35 (d, 1H), 7.41-7.57 (m, 4H), 9.83 (s, 1H).<br>$[\alpha]_D^{20}$ = +68.0°, c = 0.280, chloroform. |
| 191A | tert-Butyl 3-(4-chloro-3-{[(2S,3R)-2-(4-chlorophenyl)-4,4,4-trifluoro-3-methylbutanoyl]-amino)phenyl)-4,4,4-trifluorobutanoate (diastereomer mixture)<br>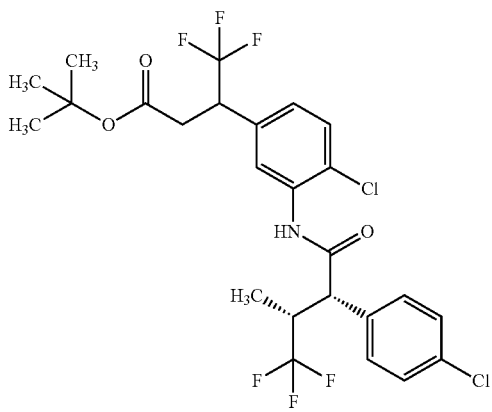 [SMILES: C[C@H]([C@H](C(=O)Nc1cc(C(CC(=O)OC(C)(C)C)C(F)(F)F)ccc1Cl)c1ccc(Cl)cc1)C(F)(F)F]<br>(from (+/−)-tert-butyl 3-(3-amino-4-chlorophenyl)-4,4,4-trifluorobutanoate and (+)-(2S,3R)-2-(4-chlorophenyl)-4,4,4-trifluoro-3-methylbutanoic acid) | LC-MS (Method 6): $R_t$ = 1.50 min; m/z = 570/572 (M − H)⁻.<br>¹H-NMR (400 MHz, DMSO-$d_6$): both diastereomers δ [ppm] = 0.80 (d, 3H), 1.21 (s, 9H), 2.74-2.81 (m, 1H), 2.88-2.99 (m, 1H), 3.34-3.46 (m, 1H), 3.95-4.10 (m, 1H), 4.11-4.19 (m, 1H), 7.25 (dd, 1H), 7.40-7.54 (m, 5H), 7.58-7.72 (m, 1H), 9.93/9.94 (2s, together 1H). |

-continued

| Example | Name/Structure/Starting Materials | Analytical Data |
|---|---|---|
| 192A | tert-Butyl 3-(4-chloro-3-{[(2S,3R)-2-(4-chlorophenyl)-4,4,4-trifluoro-3-methyl-butanoyl]amino}phenyl)-2-cyclobutylpropanoate (diastereomer mixture)<br>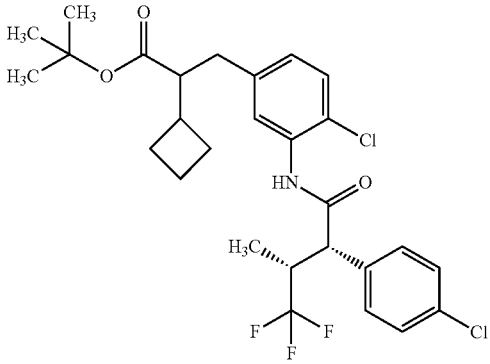 [SMILES: C[C@H]([C@H](C(=O)Nc1cc(CC(C(=O)OC(C)(C)C)C2CCC2)ccc1Cl)c1ccc(Cl)cc1)C(F)(F)F]<br>(from (+/−)-tert-butyl 3-(3-amino-4-chlorophenyl)-2-cyclobutylpropanoate and (+)-(2S,3R)-2-(4-chlorophenyl)-4,4,4-trifluoro-3-methylbutanoic acid) | LC-MS (Method 4): $R_t$ = 1.97 min; m/z = 556 (M − H)$^-$.<br>$^1$H-NMR (400 MHz, DMSO-$d_6$): both diastereomers δ [ppm] = 0.79 (d, 3H), 1.18/1.22 (2s, together 9H), 1.66-1.85 (m, 4H), 1.86-2.02 (m, 2H), 2.28-2.45 (m, 2H), 2.55-2.64 (m, 1H), 3.34-3.42 (m, 1H), 4.11/4.12 (2d, together 1H), 6.97/6.99 (2d, together 1H), 7.30-7.37 (m, 2H), 7.40-7.51 (m, 4H), 9.80/9.81 (2d, together 1H). |
| 193A | (+)-tert-Butyl 3-(4-chloro-3-{[(2S,3R)-2-(4-chlorophenyl)-4,4,4-trifluoro-3-methylbutanoyl]amino)-phenyl)-2-cyclobutylpropanoate (diastereomer A)<br>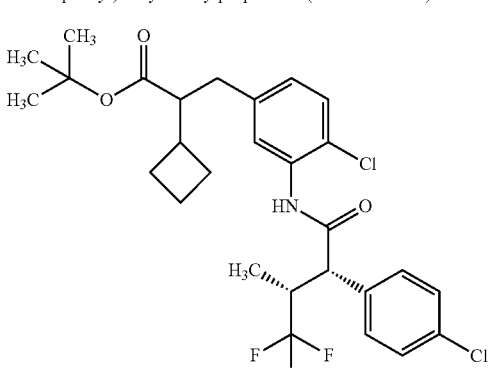<br>(from tert-butyl 3-(3-amino-4-chlorophenyl)-2-cyclobutylpropanoate (enantiomer 1) and (+)-(2S,3R)-2-(4-chlorophenyl)-4,4,4-trifluoro-3-methylbutanoic acid) | LC-MS (Method 6): $R_t$ = 1.67 min; m/z = 556 (M − H)$^-$.<br>$^1$H-NMR (400 MHz, DMSO-$d_6$): δ [ppm] = 0.79 (d, 3H), 1.22 (s, 9H), 1.68-1.82 (m, 4H), 1.86-1.93 (m, 1H), 1.94-2.03 (m, 1H), 2.31-2.47 (m, 2H), 2.56-2.63 (m, 2H), 3.36-3.43 (m, 1H), 4.12 (d, 1H), 6.98 (dd, 1H), 7.31-7.37 (m, 2H), 7.41-7.51 (m, 4H), 9.81 (s, 1H).<br>$[α]_D^{20}$ = +51.3°, c = 0.445, chloroform. |
| 194A | (+)-tert-Butyl 3-(4-chloro-3-{[(2S,3R)-2-(4-chlorophenyl)-4,4,4-trifluoro-3-methylbutanoyl]amino}-phenyl)-2-cyclobutylpropanoate (diastereomer B)<br>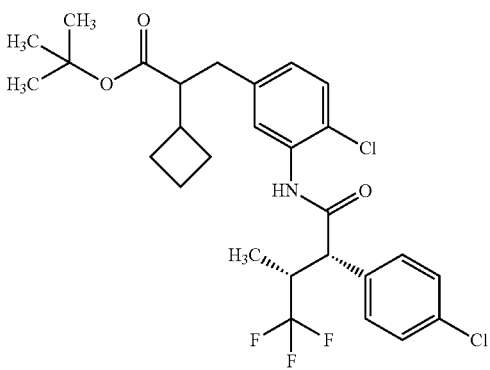 [SMILES: C[C@H]([C@H](C(=O)Nc1cc(CC(C(=O)OC(C)(C)C)C2CCC2)ccc1Cl)c1ccc(Cl)cc1)C(F)(F)F]<br>(from tert-butyl 3-(3-amino-4-chlorophenyl)-2-cyclobutylpropanoate (enantiomer 2) and (+)-(2S,3R)-2-(4-chlorophenyl)-4,4,4-trifluoro-3-methylbutanoic acid) | LC-MS (Method 6): $R_t$ = 1.58 min; m/z = 556 (M − H)$^-$.<br>$^1$H-NMR (400 MHz, DMSO-$d_6$): δ [ppm] = 0.79 (d, 3H), 1.18 (s, 9H), 1.67-1.83 (m, 4H), 1.84-1.93 (m, 1H), 1.94-2.02 (m, 1H), 2.31-2.44 (m, 2H), 2.57-2.64 (m, 1H), 3.35-3.42 (m, 1H), 4.08-4.14 (m, 1H), 6.98 (dd, 1H), 7.29-7.37 (m, 2H), 7.42-7.49 (m, 4H), 9.81 (s, 1H).<br>$[α]_D^{20}$ = +81.8°, c = 0.475, chloroform. |

| Example | Name/Structure/Starting Materials | Analytical Data |
|---|---|---|
| 195A | tert-Butyl 3-(4-chloro-3-{[(2S,3R)-2-(4-chloro-phenyl)-4,4,4-trifluoro-3-methylbutanoyl]-amino)phenyl)-2-cyclopropylpropanoate (diastereomer mixture)<br><br>(from (+/−)-tert-Butyl 3-(3-amino-4-chlorophenyl)-2-cyclopropylpropanoate and (+)-(2S,3R)-2-(4-chlorophenyl)-4,4,4-trifluoro-3-methylbutanoic acid) | LC-MS (Method 4): $R_t$ = 1.80 min; m/z = 542 (M − H)$^−$.<br>$^1$H-NMR (400 MHz, DMSO-$d_6$): both diastereomers δ [ppm] = 0.12-0.26 (m, 2H), 0.43 (q, 2H), 0.79 (d, 3H), 0.81-0.90 (m, 1H), 1.20/1.24 (2s, together 9H), 1.67-1.81 (m, 1H), 2.76-2.83 (m, 2H), 3.36-3.43 (m, 1H, 4.11/4.12 (2d, together 1H), 7.01 (dd, 1H), 7.30-7.39 (m, 2H), 7.41-7.51 (m, 4H), 9.78-9.85 (m, 1H). |

Example 196A (+)-Ethyl (2S)-3-(4-chloro-3-{[(2S,3R)-2-(4-chloro-2-fluorophenyl)-4,4,4-trifluoro-3-methylbutanoyl]amino}phenyl)-2-methylpropanoate

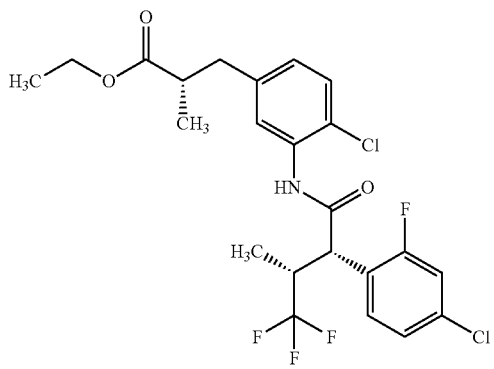 [SMILES: CCOC(=O)[C@@H](C)Cc1ccc(Cl)c(NC(=O)[C@H](c2ccc(Cl)cc2F)[C@@H](C)C(F)(F)F)c1]

280.7 mg (1.16 mmol) of ethyl (+)-(2S)-3-(3-amino-4-chlorophenyl)-2-methylpropanoate were dissolved in 1.5 ml of abs. THF, 0.26 ml (1.48 mmol) of N,N-diisopropylethylamine was added and, after cooling to −10° C., a solution of 320 mg (crude, about 1.06 mmol) of (3R)-2-(4-chloro-2-fluorophenyl)-4,4,4-trifluoro-3-methylbutanoyl chloride, prepared in situ, in 0.5 ml of abs. THF was added dropwise. After the addition had ended, the reaction mixture was stirred between −10° C. and 0° C. for 30 min After addition of a few drops of water, the mixture was then diluted with dichloromethane. The mixture was washed with 1 N hydrochloric acid and sat. sodium chloride solution, dried over magnesium sulphate and concentrated under reduced pressure. The crude product was purified initially by preparative RP-HPLC (mobile phase methanol/water) and then by chromatography on silica gel (mobile phase cyclohexane/ethyl acetate 40:1). This gave 144 mg of the target compound (26.9% of theory).

LC-MS (Method 6): $R_t$=1.42 min; m/z=508 (M+H)$^+$.
$^1$H-NMR (400 MHz, DMSO-$d_6$): δ [ppm]=0.86 (d, 3H), 1.02-1.12 (m, 6H), 2.63-2.72 (m, 2H), 2.76-2.86 (m, 1H), 3.34-3.44 (m, 1H), 3.93-4.02 (m, 2H), 4.36 (d, 1H), 7.03 (dd, 1H), 7.25-7.29 (m, 1H), 7.32-7.38 (m, 2H), 7.51 (dd, 1H), 7.61 (t, 1H), 10.02 (s, 1H).

$[α]_D^{20}$=+90°, c=0.30, chloroform.

Example 197A

Methyl 3-(4-chloro-3-{[(2S,3R)-2-(4-chlorophenyl)-4,4,4-trifluoro-3-methylbutanoyl]amino}-2-methylphenyl) propanoate

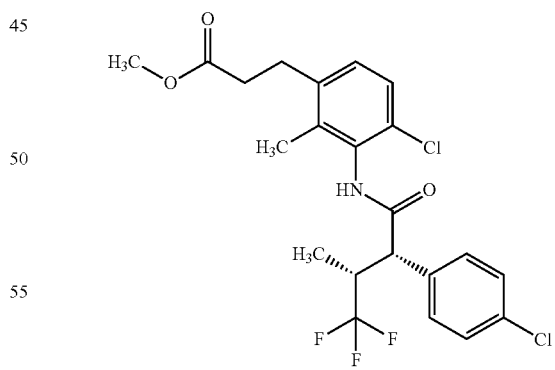

265 mg (1.16 mmol) of methyl 3-(3-amino-4-chloro-2-methylphenyl)propanoate were dissolved in 1.5 ml of abs. THF, 0.28 ml (1.63 mmol) of N,N-diisopropylethylamine was added and, after cooling to −10° C., a solution of 398 mg (crude, about 1.40 mmol) of (2S,3R)-2-(4-chlorophenyl)-4, 4,4-trifluoro-3-methylbutanoyl chloride, prepared in situ, in 0.5 ml of abs. THF was added dropwise. After the addition had ended, the reaction mixture was warmed from −10° C. to RT over 1 h and then diluted with ethyl acetate. The mixture was washed with 1 N hydrochloric acid and sat. sodium chloride solution, dried over magnesium sulphate and concentrated under reduced pressure. The crude product was purified by preparative RP-HPLC (mobile phase methanol/water). This gave 485 mg of the target compound (87.5% of theory).

LC-MS (Method 6): $R_t$=1.25 min; m/z=476 (M+H)$^+$.

Example 198A (+)-tert-Butyl (2R)-3-(4-chloro-3-{[(2S,3R)-2-(4-chlorophenyl)-4,4,4-trifluoro-3-methylbutanoyl]amino}-2-methylphenyl)-2-methylpropanoate

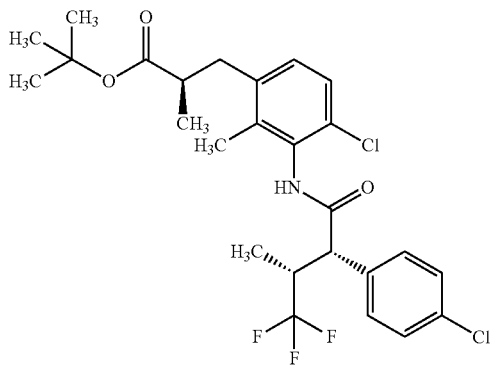

200 mg (0.705 mmol) of (−)-tert-Butyl (2R)-3-(3-amino-4-chloro-2-methylphenyl)-2-methylpropanoate were dissolved in 1 ml of abs. THF, 0.17 ml (0.987 mmol) of N,N-diisopropylethylamine was added and, after cooling to −10° C., a solution of 241 mg (crude, about 0.846 mmol) of (2S,3R)-2-(4-chlorophenyl)-4,4,4-trifluoro-3-methylbutanoyl chloride, prepared in situ, in 0.2 ml of abs. THF was added dropwise. After the addition had ended, the reaction mixture was warmed from −10° C. to RT over 2 h and then added to water. The aqueous phase was extracted three times with ethyl acetate, and the combined organic phases were washed with 1 N hydrochloric acid and sat. sodium chloride solution, dried over magnesium sulphate and concentrated under reduced pressure, and the residue was dried under high vacuum. This gave 282 mg of the target compound (75.2% of theory).

LC-MS (Method 6): $R_t$=1.45 min; m/z=530 (M−H)$^-$.

$^1$H-NMR (400 MHz, DMSO-$d_6$): δ [ppm]=0.80 (d, 3H), 1.03 (br. s, 3H), 1.30 (s, 9H), 1.50 (br. s, 1H), 2.15 (br. s, 1H), 2.42 (br. s, 1H), 2.69-2.92 (m, 1H), 3.34-3.45 (m, 1H), 3.94 (d, 1H), 7.03 (d, 1H), 7.23 (br. s, 1H), 7.45 (s, 4H), 9.83/9.91 (2 br. s, together 1H) [because of rotamers, the signals are very broad].

$[α]_D^{20}$=+68.9°, c=0.50, chloroform.

The example below was obtained in an analogous manner

Example 199A (+)-tert-Butyl (2S)-3-(4-chloro-3-{[(2S,3R)-2-(4-chlorophenyl)-4,4,4-trifluoro-3-methylbutanoyl]amino}-2-methylphenyl)-2-methylpropanoate

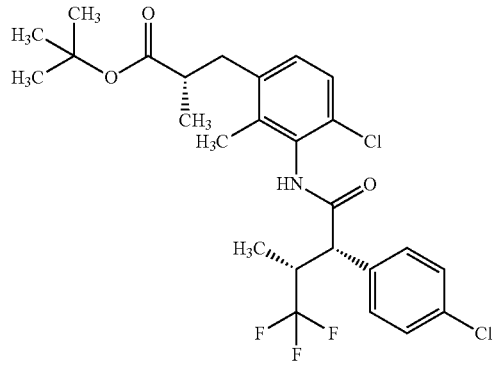

From 200 mg of (+)-tert-butyl (2S)-3-(3-amino-4-chloro-2-methylphenyl)-2-methylpropanoate and 241 mg of freshly prepared (2S,3R)-2-(4-chlorophenyl)-4,4,4-trifluoro-3-methylbutanoyl chloride, 287 mg of the target product were obtained (75.2% of theory).

LC-MS (Method 6): $R_t$=1.51 min; m/z=530 (M−H)$^-$.

$^1$H-NMR (400 MHz, DMSO-$d_6$): δ [ppm]=0.80 (d, 3H), 1.04 (br. s, 3H), 1.29 (s, 9H), 1.51 (br. s, 1H), 2.15 (br. s, 1H), 2.56-2.68 (m, 1H), 2.79 (br. s, 1H), 3.34-3.45 (m, 1H), 3.94 (br. d, 1H), 7.03 (d, 1H), 7.15 (br. s, 1H), 7.23 (br. s, 1H), 7.45 (s, 4H), 9.87 (br. s, 1H) [because of rotamers, the signals are very broad].

$[α]_D^{20}$=+116.1°, c=0.520, chloroform.

Example 200A (+)-tert-Butyl 2-(4-chloro-3-{[(2S,3R)-2-(4-chlorophenyl)-4,4,4-trifluoro-3-methylbutanoyl]amino}benzyl)-2-methylbutanoate (diastereomer A)

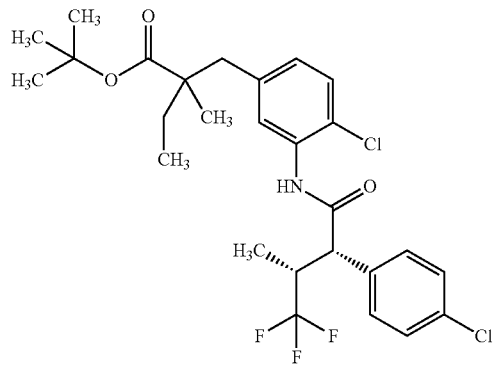 [SMILES: CCC(C)(Cc1ccc(Cl)c(NC(=O)[C@H](c2ccc(Cl)cc2)[C@@H](C)C(F)(F)F)c1)C(=O)OC(C)(C)C]

225 mg (0.756 mmol) of (−)-tert-butyl 2-(3-amino-4-chlorobenzyl)-2-methylbutanoate (enantiomer 1) and 231 mg (0.907 mmol) of (+)-(2S,3R)-2-(4-chlorophenyl)-4,4,4-trifluoro-3-methylbutanoic acid were dissolved in 0.9 ml of pyridine and 2.7 ml of DMF, and 345 mg (0.907 mmol) of HATU were added at RT. The reaction mixture was stirred at 45° C. overnight, and a further 0.5 eq. of (+)-(2S,3R)-2-(4-chlorophenyl)-4,4,4-trifluoro-3-methylbutanoic acid and 0.6 eq. of HATU were then added. The reaction mixture was stirred at 45° C. for another 3 h and then, after cooling, diluted with ethyl acetate. The mixture was washed with 1 N hydrochloric acid and sat. sodium chloride solution, dried over magnesium sulphate and concentrated under reduced pressure. The crude product was purified by preparative RP-HPLC (mobile phase acetonitrile/water) and subsequent chromatography on silica gel (mobile phase cyclohexane/ethyl acetate 40:1). This gave 177 mg of the target product (35.6% of theory).

LC-MS (Method 4): $R_t$=1.97 min; m/z=544 (M−H)⁻.

¹H-NMR (400 MHz, DMSO-$d_6$): δ [ppm]=0.76-0.83 (m, 6H), 0.91 (s, 3H), 1.31 (s, 9H), 1.33-1.40 (m, 1H), 1.57-1.67 (m, 1H), 2.57 (d, 1H), 2.85 (d, 1H), 3.35-3.43 (m, 1H), 4.07-4.13 (m, 1H), 6.95 (dd, 1H), 7.30-7.36 (m, 2H), 7.41-7.48 (m, 4H), 9.82 (s, 1H).

$[\alpha]_D^{20}$=+63.2°, c=0.365, chloroform.

Example 201A

Methyl 3-(4-chloro-3-{[(2S,3R)-2-(4-chlorophenyl)-4,4,4-trifluoro-3-methylbutanoyl]amino}-phenyl) hexanoate (diastereomer mixture)

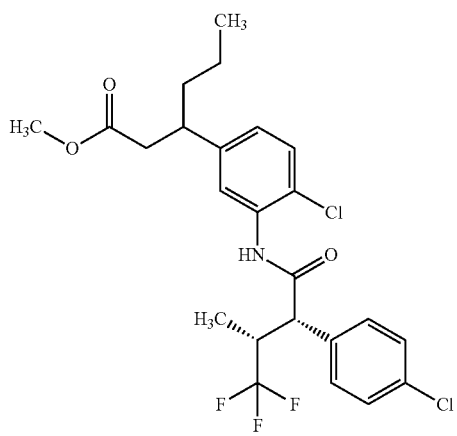 [SMILES: CCCC(CC(=O)OC)c1ccc(Cl)c(NC(=O)[C@H](c2ccc(Cl)cc2)[C@@H](C)C(F)(F)F)c1]

1.45 g (5.67 mmol) of (+/−)-methyl 3-(3-amino-4-chlorophenyl)hexanoate and 1.81 g (6.80 mmol) of (+)-(2S,3R)-2-(4-chlorophenyl)-4,4,4-trifluoro-3-methylbutanoic acid were dissolved in 5.0 ml of pyridine and 10.0 ml of DMF, and 2.80 g (7.37 mmol) of HATU were added at RT. The reaction mixture was stirred at RT overnight and then diluted with ethyl acetate. The mixture was washed with 1 N hydrochloric acid and sat. sodium chloride solution, dried over magnesium sulphate and concentrated under reduced pressure. The crude product was purified by chromatography on silica gel (mobile phase initially cyclohexane, then cyclohexane/ethyl acetate 50:1). In two fractions, in total 2.02 g of the target product were obtained (70.6% of theory).

LC-MS (Method 6): $R_t$=1.43 min; m/z=504 (M+H)⁺.

¹H-NMR (400 MHz, DMSO-$d_6$): both diastereomers δ [ppm]=0.74-0.85 (m, 6H), 0.98-1.16 (m, 2H), 1.42-1.61 (m, 2H), 2.49 (dd, about 1H, obscured), 2.64 (dd, 1H), 2.84-3.02 (m, 1H), 3.37-3.42 (m, 1H), 3.47/3.48 (2s, together 3H), 4.12 (d, 1H), 7.05 (dd, 1H), 7.31-7.38 (m, 2H), 7.41-7.55 (m, 4H), 9.83 (s, 1H).

Example 202A

Methyl 3-(4-chloro-3-{[(2S,3R)-2-(4-chlorophenyl)-4,4,4-trifluoro-3-methylbutanoyl]amino}-phenyl) pentanoate (diastereomer mixture)

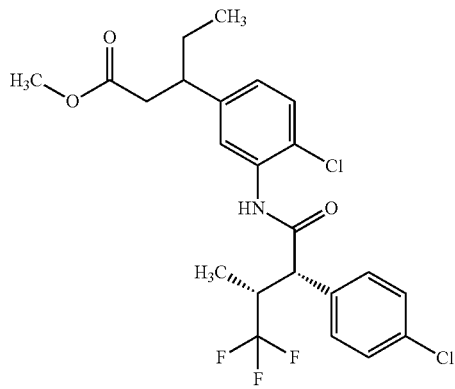 [SMILES: CCC(CC(=O)OC)c1ccc(Cl)c(NC(=O)[C@H](c2ccc(Cl)cc2)[C@@H](C)C(F)(F)F)c1]

500 mg (2.07 mmol) of (+/−)-methyl 3-(3-amino-4-chlorophenyl)pentanoate and 668.9 mg (2.48 mmol) of (+)-(2S,3R)-2-(4-chlorophenyl)-4,4,4-trifluoro-3-methylbutanoic acid were dissolved in 1.7 ml of pyridine and 3.3 ml of DMF, and 1.02 g (2.69 mmol) of HATU were added at RT. The reaction mixture was stirred at RT overnight and then diluted with ethyl acetate. The mixture was washed with 1 N hydrochloric acid and sat. sodium chloride solution, dried over magnesium sulphate and concentrated under reduced pressure. The crude product was purified by chromatography on silica gel (mobile phase initially cyclohexane, then cyclohexane/ethyl acetate 50:1). This gave 675 mg of the target product (66.6% of theory).

LC-MS (Method 6): $R_t$=1.39 min; m/z=490 (M−H)⁻.

¹H-NMR (400 MHz, DMSO-$d_6$): both diastereomers δ [ppm]=0.65-0.74 (m, 3H), 0.80 (d, 3H), 1.43-1.67 (m, 2H), 2.49 (dd, about 1H, obscured), 2.65 (dd, 1H), 2.80-2.92 (m, 1H), 3.35-3.43 (m, 1H), 3.47/3.48 (2s, together 3H), 4.13 (d, 1H), 7.05 (dd, 1H), 7.36 (dd, 2H), 7.43-7.51 (m, 4H), 9.84 (s, 1H).

Example 203A (+)-tert-Butyl (3S)-3-(4-chloro-3-{[(2S,3R)-2-(4-chlorophenyl)-4,4,4-trifluoro-3-methylbutanoyl]-amino}phenyl)-4,4,4-trifluorobutanoate

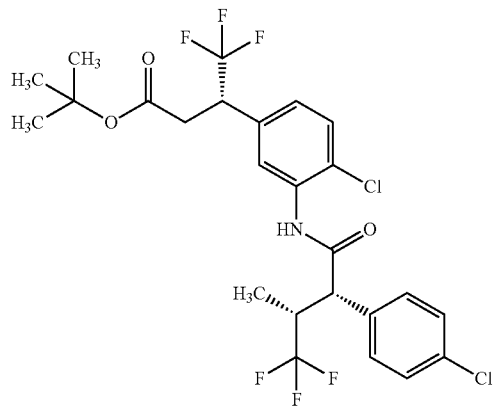

2.0 g (6.18 mmol) of (+)-tert-butyl (3S)-3-(3-amino-4-chlorophenyl)-4,4,4-trifluorobutanoate and 1.98 g (7.41 mmol) of (+)-(2S,3R)-2-(4-chlorophenyl)-4,4,4-trifluoro-3-methylbutanoic acid were dissolved in 5.0 ml of pyridine and 10.0 ml of DMF, and 3.05 g (8.03 mmol) of HATU were added at RT. The reaction mixture was stirred at RT overnight, and a further 1.98 g (7.41 mmol) of (+)-(2S,3R)-2-(4-chlorophenyl)-4,4,4-trifluoro-3-methylbutanoic acid and 3.05 g (8.03 mmol) of HATU were then added. The reaction mixture was stirred at 40° C. for another 8 h and then, after cooling, diluted with ethyl acetate. The mixture was washed with 1 N hydrochloric acid and sat. sodium chloride solution, dried over magnesium sulphate and concentrated under reduced pressure. The crude product was purified by chromatography on silica gel (mobile phase initially cyclohexane, then cyclohexane/ethyl acetate 50:1). The product obtained in this manner (2.7 g) was repurified again by another chromatography on silica gel (mobile phase cyclohexane/ethyl acetate 100:1). This gave 1.80 g of the target product (50.9% of theory).

LC-MS (Method 4): $R_t$=1.74 min; m/z=570 (M−H)⁻.

¹H-NMR (400 MHz, DMSO-$d_6$): δ [ppm]=0.80 (d, 3H), 1.21 (s, 9H), 2.77 (dd, 1H), 2.94 (dd, 1H), 3.36-3.46 (m, 1H), 3.99-4.09 (m, 1H), 4.15 (d, 1H), 7.17-7.29 (m, 1H), 7.42-7.52 (m, 5H), 7.59-7.65 (m, 1H), 9.94 (s, 1H).

$[α]_D^{20}$=+84.0°, c=0.48, chloroform.

The example below was prepared in an analogous manner:

Example 204A (+)-tert-Butyl (3R)-3-(4-chloro-3-{[(2S,3R)-2-(4-chlorophenyl)-4,4,4-trifluoro-3-methylbutanoyl]-amino}phenyl)-4,4,4-trifluorobutanoate

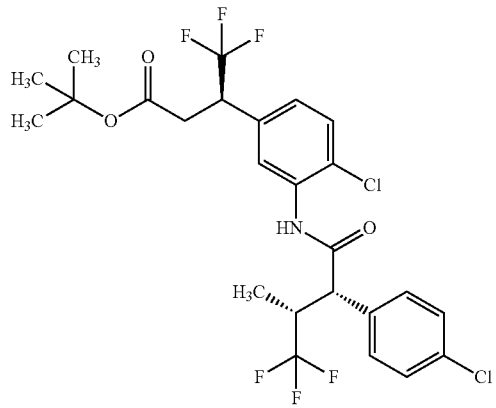 [SMILES: C[C@H]([C@H](C(=O)Nc1cc([C@@H](CC(=O)OC(C)(C)C)C(F)(F)F)ccc1Cl)c1ccc(Cl)cc1)C(F)(F)F]

From 1.0 g (3.09 mmol) of (−)-tert-butyl (3R)-3-(3-amino-4-chlorophenyl)-4,4,4-trifluorobutanoate and 988 mg (3.71 mmol) of (+)-(2S,3R)-2-(4-chlorophenyl)-4,4,4-trifluoro-3-methylbutanoic acid 1.2 g (68% of theory) of the target product were obtained.

LC-MS (Method 4): $R_t$=1.75 min; m/z=570 (M−H)⁻.

¹H-NMR (400 MHz, DMSO-$d_6$): δ [ppm]=0.80 (d, 3H), 1.21 (s, 9H), 2.78 (dd, 1H), 2.93 (dd, 1H), 3.35-3.47 (m, 1H), 3.99-4.10 (m, 1H), 4.15 (d, 1H), 7.19-7.28 (m, 1H), 7.40-7.52 (m, 5H), 7.60-7.66 (m, 1H), 9.93 (s, 1H).

$[α]_D^{20}$=+42.7°, c=0.48, chloroform.

Example 205A tert-Butyl 3-(3-amino-2-methylphenyl)propanoate

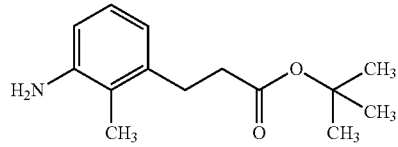

Under argon, 201 ml (1.39 mol) of tert-butyl prop-2-enoate were added dropwise to a solution of 100 g (463 mmol) of 1-bromo-2-methyl-3-nitrobenzene, 322 ml (2.31 mol) of triethylamine, 28.18 g (92.58 mmol) of tri-2-tolylphosphine and 10.39 g (46.29 mmol) of palladium(II) acetate in 2 liters of DMF, and the mixture was then stirred at 125° C. for 36 h. After cooling to room temperature, the reaction mixture was stirred with saturated aqueous ammonium chloride solution, and the organic phase was separated off. The aqueous phase was extracted three times with tert-butyl methyl ether, and the combined organic phases were washed with saturated sodium chloride solution and dried over sodium sulphate. After filtration, the solvent was removed to dryness under reduced pressure. The residue obtained was purified by flash chromatography on silica gel (mobile phase petroleum ether/ethyl acetate 9:1). This gave 89 g (338 mmol, 73% of theory) of the intermediate tert-butyl (2E)-3-(2-methyl-3-nitrophenyl)prop-2-enoate as a colourless solid.

88 g (334 mmol) of this solid were dissolved in 2 liters of ethanol, 7 g of palladium on carbon (10%) were added at room temperature and the mixture was hydrogenated under atmospheric pressure for 18 h. After the reaction had gone to completion, the reaction solution was filtered through kieselguhr and the filtrate obtained was concentrated under reduced pressure. This gave 61.3 g (260.5 mmol, 78% of theory) of the title compound as a colourless solid.

LC-MS (Method 2): $R_t$=1.84 min; m/z=236 (M+H)⁺.

¹H-NMR (400 MHz, DMSO-$d_6$, δ/ppm): 6.77 (1H, t), 6.47 (1H, d), 6.36 (1H, d), 4.72 (2H, s), 2.14 (2H, t), 2.36 (2H, t), 1.95 (3H, s), 1.39 (9H, s).

Example 206A tert-Butyl 3-(3-bromo-4-chlorophenyl)-2,2-dimethylpropanoate

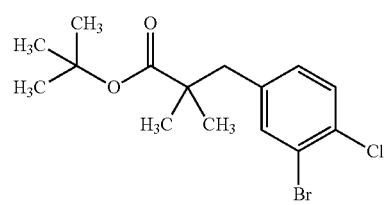 [SMILES: CC(C)(C)OC(=O)C(C)(C)Cc1ccc(Cl)c(Br)c1]

Under argon, 4.0 ml (28.8 mmol) of diisopropylamine were dissolved in 50 ml of dry THF, and the mixture was cooled to −30° C. 11.5 ml (28.8 mmol) of n-butyllithium solution (2.5 M in hexane) were added dropwise. The resulting mixture was warmed to 0° C. and then cooled to −70° C. A solution of 2.77 g (19.2 mmol) of tert-butyl-2-methylpropanoate in 20 ml of THF was then added, the temperature being kept below −60° C. After 4 h of stirring at −60° C., a solution of 6.0 g (21.1 mmol) of 2-bromo-4-(bromomethyl)-

1-chlorobenzene in 30 ml of THF was added, the reaction temperature once more being kept below −60° C. The reaction mixture was stirred overnight slowly warming to RT, and saturated aqueous ammonium chloride solution and ethyl acetate were then added. After phase separation, the aqueous phase was extracted twice with ethyl acetate. The combined organic phases were dried over magnesium sulphate and concentrated under reduced pressure. The crude product was purified by chromatography on silica gel (mobile phase cyclohexane/ethyl acetate 10:1→4:1). This gave 5.6 g (84% of theory) of the title compound.

GC-MS (Method 1): $R_t$=6.16 min; m/z=290/292 $(M-C_4H_8)^+$.

Example 207A tert-Butyl 3-[3-(benzylamino)-4-chlorophenyl]-2,2-dimethylpropanoate

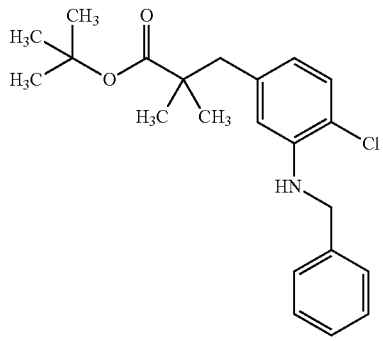 [SMILES: CC(C)(C)OC(=O)C(C)(C)Cc1ccc(Cl)c(NCc2ccccc2)c1]

Under argon, 1.73 g (17.95 mmol) of sodium tert-butoxide were weighed out into a dry flask, and 40 ml of abs. toluene were added. 5.2 g (14.96 mmol) of tert-butyl 3-(3-bromo-4-chlorophenyl)-2,2-dimethylpropanoate, 1.96 ml (17.95 mmol) of benzylamine, 685 mg (0.75 mmol) of tris(dibenzylideneacetone)dipalladium and 373 mg (0.60 mmol) of (+/−)-2,2'-bis(diphenylphosphino)-1,1'-binaphthyl were added in succession. The reaction mixture was stirred at 110° C. for 2.0 h, then cooled to RT and stirred at this temperature overnight. Saturated aqueous ammonium chloride solution and ethyl acetate were then added, and the reaction mixture was filtered off with suction through kieselguhr. After phase separation, the organic phase was washed with saturated ammonium chloride solution and saturated sodium chloride solution, dried over magnesium sulphate and concentrated under reduced pressure. The crude product was purified by preparative HPLC (mobile phase acetonitrile/water). This gave 2.78 g of the title compound (50% of theory).

LC-MS (Method 6): $R_t$=1.53 min; m/z=374/376 $(M+H)^+$.

Example 208A tert-Butyl 3-(3-amino-4-chlorophenyl)-2,2-dimethylpropanoate

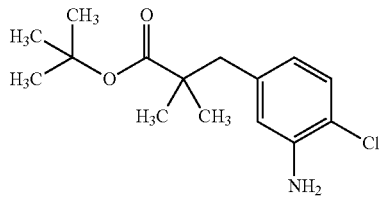 [SMILES: CC(C)(C)OC(=O)C(C)(C)Cc1ccc(Cl)c(N)c1]

2.7 g (about 7.22 mmol) of tert-butyl 3-[3-(benzylamino)-4-chlorophenyl]-2,2-dimethylpropanoate were dissolved in 150 ml of ethyl acetate, and 100 ml of palladium on carbon (10%) were added. The reaction mixture was stirred at RT under an atmosphere of hydrogen at atmospheric pressure overnight. The mixture was then filtered off with suction through kieselguhr, the residue was washed thoroughly with ethyl acetate and the combined filtrate was concentrated. The crude product was purified by chromatography on silica gel (mobile phase cyclohexane/ethyl acetate 10:1→7:1). This gave 1.49 g (72.7% of theory) of the target compound.

LC-MS (Method 4): $R_t$=1.46 min; m/z=284/286 $(M+H)^+$.

$^1$H-NMR (400 MHz, DMSO-$d_6$, δ/ppm): 7.05 (1H, d), 6.57 (1H, d), 6.32 (1H, dd), 5.20 (2H, s), 2.60 (2H, s), 1.38 (9H, s), 1.05 (6H, s).

Example 209A

N,N-Dibenzyl-5-bromo-2-chloroaniline

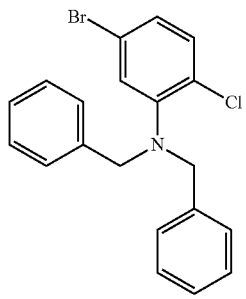 [SMILES: Clc1ccc(Br)cc1N(Cc1ccccc1)Cc1ccccc1]

Under argon, 9.69 g (242.16 mmol, 60% in mineral oil) of sodium hydride were suspended in 100 ml of THF, and the mixture was cooled to 0° C. 20.0 g (96.86 mmol) of 5-bromo-2-chloroaniline, dissolved in 50 ml of THF, were then slowly added dropwise, and the mixture was stirred at 0° C. for 30 min 39.76 g (232.47 mmol) of benzyl bromide, dissolved in 150 ml of THF, were then slowly added to the reaction mixture, and the mixture was then warmed to room temperature. The mixture was stirred at RT overnight and then carefully poured onto 150 ml of ice-water. The organic phase was separated off, and the aqueous phase was then extracted three more times with ethyl acetate. The combined organic phases were dried over sodium sulphate. After filtration, the solvent was removed under reduced pressure. Isopropanol was added to the crude product obtained, and the crystals formed were filtered off with suction and dried at 40° C. under high vacuum. This gave 14 g of the title compound. The filtrate was evaporated and the residue obtained was purified by chromatography on silica gel (mobile phase cyclohexane/ethyl acetate 20:1). This gave a further 7.57 g of the title compound (total yield: 21.57 g, 58% of theory).

LC-MS (Method 6): $R_t$=1.53 min; m/z=386/388 $(M+H)^+$.

The following compound was obtained analogously to Example 209A:

| Example | Name/Structure/Starting Materials | Analytical Data |
|---|---|---|
| 210A | N,N-Dibenzyl-2-chloro-iodoaniline<br>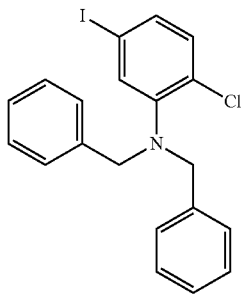 [SMILES: Clc1ccc(I)cc1N(Cc1ccccc1)Cc1ccccc1]<br>(from 2-chloro-5-iodoaniline and benzyl bromide) | LC-MS (Method 4):<br>$R_t$ = 1.86 min; m/z = 433/435 (M + H)$^+$. |

Example 211A

[4-Chloro-3-(dibenzylamino)phenyl]boronic acid

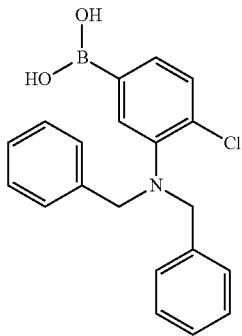 [SMILES: OB(O)c1ccc(Cl)c(N(Cc2ccccc2)Cc2ccccc2)c1]

Under argon and at −78° C., 20.2 ml (50.42 mmol) of a 2.5 M solution of n-butyllithium in hexane were slowly added dropwise to a solution of 15 g (38.79 mmol) of N,N-dibenzyl-5-bromo-2-chloroaniline in 350 ml of THF/diethyl ether (1:1). The reaction solution was stirred at −78° C. for 60 min, and 14.3 ml (62.1 mmol) of triisopropyl borate were then added slowly. The reaction solution was subsequently stirred at −78° C. for another 15 min, then slowly warmed to room temperature, and stirring at this temperature was continued overnight. 150 ml of ice-water were then metered in. The organic phase was separated off, and the aqueous phase was then extracted three more times with ethyl acetate. The combined organic phases were dried over sodium sulphate. After filtration, the solvent was removed under reduced pressure. The crude product was purified chromatographically on silica gel (mobile phase cyclohexane/ethyl acetate 10:1→4:1). This gave 9 g (66% of theory) of the title compound.

LC-MS (Method 6): $R_t$=1.21 min; m/z=352 (M+H)$^+$.

Example 212A tert-Butyl cyclobutylideneacetate

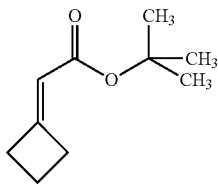

Under argon and at room temperature, 3.0 g (42.8 mmol) of cyclobutanone were dissolved in 160 ml of dichloromethane, and 20.95 g (55.64 mmol) of tert-butyl (triphenyl-$\lambda^5$-phosphanylidene) acetate and 0.68 g (5.56 mmol) of benzoic acid were then added. The reaction mixture was stirred at room temperature overnight and then concentrated to dryness. The residue was triturated with 25 ml of diethyl ether, and the mixture was stored at 4° C. for 12 h. The precipitated triphenylphosphane oxide was filtered off and the filtrate was concentrated to dryness. The crude product obtained was purified chromatographically on silica gel (mobile phase cyclohexane/ethyl acetate 20:1). This gave 9.3 g (99% of theory) of the title compound.

$^1$H-NMR (400 MHz, DMSO-d$_6$, δ/ppm): 5.47-5.41 (1H, m), 3.05-2.95 (2H, m), 2.82-2.74 (2H, m), 2.06-1.95 (2H, m), 1.50 (9H, s).

GC-MS (Method 1): $R_t$=3.01 min; m/z=112 (M−C$_4$H$_8$)$^+$.

Example 213A tert-Butyl cyclopropylideneacetate

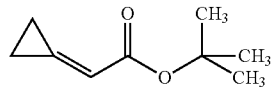

At room temperature, 55 ml (55 mmol) of a 1 M solution of tetra-n-butylammonium fluoride in THF were added dropwise to a solution of 9.65 g (55.34 mmol) of [(1-ethoxycyclopropyl)oxy](trimethyl)silane, 25 g (66.41 mmol) of tert-butyl (triphenyl-$\lambda^5$-phosphanylidene)-acetate and 8.11 g (66.41 mmol) of benzoic acid in 240 ml of THF. After 1 h of stirring, the reaction mixture was heated to 80° C. and stirred at this temperature for 2 h. Using a rotary evaporator, the solvent was then distilled off (200 mbar, bath temperature 40° C.). The residue obtained was taken up in diethyl ether and the mixture was cooled to 4° C. and allowed to stand at this temperature for 1 h. The resulting precipitate (triphenylphosphane oxide) was filtered off. Using a rotary evaporator, the filtrate was then freed from the solvent. The crude product obtained was purified chromatographically on silica gel (mobile phase cyclohexane/ethyl acetate 20:1). This gave 3.58 g (42% of theory) of the title compound.

GC-MS (Method 1): $R_t$=2.45 min; m/z=98 (M−C$_4$H$_8$)$^+$.

$^1$H-NMR (400 MHz, DMSO-d$_6$, δ/ppm): 1.18-1.26 (m, 2H), 1.34-1.41 (m, 3H), 1.44 (s, 9H), 6.06-6.13 (m, 1H).

Example 214A

Ethyl (3,3-dimethoxycyclobutylidene)acetate

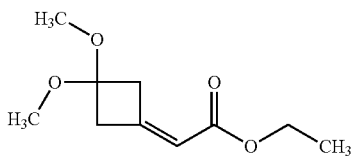

A solution of 3.93 g (44.59 mmol) of 1,1-dimethoxyethene and 5 g (44.59 mmol) of ethyl buta-2,3-dienoate in 50 ml of toluene was heated at reflux and stirred for 24 h. After cooling to room temperature, the reaction mixture was freed from the solvent, and the crude product obtained was purified chromatographically on silica gel (mobile phase cyclohexane/ethyl acetate 20:1). This gave 1.9 g (21% of theory) of the title compound as a colourless liquid which was used without further characterization for subsequent reactions.

Example 215A tert-Butyl {1-[4-chloro-3-(dibenzylamino)phenyl]cyclopropyl}acetate

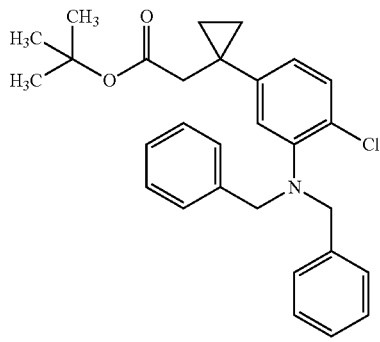 [SMILES: CC(C)(C)OC(=O)CC1(c2ccc(Cl)c(N(Cc3ccccc3)Cc3ccccc3)c2)CC1]

Preparation of solution A: under argon, 300 mg (0.69 mmol) of N,N-dibenzyl-2-chloro-5-iodoaniline were dissolved in 3 ml of THF, and the solution was cooled to −78° C. 0.4 ml (0.80 mmol) of a 2M solution of isopropylmagnesium chloride in THF was then slowly added dropwise. The reaction solution was then slowly warmed to −40° C. and stirred at this temperature for 30 min.

Preparation of solution B: under argon and at room temperature, 6 mg (0.14 mmol) of lithium chloride and 13 mg (0.07 mmol) of copper(I) chloride were suspended in 12 ml of THF, and 84 µl (0.66 mmol) of chloro(trimethyl)silane and 102 mg (0.66 mmol) of tert-butyl cyclopropylidene acetate were then added. The solution was then stirred at RT for another 1 h.

Solution B was cooled to −40° C. and slowly added dropwise to solution A. The reaction mixture obtained was then stirred at −40° C. for another 1 h. 20 ml of an ice-cold semisaturated aqueous ammonium chloride solution were then added to the reaction mixture. The phases were separated, the aqueous phase was extracted three more times with ethyl acetate and the combined organic phases were dried over magnesium sulphate, filtered and concentrated to dryness. The crude product obtained was purified chromatographically on silica gel (mobile phase cyclohexane/ethyl acetate 20:1). This gave 135 mg (42% of theory) of the title compound.

LC-MS (Method 6): $R_t$=1.73 min; m/z=462/464 (M+H)$^+$.

The following compounds were obtained analogously to Example 13A:

| Example | Name/Structure/Starting materials | Analytical data |
|---|---|---|
| 216A | tert-Butyl {1-[4-chloro-3-(dibenzylamino)phenyl]cyclobutyl}acetate 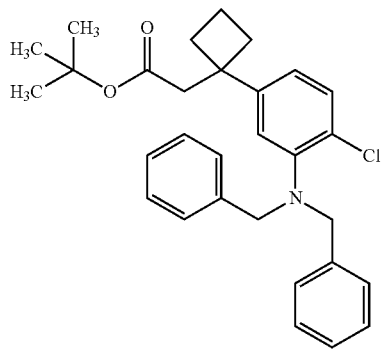 [SMILES: CC(C)(C)OC(=O)CC1(c2ccc(Cl)c(N(Cc3ccccc3)Cc3ccccc3)c2)CCC1] (from [4-chloro-3-(dibenzylamino)phenyl]boronic acid and tert-butyl cyclobutylidene acetate) | LC-MS (Method 4): $R_t$ = 1.96 min; m/z = 476/478 (M + H)$^+$. |

| Example | Name/Structure/Starting materials | Analytical data |
|---|---|---|
| 217A | Ethyl {1-[4-chloro-3-(dibenzylamino)phenyl]-3,3-dimethoxycyclobutyl}acetate 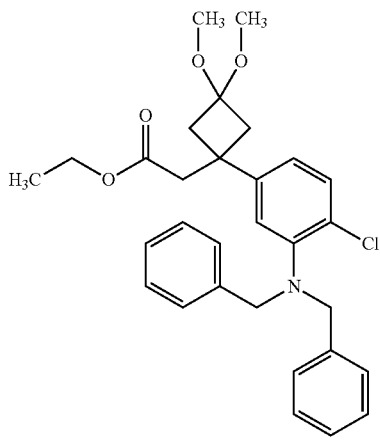 [SMILES: CCOC(=O)CC1(c2ccc(Cl)c(N(Cc3ccccc3)Cc3ccccc3)c2)CC(OC)(OC)C1] (from [4-chloro-3-(dibenzylamino)phenyl]boronic acid and ethyl (3,3-dimethoxycyclobutylidene)-acetate) | LC-MS (Method 6): $R_t$ = 1.53 min; m/z = 508/510 $(M + H)^+$. |

Example 218A

Ethyl {1-[4-chloro-3-(dibenzylamino)phenyl]-3-oxocyclobutyl}acetate

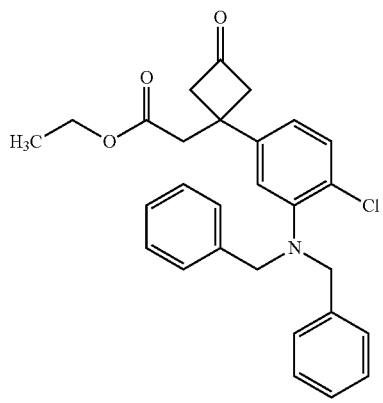 [SMILES: CCOC(=O)CC1(c2ccc(Cl)c(N(Cc3ccccc3)Cc3ccccc3)c2)CC(=O)C1]

770 mg (1.52 mmol) of ethyl {1-[4-chloro-3-(dibenzylamino)phenyl]-3,3-dimethoxycyclobutyl}-acetate were dissolved in 10 ml of THF, 2 ml of 1 M hydrochloric acid were added and the mixture was stirred at 50° C. for 1 h. The reaction solution was then diluted with 10 ml of water and 10 ml of ethyl acetate. The phases were separated, and the organic phase was then dried over magnesium sulphate, filtered and concentrated to dryness using a rotary evaporator. This gave 607 mg of the title compound (87% of theory).

LC-MS (Method 6): $R_t$=1.44 min; m/z=462/464 $(M+H)^+$.

Example 219A

Ethyl {1-[4-chloro-3-(dibenzylamino)phenyl]-3,3-difluorocyclobutyl}acetate

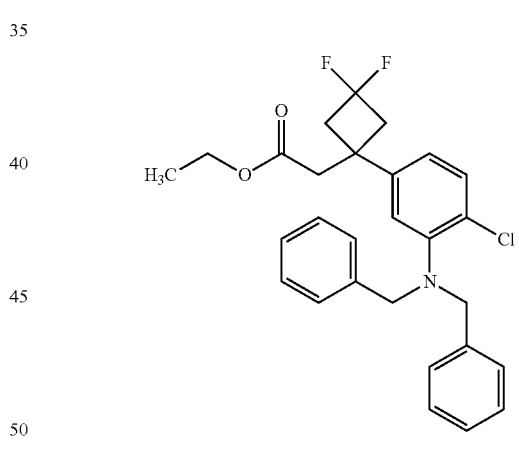

Under argon, 0.3 ml (2.27 mmol) of [ethyl(trifluoro-$\lambda^4$-sulphanyl)amino]ethane was added to 2 ml of dichloromethane. The reaction solution was cooled to 0° C., and 175 mg (0.38 mmol) of ethyl {1-[4-chloro-3-(dibenzylamino)phenyl]-3-oxocyclobutyl}acetate in 3 ml of dichloromethane were then added slowly. The solution was then slowly warmed to room temperature and stirred at this temperature overnight. The reaction mixture was then poured into 50 ml of ice-water, and the organic phase was separated off. The aqueous phase was extracted three more times with dichloromethane. The combined organic phases were dried over magnesium sulphate. After filtration, the solvent was removed under reduced pressure and the crude product obtained was purified by preparative HPLC (mobile phase methanol/water 8:2). This gave 59 mg of the title compound (32% of theory).

LC-MS (Method 6): $R_t$=1.53 min; m/z=484/486 (M+H)$^+$.

Example 220A tert-Butyl [1-(3-amino-4-chlorophenyl)cyclopropyl]acetate

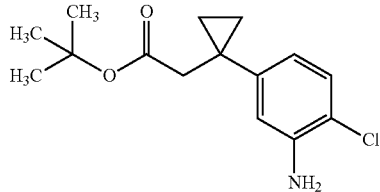 [SMILES: CC(C)(C)OC(=O)CC1(c2ccc(Cl)c(N)c2)CC1]

135 mg (0.29 mmol) of tert-butyl {1-[4-chloro-3-(dibenzylamino)phenyl]cyclopropyl}acetate were dissolved in 10 ml of ethyl acetate, 15 mg of palladium on carbon (10%) were added and the mixture was stirred at RT under an atmosphere of hydrogen at atmospheric pressure for 2 h. The reaction mixture was then filtered off through celite, the residue was washed with ethyl acetate and the filtrate was concentrated. This gave 73 mg of the title compound (89% of theory).

LC-MS (Method 6): $R_t$=1.15 min; m/z=282/284 (M+H)$^+$.

The following compounds were obtained analogously to Example 220A:

Example 223A tert-Butyl (2E)-3-(3-amino-4-cyanophenyl)-2-methylacrylate

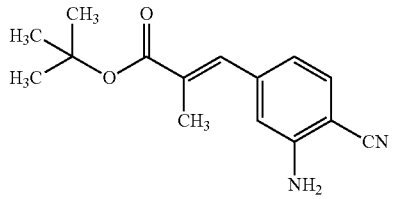 [SMILES: C/C(=C\c1ccc(C#N)c(N)c1)C(=O)OC(C)(C)C]

Under argon, a mixture of 2.0 g (10.15 mmol) of 2-amino-4-bromobenzonitrile, 2.165 g (2.5 ml, 15.23 mmol) of tert-butyl 2-methylacrylate, 93 mg (0.10 mmol) of tris(dibenzylideneacetone)-dipalladium, 41 mg (0.20 mmol) of tri-tert-butylphosphine and 2.4 ml (11.17 mmol) of N,N-dicyclohexylmethylamine in 20 ml of dioxane was heated to 120° C. and stirred at this temperature overnight. The reaction was checked (TLC, mobile phase cyclohexane/ethyl acetate 9:1), and another 10 mg of tris(dibenzylideneacetone)dipalladium, 10 mg of tri-tert-butylphosphine and 500 μl of tert-butyl 2-methylacrylate were then added and the mixture was stirred at 120° C. for a further 4 h. The reaction mixture was then filtered through celite, and the filtrate was concentrated under reduced pressure. The residue was purified by chromatography on silica gel (mobile phase cyclohexane/ethylacetate 9:1→4:1). This gave 1.375 g of the title compound (52% of theory).

LC-MS (Method 4): $R_t$=1.33 min; m/z=259 (M+H)$^+$.

| Example | Name/Structure/Starting material | Analytical Data |
|---|---|---|
| 221A | tert-butyl [1-(3-amino-4-chlorophenyl)-cyclobutyl]acetate<br><br>(from tert-butyl {1-(4-chloro-3-(dibenzylamino)-phenyl]cyclobutyl)acetate) | LC-MS (Method 6):<br>$R_t$ = 1.24 min; m/z = 296 (M + H)$^+$. |
| 222A | Ethyl [1-(3-amino-4-chlorophenyl)-3,3-difluorocyclobutyl]acetate<br><br>(from ethyl {1-[4-chloro-3-(dibenzylamino)-phenyl)-3,3-difluorocyclobutyl}acetate) | LC-MS (Method 4):<br>$R_t$ = 1.36 min; m/z = 304/306 (M + H)$^+$. |

Example 224A tert-Butyl 3-(3-amino-4-cyanophenyl)-2-methylpropanoate

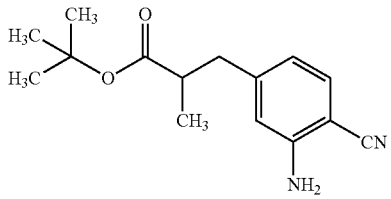 [SMILES: CC(Cc1ccc(C#N)c(N)c1)C(=O)OC(C)(C)C]

1370 mg (5.3 mmol) of tert-butyl (2E)-3-(3-amino-4-cyanophenyl)-2-methylacrylate were dissolved in 30 ml of ethyl acetate, 282 mg of palladium on carbon (10%) were added and the mixture was stirred at RT under an atmosphere of hydrogen at atmospheric pressure for three days. The reaction mixture was then filtered off through celite, the filter residue was washed with ethyl acetate and the combined filtrate was concentrated. The crude product was purified by preparative HPLC (mobile phase acetonitrile/water). This gave 870 mg of the title compound (63% of theory).

LC-MS (Method 6): $R_t$=1.04 min; m/z=261 (M+H)$^+$.

The compound below was obtained analogously to Example 54A:

| Example | Name/Structure/Starting materials | Analytical Data |
|---|---|---|
| 225A | Ethyl (3R)-2-(4-chloro-3-methoxyphenyl trifluoro-3-methylbutanoate)<br><br>(from 4-bromo-1-chloro-2-methoxybenzene and ethyl (3R)-4,4,4-trifluoro-3-methylbutanoate) | GC-MS (Method 1):<br>$R_t$ = 5.34 min;<br>m/z = 324/326 (M)$^+$. |

Example 226A

Ethyl (3R)-2-[4-(2,2-dichloro-3-oxocyclobutyl)phenyl]-4,4,4-trifluoro-3-methylbutanoate

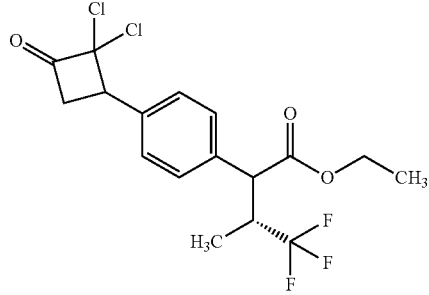 [SMILES: CCOC(=O)C(c1ccc(C2CC(=O)C2(Cl)Cl)cc1)[C@@H](C)C(F)(F)F]

3.83 g (13.38 mmol) of ethyl (3R)-4,4,4-trifluoro-3-methyl-2-(4-vinylphenyl)butanoate were dissolved in 50 ml of diethyl ether, and 2.67 g (20.74 mmol) of zinc-copper couple and 6.5 ml of 1,2-dimethoxyethane were added in succession. 4 ml (36.1 mmol) of trichloroacetyl chloride were then slowly added dropwise to the suspension obtained. The reaction solution was then heated under reflux and stirred overnight. After addition of dichloromethane, the reaction mixture was washed successively with water and saturated sodium chloride solution. The organic phase was dried over magnesium sulphate, filtered and concentrated under reduced pressure. The crude product obtained was purified chromatographically on silica gel (mobile phase: cyclohexane/ethyl acetate 4:1). This gave 4.57 g (86% of theory) of the title compound in the form of a yellowish oil which was used without further characterization in subsequent reactions.

Example 227A

Ethyl (3R)-4,4,4-trifluoro-3-methyl-2-[4-(3-oxocyclobutyl)phenyl]butanoate

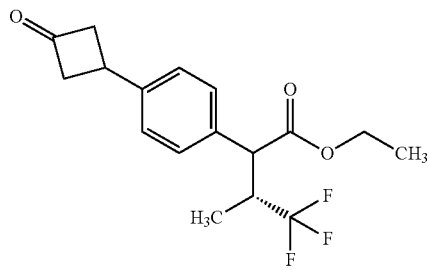 [SMILES: CCOC(=O)C(c1ccc(C2CC(=O)C2)cc1)[C@@H](C)C(F)(F)F]

100 ml of saturated aqueous ammonium chloride solution were added to 4.57 g (11.51 mmol) of ethyl (3R)-2-[4-(2,2-dichloro-3-oxocyclobutyl)phenyl]-4,4,4-trifluoro-3-methylbutanoate and 3.76 g (57.5 mmol) of zinc dust in 100 ml of THF, and the mixture was then stirred at 75° C. for 5 h. After cooling to room temperature and addition of dichloromethane, the reaction mixture was washed with water. After separation of the phases, the aqueous phase was back-extracted three times with dichloromethane. The combined organic phases were then dried over magnesium sulphate, filtered and concentrated under reduced pressure. This gave 1.21 g of the title compound (32% of theory).

GC-MS (Method 1): $R_t$=6.52 min, m/z=286 (M–C$_2$H$_2$O)$^+$ (diastereomer 1); $R_t$=6.55 min, m/z=286 (M–C$_2$H$_2$O)$^+$ (diastereomer 2).

MS (DCI): m/z=346 (M+NH$_4$)$^+$.

Example 228A

Ethyl (3R)-2-[4-(3,3-difluorocyclobutyl)phenyl]-4,4,4-trifluoro-3-methylbutanoate

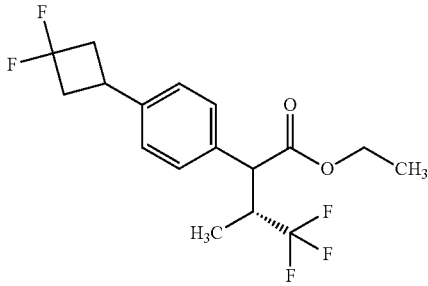 [SMILES: CCOC(=O)C(c1ccc(C2CC(F)(F)C2)cc1)[C@@H](C)C(F)(F)F]

Under argon, 7.3 ml (5.16 mmol) of a 50% strength solution of 1,1'-[(trifluoro-$\lambda^4$-sulphanyl)-imino]bis(2-methoxyethane) (Desoxofluor) in THF, diluted with 20 ml of toluene, were initially charged, the mixture was cooled to 5° C. and 47 µl (0.37 mmol) of a 1 M boron trifluoride diethyl ether complex solution were added slowly. The mixture was stirred at 5° C. for 2 h. 1.21 g (3.69 mmol) of ethyl (3R)-4,4,4-trifluoro-3-methyl-2-[4-(3-oxocyclobutyl)phenyl]butanoate, dissolved in 20 ml of toluene, were then added slowly to the reaction solution, and the mixture was then warmed to 55° C. and stirred at this temperature for 48 h. The reaction mixture was then added to a mixture, cooled to 0° C., consisting of 20 ml of toluene and 20 ml of 2 M aqueous sodium hydroxide solution. The organic phase was separated off, and the aqueous phase was extracted three more times with ethyl acetate. The combined organic phases were dried over sodium sulphate. After filtration, the solvent was removed under reduced pressure. The crude product was purified chromatographically on silica gel (mobile phase cyclohexane/ethyl acetate 10:1). This gave 558 mg (43% of theory) of the title compound as a yellowish liquid.

GC-MS (Method 1): $R_t$=5.40 min, m/z=350 (M)$^+$ (Diastereomer 1); $R_t$=5.44 min, m/z=350 (M)$^+$ (Diastereomer 2).

MS (DCI): m/z=368 (M+NH$_4$)$^+$.

Example 229A

Ethyl (3R)-2-[4-(2,2-difluorocyclopropyl)phenyl]-4,4,4-trifluoro-3-methylbutanoate

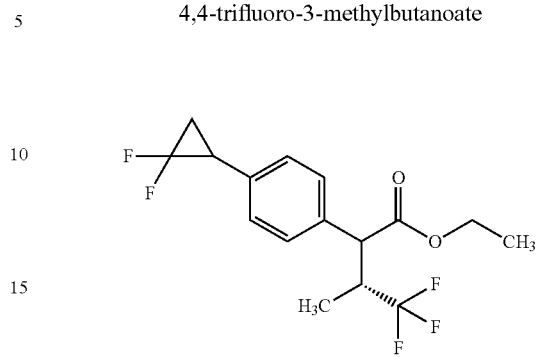

1.58 g (5.52 mmol) of ethyl (3R)-4,4,4-trifluoro-3-methyl-2-(4-vinylphenyl)butanoate, 23 mg (0.55 mmol) of sodium fluoride and 24 mg (0.11 mmol) of 2,6-di-tert-butyl 4-methylphenol were heated to 110° C. and stirred for 5 minutes. 1.9 ml (9.38 mmol) of trimethylsilyl difluoro(fluorosulphonyl)acetate were then slowly added dropwise, and the mixture was stirred at 110° C. for 60 min (caution: evolution of gas after about 30 min). After cooling to room temperature and addition of ethyl acetate and saturated aqueous sodium hydrocarbonate solution, the organic phase was separated off, dried over magnesium sulphate, filtered and concentrated to dryness. The crude product was purified chromatographically on silica gel (mobile phase cyclohexane/dichloromethane 4:1). This gave 1.5 g of the title compound (81% of theory).

GC-MS (Method 1): $R_t$=4.99 min, m/z=336 (M)$^+$ (Diastereomer 1); $R_t$=5.01 min, m/z=336 (M)$^+$ (Diastereomer 2).

MS (DCI): m/z=354 (M+NH$_4$)$^+$.

The compounds listed in the table below were prepared analogously to Example 70A:

| Example | Name/Structure/Starting materials | Analytical Data |
| --- | --- | --- |
| 230A | (2S,3R)-2-[4-(3,3-Difluorocyclobutyl)phenyl]-4,4,4-trifluoro-3-methylbutanoic acid<br><br>(from ethyl (3R)-2-[4-(3,3-difluorocyclobutyl)-phenyl]-4,4,4-trifluoro-3-methylbutanoate) | GC-MS (Method 1):<br>$R_t$ = 5.76 min; m/z = 322 (M)$^+$.<br>MS (EI): m/z = 322 (M)$^+$.<br>$^1$H-NMR (400 MHz, DMSO-d$_6$):<br>δ [ppm] = 0.76 (d, 3H), 2.58-2.76 (m, 2H), 2.91-3.05 (m, 2H), 3.17-3.28 (m, 1H), 3.34-3.45 (m, 1H), 3.60 (d, 1H), 7.27-7.36 (m, 4H), 12.63-12.81 (br. s, 1H). |

-continued

| Example | Name/Structure/Starting materials | Analytical Data |
|---|---|---|
| 231A | (2S,3R)-2-(4-Chloro-3-methoxyphenyl)-4,4,4-trifluoro-3-methylbutanoic acid<br><br>(from ethyl (3R)-2-(4-chloro-3-methoxyphenyl)-4,4,4-trifluoro-3-methylbutanoate) | $^1$H-NMR (400 MHz, DMSO-$d_6$, δ/ppm): 12.91-12.71 (1H, br. s), 7.41 (1H, d), 7.18 (1H, d), 6.98 (1H, dd), 3.86 (3H, s), 3.66 (1H, d), 3.40-3.19 (1H, m, partially obscured by signal), 0.79 (3H, d).<br>LC-MS (Method 5):<br>$R_t$ = 2.20 min; m/z = 295/297 (M − H)$^−$. |
| 232A | (2S,3R)-2-[4-(2,2-Difluorocyclopropyl)phenyl]-4,4,4-trifluoro-3-methylbutanoic acid<br><br>(from ethyl (2S,3R)-2-[4-(2,2-difluorocyclopropyl)phenyl]-4,4,4-trifluoro-3-methylbutanoate) | LC-MS (Method 6):<br>$R_t$ = 1.09 min; m/z = 307 (M − H)$^−$.<br>$^1$H-NMR (400 MHz, DMSO-$d_6$):<br>δ [ppm] = 0.76 (d, 3H), 1.86-2.04 (m, 2H), 2.92-3.06 (m, 1H), 3.18-3.29 (m, 1H), 3.61 (d, 1H), 7.27 (d, 2H), 7.34 (d, 2H), 12.72 (br. s, 1H). |

The compounds listed in the table below were prepared analogously to Example 82A:

| Example | Name/Structure | Analytical Data |
|---|---|---|
| 233A | (2S,3R)-2-[4-(3,3-Difluorocyclobutyl)phenyl]-4,4,4-trifluoro-3-methylbutanoyl chloride | (2S,3R)-2-[4-(3,3-Difluorocyclobutyl)phenyl]-4,4,4-trifluoro-3-methylbutanoic acid |
| 234A | (2S,3R)-2-[4-(2,2-Difluorocyclopropyl)phenyl]-4,4,4-trifluoro-3-methylbutanoyl chloride | (2S,3R)-2-[4-(2,2-Difluorocyclopropyl)phenyl]-4,4,4-trifluoro-3-methylbutanoic acid |

Example 235A tert-Butyl 3-(4-chloro-3-{[(2S,3R)-2-(4-chlorophenyl)-4,4,4-trifluoro-3-methylbutanoyl]amino}-phenyl)-2,2-dimethylpropanoate

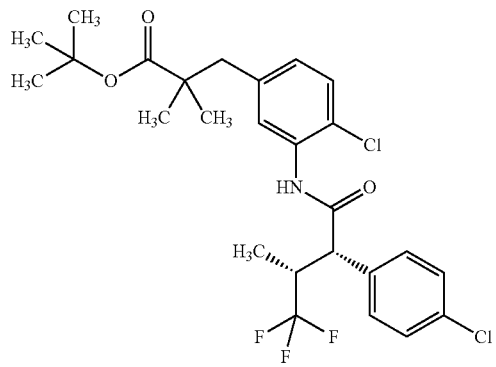 [SMILES: C[C@H]([C@H](C(=O)Nc1cc(CC(C)(C)C(=O)OC(C)(C)C)ccc1Cl)c1ccc(Cl)cc1)C(F)(F)F]

400 mg (1.50 mmol) of (2S,3R)-2-(4-chlorophenyl)-4,4,4-trifluoro-3-methylbutanoic acid were dissolved in 24 ml of dichloromethane, 320 mg (2.40 mmol) of 1-chloro-N,N,2-trimethylprop-1-ene-1-amine were added and the mixture was stirred at room temperature for 30 min. 364 µl (4.5 mmol) of pyridine and 510 mg (1.80 mmol) of tert-butyl 3-(3-amino-4-chlorophenyl)-2,2-dimethylpropanoate were then added, and the mixture was stirred at room temperature for 2 h. The reaction mixture was then concentrated under reduced pressure, and the crude product obtained was purified by chromatography on silica gel (mobile phase cyclohexane/ethylacetate 20:1). This gave 462 mg of the target compound (58% of theory).

LC-MS (Method 6): $R_t$=1.53 min; m/z=530/532 (M−H)⁻.

$^1$H-NMR (400 MHz, DMSO-$d_6$): δ [ppm]=0.79 (d, 3H), 1.02 (s, 3H), 1.05 (s, 3H), 1.26 (s, 9H), 2.65-2.78 (m, 2H), 3.27-3.44 (m, 1H, partially obscured by H₂O signal), 4.10 (d, 1H), 6.96 (dd, 1H), 7.31 (d, 1H), 7.35 (d, 1H), 7.41-7.51 (m, 4H), 9.83 (s, 1H).

The compounds listed in the table below were prepared in an analogous manner

| Example | Name/Structure/Starting materials | Analytical Data |
|---|---|---|
| 236A | tert-butyl [1-(4-chloro-3-{[(2S,3R)-2-(4-chlorophenyl)-4,4,4-trifluoro-3-methylbutanoyl]-amino}phenyl)cyclobutyl]acetate 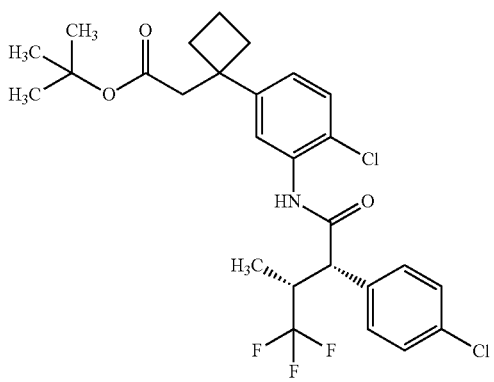 [SMILES: C[C@H]([C@H](C(=O)Nc1cc(C2(CC(=O)OC(C)(C)C)CCC2)ccc1Cl)c1ccc(Cl)cc1)C(F)(F)F] (from tert-butyl [1-(3-amino-4-chlorophenyl)-cyclobutyl]acetate and (2S,3R)-2-(4-chlorophenyl)-4,4,4-trifluoro-3-methylbutanoic acid) | LC-MS (Method 6): $R_t$ = 1.52 min; m/z = 542/544 (M − H)⁻. |
| 237A | ethyl (2S)-3-[4-chloro-3-({(2S,3R)-4,4,4-trifluoro-3-methyl-2-[4-(1,1,1-trifluoro-2-methylpropan-2-yl)-phenyl]butanoyl}amino)phenyl]-2-methylpropanoate 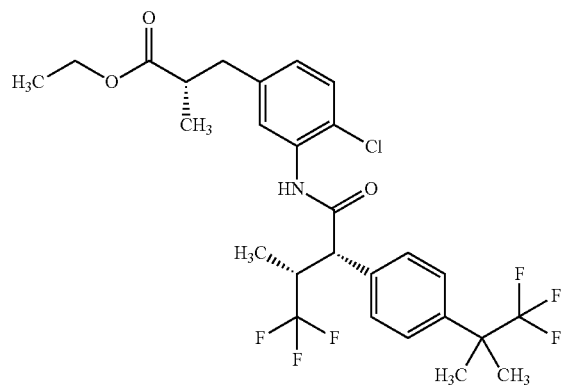 [SMILES: CCOC(=O)[C@@H](C)Cc1ccc(Cl)c(NC(=O)[C@H](c2ccc(C(C)(C)C(F)(F)F)cc2)[C@@H](C)C(F)(F)F)c1] (from ethyl (2S)-3-(3-amino-4-chlorophenyl)-2-methylpropanoate and (2S,3R)-4,4,4-trifluoro-3-methyl-2-[4-(1,1,1-trifluoro-2-methylpropan-2-yl)phenyl]butanoic acid) | LC-MS (Method 6): $R_t$ = 1.46 min; m/z = 564 (M − H)⁻. |

-continued

| Example | Name/Structure/Starting materials | Analytical Data |
|---|---|---|
| 238A | ethyl (2S)-[4-chloro-3-({4,4,4-trifluoro-3-methyl-2-[4-(2,2,2-trifluoroethyl)phenyl]butanoyl}amino)-phenyl]-2-methylpropanoate<br><br>(from ethyl (2S)-3-(3-amino-4-chlorophenyl)-2-methylpropanoate and 4,4,4-trifluoro-3-methyl-2-[4-(2,2,2-trifluoroethyl)phenyl]butanoic acid) | LC-MS (Method 6):<br>$R_t$ = 1.37 min; m/z = 536/538 (M − H)⁻. |
| 239A | ethyl (2S)-3-(4-chloro-3-{[(2S,3R)-2-(4-chloro-3-methoxyphenyl)-4,4,4-trifluoro-3-methylbutanoyl]-amino}phenyl)-2-methylpropanoate<br><br>(from ethyl (2S)-3-(3-amino-4-chlorophenyl)-2-methylpropanoate and (2S,3R)-2-(4-chloro-3-methoxyphenyl)-4,4,4-trifluoro-3-methylbutanoic acid) | LC-MS (Method 6):<br>$R_t$ = 1.37 min; m/z = 520/522 (M + H)⁺.<br>¹H-NMR (400 MHz, DMSO-$d_6$, δ/ppm): 9.80 (1H, s), 7.42 (1H, d), 7.35 (2H, d), 7.25-7.20 (1H, m), 7.06-6.96 (2H, m), 4.10 (1H, d), 3.95 (2H, q), 3.87 (3H, s), 3.49-3.34 (1H, m), 2.84-2.74 (1H, m), 2.72-2.58 (2H, m), 1.11-1.00 (6H, m), 0.83 (3H, d). |
| 240A | tert-butyl 3-(4-chloro-3-{[(2S,3R)-2-(4-chloro-3-methoxyphenyl)-4,4,4-trifluoro-3-methyl-butanoyl]amino}phenyl)propanoate<br><br>(from tert-butyl 3-(3-amino-4-chlorophenyl)-propanoate and (2S,3R)-2-(4-chloro)-3-methoxyphenyl)-4,4,4-trifluoro-3-methylbutanoic acid) | LC-MS (Method 6):<br>$R_t$ = 1.43 min; m/z = 532/534 (M + H)⁺.<br>¹H-NMR (400 MHz, DMSO-$d_6$, δ/ppm): 9.80 (1H, s), 7.42 (1H, d), 7.38 (1H, d), 7.36 (1H, d), 7.23 (1H, d), 7.07-6.99 (2H, m), 4.09 (1H, d), 3.87 (3H, s), 3.50-3.34 (1H, m), 2.76 (2H, t), 2.46 (2H, t), 1.30 (9H, s), 0.83 (3H, d). |

| Example | Name/Structure/Starting materials | Analytical Data |
|---|---|---|
| 241A | tert-butyl [1-(4-chloro-3-{[(2S,3R)-2-(4-chloro-phenyl)-4,4,4-trifluoro-3-methylbutanoyl]amino}-phenyl)cyclopropyl]acetate<br>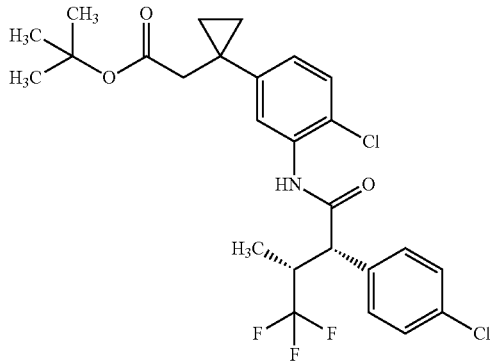 [SMILES: C[C@H]([C@H](C(=O)Nc1cc(C2(CC(=O)OC(C)(C)C)CC2)ccc1Cl)c1ccc(Cl)cc1)C(F)(F)F]<br>(from tert-butyl [1-(3-amino-4-chlorophenyl)-cyclopropyl]acetate and (2S,3R)-2-(4-chlorophenyl)-4,4,4-trifluoro-3-methylbutanoic acid) | LC-MS (Method 6):<br>$R_t$ = 1.48 min; m/z = 528/530 (M − H)⁻. |
| 242A | ethyl [1-(4-chloro-3-{[(2S,3R)-2-(4-chlorophenyl)-4,4,4-trifluoro-3-methylbutanoyl]amino}phenyl)-3,3-difluorcyclobutyl)acetate<br>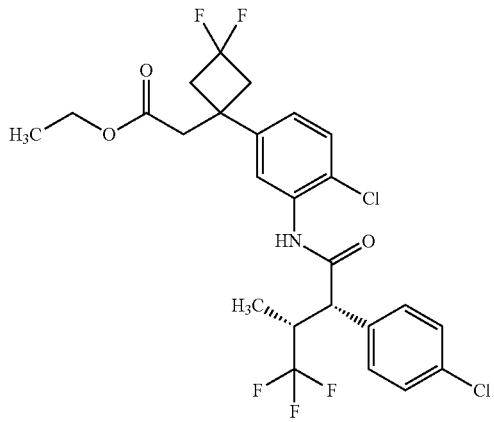 [SMILES: CCOC(=O)CC1(c2ccc(Cl)c(NC(=O)[C@H](c3ccc(Cl)cc3)[C@@H](C)C(F)(F)F)c2)CC(F)(F)C1]<br>(from ethyl [1-(3-amino-4-chlorophenyl)-3,3-difluoro-cyclobutyl]acetate and (2S,3R)-2-(4-chlorophenyl)-4,4,4-trifluoro-3-methylbutanoic acid) | LC-MS (Method 6):<br>$R_t$ = 1.39 min; m/z = 550/552 (M − H)⁻. |

-continued

| Example | Name/Structure/Starting materials | Analytical Data |
|---|---|---|
| 243A | tert-butyl 3-(3-{[(2S,3R)-2-(4-chlorophenyl)-4,4,4-trifluoro-3-methylbutanoyl]amino}-4-cyanophenyl)-2-methylpropanoate<br>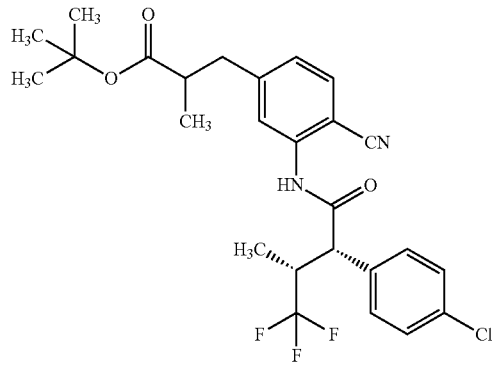 [SMILES: CC(Cc1ccc(C#N)c(NC(=O)[C@H](c2ccc(Cl)cc2)[C@@H](C)C(F)(F)F)c1)C(=O)OC(C)(C)C]<br>(from tert-butyl 3-(3-amino-4-cyanophenyl)-2-methyl-propanoate and (2S,3R)-2-(4-chlorophenyl)-4,4,4-trifluoro-3-methylbutanoic acid) | LC-MS (Method 6):<br>$R_t$ = 1.39 min; m/z = 507/509 (M − H)⁻. |

The compounds listed in the table below were prepared analogously to Example 89A:

| Example | Name/Structure/Starting materials | Analytical Data |
|---|---|---|
| 244A | tert-butyl 3-[4-chloro-3-({(2S,3R)-2-[4-(3,3-difluoro-cyclobutyl)phenyl]-4,4,4-trifluoro-3-methyl-butanoyl}amino)phenyl]propanoate<br>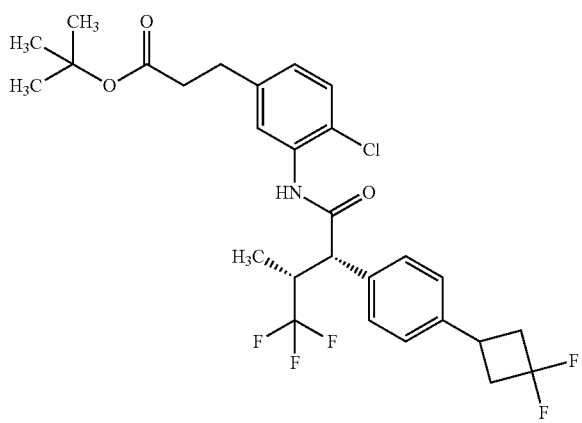 [SMILES: C[C@H]([C@H](C(=O)Nc1cc(CCC(=O)OC(C)(C)C)ccc1Cl)c1ccc(C2CC(F)(F)C2)cc1)C(F)(F)F]<br>(from (2S,3R)-2-[4-(3,3-difluorocyclobutyl)phenyl]-4,4,4-trifluoro-3-methylbutanoyl chloride and tert-butyl-3-(3-amino-4-chlorophenyl)propanoate) | $^1$H-NMR (400 MHz, DMSO-$d_6$, δ/ppm): 9.75 (1H, s), 7.44-7.37 (3H, m), 7.36-7.27 (3H, m), 7.02 (1H, dd), 4.10 (1H, d), 3.46-3.27 (2H, m, partially obscured by H$_2$O signal), 3.06-2.91 (2H, m), 2.75 (2H, t), 2.71-2.59 (2H, m), 2.45 (2H, t), 1.31 (9H, s), 0.79 (3H, d).<br>LC-MS (Method 4):<br>$R_t$ = 1.64 min; m/z = 558/560 (M − H)⁻. |

| Example | Name/Structure/Starting materials | Analytical Data |
|---|---|---|
| 245A | ethyl (2S)-3-[4-chloro-3-({(2S,3R)-2-[4-(3,3-difluoro-cyclobutyl)phenyl]-4,4,4-trifluoro-3-methyl-butanoyl}amino)phenyl]-2-methylpropanoate<br>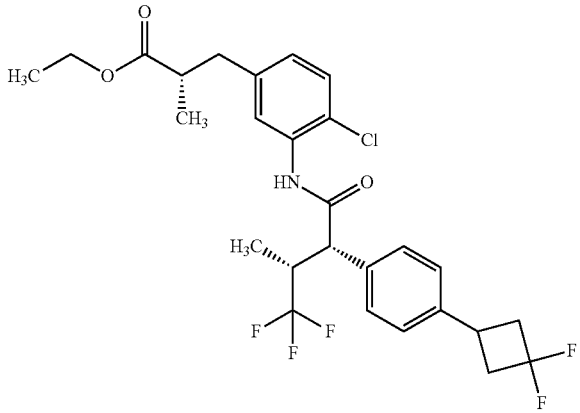 [SMILES: CCOC(=O)[C@@H](C)Cc1ccc(Cl)c(NC(=O)[C@H](c2ccc(C3CC(F)(F)C3)cc2)[C@@H](C)C(F)(F)F)c1]<br>(from (2S,3R)-2-[4-(3,3-difluorocyclobutyl)phenyl]-4,4,4-trifluoro-3-methylbutanoyl chloride and ethyl-(2S)-3-(3-amino-4-chlorophenyl)-2-methylpropanoate) | $^1$H-NMR (400 MHz, DMSO-d$_6$, δ/ppm): 9.75 (1H, s), 7.40 (3H, t), 7.32 (3H, t), 6.97 (1H, dd), 4.10 (1H, d), 3.96 (2H, q), 3.46-3.28 (2H, m, partially obscured by H$_2$O signal), 3.06-2.91 (2H, m), 2.84-2.58 (5H, m), 1.10-1.01 (6H, m), 0.79 (3H, d).<br>LC-MS (Method 6):<br>R$_t$ = 1.43 min; m/z = 544/546 (M − H)$^-$. |
| 246A | tert-butyl 3-[4-chloro-3-({(2S,3R)-2-[4-(2,2-difluoro-cyclopropyl)phenyl]-4,4,4-trifluoro-3-methyl-butanoyl}amino)phenyl]propanoate<br>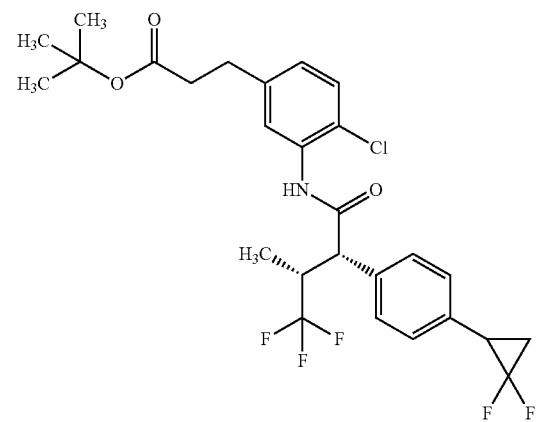 [SMILES: C[C@H]([C@H](C(=O)Nc1cc(CCC(=O)OC(C)(C)C)ccc1Cl)c1ccc(C2CC2(F)F)cc1)C(F)(F)F]<br>(from (2S,3R)-2-[4-(2,2-difluorocyclopropyl)phenyl]-4,4,4-trifluoro-3-methylbutanoyl chloride and tert-butyl-3-(3-amino-4-chlorophenyl)propanoate) | $^1$H-NMR (400 MHz, DMSO-d$_6$, δ/ppm): 9.77 (1H, s), 7.42 (3H, d), 7.34 (1H, d), 7.27 (2H, d), 7.02 (1H, dd), 4.09 (1H, d), 3.43-3.28 (1H, m, partially obscured by H$_2$O signal), 3.05-2.94 (1H, m), 2.75 (2H, t), 2.45 (2H, t), 2.04-1.86 (1H, m), 1.31 (9H, s), 0.78 (3H, d).<br>LC-MS (Method 7):<br>R$_t$ = 2.99 min; m/z = 544/546 (M − H)$^-$. |

Example 247A tert-Butyl 3-(3-{[(2S,3R)-2-(4-chlorophenyl)-4,4,4-trifluoro-3-methylbutanoyl]amino}-2-methyl-phenyl)propanoate

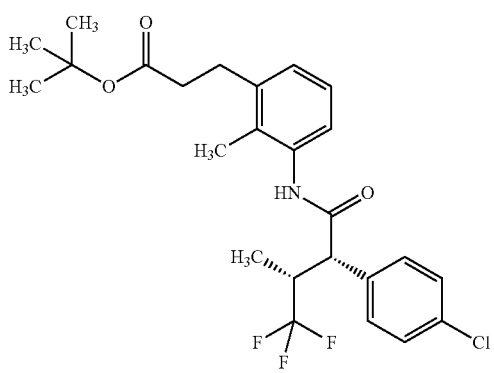 [SMILES: Cc1c(CCC(=O)OC(C)(C)C)cccc1NC(=O)[C@H](c1ccc(Cl)cc1)[C@@H](C)C(F)(F)F]

A mixture of 100 mg (0.38 mmol) of (2S,3R)-2-(4-chlorophenyl)-4,4,4-trifluoro-3-methylbutanoic acid, 88 mg (0.38 mmol) of tert-butyl 3-(3-amino-2-methylphenyl)propanoate, 213 mg (0.56 mmol) of 2-(1H-7-azabenzotriazol-1-yl)-1,1,3,3-tetramethyluronium hexafluorophosphate (HATU) and 1 ml of pyridine in 4 ml of DMF was stirred at room temperature overnight. After the reaction had ended, the reaction mixture was directly, without further work-up, separated into its components by preparative HPLC (mobile phase acetonitrile/water). This gave 151 mg (83% of theory) of the title compound as a colourless oil.

$^1$H-NMR (400 MHz, DMSO-$d_6$, δ/ppm): 9.68 (1H, s), 7.46 (4H, s), 7.09-6.93 (3H, m), 3.94 (1H, d), 3.43-3.28 (1H, m, partially obscured by H$_2$O signal), 2.78 (2H, t), 2.41 (2H, t), 1.91 (3H, s), 1.35 (9H, s), 0.80 (3H, d).

LC-MS (Method 4): R$_t$=1.57 min; m/z=482 (M−H)$^-$.

The following compound was obtained in an analogous manner:

Example 249A

Diethyl [2-(4-chlorophenyl)propan-2-yl]malonate

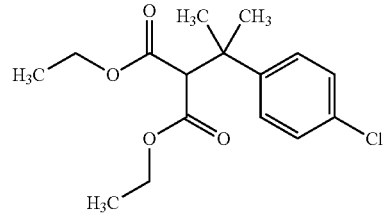

Under argon, 1 g (5.23 mmol) of 1-bromo-4-chlorobenzene in 2.5 ml of diethyl ether was added slowly to 254 mg (10.45 mmol) of magnesium turnings in 5 ml of diethyl ether. After the reaction had started, a further 1 g (5.23 mmol) of 1-bromo-4-chlorobenzene in 2.5 ml of diethyl ether was metered into the reaction mixture. The reaction mixture was stirred at room temperature for 30 min, 103 mg (1.05 mmol) of copper(I) chloride were added and the mixture was then cooled to −10° C. 2.09 g (10.45 mmol) of diethyl propan-2-ylidenemalonate were then slowly added dropwise. The reaction mixture was subsequently heated to reflux and stirred at this temperature for 3 h. 20 ml of ice-cold 1 M hydrochloric acid were then added very slowly. After separation of the phases, the aqueous phase was extracted three more times with diethyl ether. The combined organic phases were dried over magnesium sulphate and then concentrated to dryness. The crude product was purified by preparative HPLC (mobile phase methanol/water 70:30). This gave 800 mg of the title compound (25% of theory).

MS (DCI): m/z=330 (M+NH$_4$)$^+$.

GC-MS (Method 1): R$_t$=6.19 min; m/z=312 (M)$^+$.

| Example | Name/Structure/Starting Materials | Analytical Data |
|---|---|---|
| 248A | tert-butyl 3-(3-{[(2S,3R)-2-(4-chloro-3-methoxyphenyl)-4,4,4-trifluoro-3-methylbutanoyl]amino}-4-fluorophenyl)propanoate<br>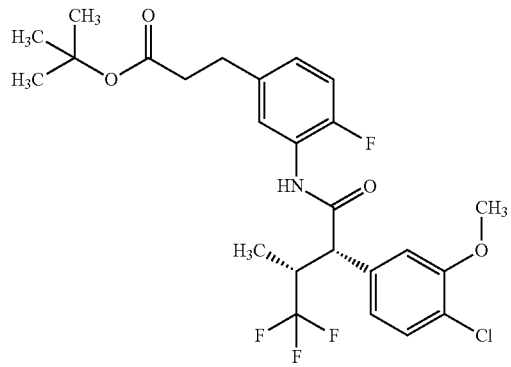 [SMILES: COc1cc([C@@H](C(=O)Nc2cc(CCC(=O)OC(C)(C)C)ccc2F)[C@@H](C)C(F)(F)F)ccc1Cl]<br>(from (2S,3R)-2-(4-chloro-3-methoxyphenyl)-4,4,4-trifluoro-3-methylbutanoic acid and tert-butyl 3-(3-amino-4-fluorophenyl)propanoate) | $^1$H-NMR (400 MHz, DMSO-$d_6$, δ/ppm): 10.00 (1H, s), 7.64 (1H, d), 7.41 (1H, d), 7.20 (1H, s), 7.13 (1H, t), 7.03-6.94 (2H, m), 4.07 (1H, d), 3.87 (3H, s), 3.48-3.34 (1H, m), 2.74 (2H, t), 2.45 (2H, t), 1.30 (9H, s), 0.82 (3H, d).<br>LC-MS (Mcihod 6): R$_t$ = 1.38 min; m/z = 516/518 (M − H)$^-$. |

Example 250A

Ethyl 3-(4-chlorophenyl)-3-methylbutanoate

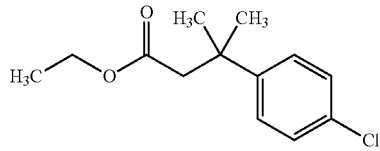 [SMILES: CCOC(=O)CC(C)(C)c1ccc(Cl)cc1]

A solution of 796 mg (2.55 mmol) of diethyl [2-(4-chlorophenyl)propan-2-yl]malonate, 216 mg (5.10 mmol) of lithium chloride and 46 μl (2.55 mmol) of water in 5 ml of DMSO was heated to reflux and stirred at this temperature for 4 h. After cooling to room temperature, 20 ml of diethyl ether and 20 ml of water were added to the reaction mixture. After separation of the phases, the organic phase was washed three more times with water, and the organic phase was dried over magnesium sulphate and then concentrated to dryness. The crude product was purified by preparative HPLC (mobile phase methanol/water 70:30). This gave 276 mg of the title compound (45% of theory).

MS (DCI): m/z=258 (M+NH$_4$)$^+$.
GC-MS (Method 1): R$_t$=4.99 min; m/z=240/242 (M)$^+$.

Example 251A

Ethyl 3-(4-chloro-3-nitrophenyl)-3-methylbutanoate

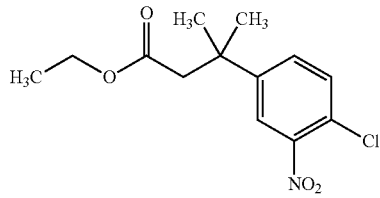

276 mg (1.45 mmol) of ethyl 3-(4-chlorophenyl)-3-methylbutanoate were dissolved in 10 ml of dichloromethane, and the mixture was cooled to 0° C. A little at a time, 278 mg (1.38 mmol) of nitronium tetrafluoroborate were then added, and the mixture was stirred at a temperature between 0° C. and 10° C. for 4 h. 10 ml of water and 10 ml of dichloromethane were then added, and the phases were separated. The organic phase was dried over magnesium sulphate and concentrated to dryness. The residue was purified by chromatography on silica gel (mobile phase cyclohexane/ethyl acetate 10:1). This gave 223 mg of the title compound (68% of theory).

MS (DCI): m/z=303 (M+NH$_4$)$^+$.
GC-MS (Method 1): R$_t$=6.39 min; m/z=285 (M)$^+$.
$^1$H-NMR (400 MHz, DMSO-d$_6$): δ [ppm]=1.00 (t, 3H), 1.38 (s, 6H), 2.74 (s, 2H), 3.89 (q, 2H), 7.66-7.76 (m, 2H), 8.03 (d, 1H).

Example 252A

Ethyl 3-(3-amino-4-chlorophenyl)-3-methylbutanoate

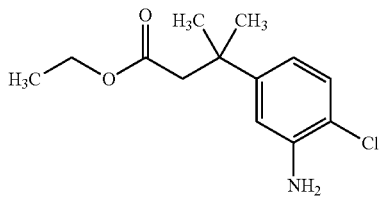 [SMILES: CCOC(=O)CC(C)(C)c1ccc(Cl)c([N+](=O)[O-])c1]

40 mg of palladium on carbon (10%) were added to a solution of 213 mg (0.75 mmol) of ethyl 3-(4-chloro-3-nitrophenyl)-3-methylbutanoate in 10 ml of ethyl acetate. The reaction mixture was hydrogenated at RT using a hydrogen pressure of 1 bar overnight. The mixture was then filtered through celite, and the filtrate was concentrated. This gave 166 mg (87% of theory) of the target compound as a yellowish oil.

LC-MS (Method 6): R$_t$=1.05 min; m/z=256/258 (M+H)$^+$.

The following compound was obtained analogously to Example 235A:

| Example | Name/Structure/Starting Materials | Analytical Data |
|---|---|---|
| 253A | Ethyl 3-(4-chloro-3-{[(2S,3R)-2-(4-chlorophenyl)-4,4,4-trifluoro-3-methylbutanoyl]amino}phenyl)-3-methylbutanoate<br><br>(from ethyl 3-(3-amino-4-chlorophenyl)-3-methylbutanoate and (2S,3R)-2-(4-chlorophenyl)-4,4,4-trifluoro-3-methylbutanoic acid) | LC-MS (Method 6): R$_t$ = 1.42 min; m/z = 504/506 (M + H)$^+$.<br>$^1$H-NMR (400 MHz, DMSO-d$_6$): δ [ppm] = 0.80 (d, 3H), 0.98 (t, 3H), 1.32 (s, 6H), 2.58 (s, 2H), 3.30-3.43 (m, 1H, partially obscured by H$_2$O signal), 3.86 (q, 2H), 4.14 (d, 1H), 7.20 (dd, 1H), 7.35 (d, 1H), 7.43-7.50 (m, 4H), 7.55 (d, 1H), 9.82 (s, 1H). |

Exemplary Embodiments

General Procedure 2

Cleavage of Tert-Butyl Esters to the Corresponding Carboxylic Acids Using Trifluoroacetic Acid At from 0° C. to RT, trifluoroacetic acid (TFA) is added dropwise to a solution of the tert-butyl ester in question in dichloromethane (concentration about 0.1 to 2.0 mol/l; additionally optionally a drop of water) until a dichloromethane/TFA ratio of about 2:1 to 1:2 (v/v) is reached. The mixture is stirred at RT for 1-24 h; if required, the mixture is warmed to 40° C. until complete conversion is achieved. The reaction mixture is then concentrated under reduced pressure. The crude product can be purified by chromatography on silica gel (elution with dichloromethane/ethyl acetate or cyclohexane/ethyl acetate mixtures, if appropriate with addition of small amounts of acetic acid, or with dichloromethane/methanol mixtures), by crystallization from acetonitrile or water/acetonitrile mixtures or by preparative RP-HPLC (mobile phase: acetonitrile/water gradient).

The following examples were prepared according to General Procedure 2:

| Example | Name/Structure/Starting Material | Analytical Data |
| --- | --- | --- |
| 1 | (+)-3-(4-chloro-3-{[(2S,3R)-4,4,4-trifluoro-2-(4-isopropylphenyl)-3-methylbutanoyl] amino}-phenyl)propanoic acid 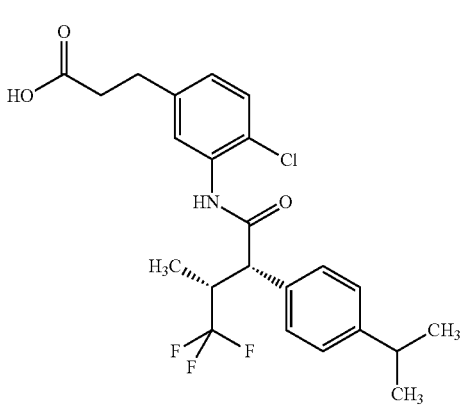 [SMILES: CC(C)c1ccc([C@@H](C(=O)Nc2cc(CCC(=O)O)ccc2Cl)[C@@H](C)C(F)(F)F)cc1] (from tert-butyl 3-(4-chloro-3-{[(2S,3R)-4,4,4-trifluoro-2-(4-isopropylphenyl)-3-methylbutanoyl]-amino}phenyl)propanoate) | $^1$H-NMR (400 MHz, DMSO-$d_6$, δ/ppm): 12.65-11.44 (1H, br. s), 9.72 (1H, s), 7.45 (1H, d), 7.35 (3H, t), 7.24 (2H, d), 7.03 (1H, dd), 4.07 (1H, d), 3.39-3.24 (1H, m), 2.94-2.81 (1H, m), 2.76 (2H, t), 2.48 (2H, t), 1.19 (6H, d), 0.79 (3H, d). LC-MS (Method 5): $R_t$ = 2.69 min; m/z = 456 (M + H)$^+$. $[α]_D^{20}$ = +102.5°, c = 0.44, methanol. |
| 2 | (+)-3-(3-{[(2S,3R)-2-(4-tert-butylphenyl)-4,4,4-trifluoro-3-methylbutanoyl]amino}-4-chlorophenyl)propanoic acid 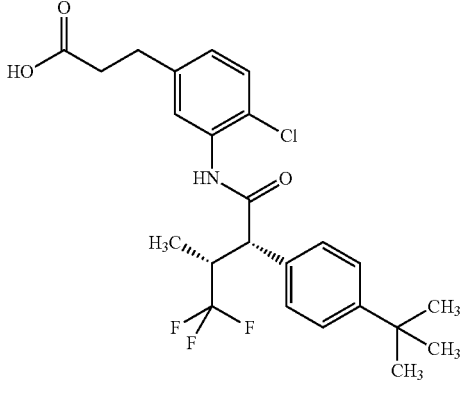 [SMILES: C[C@H]([C@H](C(=O)Nc1cc(CCC(=O)O)ccc1Cl)c1ccc(C(C)(C)C)cc1)C(F)(F)F] (from tert-butyl-3-(3-{[(2S,3R)-2-(4-tert-butyl-phenyl)-4,4,4-trifluoro-3-methylbutanoyl]amino}-4-chlorophenyl)propanoate) | $^1$H-NMR (400 MHz, DMSO-$d_6$, δ/ppm): 12.11 (1H, s), 9.72 (1H, s), 7.47 (1H, d), 7.41-7.35 (4H, m), 7.33 (1H, d), 7.03 (1H, dd), 4.08 (1H, d), 3.39-3.24 (1H, m), 2.76 (2H, t), 2.48 (2H, t), 1.27 (9H, s), 0.79 (3H, d). LC-MS (Method 4): $R_t$ = 1.47 min; m/z = 470 (M + H)$^+$. $[α]_D^{20}$ = +94.9°, c = 0.42, methanol. |

| Example | Name/Structure/Starting Material | Analytical Data |
| --- | --- | --- |
| 3 | 3-[4-chloro-3-({(2S,3R)-4,4,4-trifluoro-3-methyl-2-[4-(trifluoromethyl)phenyl]butanoyl}amino)-phenyl]propanoic acid<br>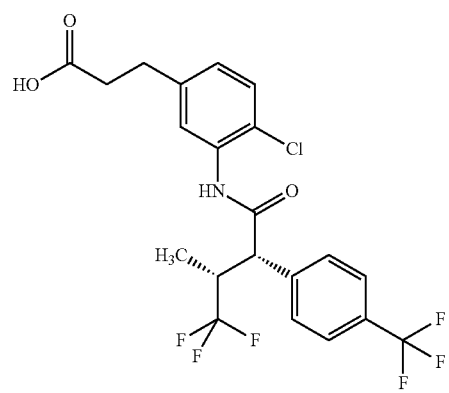 [SMILES: C[C@H]([C@H](C(=O)Nc1cc(CCC(=O)O)ccc1Cl)c1ccc(C(F)(F)F)cc1)C(F)(F)F]<br>(from tert-butyl 3-[4-chloro-3-({(2S,3R)-4,4,4-trifluoro-3-methyl-2-[4-(trifluoromethyl)phenyl]-butanoyl}amino)phenyl]propanoate) | $^1$H-NMR (400 MHz, DMSO-$d_6$, δ/ppm): 12.49-11.83 (1H, br. s), 9.89 (1H, s), 7.77 (2H, d), 7.69 (2H, d), 7.39 (1H, d), 7.35 (1H, d), 7.05 (1H, dd), 4.24 (1H, d), 3.59-3.26 (1H, m), 2.76 (2H, t), 2.48 (2H, t), 0.80 (3H, d).<br>LC-MS (Method 4): $R_t$ = 1.34 min; m/z = 482 (M + H)$^+$. |
| 4 | (+)-3-[4-chloro-3-({(2S,3R)-4,4,4-trifluoro-3-methyl-2-[4-(1,1,1-trifluoro-2-methylpropan-2-yl)phenyl]-butanoyl]amino)phenyl]propanoic acid<br>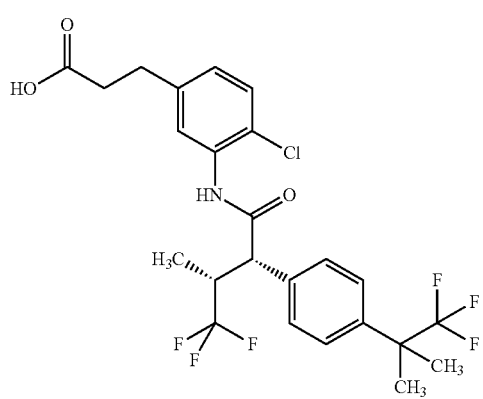 [SMILES: C[C@H]([C@H](C(=O)Nc1cc(CCC(=O)O)ccc1Cl)c1ccc(C(C)(C)C(F)(F)F)cc1)C(F)(F)F]<br>(from tert-butyl 3-[4-chloro-3-({(2S,3R)-4,4,4-trifluoro-3-methyl-2-[4-(1,1,1-trifluoro-2-methylpropan-2-yl)phenyl]butanoyl}-amino)phenyl]propanoate) | $^1$H-NMR (400 MHz, DMSO-$d_6$, δ/ppm): 12.11 (1H, s), 9.78 (1H, s), 7.54 (2H, d), 7.51-7.42 (3H, m), 7.34 (1H, d), 7.03 (1H, dd), 4.14 (1H, d), 3.42-3.26 (1H, m), 2.76 (2H, t), 2.48 (2H, t), 1.55 (6H, s), 0.79 (3H, d).<br>LC-MS (Method 6): $R_t$ = 1.24 min; m/z = 524 (M + H)$^+$.<br>$[α]_D^{20}$ = +72.1°, c = 0.43, methanol. |

-continued

| Example | Name/Structure/Starting Material | Analytical Data |
|---|---|---|
| 5 | 3-[4-Chloro-3-({4,4,4-trifluoro-3-methyl-2-[4-(2,2,2-trifluoroethyl)phenyl]butanoyl}amino)phenyl]-propanoic acid<br><br>(from tert-butyl 3-[4-chloro-3-({4,4,4-trifluoro-3-methyl-2-[4-(2,2,2-trifluoroethyl)phenyl]-butanoyl}amino)phenyl]propanoate) | $^1$H-NMR (400 MHz, DMSO-$d_6$, δ/ppm): 12.11 (1H, s), 9.79 (1H, s), 7.46 (2H, d), 7.41 (1H, d), 7.35 (3H, t), 7.04 (1H, dd), 4.11 (1H, d), 3.64 (2H, q), 3.44-3.26 (1H, m), 2.76 (2H, t), 2.48 (2H, t), 0.79 (3H, d). LC-MS (Method 4): $R_t$ = 1.33 min; m/z = 496 (M + H)$^+$. |
| 6 | 3-(4-chloro-3-{[(4-chlorophenyl)(3,3-difluoro-cyclopentyl)acetyl]amino}phenyl)propanoic acid<br><br>(from tert-butyl 3-(4-chloro-3-{[(4-chlorophenyl)-(3,3-difluorocyclopentyl)acetyl]amino}phenyl)-propanoate) | 1H-NMR (400 MHz, DMSO-$d_6$, δ/ppm): 12.13 (1H, s), 9.79 (0.5H, s), 9.75 (0.5H, s), 7.48-7.34 (6H, m), 7.07 (1H, d), 3.78 (0.5H, d), 3.75 (0.5H, d), 3.58-3.45 (0.5H, m), 3.43-3.26 (0.5H, m), 2.92-2.81 (1H, m), 2.77 (2H, t), 2.57-2.45 (2H, t), 2.44-1.80 (3H, m), 1.71-1.45 (1.5H, m), 1.35-1.20 (0.5H, m). LC-MS (Method 6): $R_t$ = 1.15 min; m/z = 456/458 (M + H)$^+$. |
| 7 | 3-(4-chloro-3-{[(2S,3R)-2-(4-ethylphenyl)-4,4,4-tri-fluoro-3-methylbutanoyl]amino}phenyl)butanoic acid (diastereomer mixture) | LC-MS (Method 6): $R_t$ = 1.24 min; m/z = 456 (M + H)$^+$. $^1$H-NMR (400 MHz, DMSO-$d_6$): δ [ppm] = 0.79 (d, 3H), 1.12-1.21 (m, 6H), 2.45 (d, 2H), 2.59 (q, 2H), 3.03-3.13 (m, 1H), 3.32 (d, 1H), 4.07 (d, 1H), 7.06 (d, 1H), 7.20 (d, 2H), 7.31-7.38 (m, 3H), 7.47 (d, 1H), 9.69 (s, 1H), 12.03 (br. s, 1H). |

-continued

| Example | Name/Structure/Starting Material | Analytical Data |
|---|---|---|
| 8 | 3-(3-{[(2S,3R)-2-(4-chlorophenyl)-4,4,4-trifluoro-3-methylbutanoyl]amino}-4-chlorophenyl)butanoic acid {diastereomer mixture}<br>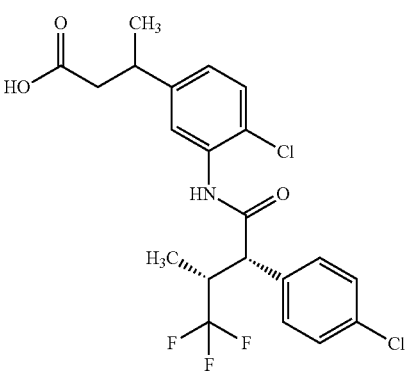 | LC-MS (Method 4): $R_t$ = 1.45 min; m/z = 462 $(M + H)^+$.<br>$^1$H-NMR (400 MHz, DMSO-$d_6$): δ [ppm] = 0.80 (d, 3H), 1.16 (d, 3H), 2.45 (d, 2H), 3.01-3.14 (m, 1H), 3.34-3.42 (m, 1H), 4.13 (d, 1H), 7.08 (dd, 1H), 7.36 (d, 1H), 7.40-7.50 (m, 5H), 9.81 (s, 1H), 12.06 (s, 1H). |
| 9 | 3-(3-{[(2S,3R)-2-(4-chlorophenyl)-4,4,4-trifluoro-3-methylbutanoyl]amino}-4-fluorophenyl)butanoic acid (diastereomer mixture)<br>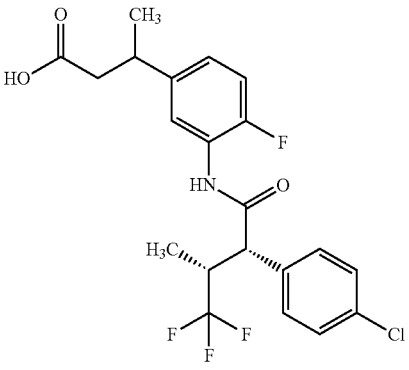 | LC-MS (Method 5): $R_t$ = 2.47 min; m/z = 446 $(M + H)^+$.<br>$^1$H-NMR (400 MHz, DMSO-$d_6$): δ [ppm] = 0.79 (d, 3H), 1.15/1.16 (2d, together 3H), 2.44 (d, 2H), 3.02-3.13 (m, 1H), 3.34-3.42 (m, 1H), 4.12 (d, 1H), 6.97-7.06 (m, 1H), 7.13 (dd, 1H), 7.40-7.49 (m, 4H), 7.67 (d, 1H), 10.03 (s, 1H), 12.05 (br. s, 1H). |
| 10 | (3S)-3-(4-chloro-3-{[(4-chlorophenyl)(2,2-difluorocyclopentyl)acetyl]amino}phenyl)butanoic acid (diastereomer mixture)<br>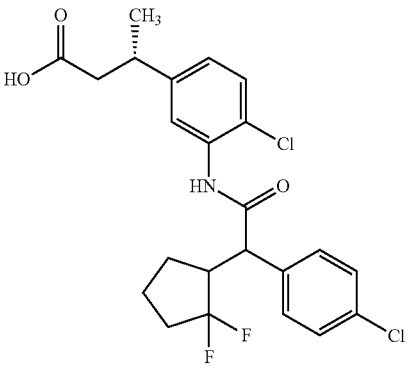 [SMILES: C[C@@H](CC(=O)O)c1ccc(Cl)c(NC(=O)C(c2ccc(Cl)cc2)C2CCCC2(F)F)c1] | LC-MS (Method 6):<br>$R_t$ = 1.17 min; m/z = 470 $(M + H)^+$ and $R_t$ = 1.19 min; m/z = 470 $(M + H)^+$.<br>$^1$NMR (400 MHz, DMSO-$d_6$): δ [ppm] = 1.11-1.19 (m, 3H), 1.45-1.78 (m, 3H), 2.00-2.26 (m, 2H), 2.45/2.46 (2d, together 2H), 2.88-3.17 (m, 2H), 4.04/4.07 (2d, together 1H), 6.99-7.13 (m, 1H), 7.30-7.44 (m, 3H), 7.44-7.52 (m, 2H), 9.64/9.84 (2s, together 1H), 12.07 (br. s, 1H). |

| Example | Name/Structure/Starting Material | Analytical Data |
|---|---|---|
| 11 | 3-(4-chloro-3-{[(4-chlorophenyl)(2,2-difluoro-cyclopentyl)acetyl]amino}phenyl)propanoic acid (diastereomer mixture) 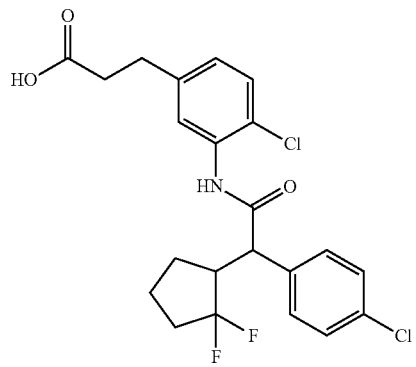 [SMILES: O=C(O)CCc1ccc(Cl)c(NC(=O)C(c2ccc(Cl)cc2)C2CCCC2(F)F)c1] | LC-MS (Method 6): R$_t$ = 1.16 min; m/z = 456 (M + H)$^+$ and R$_t$ = 1.18 min; m/z = 456 (M + H)$^+$. $^1$H-NMR (400 MHz, DMSO-d$_6$): δ [ppm] = 1.11-1.81 (m, 3H), 1.96-2.26 (m, 2H), 2.48 (t, 2H), 2.76 (t, 2H), 2.86-3.20 (m, 1H), 4.03/4.07 (2d, together 1H), 6.98-7.09 (m, 1H), 7.29-7.54 (m, 6H), 9.64/9.85 (2s, together 1H), 12.09 (br. s, 1H). |

Example 12

(+)-3-(4-Fluoro-3-{[(2S,3R)-4,4,4-trifluoro-3-methyl-2-(4-vinylphenyl)butanoyl]amino}phenyl)-propanoic acid

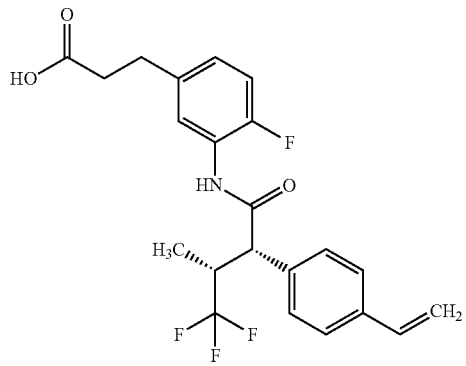 [SMILES: C=Cc1ccc([C@@H](C(=O)Nc2cc(CCC(=O)O)ccc2F)[C@@H](C)C(F)(F)F)cc1]

283 mg (0.590 mmol) of tert-butyl (+)-3-(4-fluoro-3-{[(2S,3R)-4,4,4-trifluoro-3-methyl-2-(4-vinylphenyl)butanoyl]amino}phenyl)propanoate were dissolved in 5.9 ml of a 4 N solution of hydrogen chloride in dioxane, and the mixture was stirred at RT for 24 h. The volatile components were then removed under reduced pressure. The residue was purified by two preparative RP-HPLCs (mobile phase: acetonitrile/water gradient). This gave 48 mg (19.2% of theory) of the title compound.

LC-MS (Method 6): R$_t$=1.14 min; m/z=424 (M+H)$^+$.

$^1$H-NMR (400 MHz, DMSO-d$_6$): δ [ppm]=0.79 (d, 3H), 2.63-2.82 (m, 4H), 3.58-3.66 (m, 1H), 4.08 (d, 1H), 5.27 (d, 1H), 5.83 (d, 1H), 6.72 (dd, 1H), 6.89-7.03 (m, 1H), 7.12 (dd, 1H), 7.41 (d, 2H), 7.47 (d, 2H), 7.65 (dd, 1H), 10.00 (s, 1H), 12.12 (br. s, 1H).

[α]$_D^{20}$=+149.5°, c=0.310, chloroform.

Example 13

(+)-3-(4-Chloro-3-{(2S,3R)-4,4,4-trifluoro-3-methyl-2-(4-vinylphenyl)butanoyl]amino}phenyl)-propanoic acid

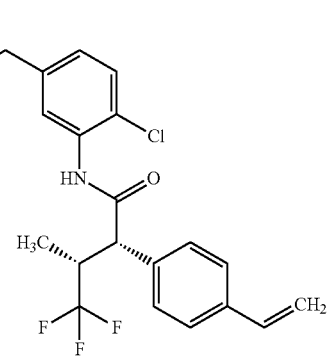

249.0 mg (0.502 mmol) of tert-butyl (+)-3-(4-chloro-3-{[(2S,3R)-4,4,4-trifluoro-3-methyl-2-(4-vinylphenyl)butanoyl]amino}phenyl)propanoate were dissolved in 3.8 ml of a 4 N solution of hydrogen chloride in dioxane, and the mixture was stirred at RT for 24 h. The reaction mixture was then frozen (−78° C.) and subsequently lyophilized under high vacuum. The residue was purified by preparative RP-HPLC (mobile phase: acetonitrile/water gradient). This gave 167.4 mg (75.8% of theory) of the title compound.

LC-MS (Method 6): R$_t$=1.16 min; m/z=440 (M+H)$^+$.

$^1$H-NMR (400 MHz, DMSO-d$_6$): δ [ppm]=0.80 (d, 3H), 2.48 (t, 2H), 2.76 (t, 2H), 3.35-3.42 (m, 1H), 4.09 (d, 1H), 5.27 (d, 1H), 5.84 (d, 1H), 6.73 (dd, 1H), 7.04 (dd, 1H), 7.34 (d, 1H), 7.39-7.52 (m, 5H), 9.79 (s, 1H), 12.14 (br. s, 1H).

[α]$_D^{20}$=+88.8°, c=0.325, chloroform.

Example 14

(+)-3-[4-Chloro-3-({(2S,3R)-4,4,4-trifluoro-2-[4-(1-fluorovinyl)phenyl]-3-methylbutanoyl}amino)-phenyl]propanoic acid

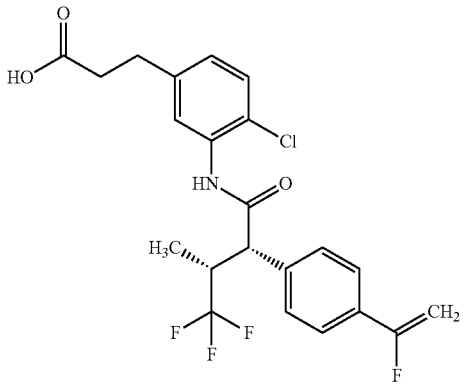 [SMILES: C=C(F)c1ccc([C@@H](C(=O)Nc2cc(CCC(=O)O)ccc2Cl)[C@@H](C)C(F)(F)F)cc1]

16.1 mg (0.674 mmol) of lithium hydroxide were added to a solution, cooled to 0° C., of 212 mg (0.449 mmol) of (+)-3-[4-chloro-3-({(2S,3R)-4,4,4-trifluoro-2-[4-(1-fluorovinyl)phenyl]-3-methylbutanoyl}amino)phenyl]propanoate in a mixture of in each case 1.0 ml of methanol, of THF and of water. The mixture was then warmed to RT and stirred at RT for 3 h, then diluted with water and acidified with 1 N hydrochloric acid (pH about 2). The mixture was extracted three times with ethyl acetate. The organic phases were combined and concentrated under reduced pressure. The crude product was initially pre-purified by RP-HPLC (mobile phase: acetonitrile/water gradient). The 2R diastereomer formed during basic hydrolysis was then removed by preparative HPLC on a chiral phase [column: Daicel Chiralpak AD-H, 5 μm, 250 mm×20 mm; injection volume: 0.25 ml; temperature: 35° C.; mobile phase: 90% isohexane/10% ethanol; flow rate: 15 ml/min; detection: 220 nm]. This gave 74.0 mg (36.0% of theory) of the title compound.

LC-MS (Method 4): $R_t$=1.33 min; m/z=458 (M+H)$^+$.

$^1$H-NMR (400 MHz, DMSO-d$_6$): δ [ppm]=0.81 (d, 3H), 2.47 (t, 2H), 2.76 (t, 2H), 3.35-3.43 (m, 1H), 4.15 (d, 1H), 4.95 (dd, 1H), 5.39 (dd, 1H), 7.04 (dd, 1H), 7.26-7.44 (m, 2H), 7.44-7.59 (m, 2H), 7.59-7.68 (m, 2H), 9.82 (s, 1H), 12.11 (br. s, 1H).

$[α]_D^{20}$=+69.2°, c=0.405, chloroform.

Example 15

(+)-3-(4-Chloro-3-{[(2S,3R)-2-(4-chlorophenyl)-4,4,4-trifluoro-3-methylbutanoyl]amino}phenyl)-propanoic acid

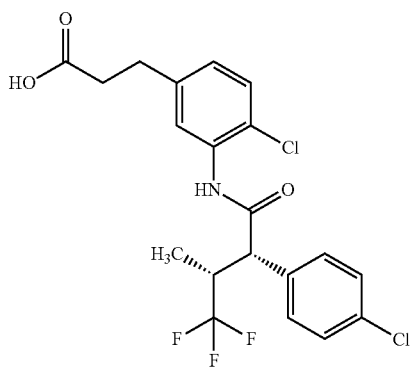 [SMILES: C[C@H]([C@H](C(=O)Nc1cc(CCC(=O)O)ccc1Cl)c1ccc(Cl)cc1)C(F)(F)F]

30.13 g (59.74 mmol) of tert-butyl 3-(4-chloro-3-{[(2S,3R)-2-(4-chlorophenyl)-4,4,4-trifluoro-3-methylbutanoyl]amino}phenyl)propanoate were dissolved in 1000 ml of dichloromethane, and 92 ml of trifluoroacetic acid were added at RT. The reaction mixture was stirred at RT for 3.5 h. Dichloromethane and water were then added. The organic phase was separated off, dried over magnesium sulphate and concentrated under reduced pressure. The residue was dried thoroughly under high vacuum. This gave 26.31 g (98.3% of theory) of the target compound.

LC-MS (Method 7): $R_t$=2.51 min; m/z=446/448 (M−H)$^-$.

$^1$H-NMR (400 MHz, DMSO-d$_6$, δ/ppm): 12.14 (1H, s), 9.83 (1H, s), 7.50-7.43 (4H, m), 7.39 (1H, d), 7.35 (1H, d), 7.05 (1H, dd), 4.12 (1H, d), 3.43-3.28 (1H, m), 2.76 (2H, t), 2.48 (2H, t), 0.80 (3H, d).

$[α]_D^{20}$=+100.1°, c=0.42, methanol.

Example 16

(+)-(2R)-3-(4-Chloro-3-{[(2S,3R)-2-(4-chlorophenyl)-4,4,4-trifluoro-3-methylbutanoyl]amino}-phenyl)-2-methylpropanoic acid

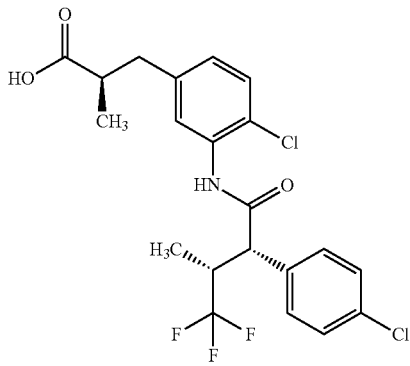 [SMILES: C[C@H](Cc1ccc(Cl)c(NC(=O)[C@H](c2ccc(Cl)cc2)[C@@H](C)C(F)(F)F)c1)C(=O)O]

990 mg (2.02 mmol) of ethyl (2R)-3-(4-chloro-3-{[(2S,3R)-2-(4-chlorophenyl)-4,4,4-trifluoro-3-methylbutanoyl]amino}phenyl)-2-methylpropanoate were dissolved in 5.7 ml of acetic acid, and 2.7 ml of concentrated hydrochloric acid were added. The mixture was stirred at 100° C. for 1 h. After cooling, the mixture was concentrated under reduced pressure. The residue was taken up in ethyl acetate and washed repeatedly with water with addition of a few drops of saturated sodium bicarbonate solution. The organic phase was dried over magnesium sulphate and concentrated under reduced pressure. The residue was purified by chromatography on silica gel (mobile phase: initially dichloromethane, then dichloromethane/ethyl acetate 10:1). This gave 652 mg (69.9% of theory) of the title compound.

LC-MS (Method 6): $R_t$=1.21 min; m/z=462 (M+H)$^+$.

$^1$H-NMR (400 MHz, DMSO-d$_6$): δ [ppm]=0.80 (d, 3H), 1.02 (d, 3H), 2.55-2.62 (m, 2H), 2.78-2.88 (m, 1H), 3.35-3.43 (m, 1H), 4.12 (d, 1H), 7.01 (dd, 1H), 7.32-7.39 (m, 2H), 7.42-7.50 (m, 4H), 9.83 (s, 1H), 12.16 (br. s, 1H).

$[α]_D^{20}$=+60.56°, c=0.530, chloroform.

Example 17

(+)-(2S)-3-(4-Chloro-3-{[(2S,3R)-2-(4-chlorophenyl)-4,4,4-trifluoro-3-methylbutanoyl]amino}-phenyl)-2-methylpropanoic acid

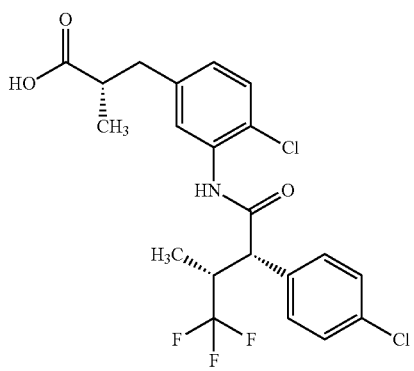 [SMILES: C[C@H]([C@H](C(=O)Nc1cc(C[C@H](C)C(=O)O)ccc1Cl)c1ccc(Cl)cc1)C(F)(F)F]

Method A:

A mixture of 2.45 g (5.0 mmol) of ethyl (2S)-3-(4-chloro-3-{[(2S,3R)-2-(4-chlorophenyl)-4,4,4-trifluoro-3-methylbutanoyl]amino}phenyl)-2-methylpropanoate, 6.0 ml of acetic acid and 20 ml of 20% strength aqueous sulphuric acid was stirred under reflux for 7 h. After cooling, the reaction mixture was added to water. The aqueous phase was extracted three times with ethyl acetate, and the combined organic phases were concentrated under reduced pressure. The residue was once more taken up in ethyl acetate and washed repeatedly with water with addition of a few drops of saturated sodium bicarbonate solution. The organic phase was dried over magnesium sulphate and concentrated under reduced pressure. The crude product was purified by chromatography on silica gel (mobile phase cyclohexane/ethyl acetate 10:1→4:1). This gave 1.88 g (81.4% of theory) of the title compound.

LC-MS (Method 6): $R_t$=1.22 min; m/z=462 (M+H)$^+$.

$^1$H-NMR (400 MHz, DMSO-$d_6$): δ [ppm]=0.80 (d, 3H), 1.02 (d, 3H), 2.55-2.61 (m, 2H), 2.78-2.88 (m, 1H), 3.35-3.43 (m, 1H), 4.12 (d, 1H), 7.01 (dd, 1H), 7.32-7.39 (m, 2H), 7.43-7.50 (m, 4H), 9.83 (s, 1H), 12.16 (br. s, 1H).

$[α]_D^{20}$=+101.2°, c=0.590, chloroform.

Method B:

A mixture of 12.99 g (26.49 mmol) of (+)-ethyl (2S)-3-(4-chloro-3-{[(2S,3R)-2-(4-chlorophenyl)-4,4,4-trifluoro-3-methylbutanoyl]amino}phenyl)-2-methylpropanoate, 60 ml of acetic acid and 60 ml of 30% strength aqueous sulphuric acid was stirred under reflux for 3 h (bath temperature 140° C.). After cooling, the reaction mixture was added to water. The aqueous phase was extracted three times with ethyl acetate, and the combined organic phases were washed with saturated sodium chloride solution, dried over sodium sulphate and concentrated under reduced pressure. The residue was dried under high vacuum overnight. The crude product obtained in this manner was stirred with 90 ml of diisopropyl ether, initially at 50° C. for 1 h and then at RT for 4 h. After filtration, the solid was dried under high vacuum. This gave 7.84 g (64% of theory) of the target compound (fraction 1). A further charge was isolated from the filtrate after concentration and renewed treatment with 30 ml of diisopropyl ether. Drying under high vacuum gave 1.65 g (13.5% of theory) of slightly contaminated target compound (fraction 2).

LC-MS (Method 4): $R_t$=1.39 min; m/z=461/463 (M+H)$^+$.

$^1$H-NMR (400 MHz, DMSO-$d_6$): δ [ppm]=0.80 (d, 3H), 1.02 (d, 3H), 2.55-2.61 (m, 2H), 2.77-2.88 (m, 1H), 3.34-3.43 (m, 1H), 4.12 (d, 1H), 7.01 (dd, 1H), 7.31-7.39 (m, 2H), 7.41-7.51 (m, 4H), 9.83 (s, 1H), 12.15 (s, 1H).

$[α]_D^{20}$=+127.6°, c=0.575, chloroform.

Example 18

(+)-[1-(3-{[(2S,3R)-2-(4-Chlorophenyl)-4,4,4-trifluoro-3-methylbutanoyl]amino}-4-fluorophenyl)-cyclopropyl]acetic acid

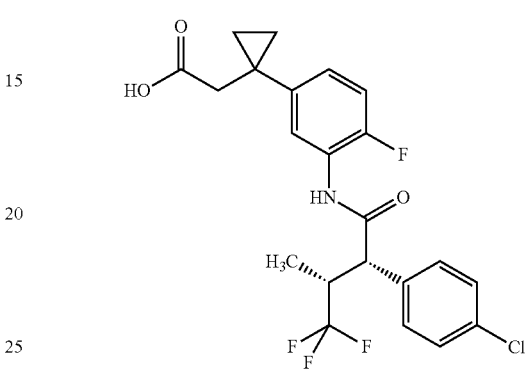

106 mg (0.23 mmol) of methyl [1-(3-{[(2S,3R)-2-(4-chlorophenyl)-4,4,4-trifluoro-3-methylbutanoyl]amino}-4-fluorophenyl)cyclopropyl]acetate were dissolved in 4 ml of glacial acetic acid and 2 ml of concentrated hydrochloric acid, and the mixture was stirred at 100° C. for 1 h. The reaction mixture was then diluted with 10 ml of water and the aqueous solution was subsequently extracted three times with in each case 10 ml of ethyl acetate. The combined organic phases were dried over magnesium sulphate and concentrated under reduced pressure. The crude product obtained was purified by preparative RP-HPLC (mobile phase: acetonitrile/water gradient). This gave 64 mg of the title compound (0.14 mmol, 89% of theory).

LC-MS (Method 4): $R_t$=1.34 min; m/z=458 (M+H)$^+$.

$^1$H-NMR (400 MHz, DMSO-$d_6$, δ/ppm): 10.03 (1H, s), 7.69-7.59 (1H, m), 7.52-7.34 (4H, m), 7.11-7.00 (2H, m), 4.11 (1H, d), 3.43-3.27 (1H, m), 2.36 (2H, s), 0.88-0.82 (2H, m), 0.78 (3H, d), 0.72-0.64 (2H, m).

$[α]_D^{20}$=+108.7°, c=0.36, methanol.

General Procedure 3

Cleavage of Ethyl or Methyl Esters to the Corresponding Carboxylic Acids Using a Mixture of Hydrochloric Acid or Sulphuric Acid with Acetic Acid A solution of the ethyl or methyl ester in question in a mixture of acetic acid and concentrated hydrochloric acid or of acetic acid and 10% strength or semi-concentrated sulphuric acid is stirred at temperatures of from 80° C. to 130° C. (if appropriate under reflux) for 30 min to 12 h. After cooling, the reaction mixture is either concentrated directly under reduced pressure or added to water, the aqueous phase is extracted with ethyl acetate or dichloromethane and the combined organic phases are concentrated under reduced pressure. The crude product can be purified by chromatography on silica gel (elution with dichloromethane/ethyl acetate or cyclohexane/ethyl acetate mixtures, if appropriate with addition of small amounts of acetic acid, or with dichloromethane/methanol mixtures), by crystallization from acetonitrile or water/acetonitrile mixtures or by preparative RP-HPLC (mobile phase: acetonitrile/water gradient).

The examples below were prepared according to General Procedure 3:

| Example | Name/Structure/Starting Material | Analytical Data |
|---|---|---|
| 19 | (+)-[1-(3-{[(2S,3R)-2-(4-ethylphenyl)-4,4,4-trifluoro-3-methylbutanoyl]amino}-4-fluorophenyl)-cyclopropyl]acetic acid<br/>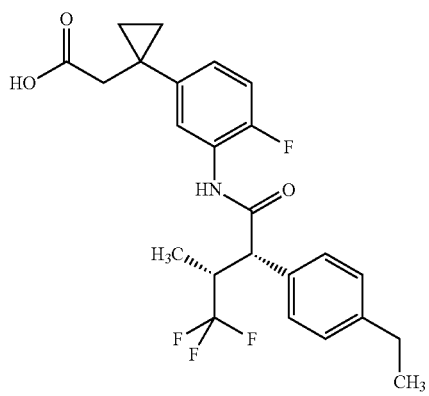 [SMILES: CCc1ccc([C@@H](C(=O)Nc2cc(C3(CC(=O)O)CC3)ccc2F)[C@@H](C)C(F)(F)F)cc1]<br/>(from methyl [1-(3-{[(2S,3R)-2-(4-ethylphenyl)-4,4,4-trifluoro-3-methylbutanoyl]amino}-4-fluorophenyl)cyclopropyl]acetate) | $^1$H-NMR (400 MHz, DMSO-$d_6$, δ/ppm): 11.97 (1H, s), 9.96 (1H, s), 7.75 (1H, dd), 7.34 (2H, d), 7.20 (2H, d), 7.09 (1H, t), 7.05-6.99 (1H, m), 4.05 (1H, d), 3.40-3.27 (1H, m), 2.59 (2H, q), 2.55-2.48 (2H, m), 1.17 (3H, t), 0.88-0.82 (2H, m), 0.79-0.74 (5H, m).<br/>LC-MS (Method 5): $R_t$ = 2.58 min; m/z = 452 (M + H)$^+$.<br/>$[α]_D^{20}$ = +125.2°, c = 0.35, methanol. |
| 20 | (2S)-3-(4-chloro-3-{[(4-chlorophenyl)(3,3-difluoro-cyclopentyl)acetyl]amino}phenyl)-2-methyl-propanoic acid<br/>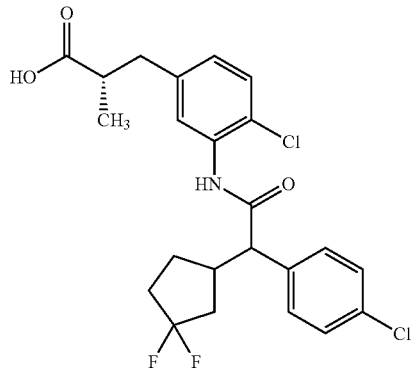<br/>(from ethyl (2S)-3-(4-chloro-3-{[(4-chlorophenyl)-(3,3-difluorocyclopentyl)acetyl]amino}phenyl)-2-methylpropanoate) | LC-MS (Method 6): $R_t$ = 1.21 min; m/z = 470/472 (M)$^+$. |

-continued

| Example | Name/Structure/Starting Material | Analytical Data |
|---|---|---|
| 21 | (2R)-3-(4-chloro-3-{[(4-chlorophenyl)(3,3-difluoro-cyclopentyl)acetyl]amino}phenyl)-2-methyl-propanoic acid<br><br>(from ethyl (2R)-3-(4-chloro-3-{[(4-chlorophenyl)-(3,3-difluorocyclopentyl)acetyl]amino}phenyl)-2-methylpropanoate) | LC-MS (Method 6): $R_t$ = min; m/z = 470/472 (M)$^+$. |
| 22 | 3-(4-chloro-3-{[(2S,3R)-2-(4-chlorophenyl)-4,4,4-trifluoro-3-methylbutanoyl]amino}phenyl)-2-methylpropanoate {diastereomer mixture} | LC-MS (Method 5): $R_t$ = 2.57 min; m/z = 462 (M + H)$^+$.<br>$^1$H-NMR (400 MHz, DMSO-$d_6$): δ [ppm] = 0.80 (d, 3H), 1.02 (d, 3H), 2.55-2.61 (m, 2H), 2.77-2.89 (m, 1H), 3.33-3.42 (m, 1H), 4.12 (d, 1H), 7.01 (dd, 1H), 7.30-7.40 (m, 2H), 7.41-7.51 (m, 4H), 9.82 (s, 1H), 12.14 (br. s, 1H). |
| 23 | 3-(3-{[(2S,3R)-2-(4-ethylphenyl)-4,4,4-trifluoio-3-methylbutanoyl]amino}-4-fluorophenyl)-2-methylpropanoic acid (diastereomer mixture) | LC-MS (Method 6): $R_t$ = 1.22 min; m/z = 440 (M + H)$^+$.<br>$^1$H-NMR (400 MHz, DMSO-$d_6$): δ [ppm] = 0.77 (d, 3H), 1.01 (d, 3H), 1.17 (t, 3H), 2.53-2.62 (m, about 4H), 2.77-2.87 (m, 1H), 3.27-3.38 (m, about 1H), 4.05 (d, 1H), 6.86-6.98 (m, 1H), 7.11 (dd, 1H), 7.16-7.23 (m, 2H), 7.29-7.37 (m, 2H), 7.66 (dt, 1H), 9.97 (s, 1H), 12.14 (br. s, 1H). |

-continued

| Example | Name/Structure/Starting Material | Analytical Data |
|---|---|---|
| 24 | 3-(4-chloro-3-{[(2S,3R)-2-(4-ethylphenyl)-4,4,4-trifluoro-3-methylbutanoyl]amino}phenyl)-2-methylpropanoic acid {diastereomer mixture}<br>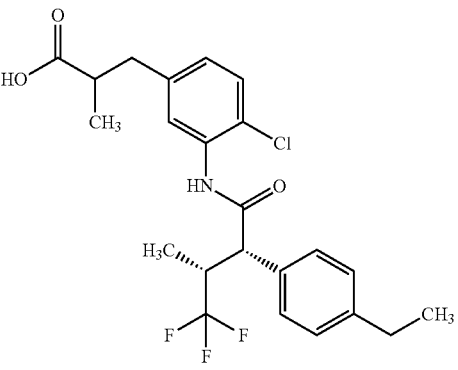 [SMILES: CCc1ccc([C@@H](C(=O)Nc2cc(CC(C)C(=O)O)ccc2Cl)[C@@H](C)C(F)(F)F)cc1] | LC-MS (Method 6): $R_t$ = 1.27 min; m/z = 456 (M + H)$^+$.<br>$^1$H-NMR (400 MHz, DMSO-$d_6$): δ [ppm] = 0.79 (d, 3H), 1.02 (d, 3H), 1.17 (t, 3H), 2.55-2.64 (m, about 4H), 2.77-2.88 (m, 1H), 3.27-3.38 (m, about 1H), 4.06 (d, 1H), 6.99 (dd, 1H), 7.21 (d, 2H), 7.34 (dd, 3H), 7.41 (d, 1H), 9.74 (s, 1H), 12.20 (br. s, 1H). |
| 25 | (2S)-3-(4-chloro-3-{[(4-chlorophenyl)(2,2-difluorocyclopentyl)acetyl]amino}phenyl)-2-methylpropanoic acid {diastereomer mixture}<br>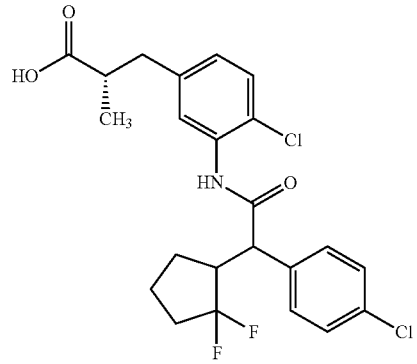 [SMILES: C[C@@H](Cc1ccc(Cl)c(NC(=O)C(c2ccc(Cl)cc2)C2CCCC2(F)F)c1)C(=O)O] | LC-MS (Method 6): $R_t$ = 1.17 min; m/z = 470 (M + H)$^+$ and $R_t$ = 1.19 min; m/z = 470 (M + H)$^+$.<br>$^1$H-NMR (400 MHz, DMSO-$d_6$): δ [ppm] = 1.02 (d, 3H), 1.11-1.26 (m, 1H), 1.48-1.78 (m, 3H), 1.99-2.24 (m, 2H), 2.55-2.62 (m, about 2H), 2.77-2.86 (m, 1H), 2.87-3.20 (m, 1H), 4.02/4.06 (2d, together 1H), 6.99/7.01 (2dd, together 1H), 7.30-7.45 (m, 4H), 7.45-7.51 (m, 2H), 9.64 (s, 1H), 12.14 (br. s, 1H). |
| 26 | 2-(4-chloro-3-{[(2S,3R)-2-(4-chlorophenyl)-4,4,4-trifluoro-3-methylbutanoyl]amino}benzyl)butanoic acid (diastereomer mixture)<br>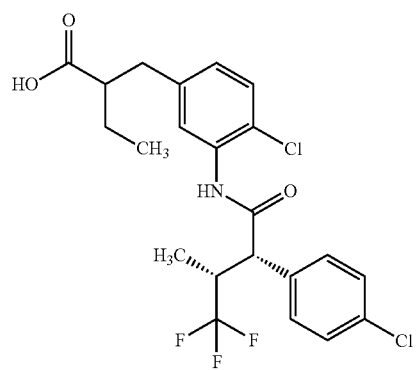 | LC-MS (Method 6): $R_t$ = 1.26 min; m/z = 476 (M + H)$^+$.<br>$^1$H-NMR (400 MHz, DMSO-$d_6$): δ [ppm] = 0.74-0.89 (m, 6H), 1.40-1.53 (m, 2H), 2.30-2.45 (m, 1H), 2.46-2.55 (m, about 1H), 2.57-2.68 (m, 1H), 2.68-2.81 (m, 1H), 3.36-3.44 (m, about 1H), 4.12 (d, 1H), 7.00 (dd, 1H), 7.29-7.40 (m, 2H), 7.41-7.51 (m, 4H), 9.82 (s, 1H), 12.15 (br. s, 1H). |

Example 27

(+)-[3-(4-Chloro-3-{[(2S,3R)-2-(4-chlorophenyl)-4,4,4-trifluoro-3-methylbutanoyl]amino}phenyl)-oxetan-3-yl]acetic acid

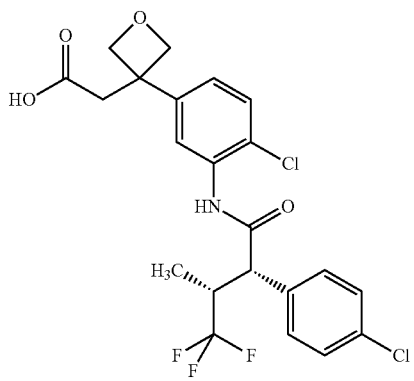 [SMILES: C[C@H]([C@H](C(=O)Nc1cc(C2(CC(=O)O)COC2)ccc1Cl)c1ccc(Cl)cc1)C(F)(F)F]

25 mg of palladium on carbon (10%) were added to a solution of 120 mg (0.21 mmol) of benzyl [3-(4-chloro-3-{[(2S,3R)-2-(4-chlorophenyl)-4,4,4-trifluoro-3-methylbutanoyl]amino}-phenyl)oxetan-3-yl]acetate in 15 ml of ethyl acetate. Under an atmosphere of hydrogen, the mixture was hydrogenated at atmospheric pressure for 2 h. The reaction mixture was then filtered through Tonsil, the filter residue was washed with ethyl acetate and the combined filtrates were concentrated on a rotary evaporator. This gave 98 mg (0.2 mmol, 97% of theory) of the title compound.

LC-MS (Method 4): $R_t$=1.28 min; m/z=488/490 (M−H)⁻.

$^1$H-NMR (400 MHz, DMSO-$d_6$, δ/ppm): 12.76-11.52 (1H, br. s), 9.88 (1H, s), 7.52 (1H, d), 7.50-7.39 (5H, m), 7.10 (1H, dd), 4.79-4.71 (2H, m), 4.71-4.64 (2H, m), 4.14 (1H, d), 3.42-3.28 (1H, m), 3.03 (2H, s), 0.80 (3H, d).

$[α]_D^{20}$=+88.4°, c=0.355, methanol.

Example 28

[1-(4-Chloro-3-{[(3R)-2-(4-chlorophenyl)-4,4,4-trifluoro-3-methylbutanoyl]amino}-phenyl)cyclobutyl]acetic acid

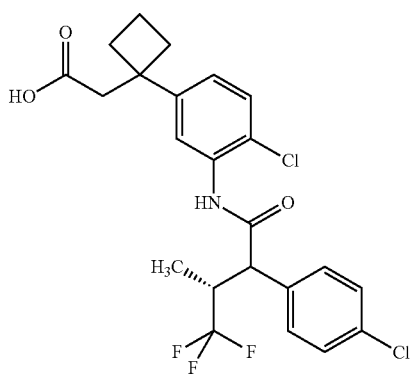 [SMILES: C[C@H](C(C(=O)Nc1cc(C2(CC(=O)O)CCC2)ccc1Cl)c1ccc(Cl)cc1)C(F)(F)F]

38 mg (0.08 mmol) of methyl-[1-(4-chloro-3-{[(3R)-2-(4-chlorophenyl)-4,4,4-trifluoro-3-methylbutanoyl]amino}phenyl)cyclobutyl]acetate were dissolved in 9.5 ml of dioxane, and 0.15 ml of 1 N aqueous sodium hydroxide solution was added. The mixture was stirred at 80° C. overnight. The reaction mixture was then acidified with 1 N hydrochloric acid to pH 1 and extracted repeatedly with ethyl acetate. The combined organic phases were washed with saturated sodium chloride solution, dried over sodium sulphate and concentrated under reduced pressure. The crude product was purified by preparative HPLC. This gave 22 mg (0.05 mmol, 60% of theory) of the target compound.

LC-MS (Method 6): $R_t$=1.28 min; m/z=488/490 (M+H)⁺.

$^1$H-NMR (400 MHz, DMSO-$d_6$, δ/ppm): 11.88 (1H, br. s), 9.95 (0.5H, s), 9.81 (0.5H, s), 7.54-7.31 (6H, m), 7.06-6.96 (1H, m), 4.14 (1H, d), 3.43-3.27 (0.5H, m), 3.27-3.14 (0.5H, m), 2.70 (1H, s), 2.69 (1H, s), 2.34-2.17 (4H, m), 2.10-1.95 (1H, m), 1.81-1.66 (1H, m), 1.25 (1.5H, d), 0.80 (1.5H, d).

Example 29

(+)-(2R)-2-(4-Chloro-3-{[(2S,3R)-2-(4-chlorophenyl)-4,4,4-trifluoro-3-methylbutanoyl]amino}-benzyl)butanoic acid

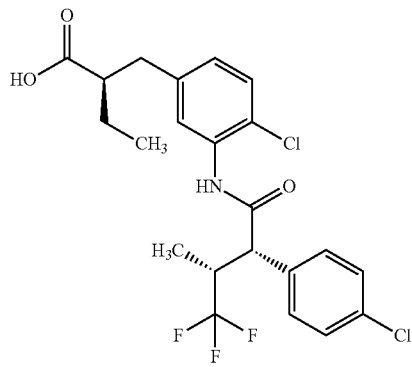 [SMILES: CC[C@H](Cc1ccc(Cl)c(NC(=O)[C@H](c2ccc(Cl)cc2)[C@@H](C)C(F)(F)F)c1)C(=O)O]

15.2 ml of acetic acid and 7.6 ml of concentrated hydrochloric acid were added to 1.96 g (3.89 mmol) of ethyl (+)-(2R)-2-(4-chloro-3-{[(2S,3R)-2-(4-chlorophenyl)-4,4,4-trifluoro-3-methylbutanoyl]amino}benzyl)butanoate. The reaction mixture was stirred under reflux for 5 h (bath temperature 140° C.). After cooling, water was added. The mixture was extracted repeatedly with dichloromethane, and the combined organic phases were washed with saturated sodium chloride solution, dried over sodium sulphate and concentrated under reduced pressure. Chromatography of the residue on silica gel (mobile phase cyclohexane/ethyl acetate 10:1→2:1) gave 1.46 g (78.6% of theory) of the title compound.

LC-MS (Method 6): $R_t$=1.25 min; m/z=476 (M+H)⁺.

$^1$H-NMR (400 MHz, DMSO-$d_6$): δ [ppm]=0.80 (d, 3H), 0.82-0.89 (m, 3H), 1.42-1.54 (m, 2H), 2.41 (t, 1H), 2.64 (dd, 1H), 2.75 (dd, 1H), 4.12 (d, 1H), 7.00 (dd, 1H), 7.31-7.39 (m, 1H), 7.42-7.50 (m, 3H), 9.82 (s, 1H), 12.16 (br. s, 1H).

$[α]_D^{20}$=+92.7°, c=0.380, methanol.

The compound below was prepared according to an analogous procedure:

Example 30

(+)-(2S)-2-(4-Chloro-3-{[(2S,3R)-2-(4-chlorophenyl)-4,4,4-trifluoro-3-methylbutanoyl]amino}-benzyl)butanoic acid

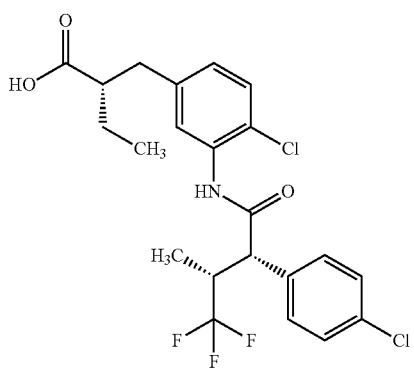

LC-MS (Method 5): $R_t$=2.66 min; m/z=476 (M+H)$^+$.

$^1$H-NMR (400 MHz, DMSO-d$_6$): δ [ppm]=0.80 (d, 3H), 0.85 (t, 3H), 1.43-1.52 (m, 2H), 2.26-2.47 (m, 1H), 2.59-2.69 (m, 1H), 2.70-2.82 (m, 1H), 3.34-3.44 (m, 1H), 4.12 (d, 1H), 7.00 (dd, 1H), 7.30-7.39 (m, 2H), 7.40-7.52 (m, 4H), 9.82 (s, 1H), 12.13 (br. s, 1H).

$[α]_D^{20}$=+143.1°, c=0.380, chloroform.

Example 31 and Example 32

3-[4-Chloro-3-({4,4,4-trifluoro-3-methyl-2-[4-(2,2,2-trifluoroethyl)phenyl]butanoyl}amino)-phenyl]propanoic acid (enantiomers 1 and 2)

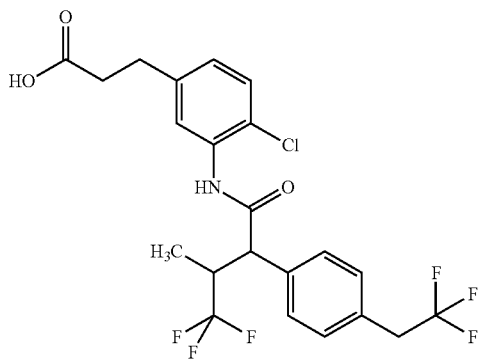 [SMILES: CC(C(C(=O)Nc1cc(CCC(=O)O)ccc1Cl)c1ccc(CC(F)(F)F)cc1)C(F)(F)F]

120 mg (0.24 mmol) of the racemic 3-[4-chloro-3-({4,4,4-trifluoro-3-methyl-2-[4-(2,2,2-trifluoroethyl)phenyl]butanoyl}amino)phenyl]propanoic acid (Example 5) were separated into the enantiomers by preparative HPLC on a chiral phase [column: Daicel Chiralpak AD-H, 5 μm, 250 mm×20 mm; mobile phase: isohexane/ethanol 85:15 (v/v); flow rate: 15 ml/min; UV detection: 220 nm; temperature: 35° C.]:

Example 31

(+)-3-[4-Chloro-3-({(2S,3R)-4,4,4-trifluoro-3-methyl-2-[4-(2,2,2-trifluoroethyl)phenyl]butanoyl}-amino)phenyl]propanoic acid (enantiomer 1)

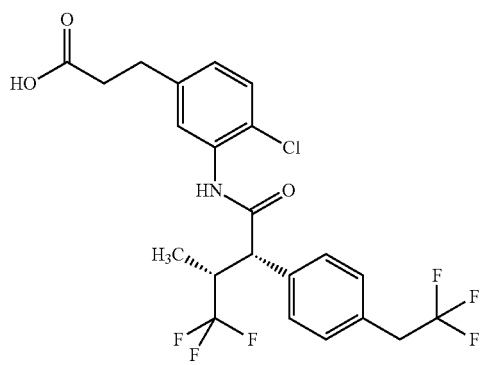 [SMILES: C[C@H]([C@H](C(=O)Nc1cc(CCC(=O)O)ccc1Cl)c1ccc(CC(F)(F)F)cc1)C(F)(F)F]

Yield: 48 mg $R_t$=5.75 min; chemical purity >99%; >99% ee
[Column: Daicel Chiralpak AD-H, 5 μm, 250 mm×4.6 mm; mobile phase: isohexane/(ethanol+0.2% TFA+1% water) 85:15 (v/v); flow rate: 1 ml/min; temperature: 35° C.; UV detection: 220 nm].

$[α]_D^{20}$=+91.8°, c=0.405, methanol.

LC-MS (Method 4): $R_t$=1.33 min; m/z=496 (M+H)$^+$.

$^1$H-NMR (400 MHz, DMSO-d$_6$, δ/ppm): 12.24-12.02 (1H, br. s), 9.80 (1H, s), 7.46 (2H, d), 7.43-7.39 (1H, m), 7.35 (3H, t), 7.04 (1H, dd), 4.11 (1H, d), 3.64 (2H, q), 3.44-3.27 (1H, m), 2.76 (2H, t), 2.48 (2H, t), 0.79 (3H, d).

Example 32

(−)-3-[4-Chloro-3-({(2R,3S)-4,4,4-trifluoro-3-methyl-2-[4-(2,2,2-trifluoroethyl)phenyl]butanoyl}-amino)phenyl]propanoic acid (enantiomer 2)

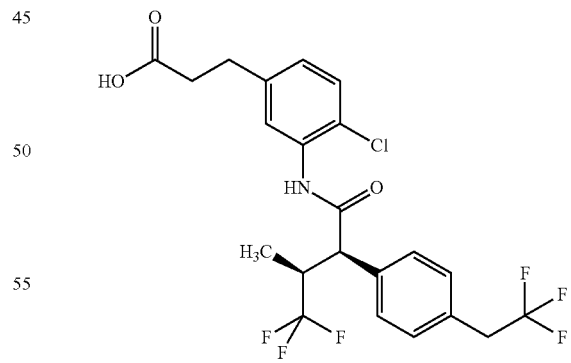

Yield: 52 mg $R_t$=6.85 min; chemical purity >97.4%; >99% ee
[Column: Daicel Chiralpak AD-H, 5 μm, 250 mm×4.6 mm; mobile phase: isohexane/(ethanol+0.2% TFA+1% water) 85:15 (v/v); flow rate: 1 ml/min; temperature: 35° C.; UV detection: 220 nm].

$[α]_D^{20}$=−94.3°, c=0.40, methanol

LC-MS (Method 4): $R_t$=1.33 min; m/z=496 (M+H)$^+$.

Examples 33-36

3-(4-Chloro-3-{[(4-chlorophenyl)(3,3-difluorocyclopentyl)acetyl]amino}phenyl)propanoic acid (isomers 1-4)

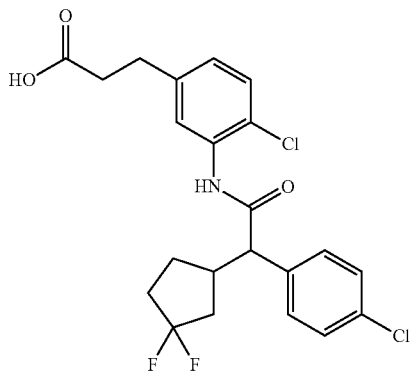 [SMILES: O=C(O)CCc1ccc(Cl)c(NC(=O)C(c2ccc(Cl)cc2)C2CCC(F)(F)C2)c1]

44 mg (0.096 mmol) of the diastereomer mixture of 3-(4-chloro-3-{[(4-chlorophenyl)(3,3-difluoro-cyclopentyl)acetyl]amino}phenyl)propanoic acid (Example 6) were separated further by preparative HPLC on a chiral phase [column: Daicel Chiralcel OJ-H, 5 μm, 250 mm×20 mm; mobile phase: isohexane/ethanol 70:30 (v/v); flow rate: 15 ml/min; UV detection: 220 nm; temperature: 35° C.]. This gave four different fractions each consisting of a mixture of two isomers. By repeat preparative HPLC on a chiral phase, these fractions were separated into the individual isomers [fractions 1 and 2: column: Daicel Chiralpak AS-H, 5 μm, 250 mm×20 mm; mobile phase: isohexane/isopropanol 75:25 (v/v); flow rate: 15 ml/min; UV detection: 220 nm; temperature: 35° C. Fractions 3 and 4: column: Daicel Chiralpak AD-H, 5 μm, 250 mm×20 mm; mobile phase: isohexane/ethanol 80:20 (v/v); flow rate: 15 ml/min; UV detection: 220 nm; temperature: 35° C.]:

Example 33

Isomer 1

Yield: 8 mg
$R_t$=6.49 min; chemical purity >99%
[Column: Daicel Chiralpak AS-H, 5 μm, 250 mm×4.6 mm; mobile phase: isohexane/isopropanol 75:25 (v/v); flow rate: 1 ml/min; UV detection: 220 nm; temperature: 35° C.].

Example 34

Isomer 2

Yield: 11 mg
$R_t$=9.08 min; chemical purity >98.5%
[Column: Daicel Chiralpak AS-H, 5 μm, 250 mm×4.6 mm; mobile phase: isohexane/isopropanol 75:25 (v/v); flow rate: 1 ml/min; UV detection: 220 nm; temperature: 35° C.].

Example 35

Isomer 3

Yield: 12 mg
$R_t$=7.19 min; chemical purity >99%
[Column: Daicel Chiralpak AD-H, 5 μm, 250 mm×4.6 mm; mobile phase: isohexane/ethanol 80:20 (v/v); flow rate: 1 ml/min; UV detection: 220 nm; temperature: 30° C.].

Example 36

Isomer 4

Yield: 9 mg
$R_t$=8.58 min; chemical purity >97.5%
[Column: Daicel Chiralpak AD-H, 5 μm, 250 mm×4.6 mm; mobile phase: isohexane/ethanol 80:20 (v/v); flow rate: 1 ml/min; UV detection: 220 nm; temperature: 30° C.].

Example 37

3-(3-{[(3R)-2-(4-Chlorophenyl)-4,4,4-trifluoro-3-methylbutanoyl]amino}-4-fluorophenyl)-2-methylpropanoic acid (diastereomer mixture)

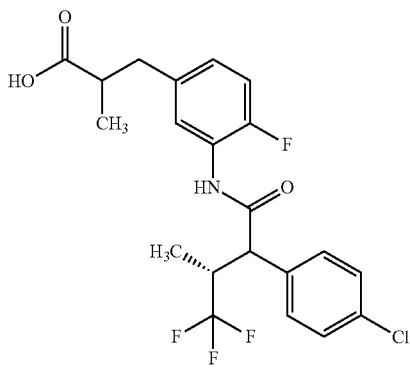

300 mg (0.633 mmol) of ethyl 3-(3-{[(2S,3R)-2-(4-chlorophenyl)-4,4,4-trifluoro-3-methylbutanoyl]amino}-4-fluorophenyl)-2-methylpropanoate (diastereomer mixture) were dissolved in a mixture of in each case 1.0 ml of methanol, THF and water, and 265.5 mg (6.33 mmol) of lithium hydroxide were added at 0° C. The mixture was stirred initially at 0° C. for 1 h and then at RT for 1 h. The solution was then diluted with water and acidified with 1 N hydrochloric acid (pH about 2). The aqueous phase was extracted three times with diethyl ether and once with ethyl acetate. The combined organic phases were dried over sodium sulphate and concentrated under reduced pressure. This gave 294 mg (99.7% of theory) of the title compound as a mixture of four diastereomers.

LC-MS (Method 6): $R_t$=1.18 min; m/z=446 (M+H)⁺.

Example 38 and Example 39

3-(3-{[(2S,3R)-2-(4-Chlorophenyl)-4,4,4-trifluoro-3-methylbutanoyl]amino}-4-fluorophenyl)-2-methylpropanoic acid (diastereomers 1 and 2)

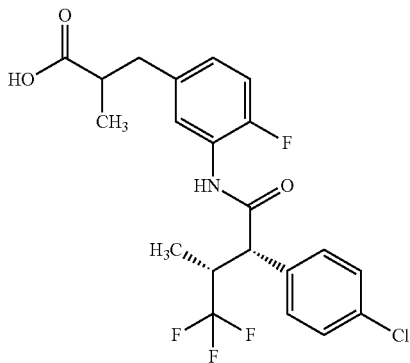

The mixture obtained above of the diastereomeric 3-(3-{[(3R)-2-(4-chlorophenyl)-4,4,4-trifluoro-3-methylbutanoyl]amino}-4-fluorophenyl)-2-methylpropanoic acids (Example 37) was separated further by preparative HPLC on a chiral phase [column: Daicel Chiralpak AS-H, 5 μm, 250 mm×20 mm; injection volume: 0.25 ml; temperature: 40° C.; mobile phase: 90% isohexane/10% (ethanol+0.2% TFA+1% water); flow rate: 15 ml/min; detection: 220 nm]. 260 mg of diastereomer mixture gave, in addition to two further isomers, 52 mg of isomer 1 (Example 38) and 54 mg of isomer 2 (Example 39):

Example 38

Diastereomer 1

(+)-(2S)-3-(3-{[(2S,3R)-2-(4-Chlorophenyl)-4,4,4-trifluoro-3-methylbutanoyl]amino}-4-fluoro-phenyl)-2-methylpropanoic acid

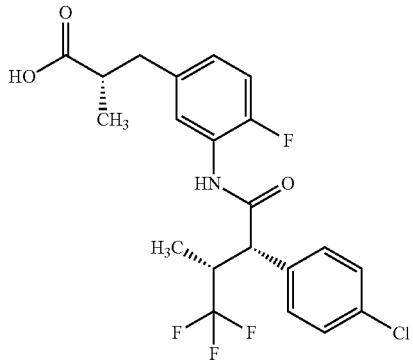 [SMILES: CC(Cc1ccc(F)c(NC(=O)C(c2ccc(Cl)cc2)[C@@H](C)C(F)(F)F)c1)C(=O)O]

Isomer 1 was repurified again by preparative RP-HPLC (mobile phase acetonitrile/water). This gave 32 mg.
LC-MS (Method 6): $R_t$=1.18 min; m/z=446 (M+H)$^+$.
$^1$H-NMR (400 MHz, DMSO-$d_6$): δ [ppm]=0.79 (d, 3H), 1.01 (d, 3H), 2.51-2.58 (m, 2H), 2.76-2.86 (m, 1H), 3.35 (dd, 1H), 4.11 (d, 1H), 6.87-7.00 (m, 1H), 7.12 (dd, 1H), 7.41-7.49 (m, 4H), 7.63 (dd, 1H), 10.04 (s, 1H), 12.11 (br. s, 1H).
$[α]_D^{20}$=+150.4°, c=0.50, chloroform.

Example 39

Diastereomer 2

(+)-(2R)-3-(3-{[(2S,3R)-2-(4-Chlorophenyl)-4,4,4-trifluoro-3-methylbutanoyl]amino}-4-fluoro-phenyl)-2-methylpropanoic acid

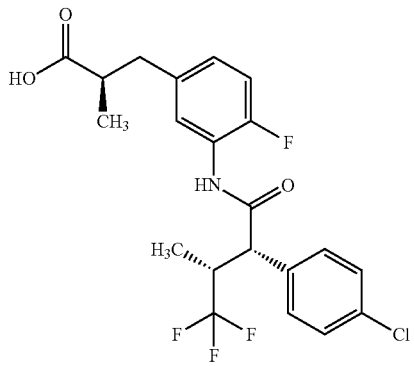 [SMILES: C[C@H](Cc1ccc(F)c(NC(=O)[C@H](c2ccc(Cl)cc2)[C@@H](C)C(F)(F)F)c1)C(=O)O]

Isomer 2 was repurified again by preparative RP-HPLC (mobile phase acetonitrile/water). This gave 21 mg.
LC-MS (Method 6): $R_t$=1.18 min; m/z=446 (M+H)$^+$.
$^1$H-NMR (400 MHz, DMSO-$d_6$): δ [ppm]=0.79 (d, 3H), 1.02 (d, 3H), 2.53-2.58 (m, 2H), 2.77-2.87 (m, 1H), 3.30-3.41 (m, 1H), 4.11 (d, 1H), 6.89-7.00 (m, 1H), 7.12 (dd, 1H), 7.41-7.48 (m, 4H), 7.63 (dd, 1H), 10.04 (s, 1H), 12.12 (br. s, 1H).
$[α]_D^{20}$=+131.6°, c=0.530, chloroform.

Example 40 and Example 41

3-(4-Chloro-3-{[(2S,3R)-2-(4-ethylphenyl)-4,4,4-trifluoro-3-methylbutanoyl]amino}phenyl)-2-methylpropanoic acid (diastereomers 1 and 2)

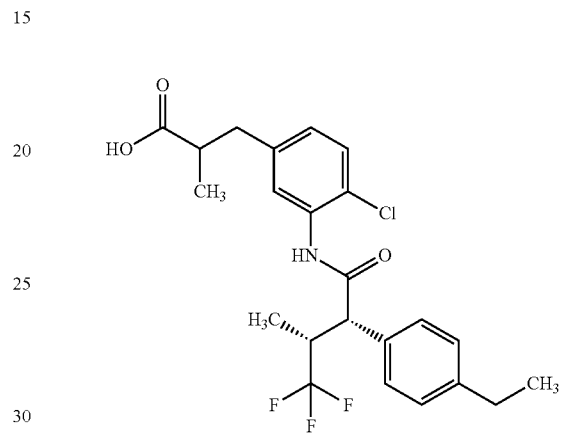

The mixture obtained above of the diastereomeric 3-(4-chloro-3-{[(2S,3R)-2-(4-ethylphenyl)-4,4,4-trifluoro-3-methylbutanoyl]amino}phenyl)-2-methylpropanoic acids (Example 24) was separated further by preparative HPLC on a chiral phase [column: chiral silica gel phase based on the selector poly(N-methacryloyl-L-isoleucin-3-pentylamide), 430 mm×40 mm; injection volume: 2.0 ml; temperature: 24° C.; mobile phase: 40% isohexane/60% ethyl acetate; flow rate: 80 ml/min; detection: 265 nm]. 514 mg of diastereomer mixture gave 178 mg of diastereomer 1 (Example 40) and 218 mg of diastereomer 2 (Example 41):

Example 40

Diastereomer 1

(+)-(2R)-3-(4-Chloro-3-{[(2S,3R)-2-(4-ethylphenyl)-4,4,4-trifluoro-3-methylbutanoyl]amino}-phenyl)-2-methylpropanoic acid

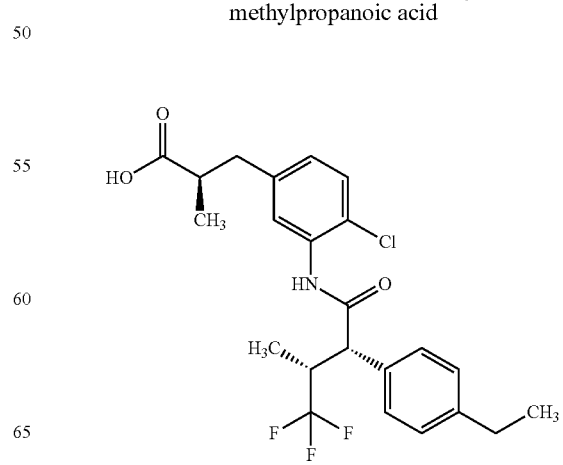

LC-MS (Method 6): $R_t$=1.25 min; m/z=456 (M+H)$^+$.

$^1$H-NMR (400 MHz, DMSO-$d_6$): δ [ppm]=0.79 (d, 3H), 0.98-1.05 (m, 3H), 1.17 (t, 3H), 2.55-2.63 (m, 4H), 2.78-2.88 (m, 1H), 3.28-3.37 (m, 1H), 4.06 (d, 1H), 6.99 (dd, 1H), 7.20 (d, 2H), 7.34 (dd, 3H), 7.41 (d, 1H), 9.73 (s, 1H), 12.15 (s, 1H).

$[α]_D^{20}$=+52°, c=0.500, chloroform.

Example 41

Diastereomer 2

(+)-(2S)-3-(4-Chloro-3-{[(2S,3R)-2-(4-ethylphenyl)-4,4,4-trifluoro-3-methylbutanoyl]amino}-phenyl)-2-methylpropanoic acid

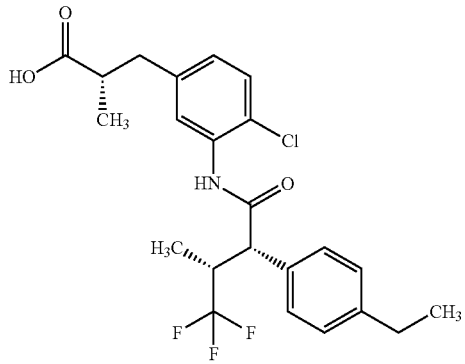 [SMILES: CCc1ccc([C@@H](C(=O)Nc2cc(C[C@H](C)C(=O)O)ccc2Cl)[C@@H](C)C(F)(F)F)cc1]

LC-MS (Method 6): $R_t$=1.27 min; m/z=456 (M+H)$^+$.

$^1$H-NMR (400 MHz, DMSO-$d_6$): δ [ppm]=0.78 (d, 3H), 1.02 (d, 3H), 1.17 (t, 3H), 2.54-2.64 (m, 4H), 2.77-2.87 (m, 1H), 3.28-3.37 (m, 1H), 4.06 (d, 1H), 6.99 (dd, 1H), 7.21 (d, 2H), 7.34 (dd, 3H), 7.41 (d, 1H), 9.74 (s, 1H), 12.16 (br. s, 1H).

$[α]_D^{20}$=+75.0°, c=0.640, chloroform.

Example 42 and Example 43

3-(3-{[(2S,3R)-2-(4-Ethylphenyl)-4,4,4-trifluoro-3-methylbutanoyl]amino}-4-fluorophenyl)-2-methyl-propanoic acid (diastereomers 1 and 2)

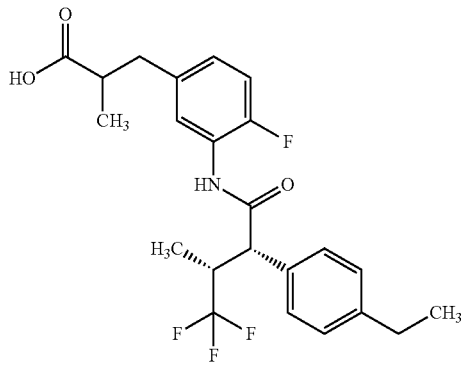 [SMILES: CCc1ccc([C@@H](C(=O)Nc2cc(CC(C)C(=O)O)ccc2F)[C@@H](C)C(F)(F)F)cc1]

The mixture obtained above of the diastereomeric 3-(3-{[(2S,3R)-2-(4-ethylphenyl)-4,4,4-trifluoro-3-methylbutanoyl]amino}-4-fluorophenyl)-2-methylpropanoic acids (Example 23) was separated further by preparative HPLC on a chiral phase [column: Daicel Chiralpak AS-H, 5 μm, 250 mm×20 mm; injection volume: 0.30 ml; temperature: 30° C.; mobile phase: 92% isohexane/8% (ethanol+0.2% TFA+1% water); flow rate: 15 ml/min; detection: 220 nm]. 509 mg of diastereomer mixture gave 209 mg of diastereomer 1 (Example 42) and 220 mg of diastereomer 2 (Example 43):

Example 42

Diastereomer 1

(+)-(2S)-3-(3-{[(2S,3R)-2-(4-Ethylphenyl)-4,4,4-trifluoro-3-methylbutanoyl]amino}-4-fluoro-phenyl)-2-methylpropanoic acid

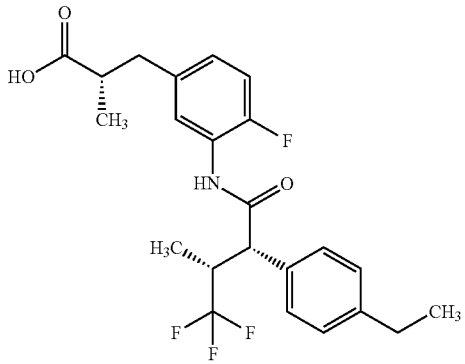 [SMILES: CCc1ccc([C@@H](C(=O)Nc2cc(C[C@H](C)C(=O)O)ccc2F)[C@@H](C)C(F)(F)F)cc1]

LC-MS (Method 6): $R_t$=1.22 min; m/z=440 (M+H)$^+$.

$^1$H-NMR (400 MHz, DMSO-$d_6$): δ [ppm]=0.77 (d, 3H), 1.01 (d, 3H), 1.17 (t, 3H), 2.55-2.63 (m, 4H), 2.76-2.86 (m, 1H), 3.25-3.39 (m, 1H), 4.05 (d, 1H), 6.88-6.98 (m, 1H), 7.11 (dd, 1H), 7.17-7.24 (m, 2H), 7.29-7.38 (m, 2H), 7.66 (dd, 1H), 9.97 (s, 1H), 12.13 (br. s, 1H).

$[α]_D^{20}$=+162.1°, c=0.500, chloroform.

Example 43

Diastereomer 2

(+)-(2R)-3-(3-{[(2S,3R)-2-(4-Ethylphenyl)-4,4,4-trifluoro-3-methylbutanoyl]amino}-4-fluoro-phenyl)-2-methylpropanoic acid

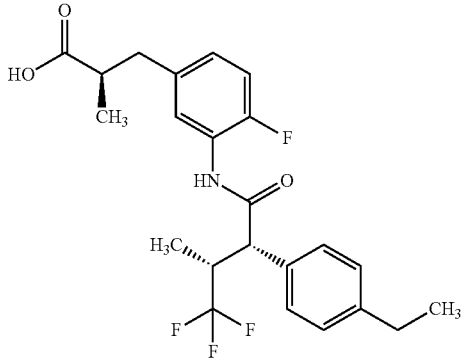 [SMILES: CCc1ccc([C@@H](C(=O)Nc2cc(C[C@@H](C)C(=O)O)ccc2F)[C@@H](C)C(F)(F)F)cc1]

LC-MS (Method 6): $R_t$=1.22 min; m/z=440 (M+H)$^+$.

$^1$H-NMR (400 MHz, DMSO-$d_6$): δ [ppm]=0.77 (d, 3H), 1.01 (d, 3H), 1.17 (t, 3H), 2.53-2.64 (m, 4H), 2.76-2.87 (m, 1H), 3.26-3.38 (m, 1H), 4.04 (d, 1H), 6.87-6.97 (m, 1H), 7.11 (dd, 1H), 7.17-7.23 (m, 2H), 7.28-7.38 (m, 2H), 7.65 (dd, 1H), 9.97 (s, 1H), 12.12 (br. s, 1H).
$[α]_D^{20}$=+94.0°, c=0.620, chloroform.

Example 44 and Example 45

3-(4-Chloro-3-{[(2S,3R)-2-(4-ethylphenyl)-4,4,4-trifluoro-3-methylbutanoyl]amino}phenyl)-butanoic acid (diastereomers 1 and 2)

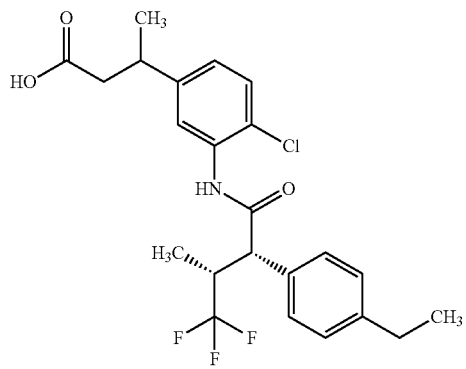 [SMILES: CCc1ccc([C@@H](C(=O)Nc2cc(C(C)CC(=O)O)ccc2Cl)[C@@H](C)C(F)(F)F)cc1]

The mixture obtained above of the diastereomeric 3-(4-chloro-3-{[(2S,3R)-2-(4-ethylphenyl)-4,4,4-trifluoro-3-methylbutanoyl]amino}phenyl)butanoic acids (Example 7) was separated further by preparative HPLC on a chiral phase [column: Daicel Chiralpak AS-H, 5 μm, 250 mm×20 mm; injection volume: 0.20 ml; temperature: 30° C.; mobile phase: 90% isohexane/10% (isopropanol+0.2% TFA+1% water); flow rate: 15 ml/min; detection: 220 nm]. 210 mg of diastereomer mixture gave 110 mg of diastereomer 1 (Example 44) and 99 mg of diastereomer 2 (Example 45):

Example 44

Diastereomer 1

(+)-(3S)-3-(4-Chloro-3-{[(2S,3R)-2-(4-ethylphenyl)-4,4,4-trifluoro-3-methylbutanoyl]amino}-phenyl) butanoic acid

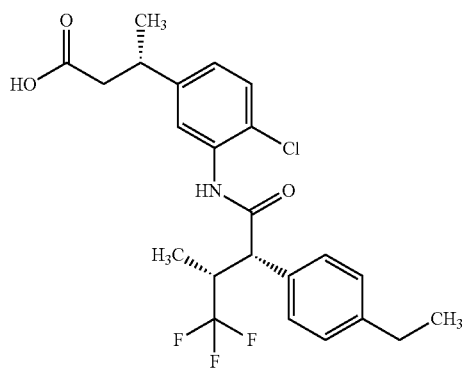 [SMILES: CCc1ccc([C@@H](C(=O)Nc2cc([C@@H](C)CC(=O)O)ccc2Cl)[C@@H](C)C(F)(F)F)cc1]

LC-MS (Method 6): $R_t$=1.26 min; m/z=456 (M+H)$^+$.

$^1$H-NMR (400 MHz, DMSO-$d_6$): δ [ppm]=0.79 (d, 3H), 1.13-1.21 (m, 6H), 2.45 (d, 2H), 2.59 (q, 2H), 3.08 (q, 1H), 3.27-3.38 (m, 1H), 4.07 (d, 1H), 7.06 (dd, 1H), 7.21 (d, 2H), 7.35 (dd, 3H), 7.46 (d, 1H), 9.72 (s, 1H), 12.05 (br. s, 1H).
$[α]_D^{20}$=+86.8°, c=0.440, chloroform.

Example 45

Diastereomer 2

(+)-(3R)-3-(4-Chloro-3-{[(2S,3R)-2-(4-ethylphenyl)-4,4,4-trifluoro-3-methylbutanoyl]amino}-phenyl) butanoic acid

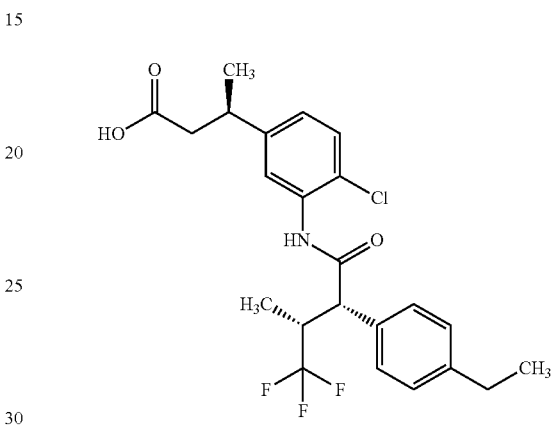

LC-MS (Method 6): $R_t$=1.26 min; m/z=456 (M+H)$^+$.

$^1$H-NMR (400 MHz, DMSO-$d_6$): δ [ppm]=0.79 (d, 3H), 1.11-1.22 (m, 6H), 2.45 (d, 2H), 2.55-2.63 (m, 2H), 3.08 (q, 1H), 3.28-3.38 (m, 1H), 4.08 (d, 1H), 7.06 (dd, 1H), 7.20 (d, 2H), 7.35 (dd, 3H), 7.47 (d, 1H), 9.72 (s, 1H), 12.05 (br. s, 1H).
$[α]_D^{20}$=+68.0°, c=0.415, chloroform.

Example 46 and Example 47

3-(3-{[(2S,3R)-2-(4-Chlorophenyl)-4,4,4-trifluoro-3-methylbutanoyl]amino}-4-chlorophenyl)butanoic acid (diastereomers 1 and 2)

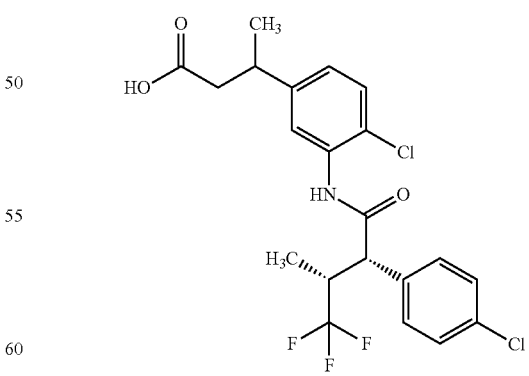

The mixture obtained above of the diastereomeric 3-(3-{[(2S,3R)-2-(4-chlorophenyl)-4,4,4-trifluoro-3-methylbutanoyl]amino}-4-chlorophenyl)butanoic acids (Example 8) was separated further by preparative HPLC on a chiral phase [column: Daicel Chiralpak AS-H, 5 μm, 250 mm×20 mm;

injection volume: 0.30 ml; temperature: 30° C.; mobile phase: 90% isohexane/10% isopropanol; flow rate: 15 ml/min; detection: 220 nm]. 250 mg of diastereomer mixture gave 116 mg of diastereomer 1 (Example 46) and 113 mg of diastereomer 2 (Example 47):

Example 46

Diastereomer 1

(+)-(3S)-3-(3-{[(2S,3R)-2-(4-Chlorophenyl)-4,4,4-trifluoro-3-methylbutanoyl]amino}-4-chlorophenyl)butanoic acid

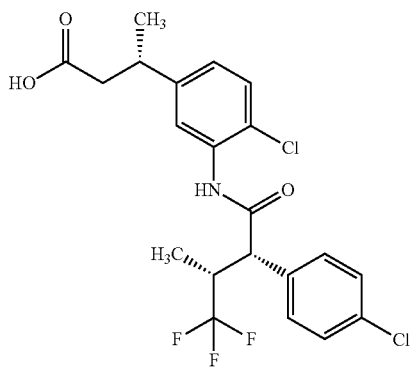

LC-MS (Method 4): $R_t$=1.36 min; m/z=462 (M+H)$^+$.
$^1$H-NMR (400 MHz, DMSO-d$_6$): δ [ppm]=0.80 (d, 3H), 1.16 (d, 3H), 2.45 (d, 2H), 3.03-3.14 (m, 1H), 3.33-3.42 (m, 1H), 4.13 (d, 1H), 7.08 (dd, 1H), 7.36 (d, 1H), 7.41 (d, 1H), 7.43-7.51 (m, 4H), 9.81 (s, 1H), 12.05 (s, 1H).
[α]$_D^{20}$=+88.6°, c=0.435, chloroform.

Example 47

Diastereomer 2

(+)-(3R)-3-(3-{[(2S,3R)-2-(4-Chlorophenyl)-4,4,4-trifluoro-3-methylbutanoyl]amino}-4-chloro-phenyl)butanoic acid

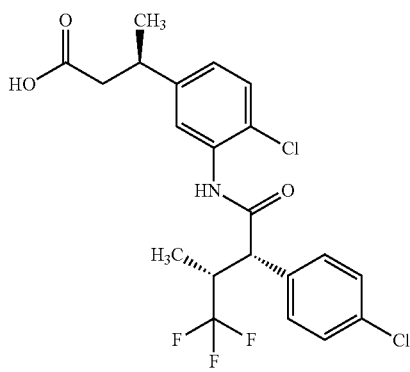

LC-MS (Method 4): $R_t$=1.36 min; m/z=462 (M+H)$^+$.
$^1$H-NMR (400 MHz, DMSO-d$_6$): δ [ppm]=0.80 (d, 3H), 1.16 (d, 3H), 2.45 (d, 2H), 3.09 (q, 1H), 3.33-3.42 (m, 1H), 4.13 (d, 1H), 7.08 (dd, 1H), 7.35 (d, 1H), 7.42 (d, 1H), 7.43-7.51 (m, 4H), 9.81 (s, 1H), 12.05 (s, 1H).
[α]$_D^{20}$=+57.9°, c=0.365, chloroform.

Example 48 and Example 49

3-(3-{[(2S,3R)-2-(4-Chlorophenyl)-4,4,4-trifluoro-3-methylbutanoyl]amino}-4-fluorophenyl)-butanoic acid (diastereomers 1 and 2)

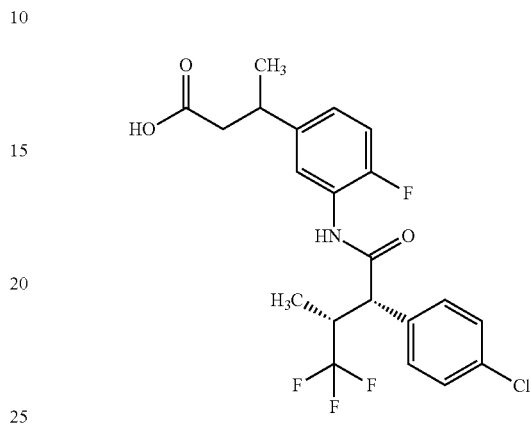

The mixture obtained above of the diastereomeric 3-(3-{[(2S,3R)-2-(4-chlorophenyl)-4,4,4-trifluoro-3-methylbutanoyl]amino}-4-fluorophenyl)butanoic acids (Example 9) was separated further by preparative HPLC on a chiral phase [column: Daicel Chiralpak AS-H, 5 μm, 250 mm×20 mm; injection volume: 0.25 ml; temperature: 30° C.; mobile phase: 85% isohexane/15% isopropanol; flow rate: 15 ml/min; detection: 220 nm]. 295 mg of diastereomer mixture gave 121 mg of diastereomer 1 (Example 48) and 111 mg of diastereomer 2 (Example 49):

Example 48

Diastereomer 1

(+)-(3S)-3-(3-{[(2S,3R)-2-(4-Chlorophenyl)-4,4,4-trifluoro-3-methylbutanoyl]amino}-4-fluoro-phenyl)butanoic acid

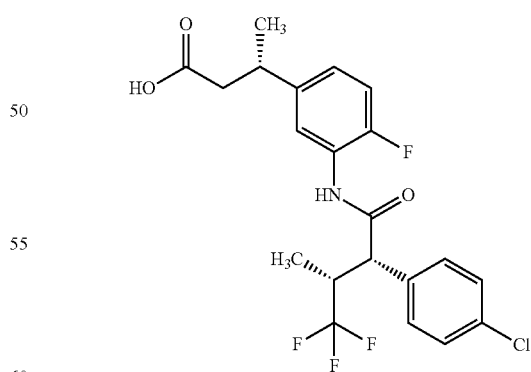

LC-MS (Method 6): $R_t$=1.14 min; m/z=446 (M+H)$^+$.
$^1$H-NMR (400 MHz, DMSO-d$_6$): δ [ppm]=0.79 (d, 3H), 1.16 (d, 3H), 2.44 (d, 2H), 3.02-3.12 (m, 1H), 3.33-3.42 (m, 1H), 4.12 (d, 1H), 7.00-7.04 (m, 1H), 7.13 (dd, 1H), 7.43-7.48 (m, 4H), 7.68 (dd, 1H), 10.04 (s, 1H), 12.03 (s, 1H).
[α]$_D^{20}$=+142.0°, c=0.350, chloroform.

Example 49

Diastereomer 2

(+)-(3R)-3-(3-{[(2S,3R)-2-(4-Chlorophenyl)-4,4,4-trifluoro-3-methylbutanoyl]amino}-4-fluoro-phenyl)butanoic acid

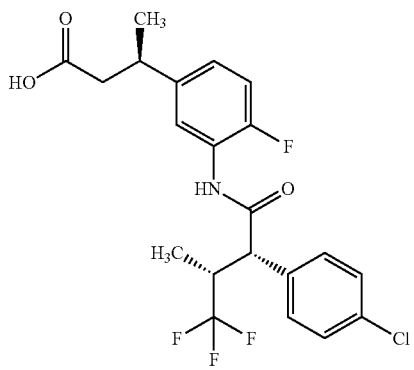 [SMILES: C[C@H](CC(=O)O)c1ccc(F)c(NC(=O)[C@H](c2ccc(Cl)cc2)[C@@H](C)C(F)(F)F)c1]

LC-MS (Method 6): $R_t$=1.14 min; m/z=446 (M+H)$^+$.

$^1$H-NMR (400 MHz, DMSO-d$_6$): δ [ppm]=0.79 (d, 3H), 1.15 (d, 3H), 2.44 (d, 2H), 3.08 (q, 1H), 3.30-3.42 (m, 1H), 4.12 (d, 1H), 6.94-7.06 (m, 1H), 7.13 (dd, 1H), 7.40-7.50 (m, 4H), 7.68 (dd, 1H), 10.04 (s, 1H), 12.04 (br. s, 1H).

$[α]_D^{20}$=+139.8°, c=0.405, chloroform.

General Procedure 4

Acidic Hydrolysis of Ethyl Esters

The ethyl ester in question is dissolved in a 7:2 mixture of glacial acetic acid and concentrated hydrochloric acid (about 10 ml/mmol of substrate) and heated at 100° C. until the reaction has gone to completion (in general between 1 h and 8 h). The mixture is then cooled, poured into water and extracted repeatedly with dichloromethane. The combined organic phases are washed three times with saturated sodium chloride solution, dried over magnesium sulphate and concentrated. If required, the residue is purified by flash chromatography or preparative HPLC.

The exemplary compounds below were prepared according to General Procedure 4:

| Example | Name/Structure | Analytical data |
|---|---|---|
| 50 | threo-3-(3-{[(2S,3R)-2-(4-chlorophenyl)-4,4,4-trifluoro-3-methylbutanoyl]amino}-4-fluorophenyl)-2-methylbutanoic acid | LC-MS (Method 6): $R_t$ = 1.21 min; m/z = 460 (M + H)$^+$. $^1$H-NMR (400 MHz, DMSO-d$_6$): δ [ppm] = 0.75-0.95 (m, 3H), 1.00-1.06 (m, 2H), 1.07-1.17 (m, 3H), 1.24 (s, 1H), 1.91 (s, 1H), 2.93 (t, 1H), 3.35-3.45 (m, 1H), 4.06-4.20 (m, 1H), 6.93-7.04 (m, 1H), 7.07-7.19 (m, 1H), 7.39-7.54 (m, 4H), 7.66 (dt, 1H), 9.98-10.09 (m, 1H), 11.96 (br. s, 1H). |
| 51 | erythro-3-(3-{[(2S,3R)-2-(4-chlorophenyl)-4,4,4-trifluoro-3-methylbutanoyl]amino}-4-fluorophenyl)-2-methylbutanoic acid | LC-MS (Method 5): $R_t$ = 2.52 min; m/z = 460 (M + H)$^+$. $^1$H-NMR (400 MHz, DMSO-d$_6$): δ [ppm] = 0.71-0.91 (m, 4H), 1.00-1.11 (m, 1H), 1.14 (d, 3H), 1.23 (br. s, 2H), 1.91 (s, 1H), 3.37-3.45 (m, 1H), 4.12 (d, 1H), 6.90-7.05 (m, 1H), 7.14 (t, 1H), 7.33-7.56 (m, 4H), 7.65 (d, 1H), 10.05 (s, 1H). |

| Example | Name/Structure | Analytical data |
|---|---|---|
| 52 | 2-(3-{[(2S,3R)-2-(4-chlorophenyl)-4,4,4-trifluoro-3-methylbutanoyl]amino}-4-fluorophenyl)-trans-cyclopropancarboxylic acid | LC-MS (Method 5): $R_t$ = 2.45 min; m/z = 444 (M + H)$^+$. $^1$H-NMR (400 MHz, DMSO-$d_6$): δ [ppm] = 0.79 (d, 3H), 1.19-1.28 (m, 1H), 1.38 (dt, 1H), 1.65-1.75 (m, 1H), 2.30-2.40 (m, 1H), 4.12 (d, 1H), 6.88-6.97 (m, 1H), 7.13 (dd, 1H), 7.37-7.52 (m, 4H), 7.62 (dd, 1H), 10.06 (s, 1H), 12.30 (br. s, 1H). |

Example 53 and Example 54

2-(3-{[(2S,3R)-2-(4-Chlorophenyl)-4,4,4-trifluoro-3-methylbutanoyl]amino}-4-fluorophenyl)-trans-cyclopropanecarboxylic acid (diastereomers 1 and 2)

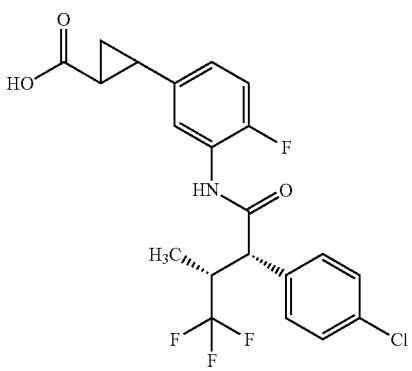 [SMILES: C[C@H]([C@H](C(=O)Nc1cc(C2CC2C(=O)O)ccc1F)c1ccc(Cl)cc1)C(F)(F)F]

71 mg of the diastereomer mixture of 2-(3-{[(2S,3R)-2-(4-chlorophenyl)-4,4,4-trifluoro-3-methylbutanoyl]amino}-4-fluorophenyl)-trans-cyclopropanecarboxylic acid (Example 52) were dissolved in 2 ml of ethanol and 2 ml of isohexane and separated further by preparative HPLC on a chiral phase [column: Daicel Chiralpak AD-H, 5 µm, 250 mm×200 mm; injection volume: 0.25 ml; temperature: 30° C.; mobile phase: 15% isopropanol/85% isohexane; flow rate: 15 ml/min; detection: 220 nm]. This gave 36 mg of diastereomer 1 (Example 53) and 37 mg of diastereomer 2 (Example 54):

Example 53

Diastereomer 1

LC-MS (Method 6): $R_t$=1.15 min; m/z=444 (M+H)$^+$.
$^1$H-NMR (400 MHz, DMSO-$d_6$): δ [ppm]=0.79 (d, 3H), 1.24 (ddd, 1H), 1.38 (dt, 1H), 1.64-1.80 (m, 1H), 2.35 (ddd, 1H), 4.12 (d, 1H), 6.85-7.01 (m, 1H), 7.13 (dd, 1H), 7.37-7.56 (m, 4H), 7.62 (dd, 1H), 10.06 (s, 1H).
$[α]_D^{20}$=+291.4°, c=0.48, chloroform.

Example 54

Diastereomer 2

LC-MS (Method 6): $R_t$=1.15 min; m/z=444 (M+H)$^+$.
$^1$H-NMR (400 MHz, DMSO-$d_6$): δ [ppm]=0.79 (d, 3H), 1.24 (ddd, 1H), 1.38 (dt, 1H), 1.64-1.76 (m, 1H), 2.29-2.40 (m, 2H), 4.12 (d, 1H), 6.92 (ddd, 1H), 7.13 (dd, 1H), 7.39-7.52 (m, 4H), 7.62 (dd, 1H), 10.06 (s, 1H).
$[α]_D^{20}$=+44.3°, c=0.40, chloroform.

Example 55

3-(3-{[(2S,3R)-2-(4-Chlorophenyl)-4,4,4-trifluoro-3-methylbutanoyl]amino}-4-cyanophenyl)-propanoic acid

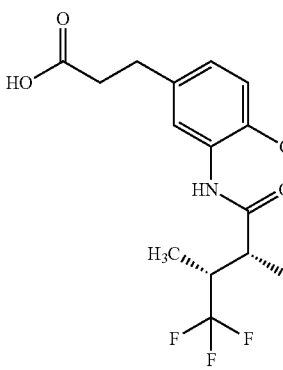

16.5 mg (33 µmol) of tert-butyl 3-(3-{[(2S,3R)-2-(4-chlorophenyl)-4,4,4-trifluoro-3-methylbutanoyl]amino}-4-cyanophenyl)propanoate were dissolved in 1.1 ml of dichloromethane, and 275 µl of trifluoroacetic acid were added. The reaction mixture was stirred at RT for 1.5 h, then diluted with 20 ml of dichloromethane and concentrated under reduced pressure. The residue was dried under high vacuum overnight. This gave 14.8 mg (97% of theory) of the title compound.
LC-MS (Method 6): $R_t$=1.10 min; m/z=439 (M+NH$_4$)$^+$.

$^1$H-NMR (400 MHz, DMSO-d$_6$): δ [ppm]=0.81 (d, 3H), 2.80-2.94 (m, 2H), 4.01 (d, 1H), 7.22 (dd, 1H), 7.32 (s, 1H), 7.40-7.52 (m, 4H), 7.69 (d, 1H), 10.48 (s, 1H).

Example 56

(+/−)-3-(3-{[2-(4-Chlorophenyl)-4,4,4-trifluoro-3-methylbutanoyl]amino}-2-fluorophenyl)propanoic acid (diastereomer 1)

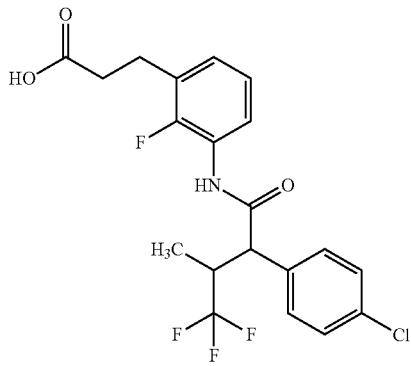

270 mg (0.553 mmol) of tert-butyl (+/−)-3-(3-{[2-(4-chlorophenyl)-4,4,4-trifluoro-3-methylbutanoyl]amino}-2-fluorophenyl) propanoic acid (diastereomer 1, Example 102A) were dissolved in 0.2 ml of dichloromethane, and 0.85 ml of trifluoroacetic acid was added at RT. The reaction mixture was stirred at RT for 4 h and then concentrated under reduced pressure. The residue was purified by preparative RP-HPLC (acetonitrile/water mixture). This gave 188 mg (78.7% of theory) of the target compound.

LC-MS (Method 6): R$_t$=1.16 min; m/z=432 (M+H)$^+$.

$^1$H-NMR (400 MHz, DMSO-d$_6$): δ [ppm]=0.79 (d, 3H), 2.48-2.53 (m, 2H), 2.82 (t, 2H), 3.35-3.48 (m, 1H), 4.13 (d, 1H), 6.88-7.13 (m, 2H), 7.37-7.51 (m, 4H), 7.54-7.76 (m, 1H), 10.04 (s, 1H), 12.19 (br. s, 1H).

The compound below was prepared in an analogous manner:

Example 57

(+/−)-3-(3-{[2-(4-Chlorophenyl)-4,4,4-trifluoro-3-methylbutanoyl]amino}-2-fluorophenyl)propanoic acid (diastereomer 2)

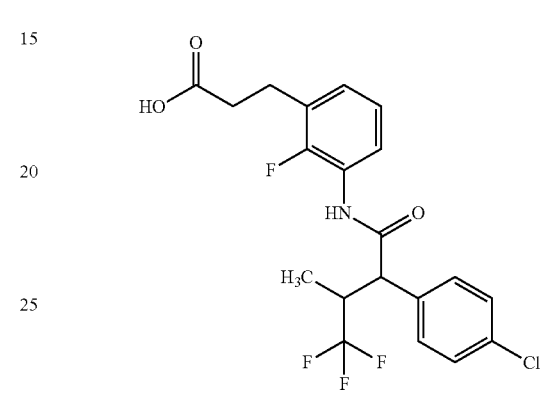

LC-MS (Method 6): R$_t$=1.15 min; m/z=432 (M+H)$^+$.

$^1$H-NMR (400 MHz, DMSO-d$_6$): δ [ppm]=1.22 (d, 3H), 2.52-2.56 (m, 2H), 2.83 (t, 2H), 3.22 (dd, 1H), 4.15 (d, 1H), 6.98-7.10 (m, 2H), 7.36-7.43 (m, 2H), 7.45-7.53 (m, 2H), 7.62 (td, 1H), 10.13 (s, 1H), 12.19 (s, 1H).

The following examples were prepared in accordance with General Procedure 2 (cleavage of tert-butyl esters to the corresponding carboxylic acids using trifluoroacetic acid):

| Example | Name/Structure/Starting material | Analytical data |
|---|---|---|
| 58 | (+)-3-(4-chloro-3-{[(2S,3R)-2-(4-chloro-3-fluorophenyl)-4,4,4-trifluoro-3-methylbutanoyl]amino}-phenyl)propanoic acid<br><br>(from (+)-tert-butyl 3-(4-chloro-3-{[(2S,3R)-2-(4-chloro-3-fluorophenyl)-4,4,4-trifluoro-3-methylbutanoyl]amino}phenyl)propanoate) | LC-MS (Method 6): R$_t$ = 1.17 min; m/z = 466 (M + H)$^+$.<br>$^1$H-NMR (400 MHz, DMSO-d$_6$): δ [ppm] = 0.83 (d, 3H), 2.49 (t, 2H), 2.76 (t, 2H), 3.34-3.46 (m, 1H), 4.14 (d, 1H), 7.06 (dd, 1H), 7.28-7.41 (m, 3H), 7.49 (dd, 1H), 7.62 (t, 1H), 9.87 (s, 1H), 12.13 (s, 1H).<br>[α]$_D^{20}$ = +79.9°, c = 0.520, chloroform. |

| Example | Name/Structure/Starting material | Analytical data |
|---|---|---|
| 59 | (+)-3-(4-chloro-3-{[(2S,3R)-2-(4-chloro-3-methyl-phenyl)-4,4,4-trifluoro-3-methylbutanoyl]amino}-phenyl)propanoic acid<br>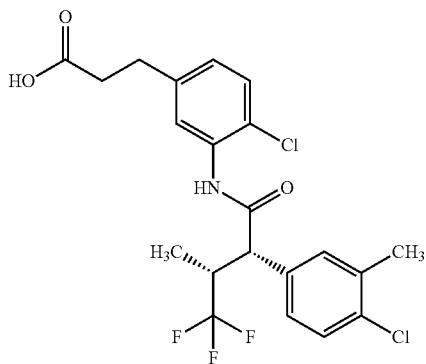<br>(from tert-butyl 3-(4-chloro-3-{[(2S,3R)-2-(4-chloro-3-methylphenyl)-4,4,4-trifluoro-3-methyl-butanoyl]-amino}phenyl)propanoate) | LC-MS (Method 6): $R_t$ = 1.20 min; m/z = 462 (M + H)$^+$.<br>$^1$H-NMR (400 MHz, DMSO-$d_6$): δ [ppm] = 0.80 (d, 3H), 2.33 (s, 3H), 2.48 (t, 2H), 2.76 (t, 2H), 3.27-3.42 (m, 1H), 4.04-4.09 (m, 1H), 7.04 (dd, 1H), 7.29 (dd, 1H), 7.32-7.36 (m, 1H), 7.38-7.45 (m, 3H), 9.81 (s, 1H), 12.16 (br. s, 1H).<br>$[α]_D^{20}$ = +86.0°, c = 0.250, chloroform. |
| 60 | (+)-3-(4-chloro-3-{[(2S,3R)-2-(3,4-dichlorophenyl)-4,4,4-trifluoro-3-methylbutanoyl]amino}phenyl)-propanoic acid<br>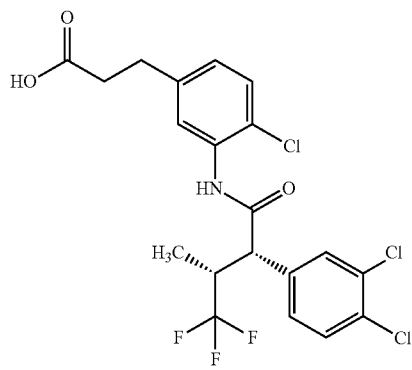<br>(from tert-butyl 3-(4-chloro-3-{[(2S,3R)-2-(3,4-dichlorophenyl)-4,4,4-trifluoro-3-methylbutanoyl]amino}phenyl)propanoate) | LC-MS (Method 6): $R_t$ = 1.23 min; m/z = 480/482 (M − H)$^-$.<br>$^1$H-NMR (400 MHz, DMSO-$d_6$): δ [ppm] = 0.83 (d, 3H), 2.47 (t, 2H), 2.72-2.81 (m, 2H), 3.35-3.47 (m, 1H), 4.09-4.17 (m, 1H), 7.06 (dd, 1H), 7.31-7.41 (m, 2H), 7.45 (dd, 1H), 7.67 (d, 1H), 7.72 (d, 1H), 9.88 (s, 1H).<br>$[α]_D^{20}$ = +98.8°, c = 0.325, methanol. |

| Example | Name/Structure/Starting material | Analytical data |
| --- | --- | --- |
| 61 | 3-(4-chloro-3-{[(2S,3R)-2-(4-chlorophenyl)-4,4,4-trifluoro-3-methylbutanoyl]amino}-2-methylphenyl)-2-methylpropanoic acid (diastereomer mixture)<br>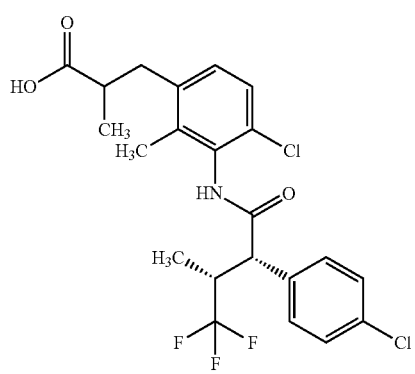<br>(from tert-butyl 3-(4-chloro-3-{[(2S,3R)-2-(4-chlorophenyl)-4,4,4-trifluoro-3-methylbutanoyl]amino}-2-methylphenyl)-2-methylpropanoate (diastereomer mixture)) | LC-MS (Method 6): $R_t$ = 1.20 min; m/z = 476 (M + H)$^+$.<br>$^1$H-NMR (400 MHz, DMSO-$d_6$): both diastereomers δ [ppm] = 0.80 (d, 3H), 1.03 (br. s, 3H), 1.51/1.57 (2 br. s, together 2H), 2.15 (br. s, about 2H), 2.86 (br. s, about 1H), 3.37-3.45 (m, about 1H), 3.90-4.00 (m, 1H), 6.99-7.12 (m, 1H), 7.16 (br. s, 1H), 7.25 (br. s, 1H), 7.35-7.54 (m, 5H), 9.88 (br. s, 1H), 12.18 (br. s, 1H) [because of rotamers, the signals are very broad]. |
| 62 | (+)-(2R)-3-(4-chloro-3-{[(2S,3R)-2-(4-chlorophenyl)-4,4,4-trifluoro-3-methylbutanoyl]amino}-2-methylphenyl)-2-methylpropanoic acid<br>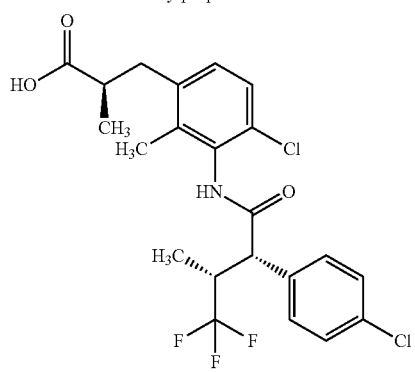<br>(from (+)-tert-butyl (2R)-3-(4-chloro-3-{[(2S,3R)-2-(4-chlorophenyl)-4,4,4-trifluoro-3-methylbutanoyl]amino}-2-methylphenyl)-2-methylpropanoate) | LC-MS (Method 6): $R_t$ = 1.26 min; m/z = 476 (M + H)$^+$.<br>$^1$H-NMR (400 MHz, DMSO-$d_6$): δ [ppm] = 0.80 (d, 3H), 1.03 (br. s, 3H), 2.42-2.62 (br. s, about 2H, partially obscured), 3.30-3.44 (m, 1H), 3.94 (d, 1H), 7.05 (d, 1H), 7.23 (br. s, 1H), 7.45 (s, 4H), 12.15 (br. s, 1H) [because of rotamers, the signals are very broad].<br>$[\alpha]_D^{20}$ = +108.9°, c = 0.510, methanol. |

| Example | Name/Structure/Starting material | Analytical data |
| --- | --- | --- |
| 63 | (+)-(2S)-3-(4-chloro-3-{[(2S,3R)-2-(4-chlorophenyl)-4,4,4-trifluoro-3-methylbutanoyl]amino}-2-methylphenyl)-2-methylpropanoic acid<br>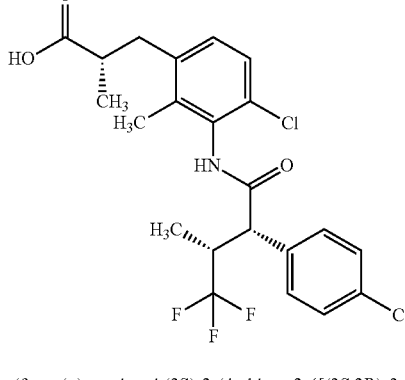<br>(from (+)-tert-butyl (2S)-3-(4-chloro-3-{[(2S,3R)-2-(4-chlorophenyl)-4,4,4-trifluoro-3-methylbutanoyl]-amino}-2-methylphenyl)-2-methylpropanoate) | LC-MS (Method 6): $R_t$ = 1.26 min; m/z = 476 (M + H)$^+$.<br>$^1$H-NMR (400 MHz, DMSO-$d_6$): δ [ppm] = 0.80 (d, 3H), 1.03 (br. s, 3H), 3.17 (d, 1H), 3.34-3.43 (m, 1H), 3.94 (d, 1H), 7.05 (d, 1H), 7.45 (br. s, 4H), 9.86 (br. s, 1H), 12.15 (br. s, 1H) [because of rotamers, the signals are very broad].<br>$[α]_D^{20}$ = +143.7°, c = 0.505, methanol. |
| 64 | 2-(4-chloro-3-{[(2S,3R)-2-(4-chlorophenyl)-4,4,4-trifluoro-3-methylbutanoyl]amino}benzyl)-2-methylbutanoic acid (diastereomer mixture)<br>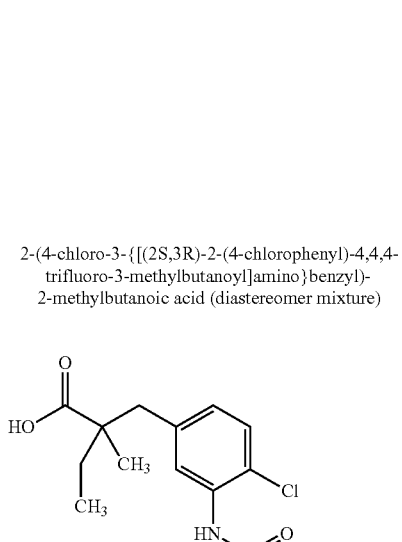<br>(from tert-butyl 2-(4-chloro-3-{[(2S,3R)-2-(4-chlorophenyl)-4,4,4-trifluoro-3-methylbutanoyl]-amino}benzyl)-2-methylbutanoate (diastereomer mixture)) | LC-MS (Method 6): $R_t$ = 1.28 min; m/z = 490 (M + H)$^+$.<br>$^1$H-NMR (400 MHz, DMSO-$d_6$): both diastereomers δ [ppm] = 0.73-0.87 (m, 6H), 0.92 (d, 3H), 1.31-1.42 (m, 1H), 1.52-1.72 (m, 1H), 2.60 (d, 1H), 2.85/2.87 (2d, together 1H), 3.32-3.36 (m, 1H), 3.94-4.18 (m, 1H), 6.95 (dd, 1H), 7.27-7.37 (m, 2H), 7.39-7.53 (m, 4H), 9.84 (s, 1H). |

| Example | Name/Structure/Starting material | Analytical data |
|---|---|---|
| 65 | (+)-2-(4-chloro-3-{[(2S,3R)-2-(4-chlorophenyl)-4,4,4-trifluoro-3-methylbutanoyl]amino}benzyl)-2-methylbutanoic acid (diastereomer B)<br>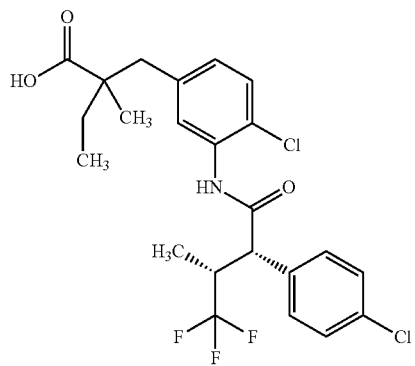<br>(from tert-butyl 2-(4-chloro-3-{[(2S,3R)-2-(4-chlorophenyl)-4,4,4-trifluoro-3-methylbutanoyl]-amino}benzyl)-2-methylbutanoate (diastereomer B) | LC-MS (Method 6): $R_t$ = 1.26 min; m/z = 490 (M + H)$^+$.<br>$^1$H-NMR (400 MHz, DMSO-$d_6$): δ [ppm] = 0.73-0.85 (m, 6H), 0.92 (s, 3H), 1.32-1.41 (m, 1H), 1.57-1.66 (m, 1H), 2.60 (d, 1H), 2.85 (d, 1H), 3.35-3.43 (m, 1H), 4.11 (d, 1H), 6.94 (d, 1H), 7.34 (d, 2H), 7.41-7.53 (m, 4H), 9.82 (s, 1H), 12.27 (br. s, 1H).<br>$[α]_D^{20}$ = +80.6°, c = 0.350, chloroform. |
| 66 | 3-(4-chloro-3-{[(2S,3R)-2-(4-chlorophenyl)-4,4,4-trifluoro-3-methylbutanoyl]amino}phenyl)-4,4,4-trifluorobutanoic acid (diastereomer mixture)<br>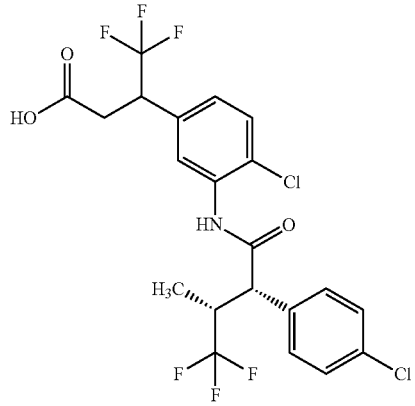<br>(from tert-butyl 3-(4-chloro-3-{[(2S,3R)-2-(4-chlorophenyl)-4,4,4-trifluoro-3-methylbutanoyl]amino}phenyl)-4,4,4-trifluorobutanoate (diastereomer mixture)) | LC-MS (Method 6): $R_t$ = 1.18 min; m/z = 516 (M + H)$^+$.<br>$^1$H-NMR (400 MHz, DMSO-$d_6$): both diastereomers<br>δ [ppm] = 0.80 (d, 3H), 2.84 (dd, 1H), 2.95 (dd, 1H), 3.35-3.44 (m, 1H), 4.01-4.09 (m, 1H), 4.14 (d, 1H), 7.26 (dd, 1H), 7.39-7.52 (m, 5H), 7.61 (dd, 1H), 9.95 (s, 1H), 12.55 (br. s, 1H). |

| Example | Name/Structure/Starting material | Analytical data |
|---|---|---|
| 67 | 3-(4-chloro-3-{[(2S,3R)-2-(4-chlorophenyl)-4,4,4-trifluoro-3-methylbutanoyl]amino}phenyl)-2-cyclobutylpropanoic acid (diastereomer mixture)<br>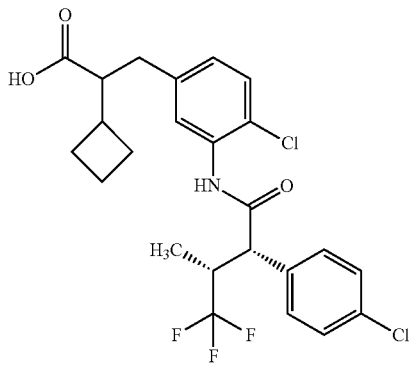<br>(from tert-butyl 3-(4-chloro-3-{[(2S,3R)-2-(4-chlorophenyl)-4,4,4-trifluoro-3-methylbutanoyl]-amino}phenyl)-2-cyclobutylpropanoate (diastereomer mixture)) | LC-MS (Method 6): $R_t$ = 1.29 min; m/z = 502 (M + H)$^+$.<br>$^1$H-NMR (400 MHz, DMSO-$d_6$): both diastereomers<br>δ [ppm] = 0.80 (d, 3H), 1.67-1.83 (m, 4H), 1.86-1.99 (m, 2H), 2.30-2.42 (m, 1H), 2.43-2.48 (m, 1H), 2.57-2.63 (m, 2H), 3.36-3.42 (m, 1H), 4.12 (d, 1H), 6.98 (d, 1H), 7.29-7.36 (m, 2H), 7.41-7.50 (m, 4H), 9.82 (s, 1H), 12.07 (s, 1H). |
| 68 | (+)-3-(4-chloro-3-{[(2S,3R)-2-(4-chlorophenyl)-4,4,4-trifluoro-3-methylbutanoyl]amino}phenyl)-2-cyclobutylpropanoic acid (diastereomer A)<br>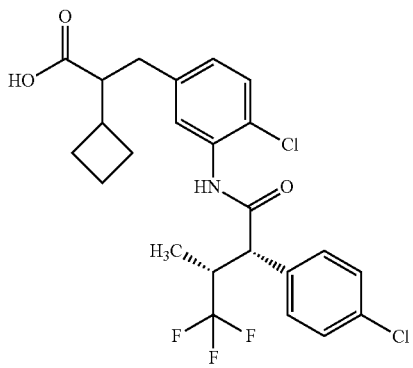<br>(from tert-butyl 3-(4-chloro-3-{[(2S,3R)-2-(4-chlorophenyl)-4,4,4-trifluoro-3-methylbutanoyl]-amino}phenyl)-2-cyclobutylpropanoate (diastereomer A)) | LC-MS (Method 6): $R_t$ = 1.32 min; m/z = 502 (M + H)$^+$.<br>$^1$H-NMR (400 MHz, DMSO-$d_6$): δ [ppm] = 0.80 (d, 3H), 1.65-1.83 (m, 4H), 1.88-1.98 (m, 2H), 2.29-2.43 (m, 1H), 2.43-2.48 (m, 1H), 2.56-2.63 (m, 2H), 3.37-3.41 (m, 1H), 4.12 (d, 1H), 6.98 (dd, 1H), 7.28-7.36 (m, 2H), 7.42-7.55 (m, 4H), 9.82 (s, 1H), 12.08 (br. s, 1H).<br>$[α]_D^{20}$ = +50.3°, c = 0.520, chloroform. |

| Example | Name/Structure/Starting material | Analytical data |
|---|---|---|
| 69 | (+)-3-(4-chloro-3-{[(2S,3R)-2-(4-chlorophenyl)-4,4,4-trifluoro-3-methylbutanoyl]amino}phenyl)-2-cyclobutylpropanoic acid (diastereomer B)<br>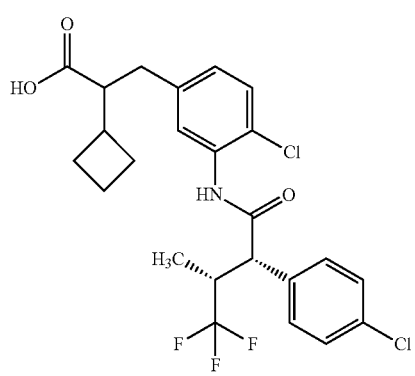<br>(from tert-butyl 3-(4-cloro-3-{[(2S,3R)-2-(4-chlorophenyl)-4,4,4-trifluoro-3-methylbutanoyl]amino}phenyl)-2-cyclobutylpropanoate (diastereomer B)) | LC-MS (Method 6): $R_t$ = 1.29 min; m/z = 502 (M + H)$^+$.<br>$^1$H-NMR (400 MHz, DMSO-$d_6$): δ [ppm] = 0.80 (d, 3H), 1.62-1.83 (m, 4H), 1.86-2.00 (m, 2H), 2.28-2.43 (m, 1H), 2.45-2.49 (m, 1H), 2.60 (d, 2H), 3.36-3.44 (m, 1H), 4.12 (d, 1H), 6.99 (dd, 1H), 7.24-7.37 (m, 2H), 7.41-7.53 (m, 4H), 9.82 (s, 1H), 12.07 (s, 1H).<br>$[\alpha]_D^{20}$ = +97.8°, c = 0.445, chloroform. |
| 70 | 3-(4-chloro-3-{[(2S,3R)-2-(4-chlorophenyl)-4,4,4-trifluoro-3-methylbutanoyl]amino}phenyl)-2-cyclopropylpropanoic acid (diastereomer mixture)<br>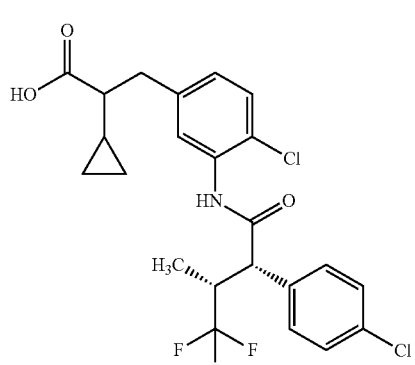<br>(from tert-butyl 3-(4-chloro-3-{[(2S,3R)-2-(4-chlorophenyl)-4,4,4-trifluoro-3-methylbutanoyl]-amino}phenyl)-2-cyclopropylpropanoate (diastereomer mixture)) | LC-MS (Method 4): $R_t$ = 1.48 min; m/z = 488 (M + H)$^+$.<br>$^1$H-NMR (400 MHz, DMSO-$d_6$): both diastereomers δ [ppm] = 0.05-0.13 (m, 1H), 0.20-0.25 (m, 1H), 0.42 (d, 2H), 0.79 (d, 3H), 0.82-0.92 (m, 1H), 1.78 (td, 1H), 2.74-2.90 (m, 2H), 3.30-3.40 (m, 1H), 4.11 (d, 1H), 7.01 (d, 1H), 7.33 (d, 1H), 7.37 (d, 1H), 7.42-7.50 (m, 4H), 9.82 (s, 1H). |

Example 71

(+)-2-(4-Chloro-3-{[(2S,3R)-2-(4-chlorophenyl)-4,4,4-trifluoro-3-methylbutanoyl]amino}benzyl)-2-methylbutanoic acid (diastereomer A)

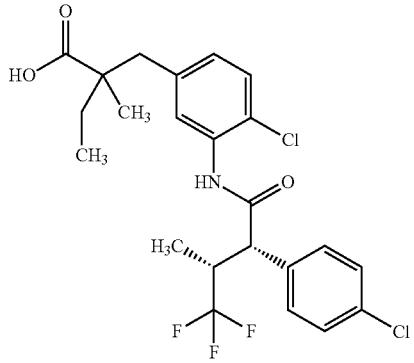 [SMILES: CCC(C)(Cc1ccc(Cl)c(NC(=O)[C@H](c2ccc(Cl)cc2)[C@@H](C)C(F)(F)F)c1)C(=O)O]

302 mg (0.553 mmol) of (+)-tert-butyl 2-(4-chloro-3-{[(2S,3R)-2-(4-chlorophenyl)-4,4,4-trifluoro-3-methylbutanoyl]amino}benzyl)-2-methylbutanoate (diastereomer A) were dissolved in 2.3 ml of dichloromethane and 2 ml of TFA were added at RT. After 30 min, the reaction mixture was concentrated under reduced pressure and the residue was dried under high vacuum. The residue was then purified by preparative RP-HPLC (mobile phase acetonitrile/water). This gave 110.8 mg of the target product (40.9% of theory).

LC-MS (Method 4): $R_t$=1.50 min; m/z=490 (M+H)$^+$.

$^1$H-NMR (400 MHz, DMSO-d$_6$): δ [ppm]=0.71-0.86 (m, 6H), 0.92 (s, 3H), 1.30-1.43 (m, 1H), 1.54-1.69 (m, 1H), 2.60 (d, 1H), 2.86 (d, 1H), 3.34-3.45 (m, 1H), 4.11 (d, 1H), 6.86-7.00 (m, 1H), 7.25-7.36 (m, 2H), 7.39-7.52 (m, 4H), 9.83 (s, 1H), 12.28 (s, 1H).

$[\alpha]_D^{20}$=+74.0°, c=0.280, chloroform.

The examples below were prepared according to General Procedure 3 (cleavage of methyl or ethyl esters to the corresponding carboxylic acids in mixtures of hydrochloric acid or sulphuric acid with acetic acid):

| Example | Name/Structure/Starting material | Analytical data |
|---|---|---|
| 72 | (+)-(2S)-3-(4-chloro-3-{[(2S,3R)-2-(4-chloro-2-fluorophenyl)-4,4,4-trifluoro-3-methylbutanoyl]amino}phenyl)-2-methylpropanoic acid<br><br>(from (+)-ethyl (2S)-3-(4-chloro-3-{[(2S,3R)-2-(4-chloro-2-fluorophenyl)-4,4,4-trifluoro-3-methylbutanoyl]amino}phenyl)-2-methylpropanoate) | LC-MS (Method 6): $R_t$ = 1.22 min; m/z = 480 (M + H)$^+$.<br>$^1$H-NMR (400 MHz, DMSO-d$_6$): δ [ppm] = 0.86 (d, 3H), 1.03 (d, 3H), 2.55-2.63 (m, 2H), 2.79-2.90 (m, 1H), 3.36-3.44 (m, 1H), 4.36 (d, 1H), 7.04 (dd, 1H), 7.26-7.39 (m, 3H), 7.52 (dd, 1H), 7.62 (t, 1H), 10.02 (s, 1H), 12.18 (br. s, 1H).<br>$[\alpha]_D^{20}$ = +92.1°, c = 0.365, chloroform. |
| 73 | (+)-(2S)-3-(4-chloro-3-{[(2S,3R)-2-(4-chloro-2-methylphenyl)-4,4,4-trifluoro-3-methylbutanoyl]amino}phenyl)-2-methylpropanoic acid<br><br>(from (+)-ethyl (2S)-3-(4-chloro-3-{[(2S,3R)-2-(4-chloro-2-methylphenyl)-4,4,4-trifluoro-3-methylbutanoyl]amino}phenyl)-2-methylpropanoate) | LC-MS (Method 6): $R_t$ = 1.26 min; m/z = 476 (M + H)$^+$.<br>$^1$H-NMR (400 MHz, DMSO-d$_6$): δ [ppm] = 0.77 (d, 3H), 1.02 (d, 3H), 2.54-2.63 (m, 2H), 2.79-2.91 (m, 1H), 3.38 (br. s, 1H), 4.15 (d, 1H), 7.03 (dd, 1H), 7.22-7.38 (m, 4H), 7.52 (d, 1H), 9.89 (s, 1H), 12.18 (br. s, 1H).<br>$[\alpha]_D^{20}$ = +124.3°, c = 0.390, chloroform. |

| Example | Name/Structure/Starting material | Analytical data |
|---|---|---|
| 74 | (+)-(2S)-3-(4-chloro-3-{[(2S,3R)-2-(4-chloro-3-fluorophenyl)-4,4,4-trifluoro-3-methylbutanoyl]-amino}phenyl)-2-methylpropanoic acid<br>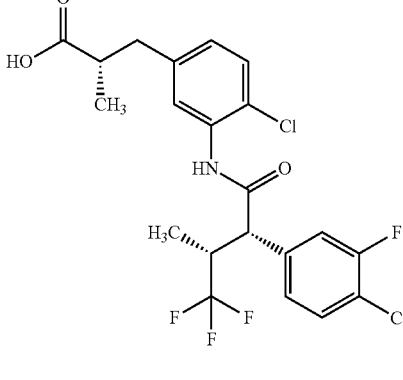<br>(from (+)-ethyl (2S)-3-(4-chloro-3-{[(2S,3R)-2-(4-chloro-3-fluorophenyl)-4,4,4-trifluoro-3-methyl-butanoyl]amino}phenyl)-2-methylpropanoate) | LC-MS (Method 6): $R_t = 1.20$ min; m/z = 480 (M + H)$^+$.<br>$^1$H-NMR (400 MHz, DMSO-$d_6$): δ [ppm] = 0.83 (d, 3H), 1.02 (d, 3H), 2.55-2.62 (m, 2H), 2.77-2.88 (m, 1H), 3.36-3.48 (m, 1H), 4.05-4.21 (m, 1H), 7.02 (dd, 1H), 7.25-7.41 (m, 3H), 7.49 (dd, 1H), 7.62 (t, 1H), 9.87 (s, 1H), 12.16 (br. s, 1H).<br>$[α]_D^{20}$ = +95.7°, c = 0.470, chloroform. |
| 75 | (+)-(2S)-3-(4-chloro-3-{[(2S,3R)-2-(4-chloro-3-methylphenyl)-4,4,4-trifluoro-3-methylbutanoyl]amino}phenyl)-2-methylpropanoic acid<br>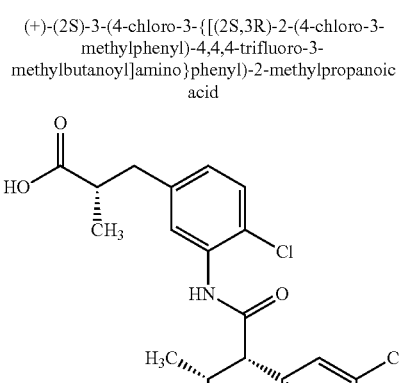<br>(from ethyl (2S)-3-(4-chloro-3-{[(2S,3R)-2-(4-chloro-3-methylphenyl)-4,4,4-trifluoro-3-methyl-butanoyl]amino}phenyl)-2-methylpropanoate) | LC-MS (Method 4): $R_t = 1.44$ min; m/z = 476 (M + H)$^+$.<br>$^1$H-NMR (400 MHz, DMSO-$d_6$): δ [ppm] = 0.78-0.85 (m, 3H), 1.02 (d, 3H), 2.33 (s, 3H), 2.55-261 (m, 2H), 2.77-2.89 (m, 1H), 3.34-3.41 (m, about 1H, obscured), 404-4.10 (m, 1H), 7.00 (dd, 1H), 7.26-7.45 (m, 5H), 9.81 (s, 1H), 12.17 (br. s, 1H).<br>$[α]_D^{20}$ = +397.5°, c = 0.340, chloroform. |

| Example | Name/Structure/Starting material | Analytical data |
|---|---|---|
| 76 | (+)-(2S)-3-(4-chloro-3-{[(2S,3R)-2-(3,4-dichlorophenyl)-4,4,4-trifluoro-3-methylbutanoyl]amino}phenyl)-2-methylpropanoic acid<br>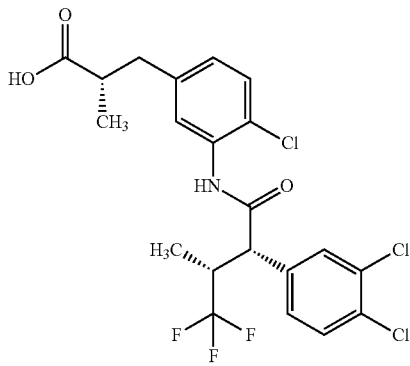<br>(from ethyl-(2S)-3-(4-chloro-3-{[(2S,3R)-2-(3,4-dichlorophenyl)-4,4,4-trifluoro-3-methylbutanoyl]amino}phenyl)-2-methylpropanoate) | LC-MS (Method 6): $R_t$ = 1.24 min; m/z = 496/498 (M + H)$^+$.<br>$^1$H-NMR (400 MHz, DMSO-$d_6$): δ [ppm] = 0.83 (d, 3H), 1.02 (d, 3H), 2.54-2.62 (m, 2H), 2.77-2.91 (m, 1H), 3.35-3.48 (m, 1H), 4.08-4.17 (m, 1H), 7.02 (dd, 1H), 7.31-7.39 (m, 2H), 7.45 (dd, 1H), 7.67 (d, 1H), 7.72 (d, 1H), 9.87 (s, 1H), 12.16 (br. s, 1H).<br>$[α]_D^{20}$ = +109.5°, c = 0.305, methanol. |
| 77 | 3-(4-chloro-3-{[(2S,3R)-2-(4-chlorophenyl)-4,4,4-trifluoro-3-methylbutanoyl]amino}-2-methylphenyl)propanoic acid<br>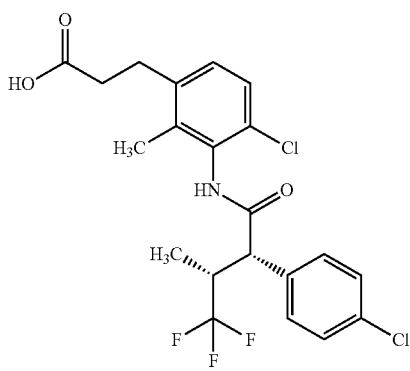<br>(from methyl 3-(4-chloro-3-{[(2S,3R)-2-(4-chlorophenyl)-4,4,4-trifluoro-3-methylbutanoyl]amino}-2-methylphenyl)propanoate) | LC-MS (Method 6): $R_t$ = 1.12 min; m/z = 462 (M + H)$^+$.<br>$^1$H-NMR (400 MHz, DMSO-$d_6$): δ [ppm] = 0.80 (d, 3H), 1.91/2.14 (2 br. s, together 3H), 2.42 (br. s, 2H), 2.73 (d, 2H), 3.34-3.43 (m, 1H), 3.96 (d, 1H), 7.04-7.14 (m, 1H), 7.14-7.35 (m, 1H), 7.45 (s, 4H), 9.91 (br. s, 1H), 12.13 (br. s, 1H) [because of rotamers, the signals are very broad]. |

| Example | Name/Structure/Starting material | Analytical data |
|---|---|---|
| 78 | 3-(3-{[(2S,3R)-2-(4-chlorophenyl)-4,4,4-trifluoro-3-methylbutanoyl]amino}-4-fluorophenyl)-4,4,4-trifluorobutanoic acid (diastereomer mixture)<br>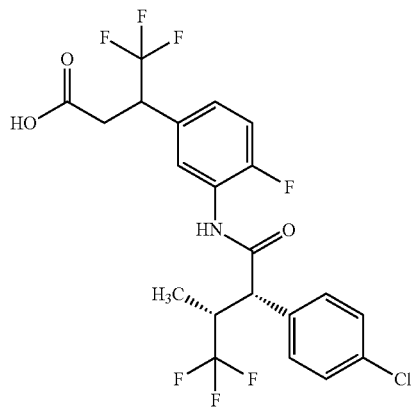<br>(from ethyl 3-(3-{[(2S,3R)-2-(4-chlorophenyl)-4,4,4-trifluoro-3-methylbutanoyl]amino}-4-fluorophenyl)-4,4,4-trifluorobutanoate) | LC-MS (Method 6): $R_t$ = 1.14 min; m/z = 500 (M + H)$^+$.<br>$^1$H-NMR (400 MHz, DMSO-$d_6$): both diastereomers δ [ppm] = 0.79 (d, 3H), 2.83 (dd, 1H), 2.95 (dd, 1H), 3.25-3.46 (m, 2H), 3.96-4.07 (m, 1H), 4.13 (d, 1H), 7.19-7.29 (m, 2H), 7.41-7.50 (m, 4H), 7.88 (d, 1H), 10.17 (s, 1H). |

Example 79 and Example 80

(+)-3-(3-{[(2S,3R)-2-(4-Chlorophenyl)-4,4,4-trifluoro-3-methylbutanoyl]amino}-4-fluorophenyl)-4,4,4-trifluorobutanoic acid (diastereomers 1 and 2)

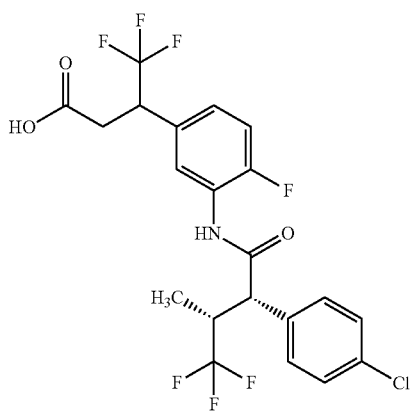 [SMILES: C[C@H]([C@H](C(=O)Nc1cc(C(CC(=O)O)C(F)(F)F)ccc1F)c1ccc(Cl)cc1)C(F)(F)F]

The mixture obtained above of the diastereomeric 3-(3-{[(2S,3R)-2-(4-chlorophenyl)-4,4,4-trifluoro-3-methylbutanoyl]amino}-4-fluorophenyl)-4,4,4-trifluorobutanoic acids (Example 78) was separated further by preparative HPLC on a chiral phase [column: Daicel Chiralpak AD-H, 5 μm, 250 mm×20 mm; flow rate: 15 ml/min; detection: 230 nm; injection volume: 0.80 ml; temperature: 45° C.; mobile phase: 92% isohexane/8% isopropanol]. 1.95 g of diastereomer mixture gave 556 mg of diastereomer 1 (Example 79) and 730 mg of diastereomer 2 (Example 80):

Example 79

Diastereomer 1

Diastereomer 1 was once more repurified by preparative RP-HPLC (mobile phase methanol/water). This gave 418 mg.

LC-MS (Method 4): $R_t$=1.49 min; m/z=500 (M+H)$^+$.

$^1$H-NMR (400 MHz, DMSO-$d_6$): δ [ppm]=0.79 (d, 3H), 2.82 (dd, 1H), 2.94 (dd, 1H), 3.37-3.44 (m, 1H), 4.02 (td, 1H), 4.13 (d, 1H), 7.17-7.30 (m, 2H), 7.40-7.50 (m, 4H), 7.87 (d, 1H), 10.18 (s, 1H), 12.53 (br. s, 1H).

$[α]_D^{20}$=+130°, c=0.29, chloroform.

Example 80

Diastereomer 2

Diastereomer 2 was once more repurified by preparative RP-HPLC (mobile phase methanol/water). This gave 352 mg.

LC-MS (Method 6): $R_t$=1.18 min; m/z=500 (M+H)$^+$.

$^1$H-NMR (400 MHz, DMSO-$d_6$): δ [ppm]=0.79 (d, 3H), 2.82 (dd, 1H), 2.94 (dd, 1H), 3.94-4.08 (m, 1H), 4.13 (d, 1H), 7.17-7.33 (m, 2H), 7.40-7.52 (m, 4H), 7.88 (d, 1H), 10.18 (s, 1H).

$[α]_D^{20}$=+104°, c=0.260, chloroform.

Example 81

3-(4-Chloro-3-{[(2S,3R)-2-(4-chlorophenyl)-4,4,4-trifluoro-3-methylbutanoyl]amino}phenyl)-hexanoic acid (diastereomer mixture)

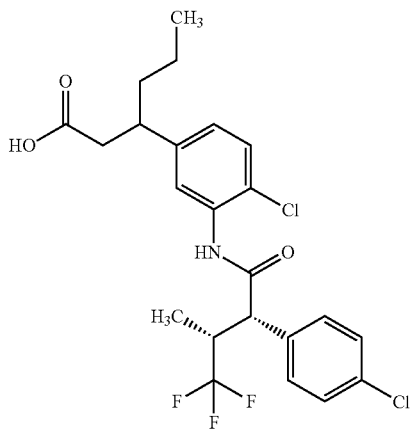 [SMILES: CCCC(CC(=O)O)c1ccc(Cl)c(NC(=O)[C@H](c2ccc(Cl)cc2)[C@@H](C)C(F)(F)F)c1]

1.50 g (2.97 mmol) of methyl 3-(4-chloro-3-{[(2S,3R)-2-(4-chlorophenyl)-4,4,4-trifluoro-3-methylbutanoyl]amino}phenyl)hexanoate (diastereomer mixture) were dissolved in 5 ml of acetic acid, 5 ml of 30% strength sulphuric acid were added and the mixture was heated at reflux (bath temperature about 140° C.). After 1.5 h, a further 2.5 ml of acetic acid were added, and the reaction mixture was stirred under reflux for another 2.5 h. After cooling, the mixture was allowed to stand at RT overnight, then added to water and extracted three times with ethyl acetate. The combined organic phases were washed with 5% strength sodium bicarbonate solution and sat. sodium chloride solution, dried over magnesium sulphate and concentrated under reduced pressure, and the residue was dried under high vacuum. This gave 1.44 g of the target product (98.8% of theory).

LC-MS (Method 6): $R_t$=1.29 min; m/z=490 (M+H)$^+$.

$^1$H-NMR (400 MHz, DMSO-$d_6$): both diastereomers δ [ppm]=0.74-0.83 (m, 6H), 0.99-1.14 (m, 2H), 1.37-1.60 (m, 2H), 2.39 (dd, 1H), 2.85-2.99 (m, 1H), 3.36-3.44 (m, 1H), 4.13 (d, 1H), 6.97-7.10 (m, 1H), 7.32-7.40 (m, 2H), 7.42-7.53 (m, 4H), 9.83 (s, 1H), 12.02 (br. s, 1H).

Example 82 and Example 83

(+)-3-(4-Chloro-3-{[(2S,3R)-2-(4-chlorophenyl)-4,4,4-trifluoro-3-methylbutanoyl]amino}phenyl)-hexanoic acid (diastereomers 1 and 2)

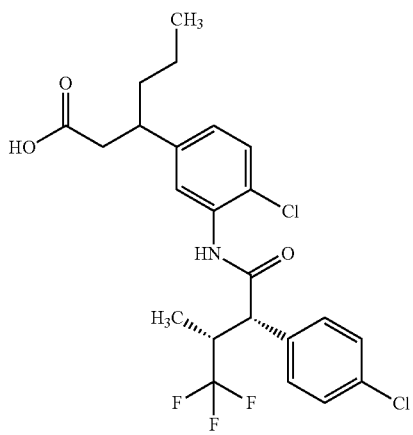 [SMILES: CCCC(CC(=O)O)c1ccc(Cl)c(NC(=O)[C@H](c2ccc(Cl)cc2)[C@@H](C)C(F)(F)F)c1]

The mixture obtained above of the diastereomeric 3-(4-chloro-3-{[(2S,3R)-2-(4-chlorophenyl)-4,4,4-trifluoro-3-methylbutanoyl]amino}phenyl)hexanoic acids (Example 81) was separated further by preparative HPLC on a chiral phase [column: Daicel Chiralpak AD-H, 5 µm, 250 mm×20 mm; flow rate: 20 ml/min; detection: 230 nm; injection volume: 0.60 ml; temperature: 25° C.; mobile phase: 95% isohexane/ 5% isopropanol]. 59.2 mg of diastereomer mixture gave 19 mg of diastereomer 1 (Example 82) and 17 mg of diastereomer 2 (Example 83):

Example 82

Diastereomer 1

(+)-(3S)-3-(4-Chloro-3-{[(2S,3R)-2-(4-chlorophenyl)-4,4,4-trifluoro-3-methylbutanoyl]amino}-phenyl)hexanoic acid

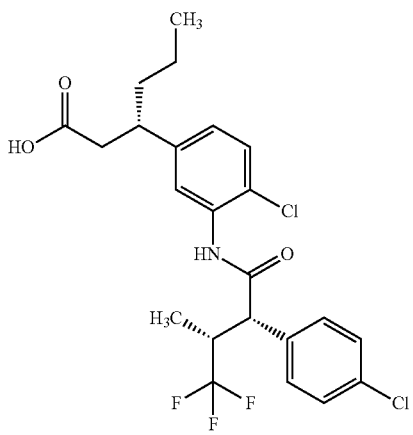 [SMILES: CCC[C@@H](CC(=O)O)c1ccc(Cl)c(NC(=O)[C@H](c2ccc(Cl)cc2)[C@@H](C)C(F)(F)F)c1]

LC-MS (Method 6): $R_t$=1.27 min; m/z=490 (M+H)$^+$.

$^1$H-NMR (400 MHz, DMSO-$d_6$): δ [ppm]=0.72-0.86 (m, 6H), 0.98-1.19 (m, 2H), 1.37-1.61 (m, 2H), 2.34-2.44 (m, 1H), 2.88-2.97 (m, 1H), 3.34-3.43 (m, 1H), 4.13 (d, 1H), 7.05 (dd, 1H), 7.26-7.40 (m, 2H), 7.41-7.63 (m, 4H), 9.82 (s, 1H), 12.02 (s, 1H).

$[α]_D^{20}$=+52°, c=0.30, chloroform.

A larger amount (1.40 g) of the diastereomeric 3-(4-chloro-3-{[(2S,3R)-2-(4-chlorophenyl)-4,4,4-trifluoro-3-methylbutanoyl]amino}phenyl)hexanoic acids (Example 81) was likewise separated by the same preparative HPLC method. In this case, the diastereomer 1 obtained was once more repurified by RP-HPLC [column: Sunfire 250 mm×20 mm; mobile phase: 80% acetonitrile/5% aq. TFA (1% strength)/15% water]. This gave 337 mg of pure diastereomer 1.

$^1$H-NMR (400 MHz, DMSO-$d_6$): δ [ppm]=0.74-0.86 (m, 6H), 0.97-1.16 (m, 2H), 1.40-1.60 (m, 2H), 2.35-2.44 (m, 1H), 2.89-2.97 (m, 1H), 3.35-3.43 (m, 1H), 4.13 (d, 1H), 7.05 (dd, 1H), 7.30-7.40 (m, 2H), 7.41-7.54 (m, 4H), 9.83 (s, 1H), 12.02 (br. s, 1H).

$[α]_D^{20}$=+86°, c=0.480, chloroform.

Example 83

Diastereomer 2

(+)-(3R)-3-(4-Chloro-3-{[(2S,3R)-2-(4-chlorophenyl)-4,4,4-trifluoro-3-methylbutanoyl]amino}-phenyl)hexanoic acid

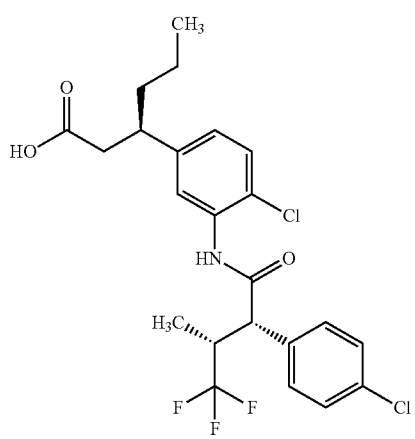 [SMILES: CCC[C@H](CC(=O)O)c1ccc(Cl)c(NC(=O)[C@H](c2ccc(Cl)cc2)[C@@H](C)C(F)(F)F)c1]

LC-MS (Method 6): $R_t$=1.27 min; m/z=490 (M+H)$^+$.

$^1$H-NMR (400 MHz, DMSO-d$_6$): δ [ppm]=0.77-0.83 (m, 6H), 1.00-1.12 (m, 2H), 1.41-1.60 (m, 2H), 2.35-2.44 (m, 1H), 2.88-2.98 (m, 1H), 3.35-3.45 (m, 1H), 4.13 (d, 1H), 7.05 (dd, 1H), 7.32-7.40 (m, 2H), 7.43-7.64 (m, 4H), 9.82 (s, 1H), 12.04 (br. s, 1H).

[α]$_D^{20}$=+22.1°, c=0.40, chloroform.

Example 84 and Example 85

(+)-3-(4-Chloro-3-{[(2S,3R)-2-(4-chlorophenyl)-4,4,4-trifluoro-3-methylbutanoyl]amino}phenyl)-4,4,4-trifluorobutanoic acid (diastereomers 1 and 2)

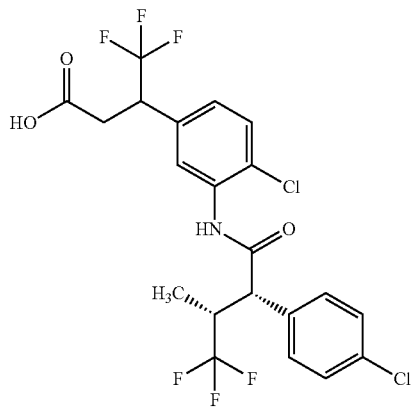 [SMILES: C[C@H]([C@H](C(=O)Nc1cc(C(CC(=O)O)C(F)(F)F)ccc1Cl)c1ccc(Cl)cc1)C(F)(F)F]

The mixture obtained above of the diastereomeric 3-(4-chloro-3-{[(2S,3R)-2-(4-chlorophenyl)-4,4,4-trifluoro-3-methylbutanoyl]amino}phenyl)-4,4,4-trifluorobutanoic acids (Example 66) was separated further by preparative HPLC on a chiral phase [column: Daicel Chiralpak AD-H, 5 μm, 250 mm×20 mm; flow rate: 15 ml/min; detection: 220 nm; injection volume: 0.25 ml; temperature: 30° C.; mobile phase: 93% isohexane/7% isopropanol]. 150 mg of diastereomer mixture gave 70 mg of diastereomer 1 (Example 84) and 79 mg of diastereomer 2 (Example 85):

Example 84

Diastereomer 1

(+)-(3S)-3-(4-Chloro-3-{[(2S,3R)-2-(4-chlorophenyl)-4,4,4-trifluoro-3-methylbutanoyl]amino}-phenyl)-4,4,4-trifluorobutanoic acid

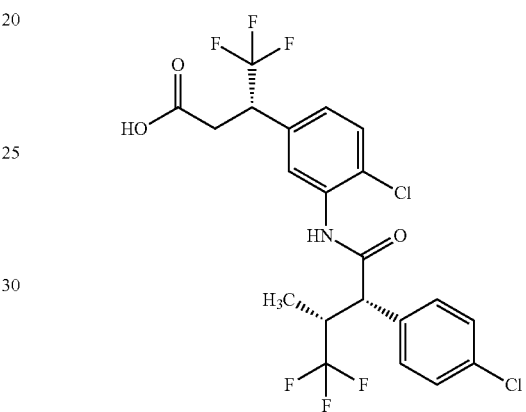

LC-MS (Method 6): $R_t$=1.18 min; m/z=516 (M+H)$^+$.

$^1$H-NMR (400 MHz, DMSO-d$_6$): δ [ppm]=0.80 (d, 3H), 2.84 (dd, 1H), 2.95 (dd, 1H), 3.36-3.43 (m, 1H), 4.06 (td, 1H), 4.14 (d, 1H), 7.26 (dd, 1H), 7.40-7.52 (m, 5H), 7.60 (d, 1H), 9.95 (s, 1H), 12.54 (br. s, 1H).

[α]$_D^{20}$=+78°, c=0.52, chloroform.

Alternatively, (+)-(3S)-3-(4-chloro-3-{[(2S,3R)-2-(4-chlorophenyl)-4,4,4-trifluoro-3-methylbutanoyl]amino}phenyl)-4,4,4-trifluorobutanoic acid could also be prepared by the following route:

1.76 g (3.08 mmol) of (+)-tert-butyl (3S)-3-(4-chloro-3-{[(2S,3R)-2-(4-chlorophenyl)-4,4,4-trifluoro-3-methylbutanoyl]amino}phenyl)-4,4,4-trifluorobutanoate (Example 203A) were dissolved in 4.9 ml of dichloromethane, and 4.7 ml of TFA were added at RT. The reaction mixture was stirred at RT for 2 h and then concentrated under reduced pressure. The residue was taken up in ethyl acetate and washed with sat. sodium bicarbonate solution and sat. sodium chloride solution, dried over magnesium sulphate and concentrated under reduced pressure. The crude product was purified by preparative RP-HPLC (mobile phase methanol/water). This gave 1.30 g of the target product (81.9% of theory).

LC-MS (Method 4): $R_t$=1.46 min; m/z=515 (M)$^+$.

$^1$H-NMR (400 MHz, DMSO-d$_6$): δ [ppm]=0.80 (d, 3H), 2.83 (dd, 1H), 2.95 (dd, 1H), 3.37-3.45 (m, 1H), 4.06 (td, 1H), 4.14 (d, 1H), 7.26 (dd, 1H), 7.43-7.52 (m, 5H), 7.60 (d, 1H), 9.95 (s, 1H), 12.56 (br. s, 1H).

[α]$_D^{20}$=+79.9°, c=0.475, chloroform.

Example 85

Diastereomer 2

(+)-(3R)-3-(4-Chloro-3-{[(2S,3R)-2-(4-chlorophenyl)-4,4,4-trifluoro-3-methylbutanoyl]amino}-phenyl)-4,4,4-trifluorobutanoic acid

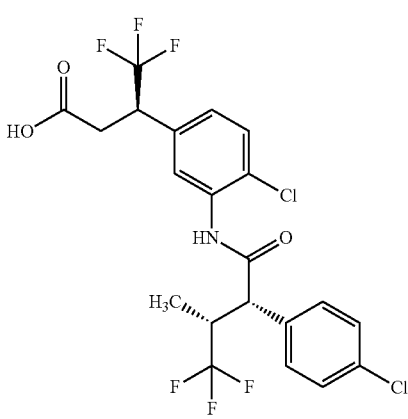 [SMILES: C[C@H]([C@H](C(=O)Nc1cc([C@@H](CC(=O)O)C(F)(F)F)ccc1Cl)c1ccc(Cl)cc1)C(F)(F)F]

LC-MS (Method 6): $R_t$=1.19 min; m/z=516 (M+H)$^+$.

$^1$H-NMR (400 MHz, DMSO-d$_6$): δ [ppm]=0.80 (d, 3H), 2.84 (dd, 1H), 2.95 (dd, 1H), 3.28-3.44 (m, 1H), 3.95-4.11 (m, 1H), 4.15 (d, 1H), 7.22-7.30 (m, 1H), 7.41-7.53 (m, 5H), 7.57-7.70 (m, 1H), 9.95 (s, 1H), 12.55 (br. s, 1H).

[α]$_D^{20}$=+40.2°, c=0.52, chloroform.

Alternatively, (+)-(3R)-3-(4-chloro-3-{[(2S,3R)-2-(4-chlorophenyl)-4,4,4-trifluoro-3-methylbutanoyl]amino}phenyl)-4,4,4-trifluorobutanoic acid could also be prepared by the following route:

1.17 g (2.04 mmol) of (+)-tert-butyl (3R)-3-(4-chloro-3-{[(2S,3R)-2-(4-chlorophenyl)-4,4,4-trifluoro-3-methylbutanoyl]amino}phenyl)-4,4,4-trifluorobutanoate (Example 204A) were dissolved in 4.9 ml of dichloromethane, and 3.2 ml of TFA were added at RT. The reaction mixture was stirred at RT for 2 h and then concentrated under reduced pressure. The residue was taken up in ethyl acetate and washed with sat. sodium bicarbonate solution and sat. sodium chloride solution, dried over magnesium sulphate and concentrated under reduced pressure. The crude product was purified by preparative RP-HPLC (mobile phase methanol/water). This gave 0.76 g of the target product (72% of theory).

LC-MS (Method 6): $R_t$=1.19 min; m/z=516 (M+H)$^+$.

$^1$H-NMR (400 MHz, DMSO-d$_6$): δ [ppm]=0.80 (d, 3H), 2.83 (dd, 1H), 2.94 (dd, 1H), 3.37-3.47 (m, 1H), 3.93-4.10 (m, 1H), 4.15 (d, 1H), 7.26 (dd, 1H), 7.43-7.52 (m, 5H), 7.58-7.66 (m, 1H), 9.95 (s, 1H), 12.57 (br. s, 1H).

[α]$_D^{20}$=+44.8°, c=0.47, chloroform.

Example 86

3-(4-Chloro-3-{[(2S,3R)-2-(4-chlorophenyl)-4,4,4-trifluoro-3-methylbutanoyl]amino}phenyl)-pentanoic acid (diastereomer mixture)

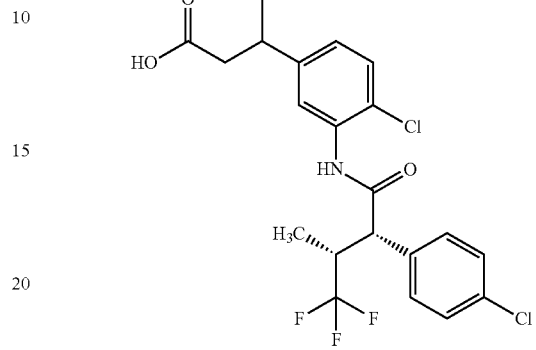

650 mg (1.33 mmol) of methyl 3-(4-chloro-3-{[(2S,3R)-2-(4-chlorophenyl)-4,4,4-trifluoro-3-methylbutanoyl]amino}phenyl)pentanoate (diastereomer mixture) were dissolved in 2 ml of acetic acid, 1 ml of 30% strength sulphuric acid was added and the mixture was heated at reflux (bath temperature about 140° C.). After 1.5 h, the reaction mixture was cooled and added to water. The mixture was extracted three times with ethyl acetate. The combined organic phases were washed with sat. sodium bicarbonate solution and sat. sodium chloride solution, dried over magnesium sulphate and concentrated under reduced pressure. After drying under high vacuum, the residue was purified by chromatography on silica gel (mobile phase cyclohexane/ethyl acetate 50:1). This gave 600 mg of the target product (95% of theory).

LC-MS (Method 6): $R_t$=1.24 min; m/z=476 (M+H)$^+$.

$^1$H-NMR (400 MHz, DMSO-d$_6$): both diastereomers δ [ppm]=0.69 (td, 3H), 0.80 (d, 3H), 1.40-1.52 (m, 1H), 1.55-1.68 (m, 1H), 2.40 (dd, 1H), 2.55-2.59 (m, 1H), 2.78-2.89 (m, 1H), 3.36-3.43 (m, 1H), 4.13 (d, 1H), 7.04 (dd, 1H), 7.31-7.41 (m, 2H), 7.42-7.57 (m, 4H), 9.84 (s, 1H), 12.04 (br. s, 1H).

Example 87 and Example 88

(+)-3-(4-Chloro-3-{[(2S,3R)-2-(4-chlorophenyl)-4,4,4-trifluoro-3-methylbutanoyl]amino}phenyl)-pentanoic acid (diastereomers 1 and 2)

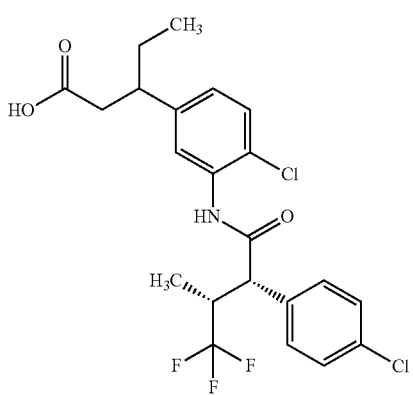 [SMILES: CCC(CC(=O)O)c1ccc(Cl)c(NC(=O)[C@H](c2ccc(Cl)cc2)[C@@H](C)C(F)(F)F)c1]

The mixture obtained above of the diastereomeric 3-(4-chloro-3-{[(2S,3R)-2-(4-chlorophenyl)-4,4,4-trifluoro-3-methylbutanoyl]amino}phenyl)pentanoic acids (Example 86) was separated further by preparative HPLC on a chiral phase [column: Daicel Chiralpak AD-H, 5 μm, 250 mm×20 mm; flow rate: 18 ml/min; detection: 230 nm; injection volume: 0.25 ml; temperature: 25° C.; mobile phase: 95% isohexane/5% isopropanol]. 545 mg of diastereomer mixture gave 140 mg of diastereomer 1 (Example 87) and 156 mg of diastereomer 2 (Example 88):

Example 87

Diastereomer 1

(+)-(3S)-3-(4-Chloro-3-{[(2S,3R)-2-(4-chlorophenyl)-4,4,4-trifluoro-3-methylbutanoyl]amino}-phenyl)pentanoic acid

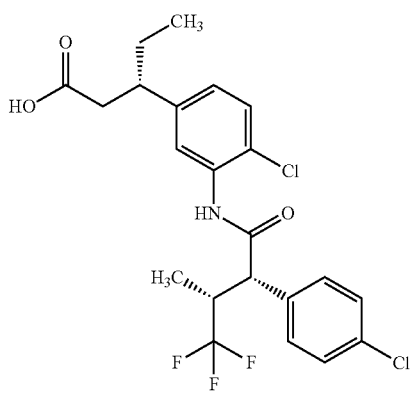 [SMILES: CC[C@@H](CC(=O)O)c1ccc(Cl)c(NC(=O)[C@H](c2ccc(Cl)cc2)[C@@H](C)C(F)(F)F)c1]

LC-MS (Method 4): $R_t$=1.47 min; m/z=476 (M+H)$^+$.
$^1$H-NMR (400 MHz, DMSO-d$_6$): δ [ppm]=0.69 (t, 3H), 0.80 (d, 3H), 1.37-1.51 (m, 1H), 1.54-1.68 (m, 1H), 2.35-2.44 (m, 1H), 2.55-2.59 (m, 1H), 2.80-2.87 (m, 1H), 3.36-3.40 (m, 1H), 4.13 (d, 1H), 7.04 (dd, 1H), 7.32-7.40 (m, 2H), 7.42-7.50 (m, 4H), 9.83 (s, 1H), 12.03 (br. s, 1H).
$[α]_D^{20}$=+87.0, c=0.47, chloroform.

Example 88

Diastereomer 2

(+)-(3R)-3-(4-Chloro-3-{[(2S,3R)-2-(4-chlorophenyl)-4,4,4-trifluoro-3-methylbutanoyl]amino}-phenyl)pentanoic acid

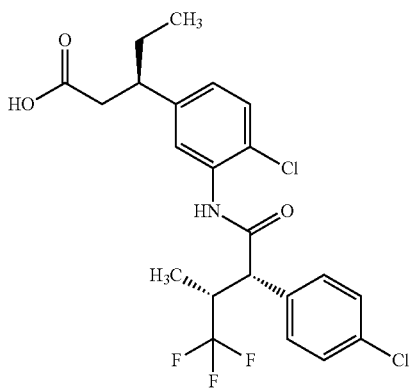 [SMILES: CC[C@H](CC(=O)O)c1ccc(Cl)c(NC(=O)[C@H](c2ccc(Cl)cc2)[C@@H](C)C(F)(F)F)c1]

LC-MS (Method 4): $R_t$=1.47 min; m/z=476 (M+H)$^+$.
$^1$H-NMR (400 MHz, DMSO-d$_6$): δ [ppm]=0.69 (t, 3H), 0.80 (d, 3H), 1.39-1.50 (m, 1H), 1.56-1.65 (m, 1H), 2.35-2.45 (m, 1H), 2.52-2.58 (m, 1H), 2.80-2.87 (m, 1H), 3.35-3.41 (m, 1H), 4.13 (d, 1H), 7.04 (dd, 1H), 7.31-7.41 (m, 2H), 7.42-7.52 (m, 4H), 9.83 (s, 1H), 12.04 (br. s, 1H).
$[α]_D^{20}$=+71.4, c=0.48, chloroform.

The examples below were prepared in accordance with General Procedure 2 (cleavage of tert-butyl esters to the corresponding carboxylic acids using trifluoroacetic acid):

| Example | Name/Structure/Starting material | Analytical data |
|---|---|---|
| 89 | 3-(4-chloro-3-{[(2S,3R)-2-(4-chlorophenyl)-4,4,4-trifluoro-3-methylbutanoyl]amino}phenyl)-2,2-dimethylpropanoic acid<br><br>(from tert-butyl 3-(4-chloro-3-{[(2S,3R)-2-(4-chlorophenyl)-4,4,4-trifluoro-3-methylbutanoyl]amino}phenyl)-2,2-dimethylpropanoate) | LC-MS (Method 6):<br>$R_t$ = 1.24 min; m/z = 476/478 (M + H)$^+$.<br>$^1$H-NMR (400 MHz, DMSO-d$_6$): δ [ppm] = 0.80 (d, 3H), 1.046 (s, 3H), 1.051 (s, 3H), 2.74 (s, 2H), 3.29-3.45 (m, 1H, partially obscured by H$_2$O signal), 4.11 (d, 1H), 6.95 (dd, 1H), 7.31-7.37 (m, 2H), 7.42-7.50 (m, 4H), 9.84 (s, 1H), 12.17-12.44 (br. s, 1H). |

| Example | Name/Structure/Starting material | Analytical data |
|---|---|---|
| 90 | [1-(4-chloro-3-{[(2S,3R)-2-(4-chlorophenyl)-4,4,4-trifluoro-3-methylbutanoyl]amino}phenyl)-cyclobutyl]acetic acid<br>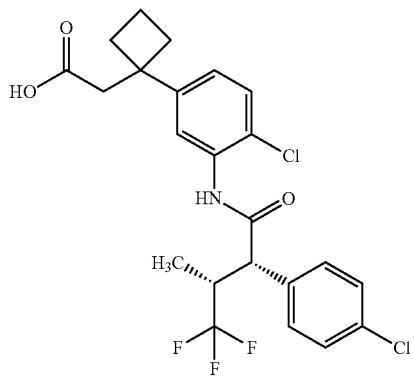<br>(from tert-butyl [1-(4-chloro-3-{[(2S,3R)-2-(4-chlorophenyl)-4,4,4-trifluoro-3-methylbutanoyl]amino}phenyl)cyclobutyl]acetate) | MS: m/z = 488 (M + H)+.<br>1H-NMR (400 MHz, DMSO-$d_6$): δ [ppm] = 0.80 (d, 3H), 1.67-1.81 (m, 1H), 1.96-2.08 (m, 1H), 2.17-2.35 (m, 4H), 2.69 (s, 2H), 3.27-3.42 (m, 1H, partially obscured by H2O signal), 4.14 (d, 1H), 6.99 (dd, 1H), 7.35 (d, 1H), 7.41 (d, 1H), 7.43-7.50 (m, 4H), 9.81 (s, 1H), 11.88 (s, 1H).<br>$[\alpha]_D^{20}$ = +88°, c = 0.290, methanol |
| 91 | 3-(3-{[(2S,3R)-2-(4-chlorophenyl)-4,4,4-trifluoro-3-methylbutanoyl]amino}-2-methylphenyl)propanoic acid<br>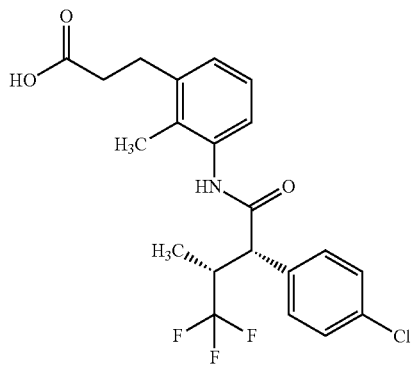<br>(from tert-butyl 3-(3-{[(2S,3R)-2-(4-chlorophenyl)-4,4,4-trifluoro-3-methylbutanoyl]amino}-2-methyl-phenyl)propanoate) | LC-MS (Method 4):<br>$R_t$ = 1.27 min; m/z = 428 (M + H)+.<br>1H-NMR (400 MHz, DMSO-$d_6$): δ [ppm] = 0.80 (d, 3H), 1.92 (s, 3H), 2.43 (t, 2H), 2.79 (t, 2H), 3.28-3.44 (m, 1H, partially obscured by H2O signal), 3.94 (d, 1H), 6.93-7.09 (m, 3H), 7.39-7.52 (m, 4H), 9.69 (s, 1H), 12.14 (s, 1H). |

| Example | Name/Structure/Starting material | Analytical data |
|---|---|---|
| 92 | 3-[4-chloro-3-({(2S,3R)-2-[4-(3,3-difluorocyclobutyl)phenyl]-4,4,4-trifluoro-3-methylbutanoyl}amino)phenyl]propanoic acid<br><br>(from tert-butyl 3-[4-chloro-3-({(2S,3R)-2-[4-(3,3-difluorocyclobutyl)phenyl]-4,4,4-trifluoro-3-methylbutanoyl}amino)phenyl]propanoate) | LC-MS (Method 6):<br>$R_t$ = 1.20 min; m/z = 502/504 (M − H)⁻.<br>¹H-NMR (400 MHz, DMSO-$d_6$): δ [ppm] = 0.79 (d, 3H), 2.48 (t, 2H, partially obscured by DMSO signal), 2.60-2.73 (m, 2H), 2.76 (t, 2H), 2.92-3.06 (m, 2H), 3.29-3.46 (m, 2H, partially obscured by $H_2O$ signal), 4.10 (d, 1H), 7.03 (dd, 1H), 7.32 (t, 3H), 7.41 (d, 3H), 9.76 (s, 1H), 12.02-12.26 (br. s, 1H). |
| 93 | 3-(4-chloro-3-{[(2S,3R)-2-(4-chloro-3-methoxyphenyl)-4,4,4-trifluoro-3-methylbutanoyl]amino}-phenyl)propanoic acid<br><br>(from tert-butyl 3-(4-chloro-3-{[(2S,3R)-2-(4-chloro-3-methoxyphenyl)-4,4,4-trifluoro-3-methylbutanoyl]amino}phenyl)propanoate) | LC-MS (Method 6):<br>$R_t$ = 1.10 min; m/z = 476/478 (M − H)⁻.<br>¹H-NMR (400 MHz, DMSO-$d_6$): δ [ppm] = 0.83 (d, 3H), 2.48 (t, 2H, partially obscured by DMSO signal), 2.77 (t, 2H), 3.33-3.48 (m, 1H), 3.87 (s, 3H), 4.09 (d, 1H), 7.00-7.08 (m, 2H), 7.23 (d, 1H), 7.35 (d, 1H), 7.40 (d, 1H), 7.42 (d, 1H), 9.81 (s, 1H), 11.50-12.57 (br. s, 1H). |

| Example | Name/Structure/Starting material | Analytical data |
|---|---|---|
| 94 | 3-(3-{[(2S,3R)-2-(4-chloro-3-methoxyphenyl)-4,4,4-trifluoro-3-methylbutanoyl]amino}-4-fluorophenyl)-propanoic acid<br>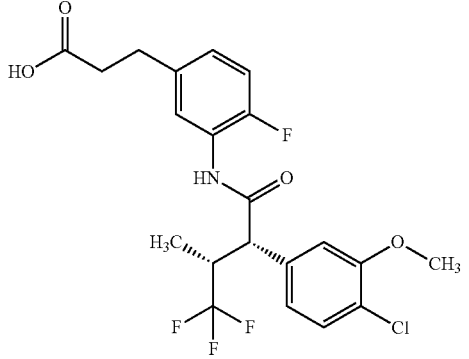<br>(from tert-butyl 3-(3-{[(2S,3R)-2-(4-chloro-3-methoxyphenyl)-4,4,4-trifluoro-3-methylbutanoyl]-amino}-4-fluorophenyl)propanoate) | LC-MS (Method 6):<br>$R_t$ = 1.06 min; m/z = 460/462 (M – H)⁻.<br>¹H-NMR (400 MHz, DMSO-$d_6$): δ [ppm] = 0.81 (d, 3H), 2.48 (t, 2H, partially obscured by DMSO signal), 2.75 (t, 2H), 3.32-3.47 (m, 1H, partially obscured by H₂O signal), 3.87 (s, 3H), 4.07 (d, 1H), 6.94-7.06 (m, 2H), 7.13 (t, 1H), 7.20 (s, 1H), 7.42 (d, 1H), 7.64 (d, 1H), 10.01 (s, 1H), 11.77-12.45 (br. s, 1H). |
| 95 | 3-[4-chloro-3-({(2S,3R)-2-[4-(2,2-difluorocyclopropyl)phenyl]-4,4,4-trifluoro-3-methylbutanoyl}amino)phenyl]propanoic acid<br>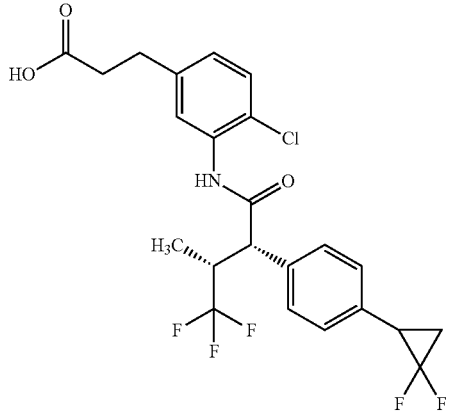<br>(from tert-butyl 3-[4-chloro-3-({(2S,3R)-2-[4-(2,2-difluorocyclopropyl)phenyl]-4,4,4-trifluoro-3-methylbutanoyl}amino)phenyl]propanoate) | LC-MS (Method 7):<br>$R_t$ = 2.52 min; m/z = 488/490 (M = H)⁻.<br>¹H-NMR (400 MHz, DMSO-$d_6$): δ [ppm] = 0.77 (d, 3H), 1.87-2.04 (m, 2H), 2.48 (t, 2H, partially obscured by DMSO signal), 2.76 (t, 2H), 2.92-3.05 (m, 1H), 3.27-3.41 (m, 1H), 4.09 (d, 1H), 7.04 (dd, 1H), 7.28 (d, 2H), 7.34 (d, 1H), 7.38-7.44 (m, 3H), 9.78 (s, 1H), 11.60-12.59 (br. s, 1H). |

| Example | Name/Structure/Starting material | Analytical data |
|---|---|---|
| 96 | [1-(4-chloro-3-{[(2S,3R)-2-(4-chlorophenyl)-4,4,4-trifluoro-3-methylbutanoyl]amino}phenyl)cyclopropyl]acetic acid<br><br>(from tert-butyl [1-(4-chloro-3-{[(2S,3R)-2-(4-chlorophenyl)-4,4,4-trifluoro-3-methylbutanoyl]amino}phenyl)cyclopropyl]acetate) | LC-MS (Method 6):<br>$R_t$ = 1.21 min; m/z = 474/476 (M + H)$^+$.<br>$^1$H-NMR (400 MHz, DMSO-$d_6$): δ [ppm] = 0.75-0.82 (m, 5H), 0.85-0.91 (m, 2H), 2.52 (s, 2H, partially obscured by DMSO signal), 3.29-3.43 (m, 1H, partially obscured by H$_2$O signal), 4.13 (d, 1H), 7.07 (dd, 1H), 7.32 (d, 1H), 7.42-7.50 (m, 5H), 9.82 (s, 1H), 11.89-12.10 (br. s, 1H). |
| 97 | 3-(3-{[(2S,3R)-2-(4-chlorophenyl)-4,4,4-trifluoro-3-methylbutanoyl]amino}-4-cyanophenyl)-2-methylpropanoic acid<br><br>(from tert-butyl 3-(3-{[(2S,3R)-2-(4-chlorophenyl)-4,4,4-trifluoro-3-methylbutanoyl]amino}-4-cyanophenyl)-2-methylpropanoate) | LC-MS (Method 6):<br>$R_t$ = 1.07 min; m/z = 453/455 (M + H)$^+$.<br>$^1$H-NMR (400 MHz, DMSO-$d_6$): δ [ppm] = 0.81 (d, 3H), 1.03 (d, 3H), 2.57-2.73 (m, 2H), 2.85-2.95 (m, 1H), 3.27-3.44 (m, 1H, partially obscured by H$_2$O signal), 4.02 (d, 1H), 7.18 (d, 1H), 7.30 (s, 1H), 7.40-7.52 (m, 4H), 7.70 (d, 1H), 10.50 (s, 1H), 12.23 (br. s, 1H). |

The examples below were prepared according to General Procedure 3 (cleavage of methyl or ethyl esters to the corresponding carboxylic acids in mixtures of hydrochloric acid or sulphuric acid with acetic acid):

| Example | Name/Structure/Starting material | Analytical data |
|---|---|---|
| 98 | (2S)-3-[4-chloro-3-({(2S,3R)-4,4,4-trifluoro-3-methyl-2-[4-(1,1,1-trifluoro-2-methylpropan-2-yl)phenyl]butanoyl}amino)phenyl]-2-methylpropanoic acid<br>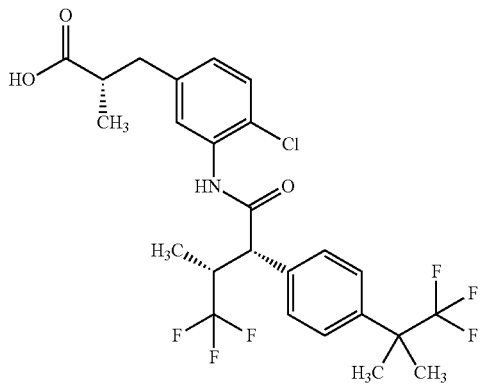<br>(from ethyl (2S)-3-[4-chloro-3-({(2S,3R)-4,4,4-trifluoro-3-methyl-2-[4-(1,1,1-trifluoro-2-methylpropan-2-yl)phenyl]butanoyl}amino)phenyl]-2-methylpropanoate) | LC-MS (Method 4): $R_t$ = 1.49 min; m/z = 536/538 (M − H)⁻.<br>¹H-NMR (400 MHz, DMSO-$d_6$): δ [ppm] = 0.69 (d, 3H), 1.02 (d, 3H), 1.54 (s, 6H), 2.51-2.62 (m, 2H, partially obscured by DMSO signal), 2.78-2.89 (m, 1H), 3.29-3.45 (m, 1H, partially obscured by H₂O signal), 4.14 (d, 1H), 7.00 (dd, 1H), 7.35 (d, 1H), 7.45 (d, 1H), 7.48 (d, 2H), 7.54 (d, 2H), 9.80 (s, 1H), 12.14 (s, 1H). |
| 99 | (2S)-3-[4-chloro-3-({4,4,4-trifluoro-3-methyl-2-[4-(2,2,2-trifluoroethyl)phenyl]butanoyl}amino)-phenyl]-2-methylpropanoic acid<br>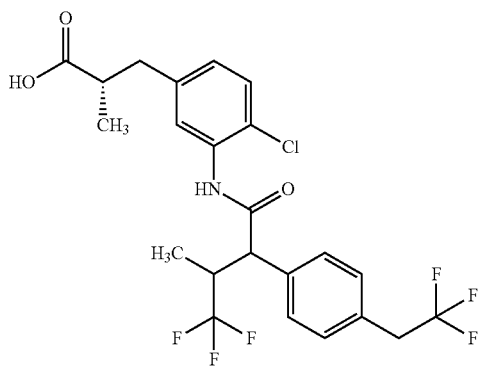<br>(from ethyl (2S)-3-[4-chloro-3-({4,4,4-trifluoro-3-methyl-2-[4-(2,2,2-trifluoroethyl)phenyl]butanoyl}-amino)phenyl]-2-methylpropanoate) | LC-MS (Method 4): $R_t$ = 1.39 min; m/z = 508/510 (M − H)⁻.<br>¹H-NMR (400 MHz, DMSO-$d_6$): δ [ppm] = 0.70 (d, 3H), 1.01 (d, 3H), 2.50-2.61 (m, 2H, partially obscured by DMSO signal), 2.78-2.90 (m, 1H), 3.29-3.45 (m, 1H, partially obscured by H₂O signal), 3.63 (q, 2H), 4.11 (d, 1H), 7.00 (dd, 1H), 7.35 (d, 2H), 7.39 (d, 2H), 7.46 (d, 2H), 9.80 (s, 1H), 12.15 (s, 1H). |

| Example | Name/Structure/Starting material | Analytical data |
|---|---|---|
| 100 | (2S)-3-[4-chloro-3-({(2S,3R)-2-[4-(3,3-difluoro-cyclobutyl)phenyl]-4,4,4-trifluoro-3-methyl-butanoyl}amino)phenyl]-2-methylpropanoic acid<br>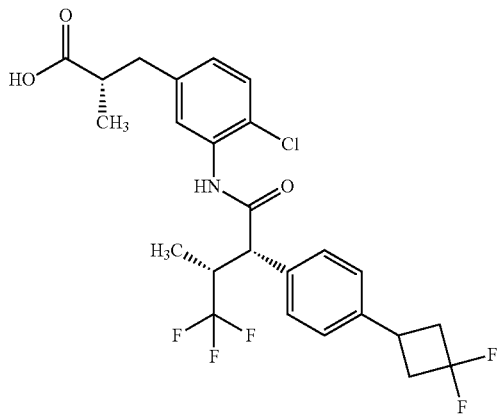<br>(from ethyl (2S)-3-[4-chloro-3-({(2S,3R)-2-[4-(3,3-difluorocyclobutyl)phenyl]-4,4,4-trifluoro-3-methyl-butanoyl}amino)phenyl]-2-methylpropanoate) | LC-MS (Method 6):<br>$R_t$ = 1.24 min; m/z = 516/518 (M − H)⁻.<br>¹H-NMR (400 MHz, DMSO-$d_6$): δ [ppm] = 0.79 (d, 3H), 1.01 (d, 3H), 2.46-2.60 (m, 2H, partially obscured by DMSO signal), 2.60-2.76 (m, 2H), 2.77-2.87 (m, 1H), 2.91-3.06 (m, 2H), 3.26-3.46 (m, 2H, partially obscured by $H_2O$ signal), 4.10 (d, 1H), 6.99 (dd, 1H), 7.33 (t, 3H), 7.42 (d, 3H), 9.76 (s, 1H), 11.86-12.37 (br. s, 1H). |
| 101 | (2S)-3-(4-chloro-3-{[(2S,3R)-2-(4-chloro-3-methoxy-phenyl)-4,4,4-trifluoro-3-methylbutanoyl]amino}-phenyl)-2-methylpropanoic acid<br>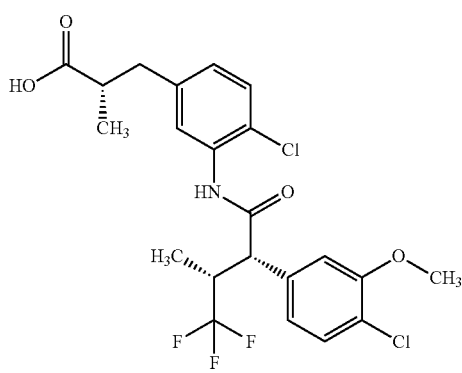<br>(from ethyl (2S)-3-(4-chloro-3-{[(2S,3R)-2-(4-chloro-3-methoxyphenyl)-4,4,4-trifluoro-3-methylbutanoyl]-amino}phenyl)-2-methylpropanoate) | LC-MS (Method 6):<br>$R_t$ = 1.15 min; m/z = 492.494 (M + H)⁺.<br>¹H-NMR (400 MHz, DMSO-$d_6$): δ [ppm] = 0.83 (d, 3H), 1.02 (d, 3H), 2.46-2.61 (m, 2H, partially obscured by DMSO signal), 2.77-2.88 (m, 1H), 3.36-3.47 (m, 1H), 3.87 (s, 3H), 4.09 (d, 1H), 6.98-7.06 (m, 2H), 7.23 (d, 1H), 7.36 (d, 1H), 7.38 (d, 1H), 7.43 (d, 1H), 9.81 (s, 1H), 12.04-12.26 (br. s, 1H). |

| Example | Name/Structure/Starting material | Analytical data |
|---|---|---|
| 102 | [1-(4-chloro-3-{[(2S,3R)-2-(4-chlorophenyl)-4,4,4-trifluoro-3-methylbutanoyl]amino}phenyl)-3,3-difluorocyclobutyl]acetic acid<br>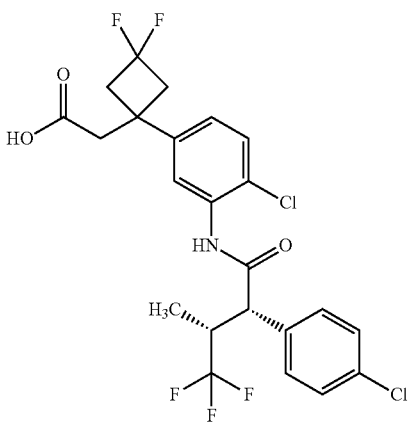<br>(from ethyl [1-(4-chloro-3-{[(2S,3R)-2-(4-chlorophenyl)-4,4,4-trifluoro-3-methylbutanoyl]amino}phenyl)-3,3-difluorocyclobutyl]acetate) | LC-MS (Method 6):<br>$R_t$ = 1.22 min; m/z = 524/526 $(M + H)^+$.<br>$^1$H-NMR (400 MHz, DMSO-$d_6$): δ [ppm] = 0.80 (d, 3H), 2.76 (s, 2H), 2.81-2.94 (m, 2H), 2.95-3.09 (m, 2H), 3.29-3.44 (m, 1H, partially obscured by H$_2$O signal), 4.15 (d, 1H), 7.12 (dd, 1H), 7.41 (d, 1H), 7.42-7.49 (m, 4H), 7.50 (d, 1H), 9.88 (s, 1H), 12.09-12.24 (br. s, 1H). |

Example 103 and Example 104

(2S)-3-[4-Chloro-3-({4,4,4-trifluoro-3-methyl-2-[4-(2,2,2-trifluoroethyl)phenyl]butanoyl}amino)-phenyl]-2-methylpropanoic acid (diastereomers 1 and 2)

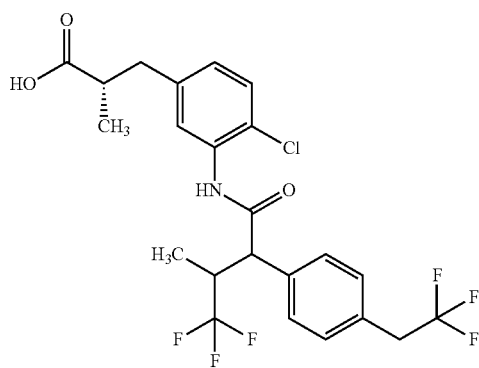 [SMILES: CC(C(C(=O)Nc1cc(C[C@H](C)C(=O)O)ccc1Cl)c1ccc(CC(F)(F)F)cc1)C(F)(F)F]

74 mg (0.15 mmol) of the isomer mixture of (2S)-3-[4-chloro-3-({[4,4,4-trifluoro-3-methyl-2-[4-(2,2,2-trifluoroethyl)phenyl]butanoyl}amino]phenyl]-2-methylpropanoic acid (Example 99) were separated further by preparative HPLC on a chiral phase [column: Daicel Chiralpak AY-H, 5 μm, 250 mm×20 mm; mobile phase: isohexane/ethanol 1:1 (v/v); flow rate: 15 ml/min; UV detection: 220 nm; temperature: 45° C.]:

Example 103

Diastereomer 1

Yield: 39 mg
$R_t$=3.72 min; chemical purity >98%; >99% de
[column: Daicel Chiralpak AY-H, 5 μm, 250 mm×4 mm; mobile phase: isohexane/(isopropanol+0.2% TFA+1% water) 70:30 (v/v); flow rate: 1 ml/min; temperature: 45° C.; UV detection: 220 nm].
LC-MS (Method 6): $R_t$=1.16 min; m/z=508/510 (M−H)$^-$.

Example 104

Diastereomer 2

Yield: 39 mg
$R_t$=6.09 min; chemical purity >98%; >99% de
[column: Daicel Chiralpak AY-H, 5 μm, 250 mm×4 mm; mobile phase: isohexane/(isopropanol+0.2% TFA+1% water) 70:30 (v/v); flow rate: 1 ml/min; temperature: 45° C.; UV detection: 220 nm].
LC-MS (Method 6): $R_t$=1.16 min; m/z=508/510 (M−H)$^-$.

Examples 105-108

(2S)-3-(4-Chloro-3-{[(4-chlorophenyl)(3,3-difluorocyclopentyl)acetyl]amino}phenyl)-2-methylpropanoic acid (isomers 1-4)

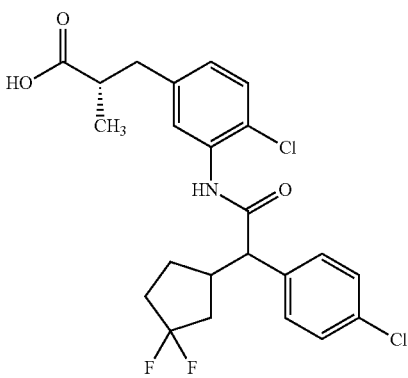 [SMILES: C[C@@H](Cc1ccc(Cl)c(NC(=O)C(c2ccc(Cl)cc2)C2CCC(F)(F)C2)c1)C(=O)O]

205 mg (0.44 mmol) of the diastereomer mixture of (2S)-3-(4-chloro-3-{[(4-chlorophenyl)(3,3-difluorocyclopentyl)acetyl]amino}phenyl)-2-methylpropanoic acid (Example 20) were separated further by preparative HPLC on a chiral phase [column: Daicel Chiralcel OJ-H, 5 µm, 250 mm×20 mm; mobile phase: isohexane/ethanol 70:30 (v/v); flow rate: 25 ml/min; UV detection: 230 nm; temperature: 25° C.]. This gave two different fractions each consisting of a mixture of two isomers. These two fractions were separated into the individual isomers by another preparative HPLC on a chiral phase [Fraction 1: column: Daicel Chiralpak AD-H, 5 µm, 250 mm×20 mm; mobile phase: isohexane/isopropanol 80:20 (v/v); flow rate: 20 ml/min; UV detection: 230 nm; temperature: 25° C. Fraction 2: column: Daicel Chiralpak AD-H, 5 µm, 250 mm×20 mm; mobile phase: isohexane/ethanol 90:10 (v/v); flow rate: 20 ml/min; UV detection: 230 nm; temperature: 25° C.]:

Example 105

Isomer 1

Yield: 30 mg
$R_t$=15.70 min; chemical purity >89.8%
[Column: Daicel Chiralpak AD-H, 5 µm, 250 mm×4 mm; mobile phase: isohexane/isopropanol 70:30 (v/v); flow rate: 1 ml/min; UV detection: 230 nm; temperature: 25° C.].
LC-MS (Method 6): $R_t$=1.22 min; m/z=470/472 (M+H)$^+$.
$^1$H-NMR (400 MHz, DMSO-d$_6$): δ [ppm]=1.02 (d, 3H), 1.21-1.35 (m, 1H), 1.45-1.58 (m, 1H), 1.84-2.20 (m, 3H), 2.28-2.43 (m, 1H), 2.53-2.62 (m, 2H, partially obscured by DMSO signal), 2.76-2.90 (m, 2H), 3.75 (d, 1H), 7.03 (dd, 1H), 7.32-7.49 (m, 6H), 9.74 (s, 1H), 12.04-12.35 (br. s, 1H).

Example 106

Isomer 2

Yield: 35 mg
$R_t$=20.07 min; chemical purity >98.9%
[Column: Daicel Chiralpak AD-H, 5 µm, 250 mm×4 mm; mobile phase: isohexane/isopropanol 70:30 (v/v); flow rate: 1 ml/min; UV detection: 230 nm; temperature: 25° C.].
LC-MS (Method 5): $R_t$=2.58 min; m/z=470/472 (M+H)$^+$.
$^1$H-NMR (400 MHz, DMSO-d$_6$): δ [ppm]=1.02 (d, 3H), 1.52-1.69 (m, 2H), 1.81-1.96 (m, 1H), 1.98-2.29 (m, 3H), 2.52-2.62 (m, 2H, partially obscured by DMSO signal), 2.78-2.92 (m, 2H), 3.78 (d, 1H), 7.03 (dd, 1H), 7.33-7.48 (m, 6H), 9.78 (s, 1H), 12.04-12.26 (br. s, 1H).

Example 107

Isomer 3

Yield: 37 mg
$R_t$=14.17 min; chemical purity >95.7%
[Column: Daicel Chiralpak AD-H, 5 µm, 250 mm×4 mm; mobile phase: isohexane/ethanol 90:10 (v/v); flow rate: 1 ml/min; UV detection: 230 nm; temperature: 25° C.].
LC-MS (Method 5): $R_t$=2.57 min; m/z=470/472 (M+H)$^+$.
$^1$H-NMR: see Example 106 (isomer 2).

Example 108

Isomer 4

Yield: 29 mg
$R_t$=17.77 min; chemical purity >99.5%
[Column: Daicel Chiralpak AD-H, 5 µm, 250 mm×4 mm; mobile phase: isohexane/ethanol 90:10 (v/v); flow rate: 1 ml/min; UV detection: 230 nm; temperature: 25° C.].
LC-MS (Method 5): $R_t$=2.58 min; m/z=470/472 (M+H)$^+$.
$^1$H-NMR: see Example 105 (isomer 1).

Examples 109-112

(2R)-3-(4-Chloro-3-{[(4-chlorophenyl)(3,3-difluorocyclopentyl)acetyl]amino}phenyl)-2-methylpropanoic acid (isomers 1-4)

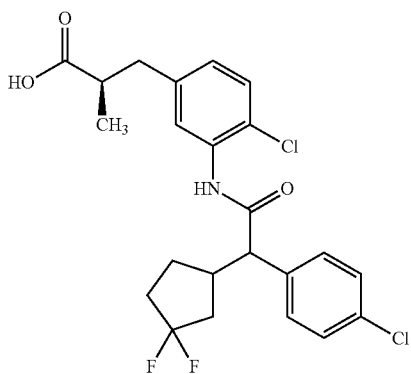

160 mg (0.32 mmol) of the diastereomer mixture of (2R)-3-(4-chloro-3-{[(4-chlorophenyl)(3,3-difluorocyclopentyl)acetyl]amino}phenyl)-2-methylpropanoic acid (Example 21) were separated into the four isomers by preparative HPLC [column: Daicel Chiralcel OJ-H, 5 µm, 250 mm×20 mm; mobile phase: isohexane/ethanol/methanol 90:5:5 (v/v); flow rate: 20 ml/min; UV detection: 230 nm; temperature: 25° C.]:

Example 109

Isomer 1

Yield: 16.7 mg
$R_t$=10.49 min; chemical purity >92.8%
[Column: Daicel Chiralpak OJ-H, 5 µm, 250 mm×4 mm; mobile phase: isohexane/ethanol/methanol 90:5:5 (v/v); flow rate: 1 ml/min; UV detection: 230 nm; temperature: 25° C.].
LC-MS (Method 4): $R_t$=1.39 min; m/z=470/472 (M+H)$^+$.

Example 110

Isomer 2

Yield: 24.4 mg
$R_t$=12.26 min; chemical purity >94.7%
[Column: Daicel Chiralpak OJ-H, 5 µm, 250 mm×4 mm; mobile phase: isohexane/ethanol/methanol 90:5:5 (v/v); flow rate: 1 ml/min; UV detection: 230 nm; temperature: 25° C.].
LC-MS (Method 4): $R_t$=1.39 min; m/z=470/472 (M+H)$^+$.

Example 111

Isomer 3

Yield: 22 mg
$R_t$=18.89 min; chemical purity >97.8%

[Column: Daicel Chiralpak OJ-H, 5 µm, 250 mm×4 mm; mobile phase: isohexane/ethanol/methanol 90:5:5 (v/v); flow rate: 1 ml/min; UV detection: 230 nm; temperature: 25° C.].
LC-MS (Method 4): $R_t$=1.39 min; m/z=470/472 (M+H)$^+$.

Example 112

Isomer 4

Yield: 25 mg
$R_t$=28.37 min; chemical purity >97.8%
[Column: Daicel Chiralpak OJ-H, 5 µm, 250 mm×4 mm; mobile phase: isohexane/ethanol/methanol 90:5:5 (v/v); flow rate: 1 ml/min; UV detection: 230 nm; temperature: 25° C.].
LC-MS (Method 4): $R_t$=1.39 min; m/z=470/472 (M+H)$^+$.
The example below was prepared according to General Procedure 3:

| Example | Name/Structure/Starting Material | Analytical Data |
|---|---|---|
| 113 | 3-(4-Chloro-3-{[(2S,3R)-2-(4-chlorophenyl)-4,4,4-trifluoro-3-methylbutanoyl]amino}phenyl)-3-methylbutanoic acid<br>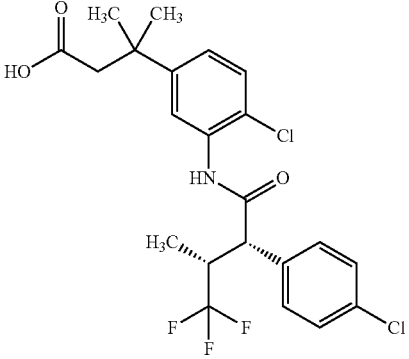<br>(from ethyl 3-(4-chloro-3-{[(2S,3R)-2-(4-chlorophenyl)-4,4,4-trifluoro-3-methyl-butanoyl]amino}phenyl)-3-methylbutanoate) | LC-MS (Method 6): $R_t$ = 1.23 min; m/z = 476/478 (M + H)$^+$.<br>$^1$H-NMR (400 MHz, DMSO-$d_6$): δ [ppm] = 0.80 (d, 3H), 1.31 (s, 6H), 2.53 (s, 2H, partially obscured by DMSO signal), 3.30-3.44 (m, 1H, partially obscured by H$_2$O signal), 4.14 (d, 1H), 7.20 (dd, 1H), 7.35 (d, 1H), 7.42-7.50 (m, 4H), 7.56 (d, 1H), 9.83 (s, 1H), 11.85-11.97 (br. s, 1H). |

B. Assessment of the Pharmacological Activity

The pharmacological effect of the compounds according to the invention can be shown in the following assays:
B-1. Stimulation of Recombinant Soluble Guanylate Cyclase (sGC) In Vitro:

Investigations on the stimulation of recombinant soluble guanylate cyclase (sGC) by the compounds according to the invention with and without sodium nitroprusside, and with and without the haem-dependent sGC inhibitor 1H-1,2,4-oxadiazolo-(4,3a)-quinoxalin-1-one (ODQ) are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. The haem-free guanylate cyclase is obtained by adding Tween 20 to the sample buffer (0.5% in the final concentration).

The activation of sGC by a test substance is reported as x-fold stimulation of the basal activity. The result for Example 15 is shown in Table 1A and that for Example 17 in Table 1B:

TABLE 1A

Stimulation (x-fold) of recombinant soluble guanylate cyclase (sGC) in vitro by Example 15

| Concentration | Haem-containing sGC | | | Haem-free sGC |
|---|---|---|---|---|
| Example 15 [µM] | Basal (n = 8) | +0.01 µM DEA/NO | +10 µM ODQ | Basal (n = 8) |
| 0 | 1.0 ± 0.0 | 6.5 ± 0.8 | 4.4 ± 0.8 | 1.0 ± 0.0 |
| 0.01 | 1.1 ± 0.1 | 5.9 ± 0.7 | 4.6 ± 0.8 | 1.7 ± 0.3 |
| 0.1 | 1.0 ± 0.1 | 7.4 ± 0.8 | 4.5 ± 0.6 | 1.8 ± 0.2 |
| 1.0 | 0.9 ± 0.1 | 8.5 ± 0.7 | 4.8 ± 0.8 | 3.0 ± 0.5 |
| 10 | 3.1 ± 0.3 | 11.5 ± 0.9 | 16.3 ± 1.3 | 17.9 ± 3.1 |
| 100 | 31.6 ± 2.6 | 45.9 ± 3.1 | 97.3 ± 7.7 | 40.3 ± 6.6 |

TABLE 1B

Stimulation (x-fold) of recombinant soluble guanylate cyclase (sGC) in vitro by Example 17

| Concentration | Haem-containing sGC | | | Haem-free sGC |
|---|---|---|---|---|
| Example 17 [µM] | Basal (n = 6) | +0.01 µM DEA/NO | +10 µM ODQ | Basal (n = 6) |
| 0 | 1.0 ± 0.0 | 7.9 ± 0.7 | 2.8 ± 0.6 | 1.0 ± 0.0 |
| 0.01 | 0.7 ± 0.2 | 9.6 ± 0.8 | 4.9 ± 1.2 | 1.7 ± 0.2 |
| 0.1 | 0.6 ± 0.1 | 8.8 ± 1.2 | 5.3 ± 1.3 | 2.0 ± 0.3 |
| 1.0 | 0.6 ± 0.1 | 9.8 ± 1.2 | 4.5 ± 1.1 | 4.1 ± 0.3 |
| 10 | 1.8 ± 0.3 | 10.7 ± 1.0 | 8.3 ± 1.4 | 22.9 ± 1.8 |
| 100 | 4.9 ± 0.7 | 11.4 ± 1.2 | 15.0 ± 2.0 | 33.5 ± 3.3 |

[DEA/NO = 2-(N,N-diethylamino)diazenolate 2-oxide; ODQ = 1H,2,4-oxadiazolo[4,3-a]quin-oxalin-1-one].

It is evident from Tables 1A and 1B that stimulation both of the haem-containing and of the haem-free enzyme is achieved. Furthermore, combination of Example 15 or Example 17 and 2-(N,N-diethylamino)diazenolate 2-oxide (DEA/NO), an NO donor, shows no synergistic effect, i.e. the effect of DEA/NO is not potentiated as would be expected with an sGC activator acting via a haem-dependent mechanism. In addition, the effect of the sGC activator according to the invention is not blocked by the haem-dependent inhibitor of soluble guanylate cyclase 1H-1,2,4-oxadiazolo-[4,3-a]quinoxalin-1-one (ODQ), but is in fact increased by it. The results in Tables 1A and 1B thus confirm the mechanism of action of the compounds according to the invention as activators of soluble guanylate cyclase.

B-2. Action at Recombinant Guanylate Cyclase Reporter Cell Line

The cellular action of the compounds according to the invention is determined at a recombinant guanylate cyclase reporter cell line, as described in F. Wunder et al., *Anal. Biochem.* 339, 104-112 (2005).

Representative results for the compounds according to the invention are listed in Table 2:

TABLE 2 sGC-activating activity in the CHO reporter cell in vitro

| Example No. | MEC [nM] |
| --- | --- |
| 2 | 0.3 |
| 5 | 3.0 |
| 7 | 0.2 |
| 10 | 5.2 |
| 15 | 10 |
| 17 | 4.8 |
| 18 | 10 |
| 28 | 1.0 |
| 30 | 0.3 |
| 37 | 10 |
| 50 | 30 |
| 53 | 300 |
| 71 | 10 |
| 81 | 0.3 |
| 82 | 0.23 |
| 84 | 1 |
| 87 | 1 |
| 89 | 3 |
| 90 | 1 |
| 96 | 1 |
| 99 | 10 |
| 100 | 3 |
| 102 | 1 |
| 105 | 30 |

(MEC = minimal effective concentration).

B-3. Stimulation of sGC Enzyme Activity

Soluble guanylate cyclase (sGC) converts on stimulation GTP into cGMP and pyrophosphate (PPi). PPi is detected with the aid of the assay described below. The signal produced in the assay increases as the reaction progresses and serves as a measure of the sGC enzyme activity under the given stimulation.

To carry out the assay, 29 μl of enzyme solution [0-10 nM soluble guanylate cyclase (prepared according to Hönicka et al., *J. Mol. Med.* 77, 14-23 (1999)) in 50 mM TEA, 2 mM $MgCl_2$, 0.1% BSA (fraction V), 0.005% Brij®, pH 7.5] are initially introduced into a microplate, and 1 μl of the substance to be tested (as a serially diluted solution in DMSO) is added. The mixture is incubated at room temperature for 10 min. Then 20 μl of detection mix [1.2 nM Firefly Luciferase (*Photinus pyralis* luciferase, Promega), 29 μM dehydroluciferin (prepared according to Bitler & McElroy, *Arch. Biochem. Biophys.* 72, 358 (1957)), 122 μM luciferin (Promega), 153 μM ATP (Sigma) and 0.4 mM DTT (Sigma) in 50 mM TEA, 2 mM $MgCl_2$, 0.1% BSA (fraction V), 0.005% Brij®, pH 7.5] are added. The enzyme reaction is started by adding 20 μl of substrate solution [1.25 mM guanosine 5'-triphosphate (Sigma) in 50 mM TEA, 2 mM $MgCl_2$, 0.1% BSA (fraction V), 0.005% Brij®, pH 7.5] and measured continuously in a luminometer. The extent of the stimulation by the substance to be tested can be determined relative to the signal of the unstimulated reaction.

The activation of haem-free guanylate cyclase is examined by addition of 25 μM of 1H-1,2,4-oxadiazolo[4,3-a]quinoxalin-1-one (ODQ) to the enzyme solution and subsequent incubation for 30 minutes, and compared to the stimulation of the native enzyme.

Representative results for the compounds according to the invention are listed in Table 3:

TABLE 3

Activating action at the sGC enzyme in vitro

| Example No. | MEC [nM] | $EC_{50}$ [nM] |
| --- | --- | --- |
| 15 | 10 | 290 |
| 17 | 7 | 130 |

(MEC = minimal effective concentration; $EC_{50}$ = concentration at 50% of maximum efficacy).

B-4. Radiotelemetric Measurement of Blood Pressure and Heart Rate on Conscious SH Rats A commercially available telemetry system from Data Sciences International DSI, USA, is employed for the measurements on conscious SH rats described below.

The system consists of 3 main components: (1) implantable transmitters, (2) receivers, which are linked via a multiplexer to a (3) data acquisition computer. The telemetry system makes it possible to continuously record the blood pressure and heart rate of conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 am and at 7.00 pm.

The telemetry transmitters (TAM PA-C40, DSI) as employed are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi, 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and layered closure of the wound is performed. An antibiotic (Tardomyocel COMP, Bayer, 1 ml/kg s.c.) is administered postoperatively for prophylaxis of infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated externally by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file created for this purpose and bearing the experiment number.

In the standard procedure, the following are measured for 10-second periods in each case: (1) systolic blood pressure (SBP), (2) diastolic blood pressure (DBP), (3) mean arterial pressure (MAP) and (4) heart rate (HR).

The acquisition of measured values is repeated under computer control at 5-minute intervals. The source data obtained as absolute value are corrected in the diagram with the currently measured barometric pressure and stored as individual data. Further technical details are given in the documentation from the manufacturing company (DSI).

The test substances are administered at 9.00 am on the day of the experiment. Following the administration, the parameters described above are measured over 24 hours. After the end of the experiment, the acquired individual data are sorted using the analysis software (Dataquest™ A.R.T. Analysis). The void value is assumed to be the time 2 hours before administration of the substance, so that the selected data set includes the period from 7.00 am on the day of the experiment to 9.00 am on the following day.

The data are smoothed over a presettable time by determination of the average (15-minute average, 30-minute average) and transferred as a text file to a storage medium. The measured values presorted and compressed in this way are transferred into Excel templates and tabulated.

C. Exemplary Embodiments of Pharmaceutical Compositions

The compounds according to the invention can be converted into pharmaceutical preparations in the following ways:

Tablet:
Composition:
100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.
Production:

The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.
Production:
The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:
500 mg of the compound according to the invention, 2.5 g of polysorbate and 97 g of polyethylene glycol 400.20 g of oral solution correspond to a single dose of 100 mg of the compound according to the invention.
Production:
The compound according to the invention is suspended in the mixture of polyethylene glycol and polysorbate with stirring. The stirring process is continued until the compound according to the invention has completely dissolved.

i.v. Solution:
The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of the formula (I)

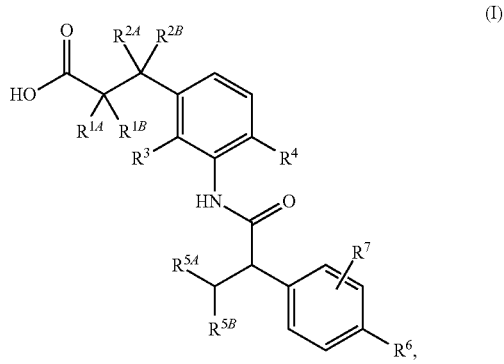

in which
R$^{1A}$ represents hydrogen, fluorine, methyl, trifluoromethyl, ethyl, 1,1-difluoroethyl, 2,2,2-trifluoroethyl, n-propyl,
R$^{1B}$ represents hydrogen or methyl,
R$^{2A}$ represents hydrogen, methyl, trifluoromethyl, ethyl, 1,1-difluoroethyl, 2,2,2-trifluoroethyl or n-propyl, and
R$^{2B}$ represents hydrogen or methyl,
R$^3$ represents hydrogen, fluorine, methyl or trifluoromethyl,
R$^4$ represents hydrogen, fluorine, chlorine, cyano, methyl, trifluoromethyl or ethyl,
R$^{5A}$ represents methyl, trifluoromethyl or ethyl, and
R$^{5B}$ represents trifluoromethyl, or R$^{5A}$ and R$^{5B}$ are attached to one another and together with the carbon atom to which they are attached form a difluoro-substituted cycloalkyl ring of the formula

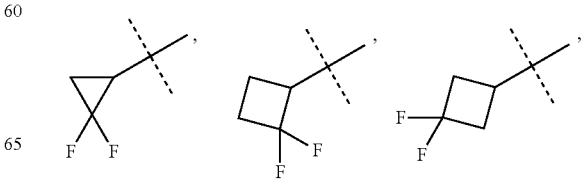

-continued

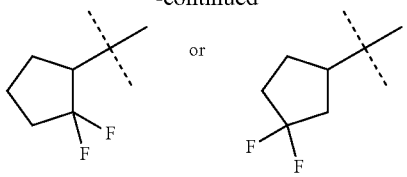

$R^6$ represents hydrogen, fluorine, chlorine, bromine, cyano, ($C_1$-$C_4$)-alkyl, ($C_2$-$C_4$)-alkenyl, cyclopropyl or cyclobutyl, where
($C_1$-$C_4$)-alkyl and ($C_2$-$C_4$)-alkenyl may be substituted up to three times by fluorine
and
cyclopropyl and cyclobutyl may be substituted up to two times by fluorine,
and
$R^7$ represents hydrogen, fluorine, chlorine, cyano, methyl, trifluoromethyl, ethyl, methoxy or trifluoromethoxy,
or a salt thereof.

2. The compound according to claim 1 in which
$R^{1A}$ represents hydrogen, methyl, trifluoromethyl, ethyl, n-propyl,
$R^{1B}$ represents hydrogen or methyl,
$R^{2A}$ represents hydrogen, methyl, trifluoromethyl, ethyl or n-propyl,
$R^{2B}$ represents hydrogen or methyl,
$R^3$ represents hydrogen, fluorine or methyl,
$R^4$ represents hydrogen, fluorine, chlorine, cyano, methyl or trifluoromethyl,
$R^{5A}$ represents methyl or ethyl,
$R^{5B}$ represents trifluoromethyl,
or
$R^{5A}$ and $R^{5B}$ are attached to one another and together with the carbon atom to which they are attached form a difluoro-substituted cycloalkyl ring of the formula

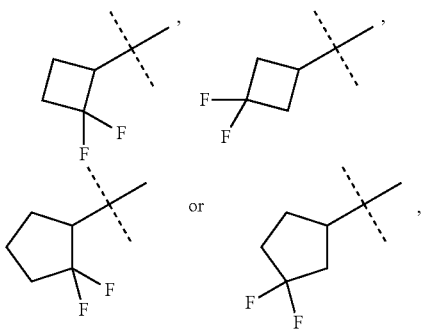

$R^6$ represents fluorine, chlorine, ($C_1$-$C_4$)-alkyl, ($C_2$-$C_3$)-alkenyl, cyclopropyl or cyclobutyl, where
($C_1$-$C_4$)-alkyl and ($C_2$-$C_3$)-alkenyl may be substituted up to three times by fluorine
and
cyclopropyl and cyclobutyl may be substituted up to two times by fluorine,
and
$R^7$ represents hydrogen, fluorine, chlorine, methyl or methoxy,
or a salt thereof.

3. The compound according to claim 1 in which
$R^{1A}$ represents hydrogen, methyl or ethyl,
$R^{1B}$ represents hydrogen,
$R^{2A}$ represents hydrogen, methyl, trifluoromethyl, ethyl or n-propyl,
$R^{2B}$ represents hydrogen or methyl,
$R^3$ represents hydrogen,
$R^4$ represents fluorine, chlorine or methyl,
$R^{5A}$ represents methyl,
$R^{5B}$ represents trifluoromethyl,
or
$R^{5A}$ and $R^{5B}$ are attached to one another and together with the carbon atom to which they are attached form a difluoro-substituted cyclopentyl ring of the formula

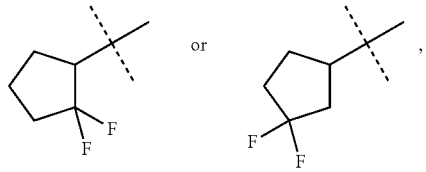

$R^6$ represents fluorine, chlorine, methyl, trifluoromethyl, ethyl, 1,1-difluoroethyl, 2,2,2-trifluoroethyl, isopropyl, tert-butyl, 1,1,1-trifluoro-2-methylpropan-2-yl, vinyl, 1-fluorovinyl, cyclopropyl, 2,2-difluorocyclopropyl, cyclobutyl or 3,3-difluorocyclobutyl,
and
$R^7$ represents hydrogen, fluorine, chlorine or methyl,
or a salt thereof.

4. The compound according to claim 1, wherein the compound is
(+)-3-(3-{[(2S,3R)-2-(4-tert-butylphenyl)-4,4,4-trifluoro-3-methylbutanoyl]amino}-4-chlorophenyl)propanoic acid;
3-[4-Chloro-3-({4,4,4-trifluoro-3-methyl-2-[4-(2,2,2-trifluoroethyl)phenyl]butanoyl}amino)phenyl]propanoic acid;
3-(4-chloro-3-{[(2S,3R)-2-(4-ethylphenyl)-4,4,4-trifluoro-3-methylbutanoyl]amino}phenyl)butanoic acid;
(3S)-3-(4-chloro-3-{[(4-chlorophenyl)(2,2-difluorocyclopentyl)acetyl]amino}phenyl)butanoic acid;
(+)-3-(4-Chloro-3-{[(2S,3R)-2-(4-chlorophenyl)-4,4,4-trifluoro-3-methylbutanoyl]amino}phenyl)propanoic acid;
(+)-(2S)-3-(4-Chloro-3-{[(2S,3R)-2-(4-chlorophenyl)-4,4,4-trifluoro-3-methylbutanoyl]amino}phenyl)-2-methylpropanoic acid;
(+)-(2S)-2-(4-Chloro-3-{[(2S,3R)-2-(4-chlorophenyl)-4,4,4-trifluoro-3-methylbutanoyl]amino}benzyl)butanoic acid;
3-(3-{[(3R)-2-(4-Chlorophenyl)-4,4,4-trifluoro-3-methylbutanoyl]amino}-4-fluorophenyl)-2-methylpropanoic acid;
threo-3-(3-{[(2S,3R)-2-(4-chlorophenyl)-4,4,4-trifluoro-3-methylbutanoyl]amino}-4-fluorophenyl)-2-methylbutanoic acid;
(+)-2-(4-Chloro-3-{[(2S,3R)-2-(4-chlorophenyl)-4,4,4-trifluoro-3-methylbutanoyl]amino}benzyl)-2-methylbutanoic acid;
3-(4-Chloro-3-{[(2S,3R)-2-(4-chlorophenyl)-4,4,4-trifluoro-3-methylbutanoyl]amino}phenyl)hexanoic acid;
(+)-3-(4-Chloro-3-{[(2S,3R)-2-(4-chlorophenyl)-4,4,4-trifluoro-3-methylbutanoyl]amino}phenyl)hexanoic acid;
(+)-3-(4-Chloro-3-{[(2S,3R)-2-(4-chlorophenyl)-4,4,4-trifluoro-3-methylbutanoyl]amino}phenyl)-4,4,4-trifluorobutanoic acid;

(+)-3-(4-Chloro-3-{[(2S,3R)-2-(4-chlorophenyl)-4,4,4-trifluoro-3-methylbutanoyl]amino}phenyl)pentanoic acid;

3-(4-chloro-3-{[(2S,3R)-2-(4-chlorophenyl)-4,4,4-trifluoro-3-methylbutanoyl]amino}phenyl)-2,2-dimethylpropanoic acid;

(2S)-3-[4-chloro-3-({4,4,4-trifluoro-3-methyl-2-[4-(2,2,2-trifluoroethyl)phenyl]butanoyl}amino)phenyl]-2-methylpropanoic acid;

(2S)-3-[4-chloro-3-({(2S,3R)-2-[4-(3,3-difluorocyclobutyl)phenyl]-4,4,4-trifluoro-3-methylbutanoyl}amino)phenyl]-2-methylpropanoic acid;

[1-(4-chloro-3-{[(2S,3R)-2-(4-chlorophenyl)-4,4,4-trifluoro-3-methylbutanoyl]amino}phenyl)-3,3-difluorocyclobutyl]acetic acid; or (2S)-3-(4-Chloro-3-{[(4-chlorophenyl)(3,3-difluorocyclopentyl)acetyl]amino}phenyl)-2-methylpropanoic acid.

5. A process for preparing a compound according to claim 1, wherein (a) a carboxylic acid of the formula (II)

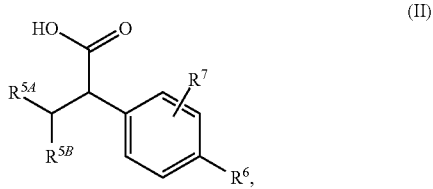

(II)

in which $R^{5A}$, $R^{5B}$, $R^6$ and $R^7$ have the meanings given in claim 1 is coupled with an amine of the formula (III)

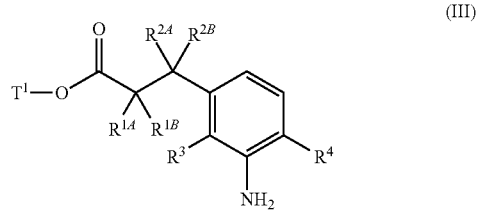

(III)

in which $R^{1A}$, $R^{1B}$, $R^{2A}$, $R^{2B}$, $R^3$ and $R^4$ have the meanings given in claim 1 and $T^1$ represents $(C_1\text{-}C_4)$-alkyl or benzyl, to give a carboxamide of the formula (IV)

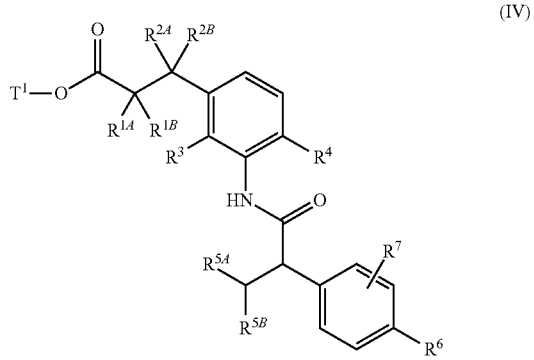

(IV)

in which $R^{1A}$, $R^{1B}$, $R^{2A}$, $R^{2B}$, $R^3$, $R^4$, $R^{5A}$, $R^{5B}$, $R^6$, $R^7$ and $T^1$ have the meanings given above, (b) the ester radical $T^1$ is removed to give the compound of formula (I), and (c) the compound of formula (I) is optionally separated into its enantiomers and/or diastereomers, and/or optionally reacted with one or more (i) solvents and/or (ii) bases to give a solvate, salt and/or solvate of a salt thereof.

6. The process according to claim 5, wherein step (a) is performed via a carbonyl chloride intermediate in the presence of a base.

7. The process according to claim 5, wherein in step (b) the ester radical $T^1$ is removed by basic or acidic solvolysis and, if $T^1$ represents benzyl, also by hydrogenolysis.

8. A pharmaceutical composition comprising a compound according to claim 1 and an inert, non-toxic, pharmaceutically suitable excipient.

9. A pharmaceutical composition comprising a compound according to claim 2 and an inert, non-toxic, pharmaceutically suitable excipient.

10. A pharmaceutical composition comprising a compound according to claim 3 and an inert, non-toxic, pharmaceutically suitable excipient.

11. A pharmaceutical composition comprising a compound according to claim 4 and an inert, non-toxic, pharmaceutically suitable excipient.

12. A pharmaceutical composition comprising a compound according to claim 1 in combination with one or more further active compounds selected from the group consisting of organic nitrates, NO donors, cGMP-PDE inhibitors, stimulators of guanylate cyclase, agents having antithrombotic activity, agents lowering blood pressure, and agents altering lipid metabolism.

13. A pharmaceutical composition comprising a compound according to claim 2 in combination with one or more further active compounds selected from the group consisting of organic nitrates, NO donors, cGMP-PDE inhibitors, stimulators of guanylate cyclase, agents having antithrombotic activity, agents lowering blood pressure, and agents altering lipid metabolism.

14. A pharmaceutical composition comprising a compound according to claim 3 in combination with one or more further active compounds selected from the group consisting of organic nitrates, NO donors, cGMP-PDE inhibitors, stimulators of guanylate cyclase, agents having antithrombotic activity, agents lowering blood pressure, and agents altering lipid metabolism.

15. A pharmaceutical composition comprising a compound according to claim 4 in combination with one or more further active compounds selected from the group consisting of organic nitrates, NO donors, cGMP-PDE inhibitors, stimulators of guanylate cyclase, agents having antithrombotic activity, agents lowering blood pressure, and agents altering lipid metabolism.

16. The process according to claim 5, wherein step (a) is performed in the presence of an inert solvent with the aid of a condensing agent.

* * * * *